US009896621B2

(12) United States Patent
Kim et al.

(10) Patent No.: US 9,896,621 B2
(45) Date of Patent: Feb. 20, 2018

(54) ORGANIC LIGHT-EMITTING DEVICE

(71) Applicant: SAMSUNG DISPLAY CO., LTD., Yongin-si, Gyeonggi-Do (KR)

(72) Inventors: Myeong-Suk Kim, Yongin-si (KR); Tae-Kyung Kim, Yongin-si (KR); Sung-Wook Kim, Yongin-si (KR); Hwan-Hee Cho, Yongin-si (KR); Chang-Woong Chu, Yongin-si (KR)

(73) Assignee: Samsung Display Co., Ltd., Yongin-si, Gyeonggi-do (KR)

( * ) Notice: Subject to any disclaimer, the term of this patent is extended or adjusted under 35 U.S.C. 154(b) by 157 days.

(21) Appl. No.: 14/923,850

(22) Filed: Oct. 27, 2015

(65) Prior Publication Data

US 2016/0260901 A1 Sep. 8, 2016

(30) Foreign Application Priority Data

Mar. 6, 2015 (KR) ........................ 10-2015-0031964

(51) Int. Cl.
*C09K 11/02* (2006.01)
*H01L 51/00* (2006.01)
(Continued)

(52) U.S. Cl.
CPC .......... *C09K 11/025* (2013.01); *C07C 211/43* (2013.01); *C07C 211/44* (2013.01);
(Continued)

(58) Field of Classification Search
CPC ............... H01L 51/006; H01L 51/0067; H01L 51/0072; H01L 51/0058; H01L 51/0052;
(Continued)

(56) References Cited

U.S. PATENT DOCUMENTS 5,968,675 A * 10/1999 Tamano ............... C08G 73/026 313/504
6,251,531 B1 * 6/2001 Enokida ................ C07C 211/61 313/504
(Continued)

FOREIGN PATENT DOCUMENTS

JP 10265773 A * 10/1998
JP 2000150152 A * 5/2000
(Continued)

*Primary Examiner* — Amanda C Walke
(74) *Attorney, Agent, or Firm* — Lee & Morse, P.C.

(57) ABSTRACT

An organic light-emitting device includes a first electrode, a second electrode facing the first electrode, an emission layer between the first electrode and the second electrode, a hole transport region between the first electrode and the emission layer, and an electron transport region between the second electrode and the emission layer. The hole transport region includes a first compound represented by one of Formulae 1A, 1B, and 1C, and the electron transport region includes a second compound represented by one of Formulae 40A and 40B:

<Formula 1A>

(Continued)

-continued

<Formula 1B>

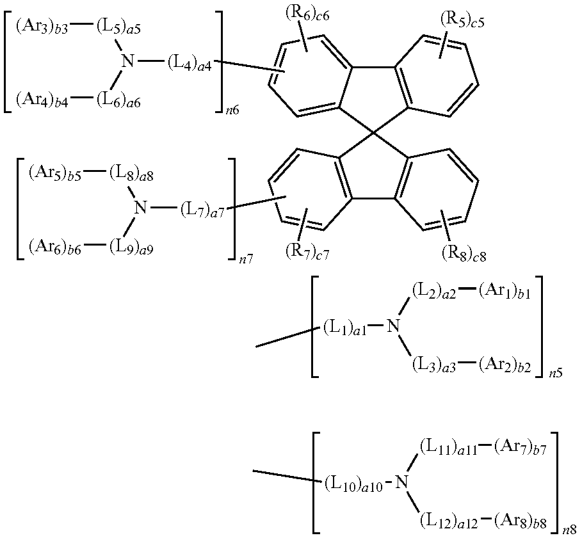

<Formula 1C>

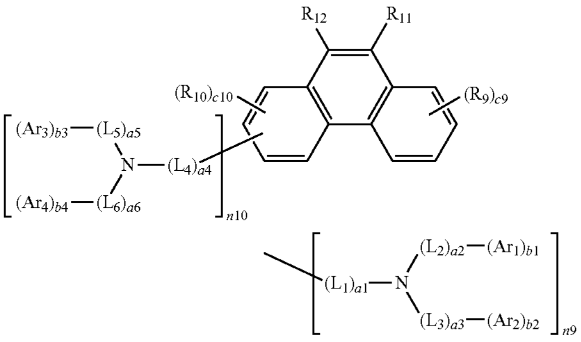

<Formula 40A>

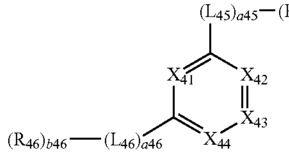

<Formula 40B>

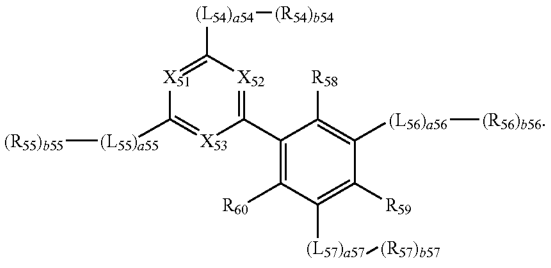

20 Claims, 1 Drawing Sheet

(51) Int. Cl.

| | |
|---|---|
| ***C07C 211/43*** | (2006.01) |
| ***C07D 403/10*** | (2006.01) |
| ***C07C 211/61*** | (2006.01) |
| ***C07D 401/14*** | (2006.01) |
| ***C07C 211/49*** | (2006.01) |
| ***C07C 211/44*** | (2006.01) |
| *H01L 51/50* | (2006.01) |

(52) U.S. Cl.

CPC .......... *C07C 211/49* (2013.01); *C07C 211/61* (2013.01); *C07D 401/14* (2013.01); *C07D 403/10* (2013.01); *H01L 51/006* (2013.01); *H01L 51/0052* (2013.01); *H01L 51/0059* (2013.01); *H01L 51/0067* (2013.01); *H01L 51/0072* (2013.01); *H01L 51/5056* (2013.01); *H01L 51/5072* (2013.01); *H01L 51/5088* (2013.01)

(58) Field of Classification Search

CPC ............ H01L 51/0074; H01L 51/0054; C09K 11/025; C07D 401/14; C07D 403/10; C07C 211/61; C07C 211/43; C07C 211/44; C07C 211/49

USPC .......................... 564/426, 431; 428/690, 917

See application file for complete search history.

(56) References Cited

U.S. PATENT DOCUMENTS 7,357,992 B2 * 4/2008 Kato .................. H01L 51/0059 313/504
7,405,326 B2 * 7/2008 Kawamura ........... C07C 211/61 564/427
8,558,221 B2 * 10/2013 Ito .......................... C08G 61/12 257/40
8,906,893 B2 * 12/2014 Anemian .............. C07C 13/567 514/180
9,028,978 B2 * 5/2015 Kim ...................... C07C 255/58 257/40
9,112,157 B2 * 8/2015 Brown .................. H01L 51/006
9,634,259 B2 * 4/2017 Kim .................... H01L 51/0071
2004/0183495 A1 * 9/2004 Iwashita .............. G05B 19/404 318/638
2005/0064233 A1 3/2005 Matsuura et al.
2006/0049397 A1 3/2006 Pfeiffer et al.
2006/0063027 A1 * 3/2006 Vestweber .............. C07C 13/72 428/690
2007/0082226 A1 * 4/2007 Yu ......................... H01L 51/006 428/690
2008/0194878 A1 8/2008 Nishiyama et al.
2008/0233434 A1 * 9/2008 Kawamura ........... C07C 211/61 428/704
2009/0008605 A1 1/2009 Kawamura et al.
2009/0026919 A1 1/2009 Stossel et al.
2009/0261711 A1 10/2009 Ito et al.
2010/0187552 A1 * 7/2010 Lee ........................ H05B 33/10 257/98
2011/0156013 A1 * 6/2011 Kim ..................... C07D 401/10 257/40
2011/0260153 A1 10/2011 In et al.
2012/0211736 A1 * 8/2012 Kim ....................... C09K 11/06 257/40
2012/0214993 A1 8/2012 Aihara et al.
2012/0235123 A1 * 9/2012 Lee ..................... H01L 51/0072 257/40
2013/0001532 A1 * 1/2013 Hwang ............... H01L 51/0058 257/40
2013/0119355 A1 5/2013 Han et al.
2013/0207046 A1 8/2013 Pflumm et al.
2013/0299794 A1 11/2013 Jung et al.
2014/0054559 A1 * 2/2014 Kim .................... H01L 51/0094 257/40
2014/0183466 A1 * 7/2014 Lee ....................... H01L 51/006 257/40
2014/0306198 A1 * 10/2014 Im ....................... H01L 51/0013 257/40

(56) References Cited

U.S. PATENT DOCUMENTS

| | | | | |
|---|---|---|---|---|
| 2014/0339518 | A1* | 11/2014 | Yamamoto | C09K 11/06 257/40 |
| 2015/0053941 | A1* | 2/2015 | Jung | H01L 51/0072 257/40 |
| 2015/0065730 | A1 | 3/2015 | Montenegro et al. | |
| 2015/0102301 | A1* | 4/2015 | Cho | H01L 51/0054 257/40 |
| 2015/0171342 | A1* | 6/2015 | Jung | C07D 405/14 257/40 |
| 2015/0349275 | A1* | 12/2015 | Jeong | H01L 51/0072 257/40 |

FOREIGN PATENT DOCUMENTS

| | | | |
|---|---|---|---|
| JP | 2008-515936 | A | 5/2008 |
| JP | 2013-136563 | A | 7/2013 |
| KR | 10-2007-0018813 | A | 2/2007 |
| KR | 10-2008-0052589 | A | 6/2008 |
| KR | 10-2011-0076488 | A | 7/2011 |
| KR | 10-2012-0013917 | | 2/2012 |
| KR | 10-2012-0078326 | A | 7/2012 |
| KR | 10-2012-0118051 | A | 10/2012 |
| KR | 10-2013-0051807 | A | 5/2013 |
| KR | 10-2013-0099098 | A | 9/2013 |
| WO | WO 2009/008215 | A1 | 1/2009 |
| WO | WO 2011/021689 | A1 | 2/2011 |
| WO | WO 2013/120577 | A1 | 8/2013 |

* cited by examiner

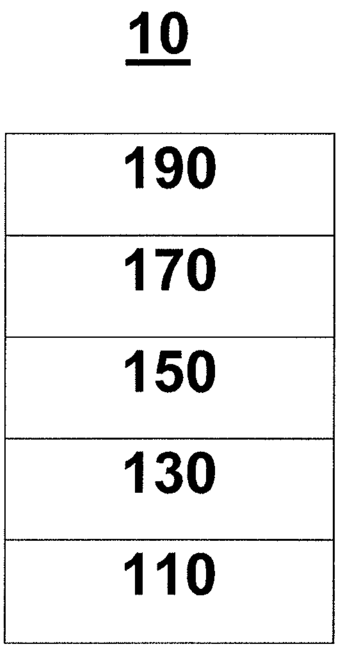
10
190
170
150
130
110

ORGANIC LIGHT-EMITTING DEVICE

CROSS-REFERENCE TO RELATED APPLICATION

Korean Patent Application No. 10-2015-0031964, filed on Mar. 6, 2015, in the Korean Intellectual Property Office, and entitled: "Organic Light-Emitting Device," is incorporated by reference herein in its entirety.

BACKGROUND

1. Field

Embodiments relate to an organic light-emitting device.

2. Description of the Related Art

Organic light-emitting devices (OLEDs) are self-emission devices that have wide viewing angles, high contrast ratios, and short response times. In addition, the OLEDs exhibit excellent luminance, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. The holes and the electrons are recombined in the emission layer to produce excitons. These excitons change from an excited state to a ground state to thereby generate light.

SUMMARY

Embodiments are directed to an organic light-emitting device that includes a first electrode; a second electrode facing the first electrode; an emission layer between the first electrode and the second electrode; a hole transport region between the first electrode and the emission layer; and an electron transport region between the emission layer and the second electrode, wherein the hole transport region includes a first compound represented by one of Formulae 1A, 1B, and 1C, and the electron transport region includes a second compound represented by one of Formulae 40A and 40B:

<Formula 1A>

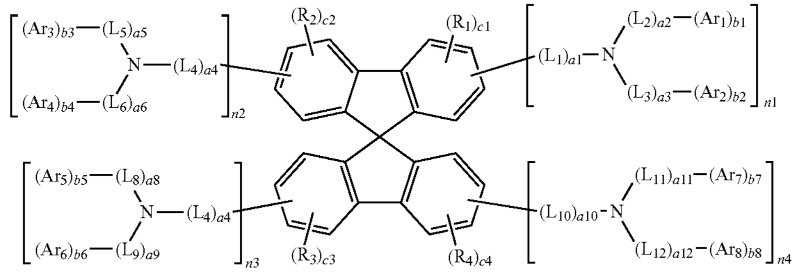

<Formula 1B>

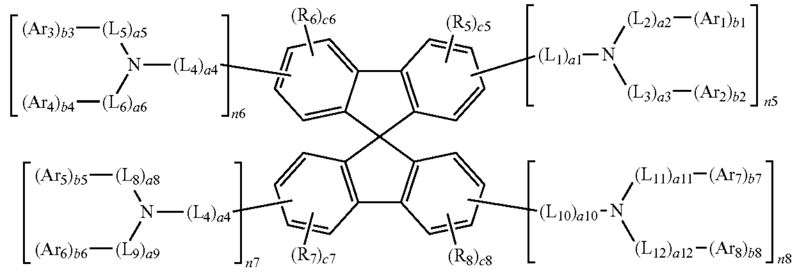

<Formula 1C>

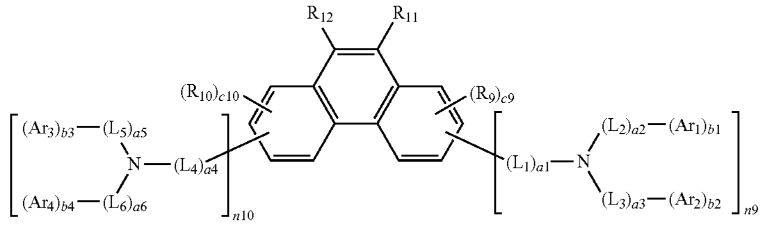

<Formula 40A>

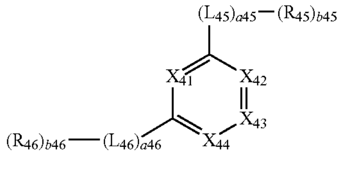

-continued

<Formula 40B>

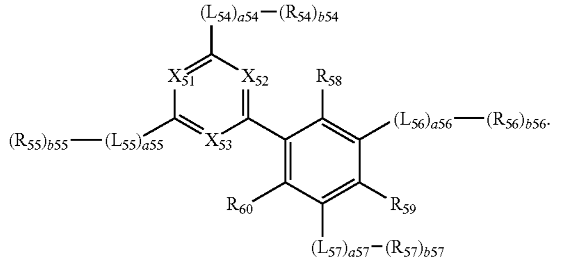

In Formulae 1A, 1B, 1C, 40A, and 40B, $X_{41}$ is N or C-$(L_{41})_{a41}$-$(R_{41})_{b41}$, $X_{42}$ is N or C-$(L_{42})_{a42}$-$(R_{42})_{b42}$, $X_{43}$ is N or C-$(L_{43})_{a43}$-$(R_{43})_{b43}$, $X_{44}$ is N or C-$(L_{44})_{a44}$-$(R_{44})_{b44}$, and at least one selected from $X_{41}$ to $X_{44}$ is N;

$X_{51}$ is N or C-$(L_{51})_{a51}$-$(R_{51})_{b51}$, $X_{52}$ is N or C-$(L_{52})_{a52}$-$(R_{52})_{b52}$, $X_{53}$ is N or C-$(L_{53})_{a53}$-$(R_{53})_{b53}$, and at least one selected from $X_{51}$ to $X_{53}$ is N;

$L_1$ to $L_{12}$, $L_{41}$ to $L_{46}$, and $L_{51}$ to $L_{57}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a1 to a12, a41 to a46, and a51 to a57 are each independently an integer selected from 0 to 3;

$Ar_1$ to $Ar_8$, $R_{41}$ to $R_{46}$, and $R_{51}$ to $R_{57}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted monovalent non-aromatic condensed polycyclic group, and a substituted or unsubstituted monovalent non-aromatic condensed heteropolycyclic group;

$Ar_1$ and $Ar_2$ are optionally linked to each other to form a saturated or unsaturated ring, $Ar_3$ and $Ar_4$ are optionally linked to each other to form a saturated or unsaturated ring, $Ar_5$ and $Ar_6$ are optionally linked to each other to form a saturated or unsaturated ring, and $Ar_7$ and $Ar_8$ are optionally linked to each other to form a saturated or unsaturated ring;

at least one of $R_{41}$ to $R_{46}$ or at least one of $R_{51}$ to $R_{57}$ is selected from a substituted or unsubstituted $C_1$-$C_{10}$ heterocycloalkyl group, a substituted or unsubstituted $C_1$-$C_{10}$ heterocycloalkenyl group, a substituted or unsubstituted $C_1$-$C_{60}$ heteroaryl group, and a substituted or unsubstituted monovalent non-aromatic condensed heteropolycyclic group;

b1 to b8, b41 to b46, and b51 to b57 are each independently an integer selected from 1 to 4;

$R_1$ to $R_{12}$ and $R_{58}$ to $R_{60}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si$(Q_1)(Q_2)(Q_3)$;

$R_{11}$ and $R_{12}$ are optionally linked to each other to form a $C_5$ to $C_{20}$ saturated or unsaturated ring;

c1 to c10 are each independently an integer selected from 0 to 4;

n1 to n4 and n7 to n10 are each independently an integer selected from 0 to 4, and n5 and n6 are each independently an integer selected from 0 to 5, provided that n1+n2+n3+n4 is 1 or more, n5+n6+n7+n8 is 1 or more, and n9+n10 is 1 or more;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group (arylthio), a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_2$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$);

and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

BRIEF DESCRIPTION OF THE DRAWINGS

Features will become apparent to those of skill in the art by describing in detail exemplary embodiments with reference to the attached drawings in which:

FIG. 1 illustrates a schematic view of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURES, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

Expressions such as "at least one of" when preceding a list of elements, modify the entire list of elements and do not modify the individual elements of the list.

FIG. 1 illustrates a schematic view of an organic light-emitting according to an embodiment. The organic light-emitting device may include a first electrode 110, a hole transport region 130, an emission layer 150, an electron transport region 170, and a second electrode 190.

Hereinafter, a structure and a method of manufacturing the organic light-emitting device according to an embodiment will be described with reference to FIG. 1.

Referring to FIG. 1, a substrate may be additionally disposed under the first electrode 110 or on the second electrode 190. The substrate may be a substrate with excellent mechanical strength, thermal stability, transparency, surface smoothness, ease of handling, and water resistance. For example, the substrate may be a glass substrate or a transparent plastic substrate.

The first electrode 110 may be formed by depositing or sputtering a material for forming the first electrode on the substrate. When the first electrode 110 is an anode, the material for the first electrode may be selected from materials with a high work function to make holes be easily injectable. The first electrode 110 may be a reflective electrode, a semi-transmissive electrode, or a transmissive electrode. The material for the first electrode may be a transparent and highly conductive material. Examples of such a material include indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one selected from magnesium (Mg), aluminum (Al), aluminum-lithium (Al—Li), calcium (Ca), magnesium-indium (Mg—In), and magnesium-silver (Mg—Ag) may be used.

The first electrode 110 may have a single-layer structure, or a multi-layer structure including a plurality of layers. For example, the first electrode 110 may have a triple-layer structure of ITO/Ag/ITO.

The hole transport region 130, the emission layer 150, and the electron transport region 170 may be sequentially stacked on the first electrode 110.

The hole transport region may include a first compound represented by one of Formulae 1A, 1B, and 1C, and the electron transport region may include a second compound represented by Formulae 40A and 40B:

<Formula 1A>

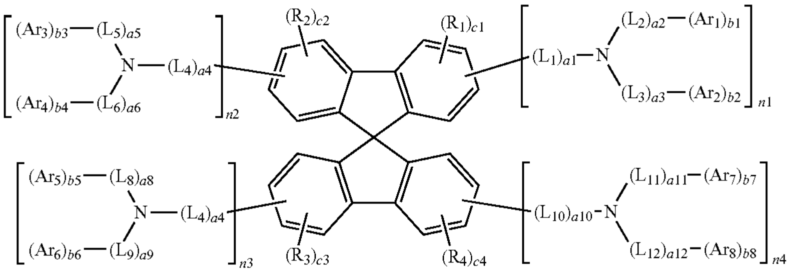

<Formula 1B>

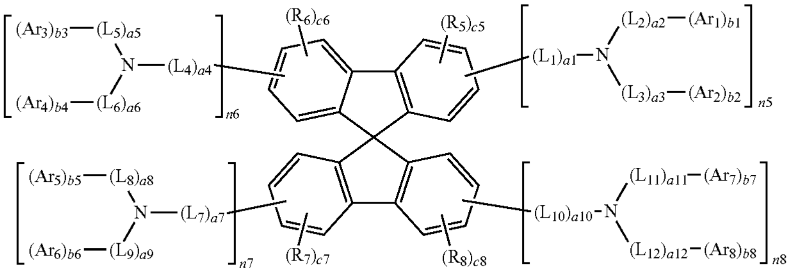

<Formula 1C>

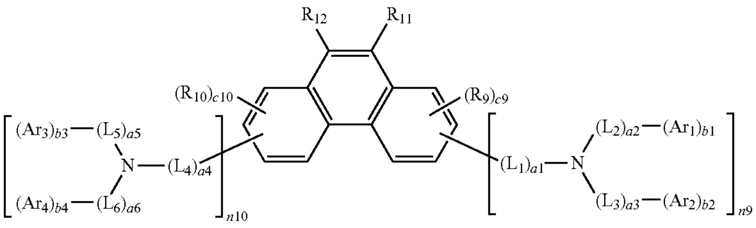

<Formula 40A>

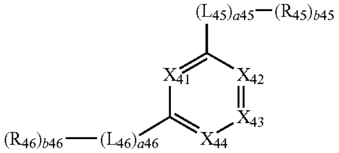

<Formula 40B>

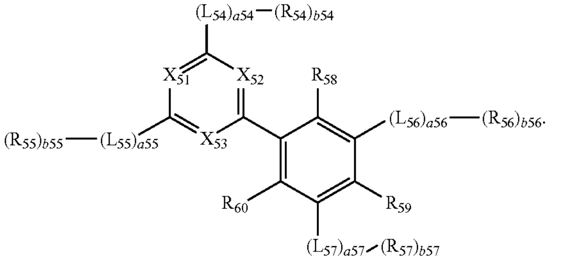

In the Formulae above, $L_1$ to $L_{12}$, $L_{41}$ to $L_{46}$, and $L_{51}$ to $L_{57}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

In some embodiments, in the Formulae above, $L_1$ to $L_{12}$, $L_{41}$ to $L_{46}$, and $L_{51}$ to $L_{57}$ may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, and a dibenzocarbazolylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, and an imidazopyridinyl group.

In some embodiments, in the Formulae above, $L_1$ to $L_{12}$, $L_{41}$ to $L_{46}$, and $L_{51}$ to $L_{57}$ may be each independently selected from a phenylene group, a naphthylene group, a fluorenylene group, a spiro-fluorenylene group, a phenanthrenylene group, an anthracenylene group, a fluoranthenylene group, a triphenylenylene group, a pyrenylene group, and a chrysenylene group; and a phenylene group, a naphthylene group, a fluorenylene group, a spiro-fluorenylene group, a phenanthrenylene group, an anthracenylene group, a fluoranthenylene group, a triphenylenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a Spiro-fluorenyl group, a phenanthrenyl group, an anthracenyl group, a fluoranthenyl group, a triphenylenyl group, a pyrenyl group, a chrysenyl group, a biphenyl group, a terphenyl group, and $—Si(Q_{31})(Q_{32})(Q_{33})$;

wherein $Q_{31}$ to $Q_{33}$ may be each independently selected from a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a biphenyl group, and a terphenyl group.

In some embodiments, in the Formulae above, $L_1$ to $L_{12}$ may be each independently selected from groups represented by Formulae 3-1 to 3-41, and $L_{41}$ to $L_{46}$ and $L_{51}$ to $L_{57}$ may be each independently selected from groups represented by Formulae 3-1 to 3-9, 3-25, and 3-33 to 3-41 (provided that $Y_1{=}C(Z_3)(Z_4)$ in Formulae 3-3 and 3-4):

Formula 3-1

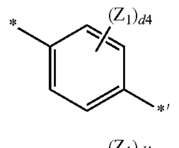

Formula 3-2

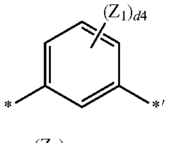

Formula 3-3

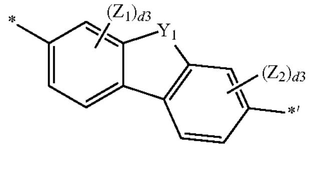

-continued
Formula 3-4
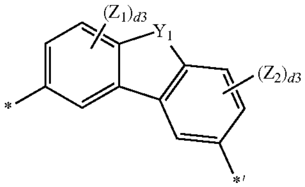
Formula 3-5
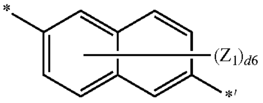
Formula 3-6
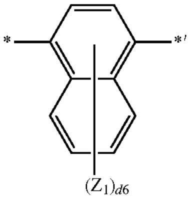
Formula 3-7
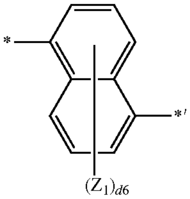
Formula 3-8
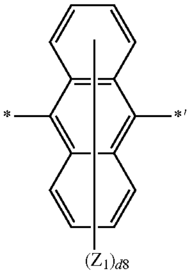
Formula 3-9
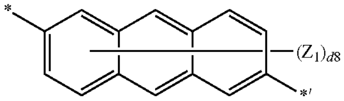
Formula 3-10
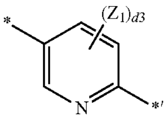
Formula 3-11
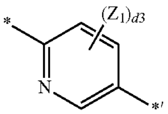
Formula 3-12
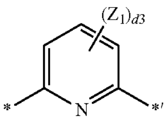
-continued
Formula 3-13
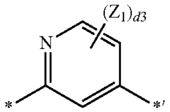
Formula 3-14
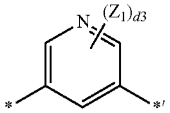
Formula 3-15
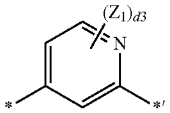
Formula 3-16
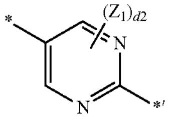
Formula 3-17
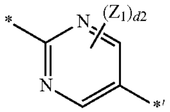
Formula 3-18
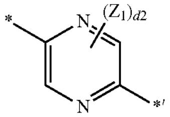
Formula 3-19
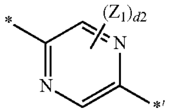
Formula 3-20
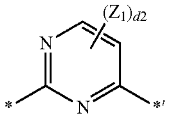
Formula 3-21
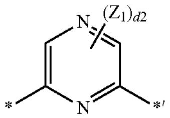
Formula 3-22
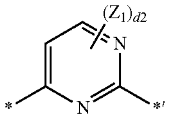
Formula 3-23
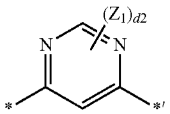
Formula 3-24
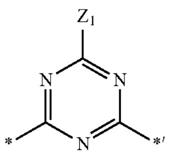

-continued
Formula 3-25
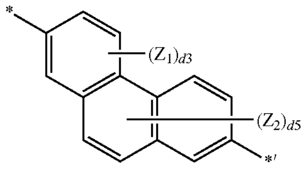
Formula 3-26
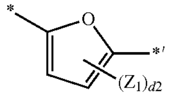
Formula 3-27
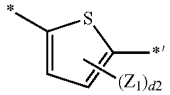
Formula 3-28
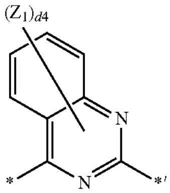
Formula 3-29
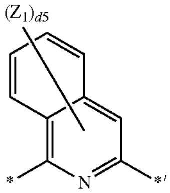
Formula 3-30
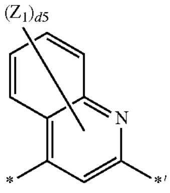
Formula 3-31
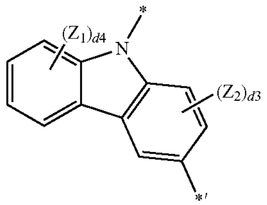
Formula 3-32
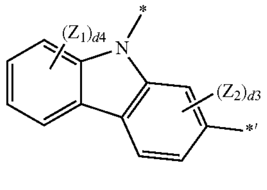
Formula 3-33
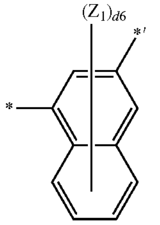
-continued
Formula 3-34
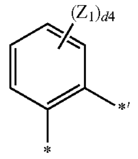
Formula 3-35
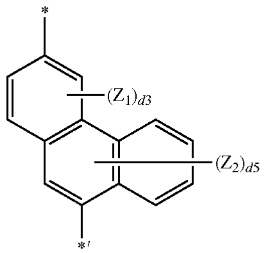
Formula 3-36
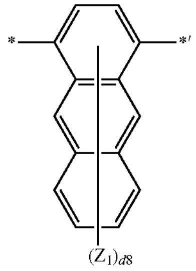
Formula 3-37
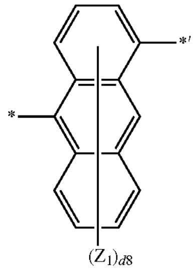
Formula 3-38
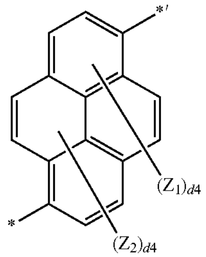
Formula 3-39
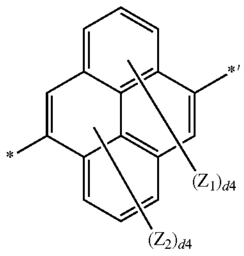

-continued

Formula 3-40

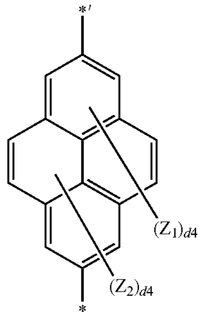

Formula 3-41

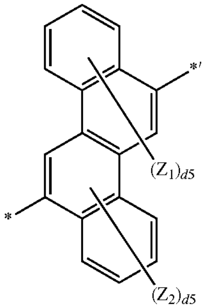

wherein, in Formulae 3-1 to 3-41, $Y_1$ may be O, S, $C(Z_3)(Z_4)$, $N(Z_5)$, or $Si(Z_6)(Z_7)$;

$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group; and —$Si(Q_{31})(Q_{32})(Q_{33})$;

wherein $Q_1$ to $Q_3$ and $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, and a carbazolyl group;

d2 may be an integer selected from 1 and 2;

d3 may be an integer selected from 1 to 3;

d4 may be an integer selected from 1 to 4;

d5 may be an integer selected from 1 to 5;

d6 may be an integer selected from 1 to 6;

d8 may be an integer selected from 1 to 8; and

* and *' each indicate a binding site to an adjacent atom.

In some embodiments, in the Formulae above, $L_1$ to $L_{12}$ may be each independently selected from groups represented by Formulae 4-1 to 4-36, and $L_{41}$ to $L_{46}$ and $L_{51}$ to $L_{57}$ may be each independently selected from groups represented by Formulae 4-1, 4-3, 4-5, 4-7 to 4-13, 4-17, and 4-24 to 4-36:

Formula 4-1

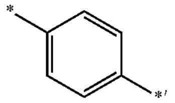

Formula 4-2

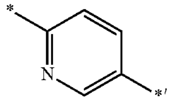

Formula 4-3

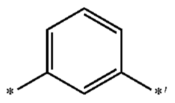

Formula 4-4

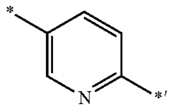

Formula 4-5

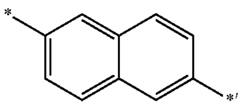

Formula 4-6

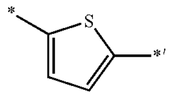

Formula 4-7

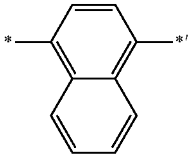

Formula 4-8

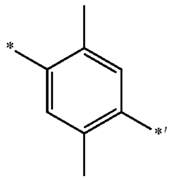

-continued
Formula 4-9
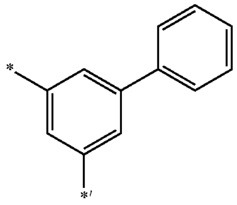
Formula 4-10
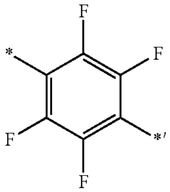
Formula 4-11
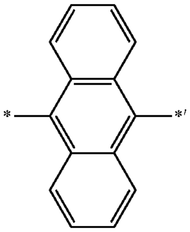
Formula 4-12
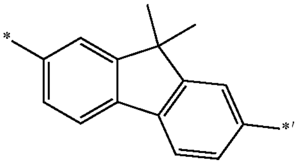
Formula 4-13
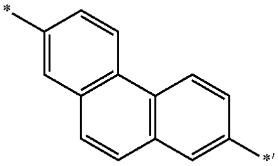
Formula 4-14
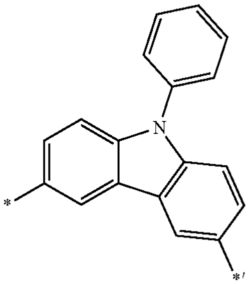
Formula 4-15
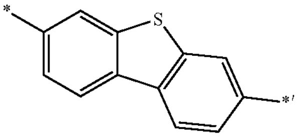
Formula 4-16
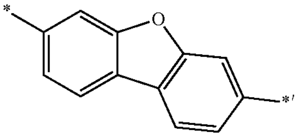
-continued
Formula 4-17
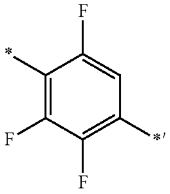
Formula 4-18
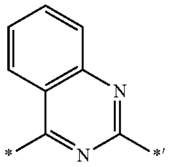
Formula 4-19
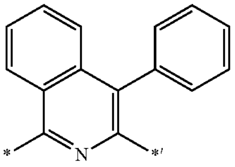
Formula 4-20
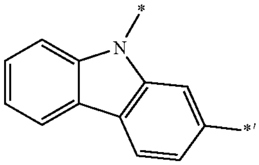
Formula 4-21
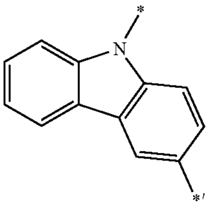
Formula 4-22
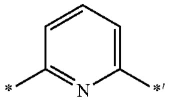
Formula 4-23
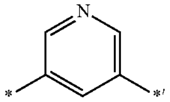
Formula 4-24
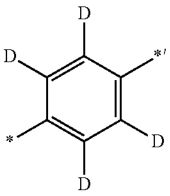
Formula 4-25
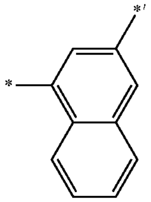

-continued

Formula 4-26

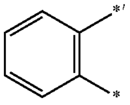

Formula 4-27

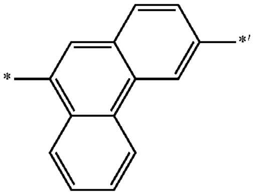

Formula 4-28

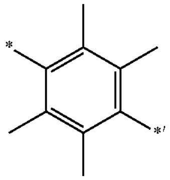

Formula 4-29

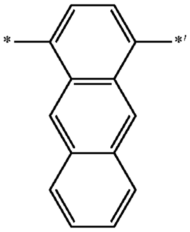

Formula 4-30

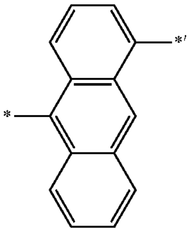

Formula 4-31

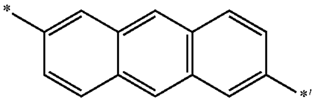

Formula 4-32

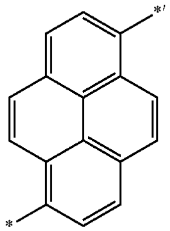

Formula 4-33

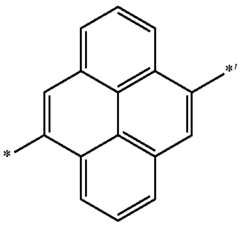

-continued

Formula 4-34

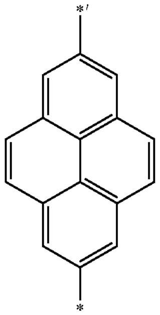

Formula 4-35

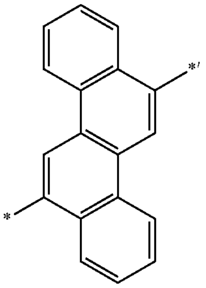

Formula 4-36

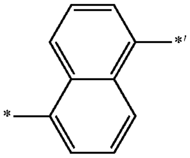

wherein, in Formulae 4-1 to 4-36, * and *' each indicate a binding site to an adjacent atom.

In the Formulae above, a1 to a12, a41 to a46, and a51 to a57 may each independently be an integer selected from 0 to 3. a1 indicates the number of $L_1$. When a1 is 0, $-(L_1)_{a1}-$ may be a single bond. When a1 is two or more, a plurality of a1 $L_1$ may be identical to or different from each other. a2 to a12, a41 to a46, and a51 to a57 may be understood by referring to the descriptions of a1 and the structures of Formulae 1A to 1C and Formulae 40A and 40B.

In some embodiments, a1 to a12, a41 to a46, and a51 to a57 may each independently be 0, 1, or 2, or, for example, 0 or 1.

In the Formulae above, $Ar_1$ to $Ar_8$, $R_{41}$ to $R_{46}$, and $R_{51}$ to $R_{57}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and $Ar_1$ and $Ar_2$ may be optionally linked to each other to form a $C_5$ to $C_{20}$ saturated or unsaturated ring, $Ar_3$ and $Ar_4$ may be optionally linked to each other to form a $C_5$ to $C_{20}$ saturated or unsaturated ring, $Ar_5$ and $Ar_6$ may be optionally linked to each other to form a $C_5$ to $C_{20}$ saturated or unsaturated ring, and $Ar_7$ and $Ar_8$ may be optionally linked to each other to form a $C_5$ to $C_{20}$ saturated or unsaturated ring.

In some embodiments, in the Formulae above, $Ar_1$ to $Ar_8$, $R_{41}$ to $R_{46}$, and $R_{51}$ to $R_{57}$ may be each independently selected from a phenyl group, a pentalenyl group, an indenyl group, a naphthyl group, an azulenyl group, a heptalenyl group, an indacenyl group, an acenaphthyl group, a fluorenyl group, a Spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{33}$)($Q_{34}$)($Q_{35}$);

wherein $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

In some embodiments, in Formulae 1A to 1C, $Ar_1$ to $Ar_8$, $R_{41}$ to $R_{46}$, and $R_{51}$ to $R_{57}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —$Si(Q_{31})(Q_{32})(Q_{33})$;

wherein $Q_{31}$ to $Q_{33}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group, as examples.

In some embodiments, $Ar_1$ to $Ar_8$ in Formulae 1A to 1C may be each independently selected from groups represented by Formulae 5-1 to 5-87:

Formula 5-1

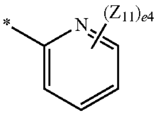

Formula 5-2

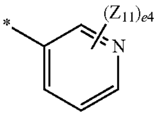

Formula 5-3

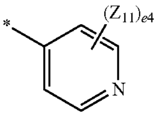

Formula 5-4

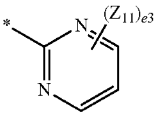

Formula 5-5

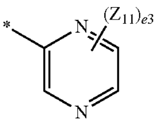

-continued

Formula 5-6

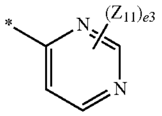

Formula 5-7

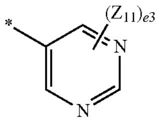

Formula 5-8

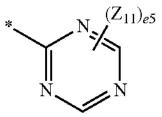

Formula 5-9

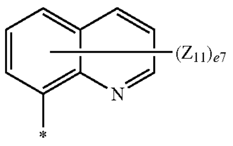

Formula 5-10

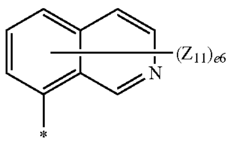

Formula 5-11

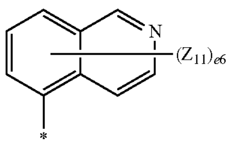

Formula 5-12

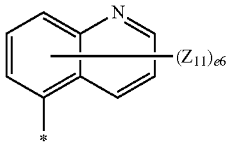

Formula 5-13

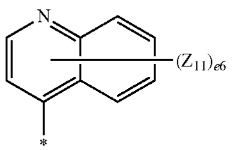

Formula 5-14

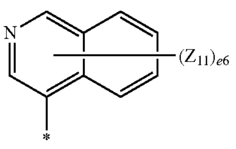

Formula 5-15

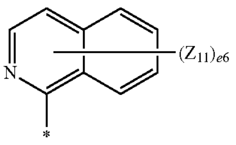

Formula 5-16

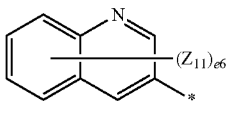

-continued
Formula 5-17
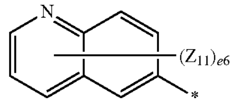
Formula 5-18
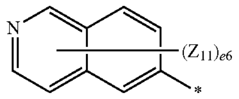
Formula 5-19
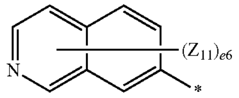
Formula 5-20
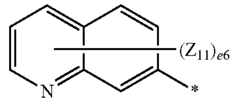
Formula 5-21
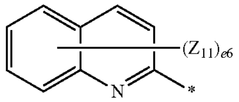
Formula 5-22
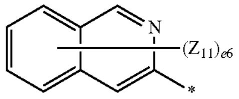
Formula 5-23
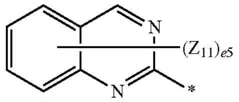
Formula 5-24
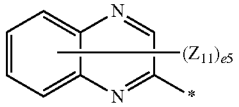
Formula 5-25
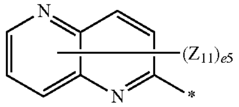
Formula 5-26
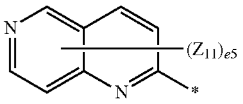
Formula 5-27
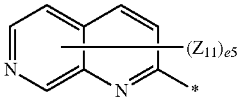
Formula 5-28
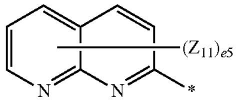
Formula 5-29
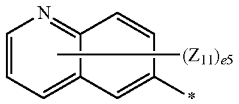
Formula 5-30
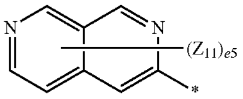
-continued
Formula 5-31
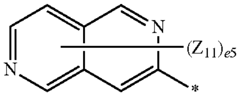
Formula 5-32
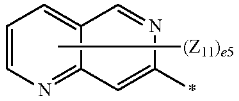
Formula 5-33
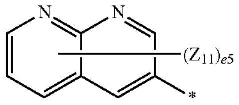
Formula 5-34
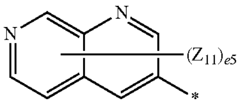
Formula 5-35
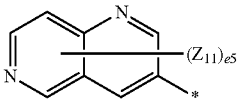
Formula 5-36
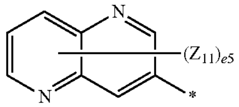
Formula 5-37
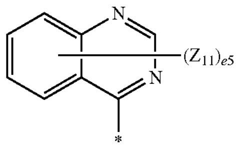
Formula 5-38
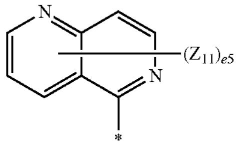
Formula 5-39
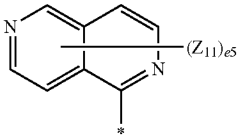
Formula 5-40
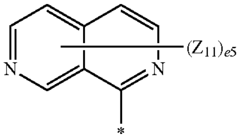
Formula 5-41
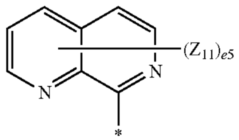

-continued
Formula 5-42
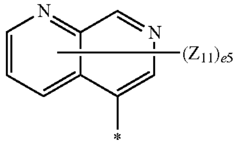
Formula 5-43
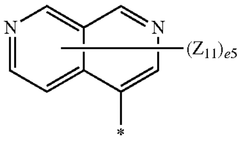
Formula 5-44
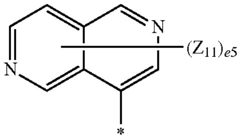
Formula 5-45
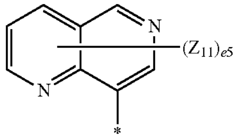
Formula 5-46
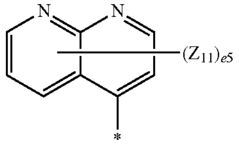
Formula 5-47
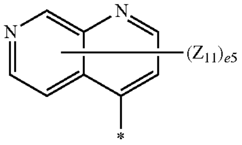
Formula 5-48
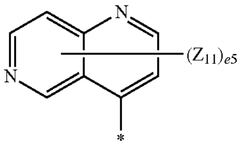
Formula 5-49
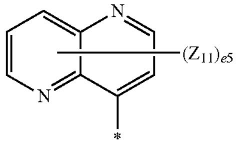
Formula 5-50
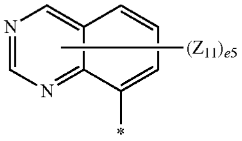
Formula 5-51
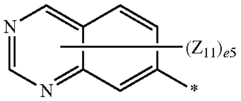
-continued
Formula 5-52
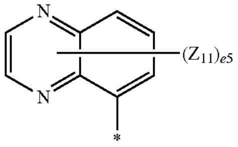
Formula 5-53
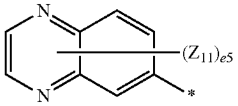
Formula 5-54
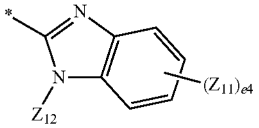
Formula 5-55
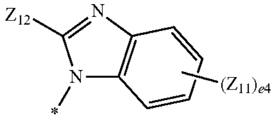
Formula 5-56
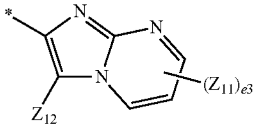
Formula 5-57
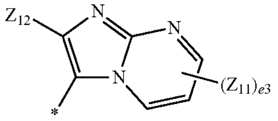
Formula 5-58
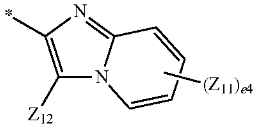
Formula 5-59
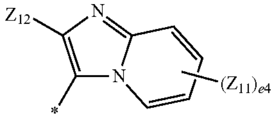
Formula 5-60
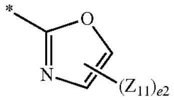
Formula 5-61
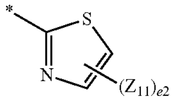
Formula 5-62
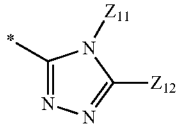
Formula 5-63
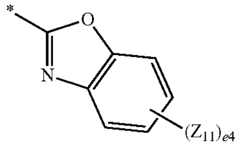

-continued
Formula 5-64
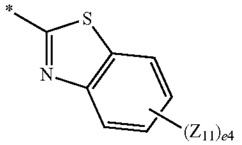
Formula 5-65
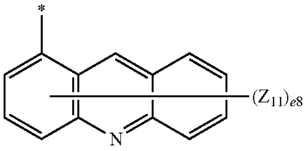
Formula 5-66
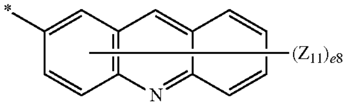
Formula 5-67
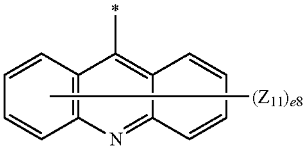
Formula 5-68
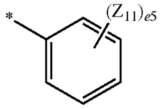
Formula 5-69
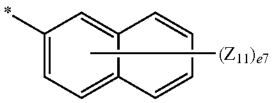
Formula 5-70
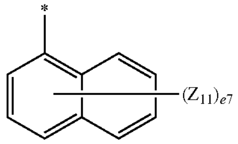
Formula 5-71
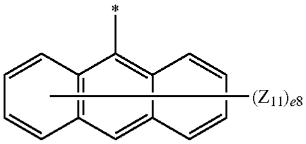
Formula 5-72
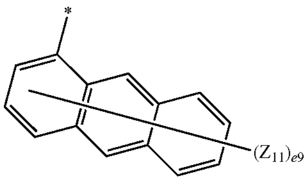
Formula 5-73
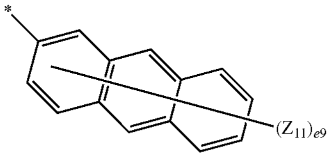
-continued
Formula 5-74
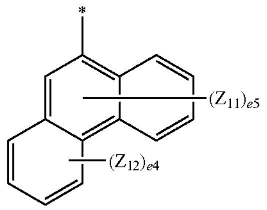
Formula 5-75
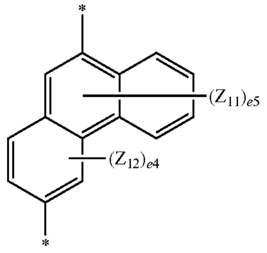
Formula 5-76
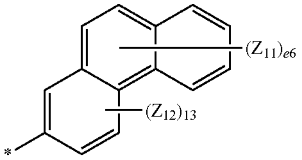
Formula 5-77
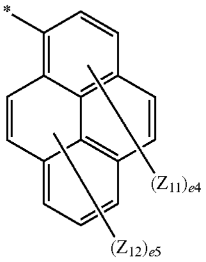
Formula 5-78
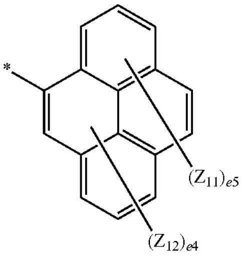
Formula 5-79
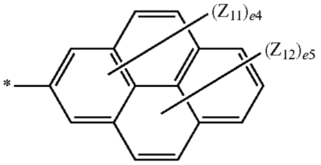
Formula 5-80
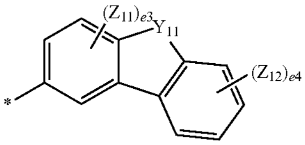

-continued

Formula 5-81

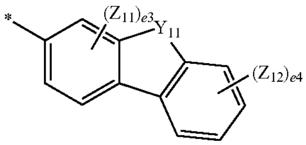

Formula 5-82

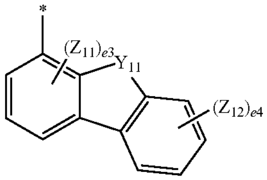

Formula 5-83

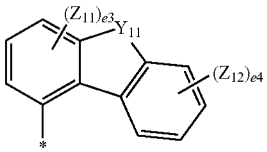

Formula 5-84

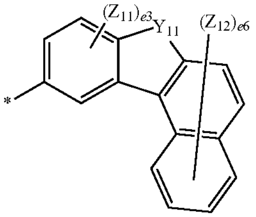

Formula 5-85

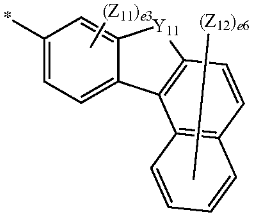

Formula 5-86

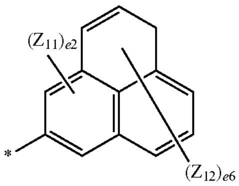

Formula 5-87

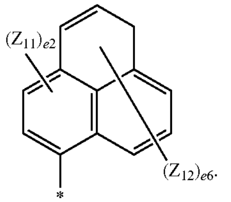

In Formulae 5-1 to 5-87, $Y_{11}$ may be O, S, $C(Z_{13})(Z_{14})$, $N(Z_{15})$, or $Si(Z_{16})(Z_{17})$;

$Z_{11}$ to $Z_{17}$ may be each independently selected from a hydrogen, a deuterium, —F, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, and a dibenzofuranyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, and a dibenzofuranyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group;

and $—Si(Q_{31})(Q_{32})(Q_{33})$; and $Z_{11}$ and $Z_{12}$ may be optionally linked to each other to form a saturated or unsaturated ring, and $Z_{13}$ and $Z_{14}$ may be optionally linked to each other to form a saturated or unsaturated ring;

wherein $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group;

e2 may be an integer selected from 1 and 2;

e3 may be an integer selected from 1 to 3;

e4 may be an integer selected from 1 to 4;

e5 may be an integer selected from 1 to 5;

e6 may be an integer selected from 1 to 6;

e7 may be an integer selected from 1 to 7;

e8 may be an integer selected from 1 to 8;

e9 may be an integer selected from 1 to 9; and

* indicates a binding site to an adjacent atom.

In some embodiments, $Ar_1$ to $Ar_8$, $R_{41}$ to $R_{46}$, and $R_{51}$ to $R_{57}$ in Formulae 1A to 1C may be each independently selected from groups represented by Formulae 6-1 to 6-170:

Formula 6-1

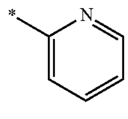

Formula 6-2

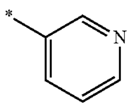

-continued
Formula 6-3
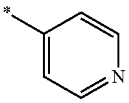
Formula 6-4
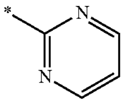
Formula 6-5
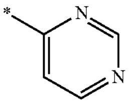
Formula 6-6
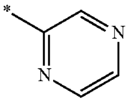
Formula 6-7
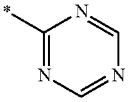
Formula 6-8
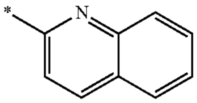
Formula 6-9
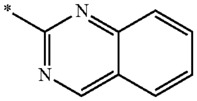
Formula 6-10
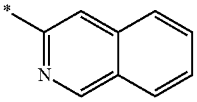
Formula 6-11
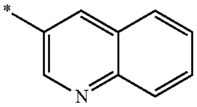
Formula 6-12
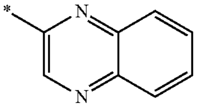
Formula 6-13
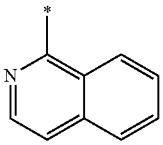
Formula 6-14
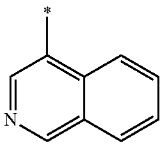
-continued
Formula 6-15
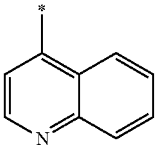
Formula 6-16
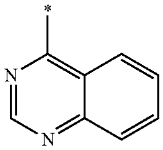
Formula 6-17
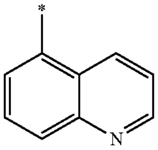
Formula 6-18
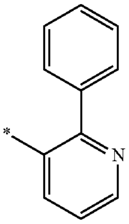
Formula 6-19
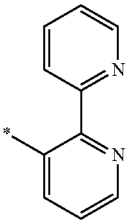
Formula 6-20
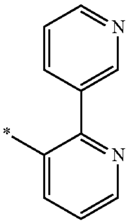
Formula 6-21
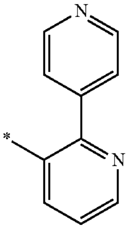

-continued
Formula 6-22
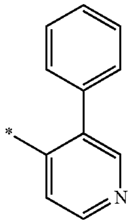
Formula 6-23
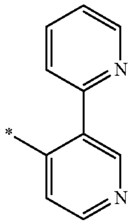
Formula 6-24
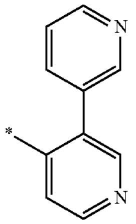
Formula 6-25
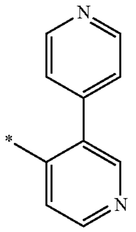
Formula 6-26
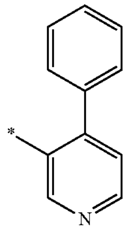
Formula 6-27
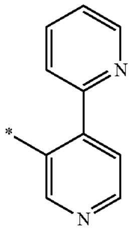
-continued
Formula 6-28
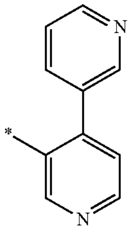
Formula 6-29
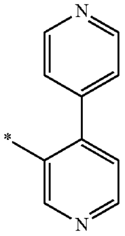
Formula 6-30
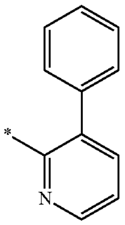
Formula 6-31
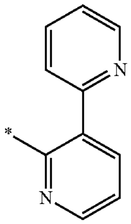
Formula 6-32
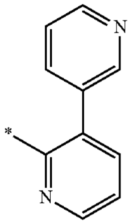
Formula 6-33
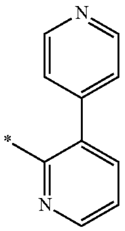

-continued
Formula 6-34
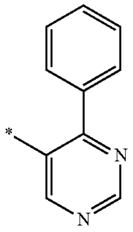
Formula 6-35
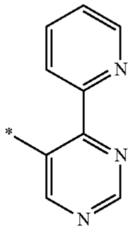
Formula 6-36
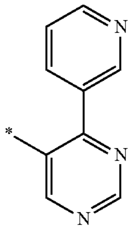
Formula 6-37
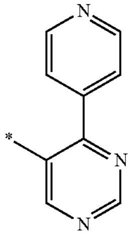
Formula 6-38
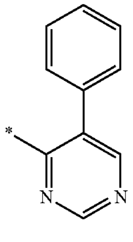
Formula 6-39
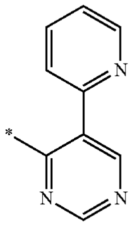
-continued
Formula 6-40
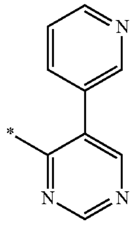
Formula 6-41
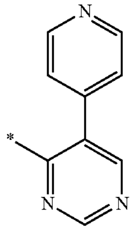
Formula 6-42
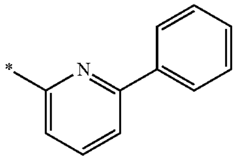
Formula 6-43
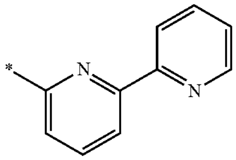
Formula 6-44
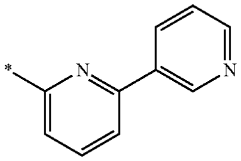
Formula 6-45
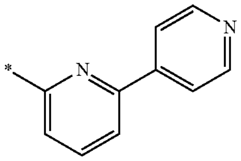
Formula 6-46
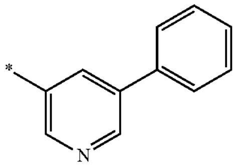
Formula 6-47
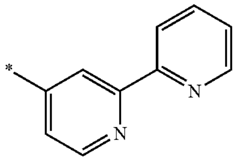

-continued
Formula 6-48
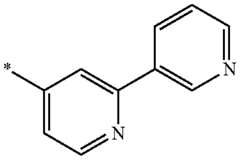
Formula 6-49
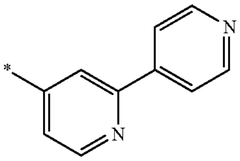
Formula 6-50
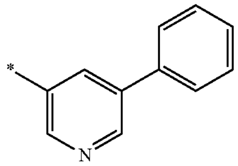
Formula 6-51
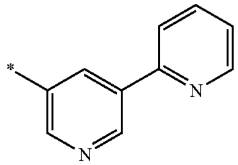
Formula 6-52
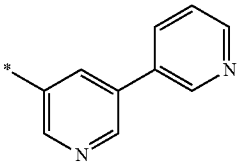
Formula 6-53
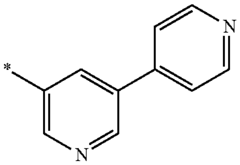
Formula 6-54
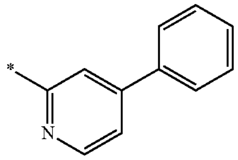
Formula 6-55
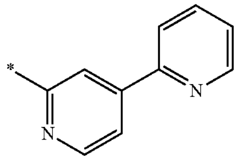
Formula 6-56
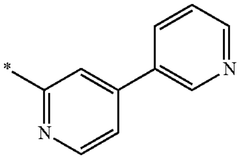
-continued
Formula 6-57
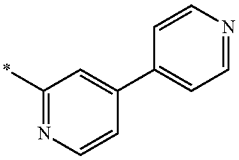
Formula 6-58
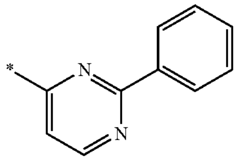
Formula 6-59
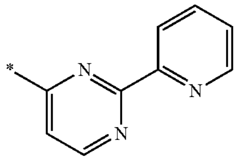
Formula 6-60
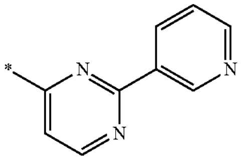
Formula 6-61
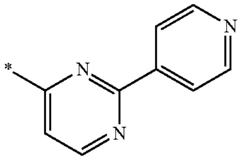
Formula 6-62
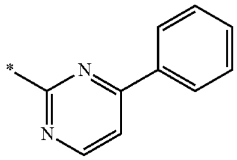
Formula 6-63
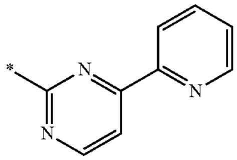
Formula 6-64
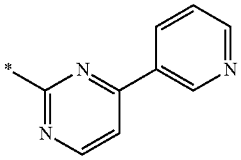
Formula 6-65
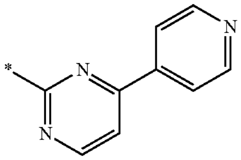

-continued
Formula 6-66
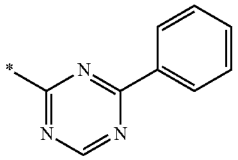
Formula 6-67
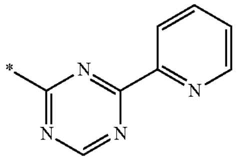
Formula 6-68
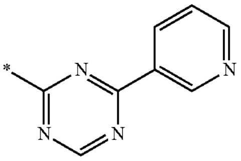
Formula 6-69
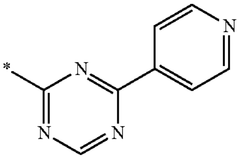
Formulat 6-70
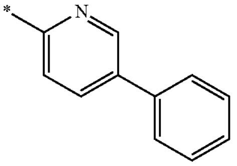
Formula 6-71
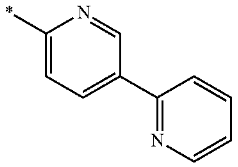
Formula 6-72
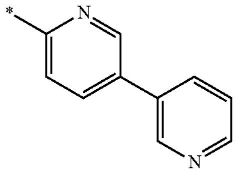
Formula 6-73
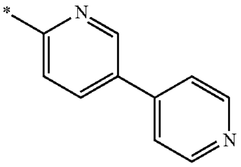
Formula 6-74
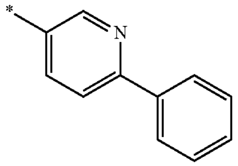
-continued
Formula 6-75
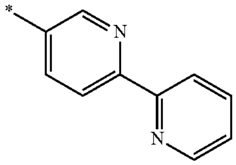
Formula 6-76
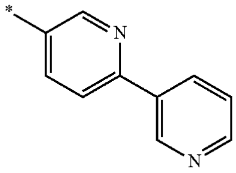
Formula 6-77
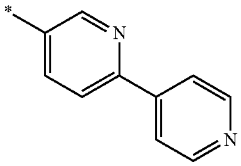
Formula 6-78
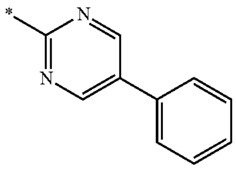
Formula 6-79
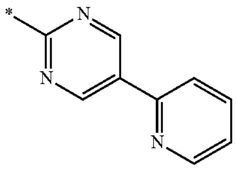
Formula 6-80
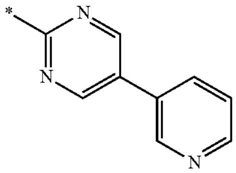
Formula 6-81
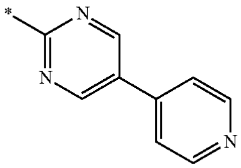
Formula 6-82
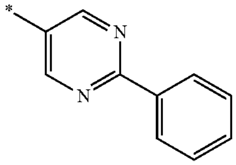
Formula 6-83
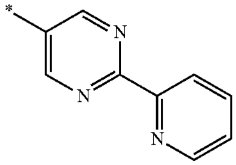

-continued
Formula 6-84
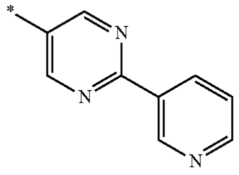
Formula 6-85
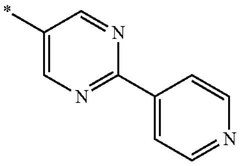
Formula 6-86
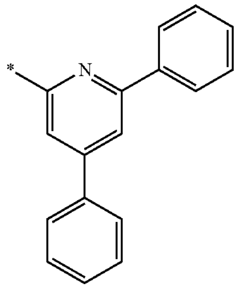
Formula 6-87
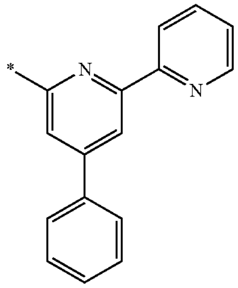
Formula 6-88
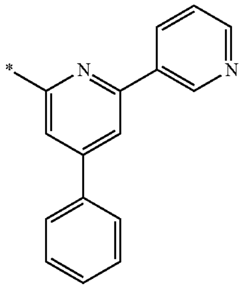
Formula 6-89
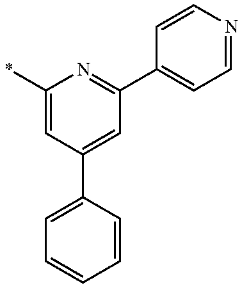
-continued
Formula 6-90
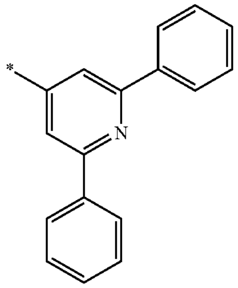
Formula 6-91
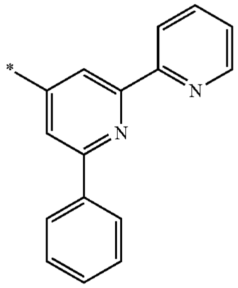
Formula 6-92
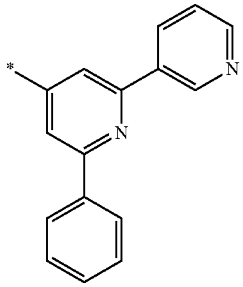
Formula 6-93
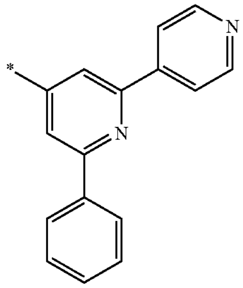
Formula 6-94
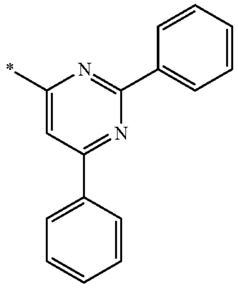

-continued
Formula 6-95
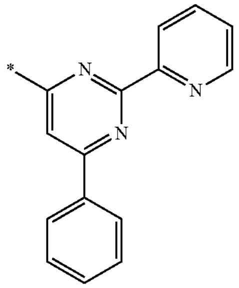
Formula 6-96
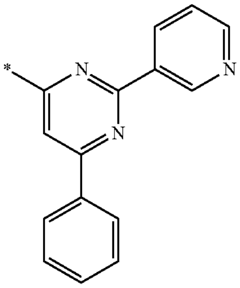
Formula 6-97
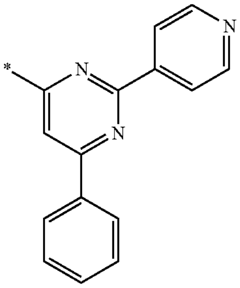
Formula 6-98
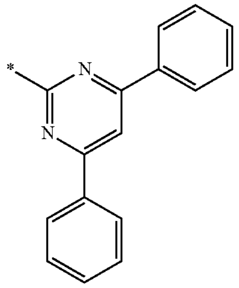
Formula 6-99
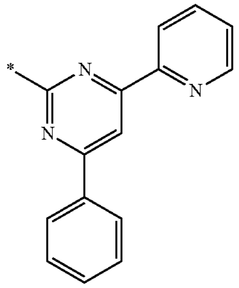
-continued
Formula 6-100
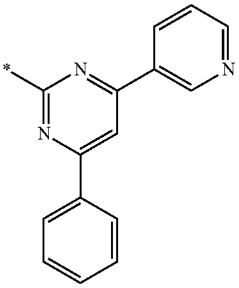
Formula 6-101
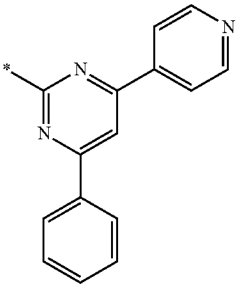
Formula 6-102
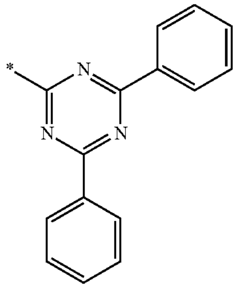
Formula 6-103
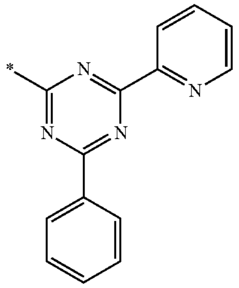
Formula 6-104
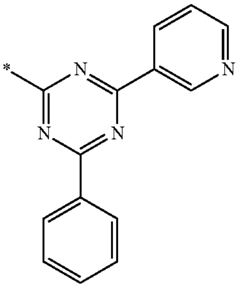

-continued
Formula 6-105
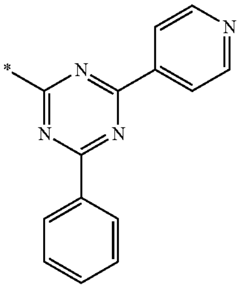
Formula 6-106
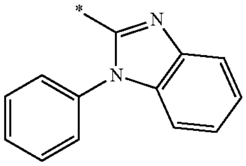
Formula 6-107
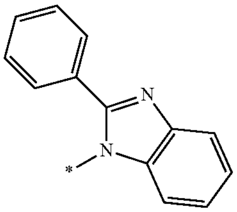
Formula 6-108
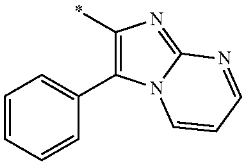
Formula 6-109
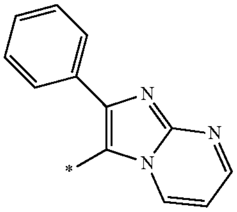
Formula 6-110
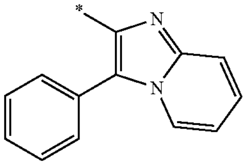
Formula 6-111
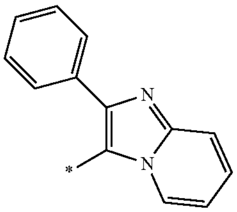
-continued
Formula 6-112
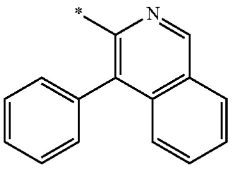
Formula 6-113
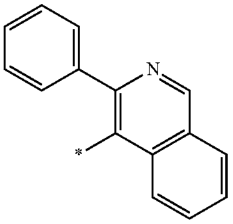
Formula 6-114
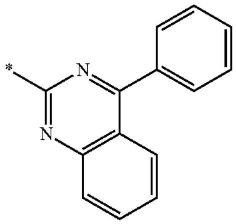
Formula 6-115
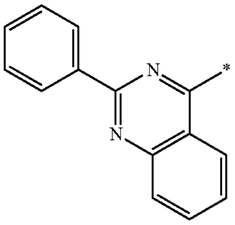
Formula 6-116
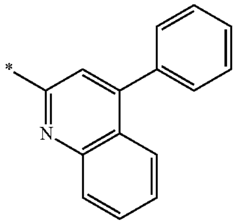
Formula 6-117
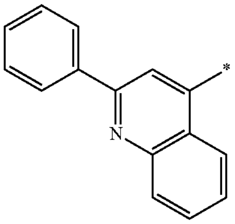
Formula 6-118
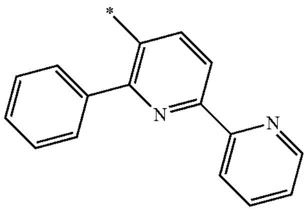

-continued
Formula 6-119
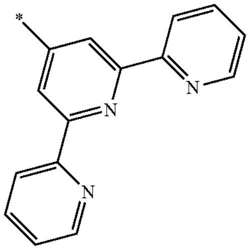
Formula 6-120
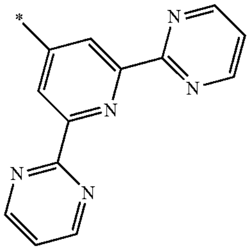
Formula 6-121
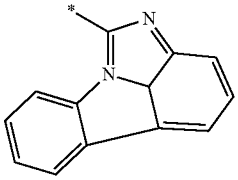
Formula 6-122
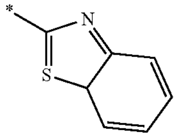
Formula 6-123
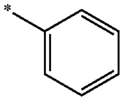
Formula 6-124
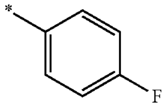
Formula 6-125
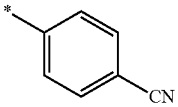
Formula 6-126
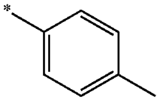
Formula 6-127
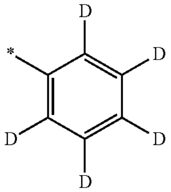
-continued
Formula 6-128
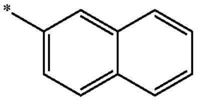
Formula 6-129
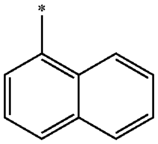
Formula 6-130
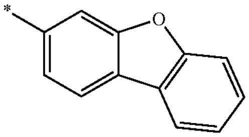
Formula 6-131
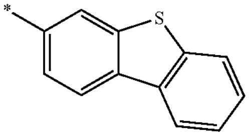
Formula 6-132
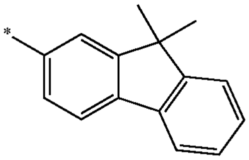
Formula 6-133
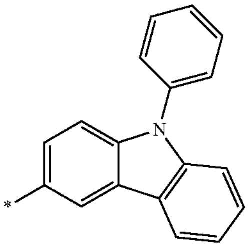
Formula 6-134
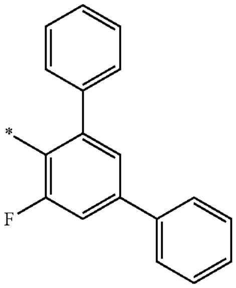
Formula 6-135
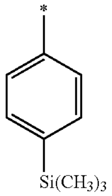

-continued
Formula 6-136
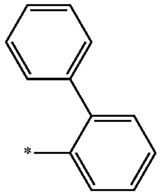
Formula 6-137
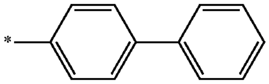
Formula 6-138
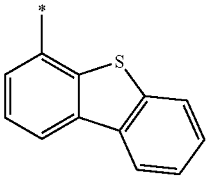
Formula 6-139
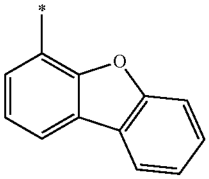
Formula 6-140
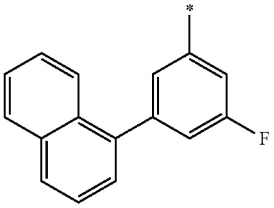
Formula 6-141
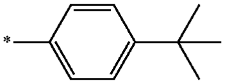
Formula 6-142
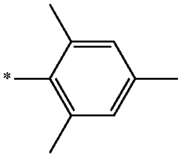
Formula 6-143
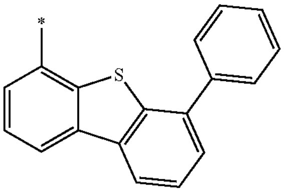
Formula 6-144
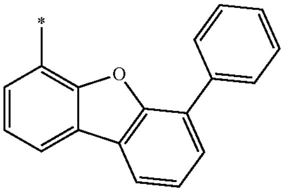
-continued
Formula 6-145
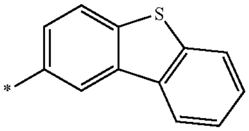
Formula 6-146
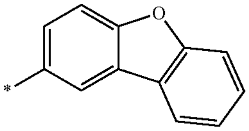
Formula 6-147
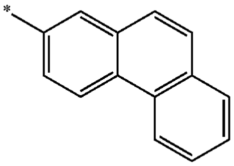
Formula 6-148
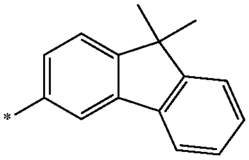
Formula 6-149
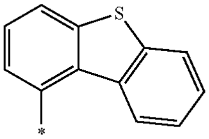
Formula 6-150
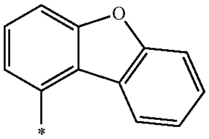
Formula 6-151
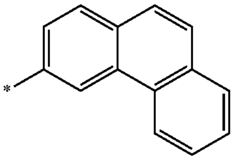
Formula 6-152
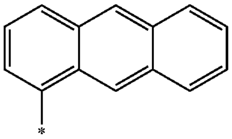
Formula 6-153
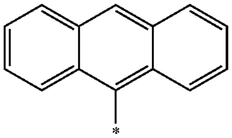
Formula 6-154
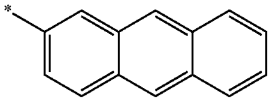

-continued
Formula 6-155
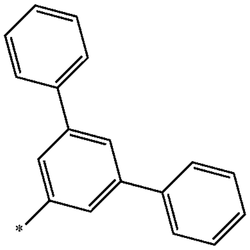
Formula 6-156
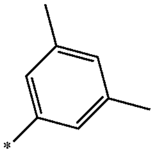
Formula 6-157
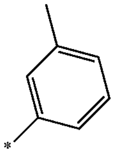
Formula 6-158
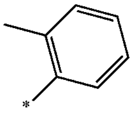
Formula 6-159
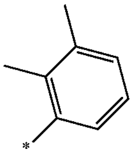
Formula 6-160
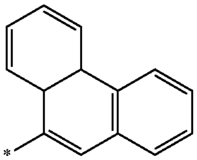
Formula 6-161
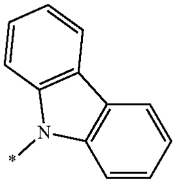
Formula 6-162
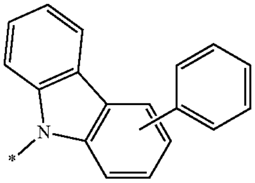
Formula 6-163
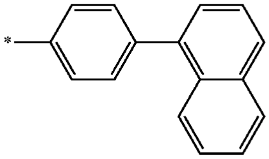
-continued
Formula 6-164
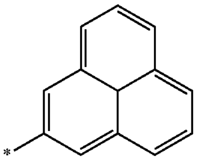
Formula 6-165
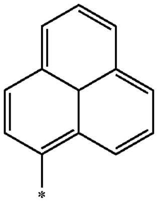
Formula 6-166
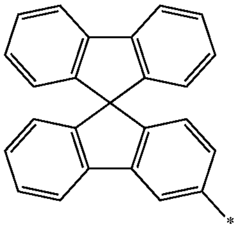
Formula 6-167
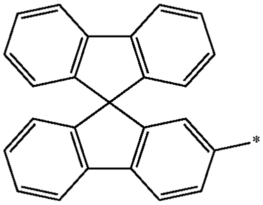
Formula 6-168
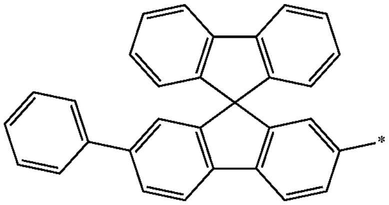
Formula 6-169
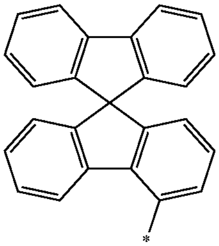
Formula 6-170
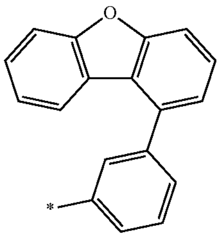
wherein, in Formulae 6-1 to 6-170, * indicates a binding site to an adjacent atom.

In some embodiments, in Formulae 1A to 1C, at least one of

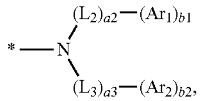
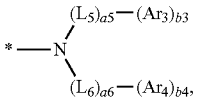
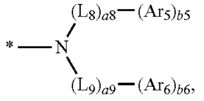
and
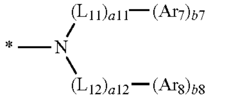

may be selected from groups represented by Formulae 7-1 and 7-2:

Formula 7-1

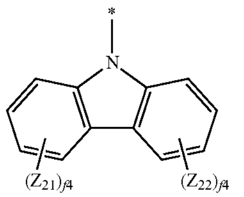

Formula 7-2

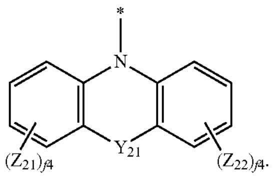

In Formulae 7-1 and 7-2, $Y_{21}$ may be selected from O, S, $C(Z_{23})(Z_{24})$. $N(Z_{25})$, and $Si(Z_{26})(Z_{27})$; and $Z_{21}$ to $Z_{27}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and $—Si(Q_{31})(Q_{32})(Q_{33})$;

wherein $Q_{31}$ to $Q_{33}$ may be each independently selected from a $C_1$-$C_{10}$ alkyl group, a $C_1$-$C_{20}$ alkoxy group, a phenyl group, and a naphthyl group;

f4 may be an integer selected from 1 to 4, and * indicates a binding site to an adjacent atom.

In the Formulae above, b1 to b8, b41 to b46, and b51 to b57 may each independently be an integer selected from 1 to 4. b1 indicate the number of $Ar_1$, and when b1 is two or more, a plurality of $Ar_1$ may be identical to or different from each other. b2 to b8, b41 to b46, and b51 to b57 may be understood by referring to the descriptions of b1 and the structures of Formulae 1A to 1C and Formulae 40A and 40B.

In some embodiments, b1 to b8, b41 to b46, and b51 to b57 may each independently be 1 or 2, or, for example, may each be 1.

In Formulae 40A and 40B, $X_{41}$ may be N or $C$-$(L_{41})_{a41}$-$(R_{41})_{b41}$, $X_{42}$ may be N or $C$-$(L_{42})_{a42}$-$(R_{42})_{b42}$, $X_{43}$ may be N or $C$-$(L_{43})_{a43}$-$(R_{43})_{b43}$, $X_{44}$ may be N or $C$-$(L_{44})_{a44}$-$(R_{44})_{b44}$, and at least one of $X_{41}$ to $X_{44}$ may be N; and $X_{51}$ may be N or $C$-$(L_{51})_{a51}$-$(R_{51})_{b51}$, $X_{52}$ may be N or $C$-$(L_{52})_{a52}$-$(R_{52})_{b52}$, $X_{53}$ may be N or $C$-$(L_{53})_{a53}$-$(R_{53})_{b53}$, and at least one of $X_{51}$ to $X_{53}$ may be N. In some embodiments, in Formula 40A, $X_{41}$, $X_{42}$, and $X_{44}$ may be N, and $X_{43}$ may be $C(R_{43})$; $X_{41}$ and $X_{44}$ may be N, $X_{42}$ may be $C(R_{42})$, and $X_{43}$ may be $C(R_{43})$; or $X_{41}$ and $X_{43}$ may be N, $X_{42}$ may be $C(R_{42})$, and $X_{44}$ may be $C(R_{44})$. In Formula 40B, $X_{51}$, $X_{52}$, and $X_{53}$ may be N; or $X_{52}$ and $X_{53}$ may be N, and $X_{51}$ may be $C(R_{51})$.

In Formulae 40A and 40B, at least one selected from $R_{41}$ to $R_{46}$ or at least one selected from $R_{51}$ to $R_{57}$ may be selected from a substituted or unsubstituted $C_1$-$C_{10}$ heterocycloalkyl group, a substituted or unsubstituted $C_1$-$C_{10}$ heterocycloalkenyl group, a substituted or unsubstituted $C_1$-$C_{60}$ heteroaryl group, and a substituted or unsubstituted monovalent non-aromatic condensed heteropolycyclic group.

In some embodiments, in Formula 40A, at least one selected from $R_{41}$ to $R_{46}$ may be an electron transporting group including at least one N as a ring-forming atom, and at least one carbon of at least one selected from $R_{41}$ to $R_{46}$ may be bound to a carbon in the core in Formula 40A or each be bound to at least one selected from $L_{41}$ to $L_{46}$; and in Formula 40B, at least one selected from $R_{51}$ to $R_{57}$ may be an electron transporting group including at least one N as a ring-forming atom, and at least one carbon of at least one selected from $R_{51}$ to $R_{57}$ may be bound to a carbon in the core in Formula 40B or each be bound to at least one selected from $L_{51}$ to $L_{57}$.

In some embodiments, at least one selected from $R_{41}$ to $R_{46}$ in Formula 40A or at least one selected from $R_{51}$ to $R_{57}$ in Formula 40B may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$);

wherein $Q_{31}$ to $Q_{33}$ may be each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

In some embodiments, at least one selected from $R_{41}$ to $R_{46}$ in Formula 40A or at least one selected from $R_{51}$ to $R_{57}$ in Formula 40B may be selected from a pyridinyl group, a pyrazinyl group, a pyrimidinyl group, a pyridazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group; and a pyridinyl group, a pyrazinyl group, a pyrimidinyl group, a pyridazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a naphthyl group, a fluorenyl group, a spiro-fluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, an imidazopyrimidinyl group, a biphenyl group, a terphenyl group, and —Si($Q_{31}$)($Q_{32}$)($Q_{33}$);

wherein $Q_{31}$ to $Q_{33}$ may be each independently selected from a $C_1$-$C_{10}$ alkyl group, a $C_1$-$C_{10}$ alkoxy group, a phenyl group, a naphthyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, and a terphenyl group.

In some embodiments, at least one selected from $R_{41}$ to $R_{46}$ in Formula 40A or at least one selected from $R_{51}$ to $R_{57}$ in Formula 40B may be selected from groups represented by Formulae 5-1 to 5-67:

Formula 5-1

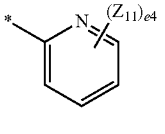

Formula 5-2

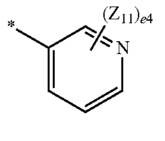

Formula 5-3

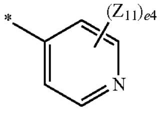

-continued
Formula 5-4
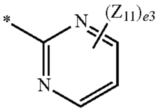
Formula 5-5
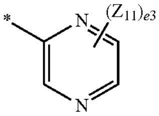
Formula 5-6
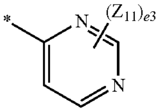
Formula 5-7
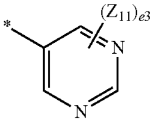
Formula 5-8
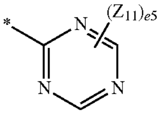
Formula 5-9
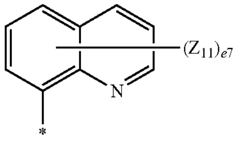
Formula 5-10
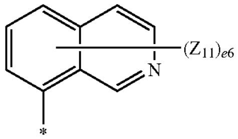
Formula 5-11
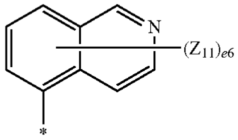
Formula 5-12
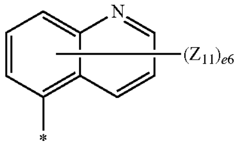
Formula 5-13
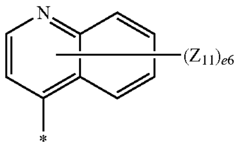
Formula 5-14
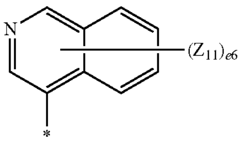
-continued
Formula 5-15
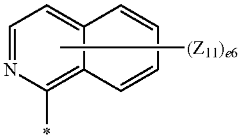
Formula 5-16
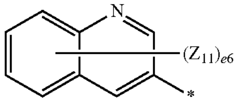
Formula 5-17
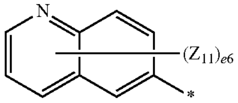
Formula 5-18
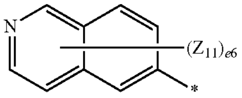
Formula 5-19
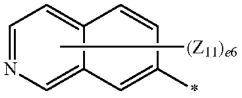
Formula 5-20
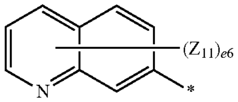
Formula 5-21
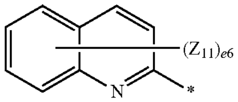
Formula 5-22
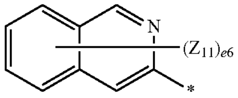
Formula 5-23
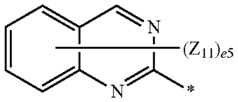
Formula 5-24
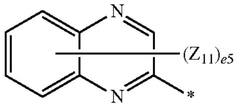
Formula 5-25
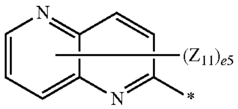
Formula 5-26
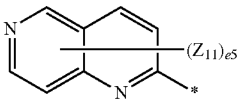
Formula 5-27
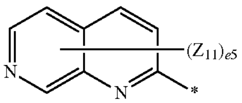

-continued
Formula 5-28
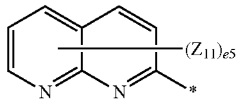
Formula 5-29
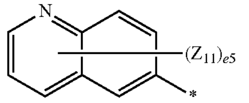
Formula 5-30
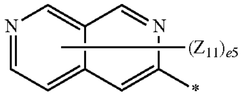
Formula 5-31
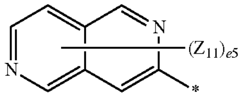
Formula 5-32
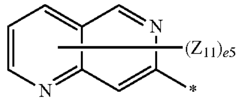
Formula 5-33
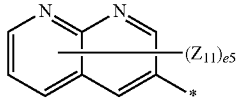
Formula 5-34
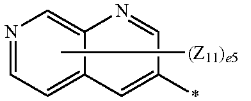
Formula 5-35
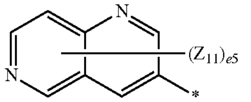
Formula 5-36
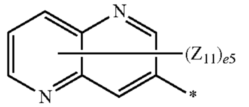
Formula 5-37
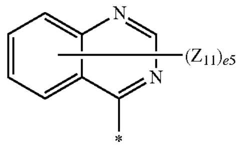
Formula 5-38
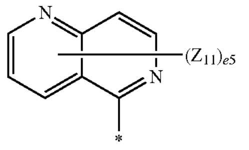
Formula 5-39
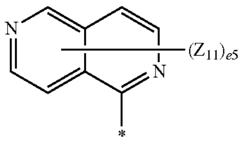
-continued
Formula 5-40
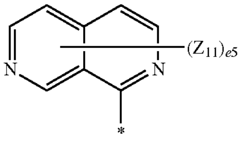
Formula 5-41
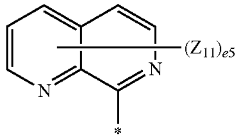
Formula 5-42
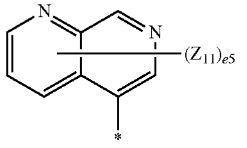
Formula 5-43
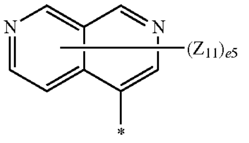
Formula 5-44
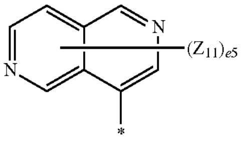
Formula 5-45
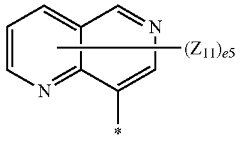
Formula 5-46
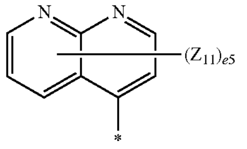
Formula 5-47
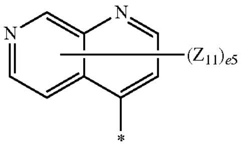
Formula 5-48
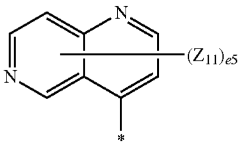
Formula 5-49
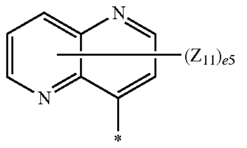

-continued

Formula 5-50

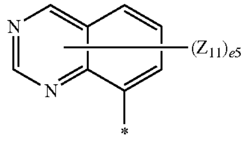

Formula 5-51

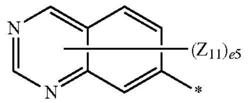

Formula 5-52

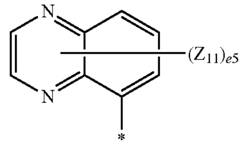

Formula 5-53

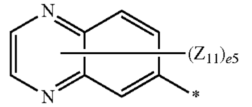

Formula 5-54

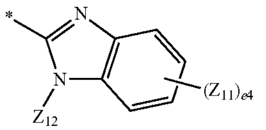

Formula 5-55

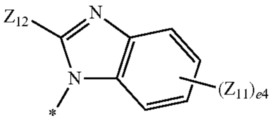

Formula 5-56

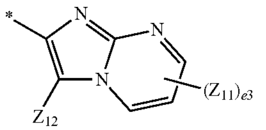

Formula 5-57

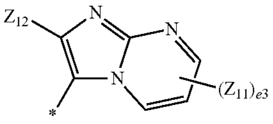

Formula 5-58

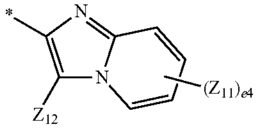

Formula 5-59

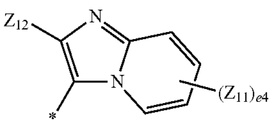

Formula 5-60

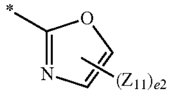

Formula 5-61

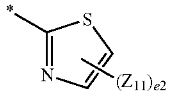

-continued

Formula 5-62

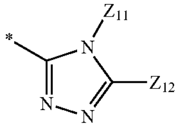

Formula 5-63

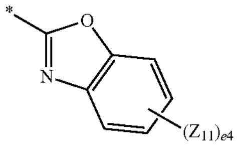

Formula 5-64

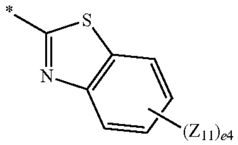

Formula 5-65

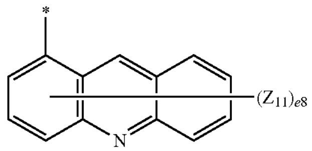

Formula 5-66

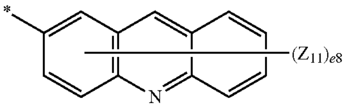

Formula 5-67

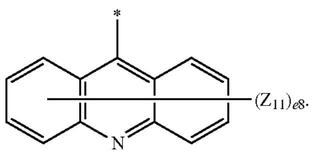

In Formulae 5-1 to 5-67, $Z_{11}$ and $Z_{12}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group; and —$Si(Q_{31})(Q_{32})(Q_{33})$;

$Z_{11}$ and $Z_{12}$ may be optionally linked to each other to form a $C_5$ to $C_{20}$ saturated or unsaturated ring;

wherein $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group;

e2 may be an integer selected from 1 and 2;

e3 may be an integer selected from 1 to 3;

e4 may be an integer selected from 1 to 4;

e5 may be an integer selected from 1 to 5;

e6 may be an integer selected from 1 to 6;

e7 may be an integer selected from 1 to 7;

e8 may be an integer selected from 1 to 8;

e9 may be an integer selected from 1 to 9; and

* indicates a binding site to an adjacent atom.

In some embodiments, at least one selected from $R_{41}$ to $R_{46}$ in Formula 40A or at least one selected from $R_{51}$ to $R_{57}$ in Formula 40B may be selected from groups represented by Formulae 10-1 to 10-122:

Formula 10-1

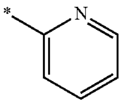

Formula 10-2

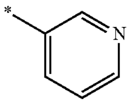

Formula 10-3

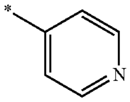

Formula 10-4

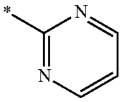

Formula 10-5

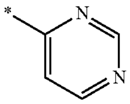

Formula 10-6

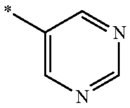

Formula 10-7

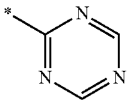

-continued

Formula 10-8

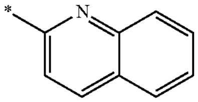

Formula 10-9

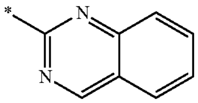

Formula 10-10

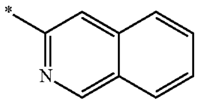

Formula 10-11

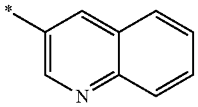

Formula 10-12

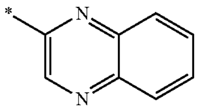

Formula 10-13

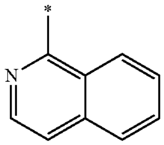

Formula 10-14

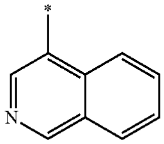

Formula 10-15

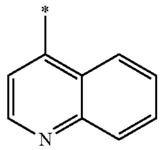

Formula 10-16

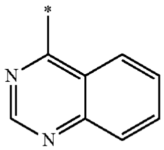

Formula 10-17

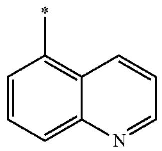

Formula 10-18

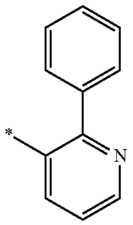

-continued
Formula 10-19
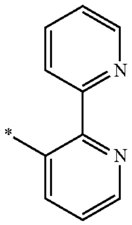
Formula 10-20
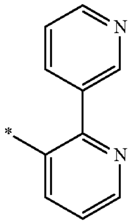
Formula 10-21
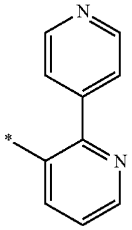
Formula 10-22
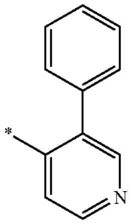
Formula 10-23
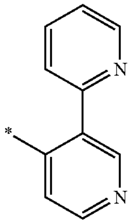
Formula 10-24
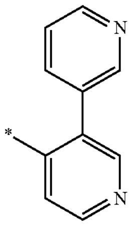
Formula 10-25
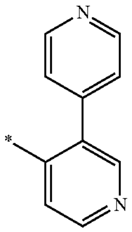
-continued
Formula 10-26
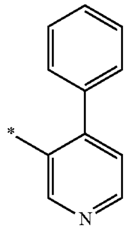
Formula 10-27
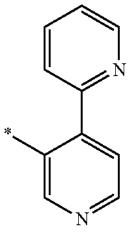
Formula 10-28
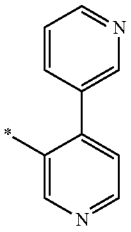
Formula 10-29
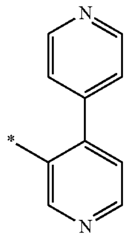
Formula 10-30
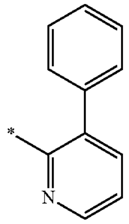
Formula 10-31
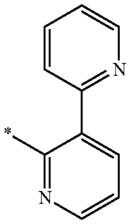

-continued
Formula 10-32
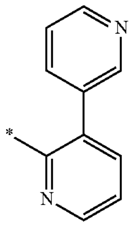
Formula 10-33
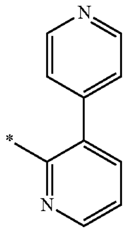
Formula 10-34
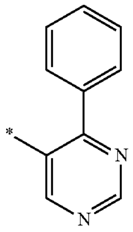
Formula 10-35
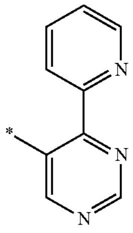
Formula 10-36
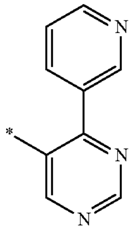
Formula 10-37
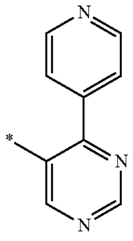
-continued
Formula 10-38
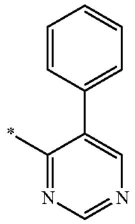
Formula 10-39
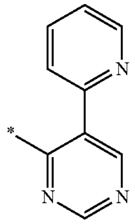
Formula 10-40
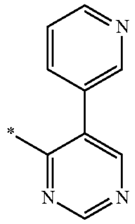
Formula 10-41
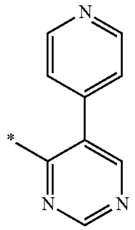
Formula 10-42
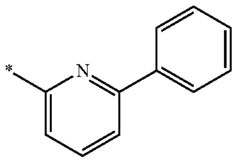
Formula 10-43
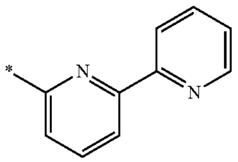
Formula 10-44
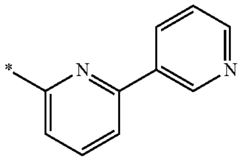
Formula 10-45
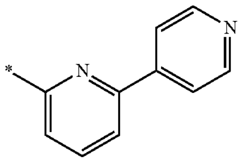

-continued
Formula 10-46
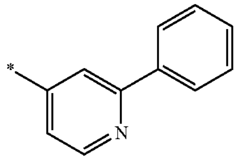
Formula 10-47
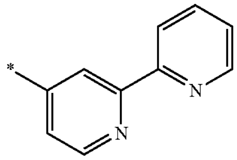
Formula 10-48
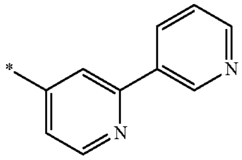
Formula 10-49
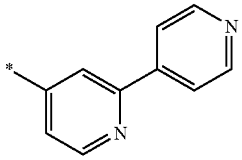
Formula 10-50
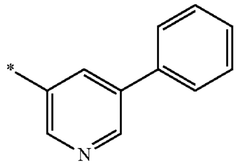
Formula 10-51
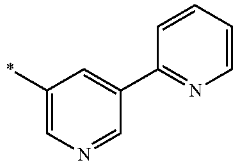
Formula 10-52
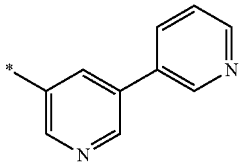
Formula 10-53
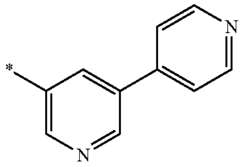
Formula 10-54
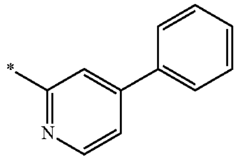
-continued
Formula 10-55
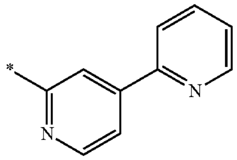
Formula 10-56
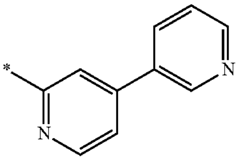
Formula 10-57
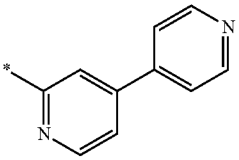
Formula 10-58
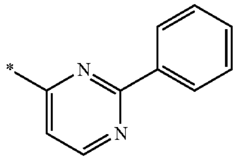
Formula 10-59
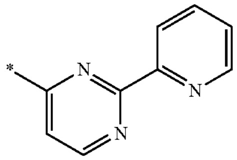
Formula 10-60
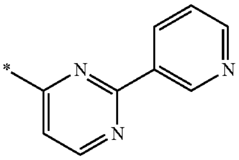
Formula 10-61
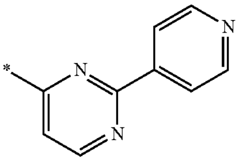
Formula 10-62
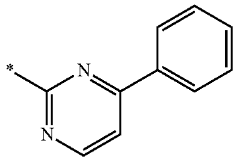
Formula 10-63
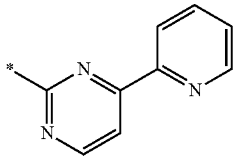

-continued
Formula 10-64
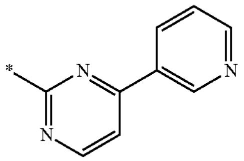
Formula 10-65
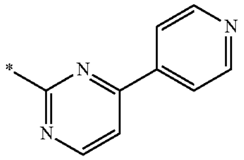
Formula 10-66
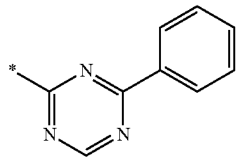
Formula 10-67
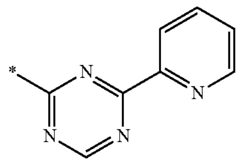
Formula 10-68
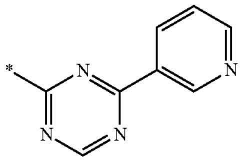
Formula 10-69
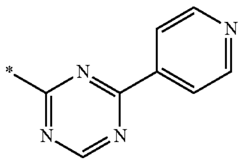
Formula 10-70
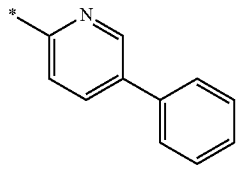
Formula 10-71
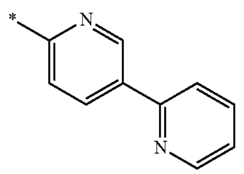
Formula 10-72
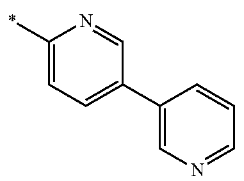
-continued
Formula 10-73
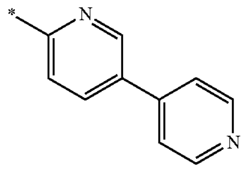
Formula 10-74
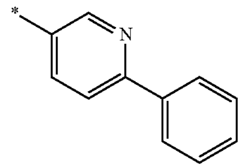
Formula 10-75
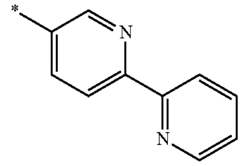
Formula 10-76
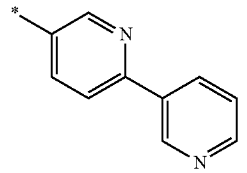
Formula 10-77
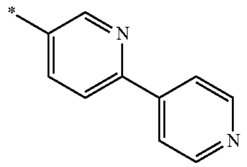
Formula 10-78
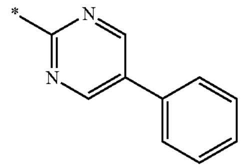
Formula 10-79
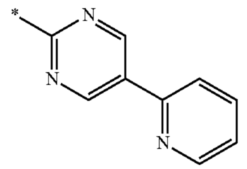
Formula 10-80
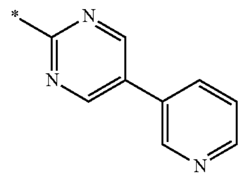
Formula 10-81
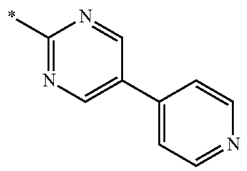

-continued
Formula 10-82
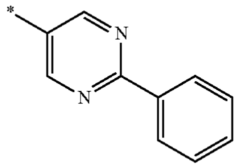
Formula 10-83
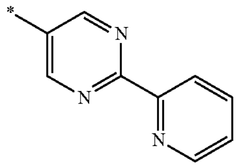
Formula 10-84
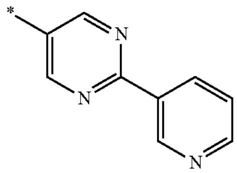
Formula 10-85
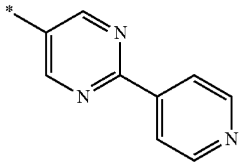
Formula 10-86
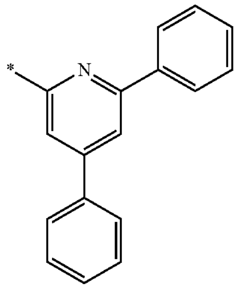
Formula 10-87
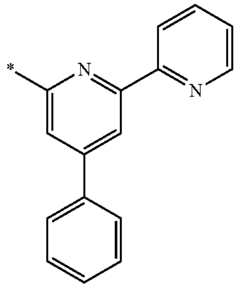
Formula 10-88
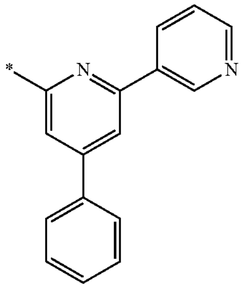
-continued
Formula 10-89
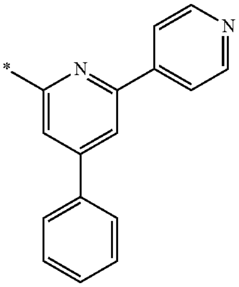
Formula 10-90
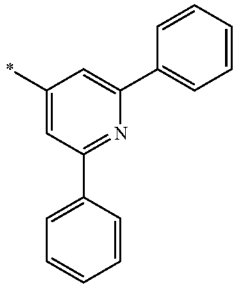
Formula 10-91
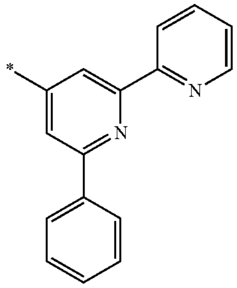
Formula 10-92
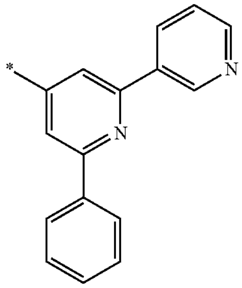
Formula 10-93
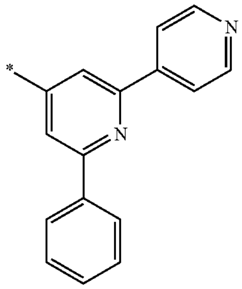

-continued
Formula 10-94
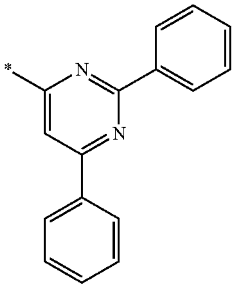
Formula 10-95
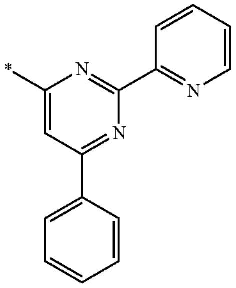
Formula 10-96
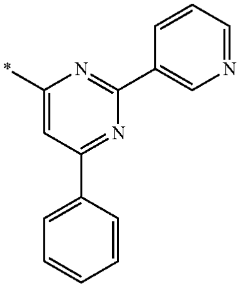
Formula 10-97
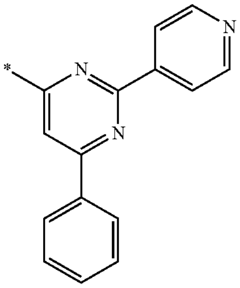
Formula 10-98
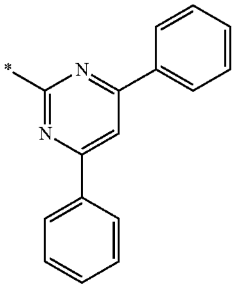
-continued
Formula 10-99
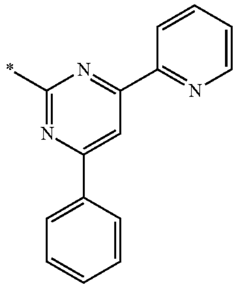
Formula 10-100
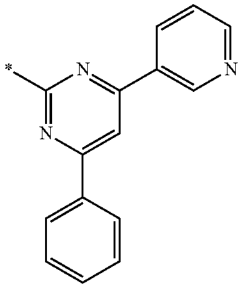
Formula 10-101
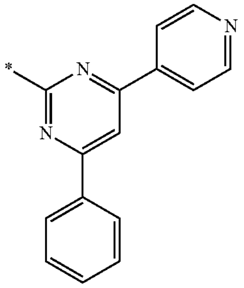
Formula 10-102
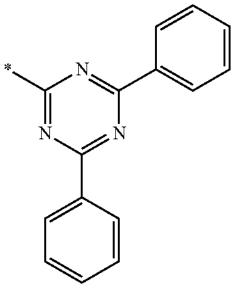
Formula 10-103
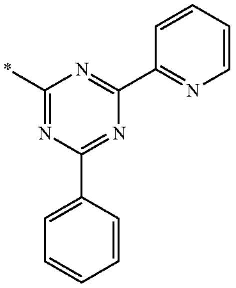

-continued
Formula 10-104
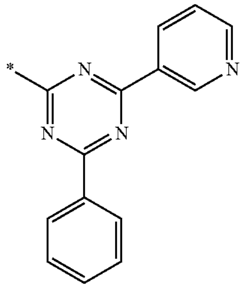
Formula 10-105
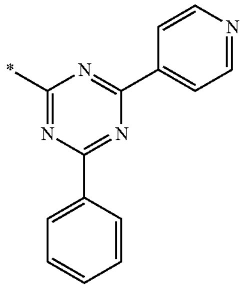
Formula 10-106
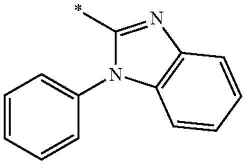
Formula 10-107
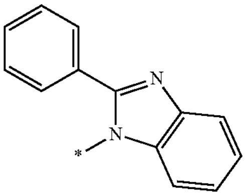
Formula 10-108
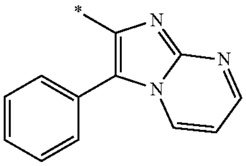
Formula 10-109
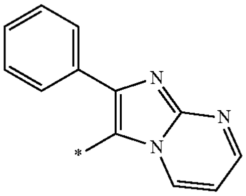
Formula 10-110
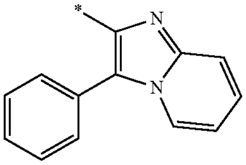
-continued
Formula 10-111
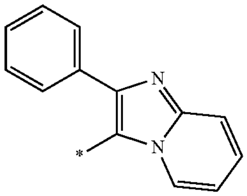
Formula 10-112
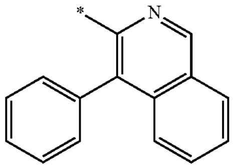
Formula 10-113
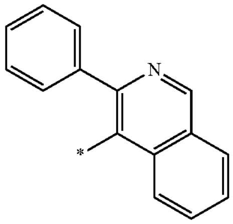
Formula 10-114
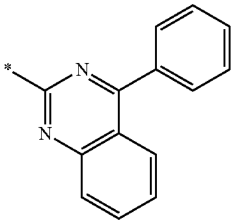
Formula 10-115
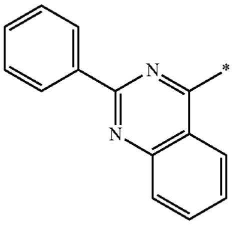
Formula 10-116
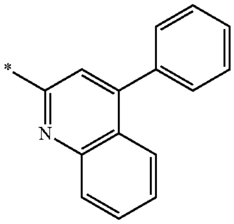
Formula 10-117
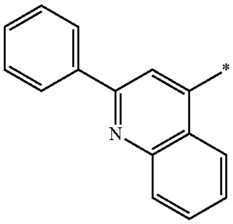

-continued

Formula 10-118

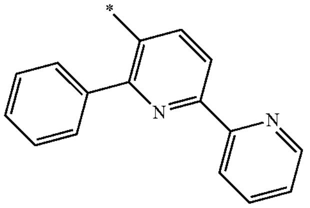

Formula 10-119

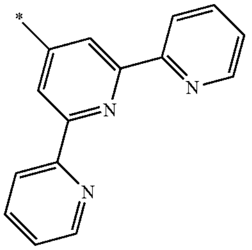

Formula 10-120

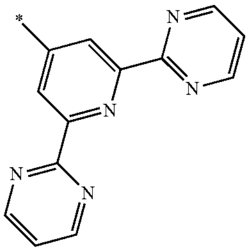

Formula 10-121

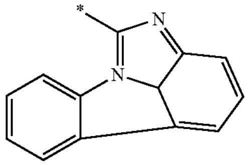

Formula 10-122

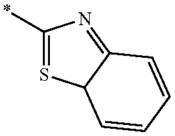

Formula 10-123

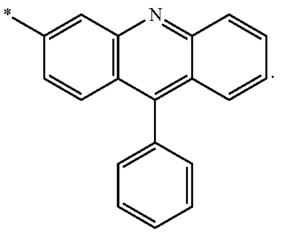

In Formulae 10-1 to 10-123, * indicates a binding site to an adjacent atom.

In some embodiments, $R_4$ in Formula 40A or at least one selected from $R_{56}$ and $R_{57}$ in Formula 40B may be selected from groups represented by Formulae 10-1 to 10-123.

in the Formulae above, $R_1$ to $R_{12}$ and $R_{58}$ to $R_{60}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$); and $R_{11}$ and $R_{12}$ may be optionally linked to each other to form a $C_5$ to $C_{20}$ saturated or unsaturated ring. Here, descriptions of $Q_1$ to $Q_5$ may be referred to the descriptions below.

In some embodiments, in the Formulae above, $R_1$ to $R_{12}$ and $R_{58}$ to $R_{60}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a Spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, a biphenyl group, a terphenyl group, and —Si($Q_{31}$)($Q_{32}$)($Q_{33}$); and —Si($Q_1$)($Q_2$)($Q_3$).

wherein $Q_1$ to $Q_3$ and $Q_{31}$ to $Q_{33}$ may be each independently selected from a $C_1$-$C_{10}$ alkyl group, a $C_1$-$C_{10}$ alkoxy group, a phenyl group, and a naphthyl group.

In some embodiments, in the Formulae above, $R_1$ to $R_{12}$ and $R_{58}$ to $R_{60}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a phenyl group, a naphthyl group, a pyridinyl group, a pyrimidinyl group, and a triazinyl group;

a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a $C_1$-$C_{10}$ alkyl group, a $C_1$-$C_{10}$ alkoxy group, a phenyl group, and a naphthyl group.

In some embodiments, in the Formulae above, $R_1$ to $R_{12}$ and $R_{58}$ to $R_{60}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, and a naphthyl group, as examples.

In the Formulae above, c1 to c10 may each independently be an integer selected from 0 to 4. c1 indicates the number of $R_1$, and when c1 is two or more, a plurality of $R_1$ may be identical to or different from each other. c2 to c10 may be understood by referring to the descriptions of c1 and structures of Formulae 1A to 1C and Formulae 40A and 40B.

In some embodiments, c1 to c10 may each independently be 0, 1, or 2; or, for example, may each independently be 0 or 1.

In Formulae 1A to 1C, n1 to n4 and n7 to n10 may each independently be an integer selected from 0 to 4, and n5 and n6 may each independently be an integer selected from 0 to 5, provided that n1+n2+n3+n4 may be 1 or more, n5+n6+n7+n8 may be 1 or more, and n9+n10 may be 1 or more.

In some embodiments, the first compound may be represented by one of Formulae 1A-1 to 1A-10, 1B-1 to 1B-4, 1C-1, and 1C-2, and the second compound may be represented by one of Formulae 40A-1 to 40A-3, 40B-1, and 40B-2:

<Formula 1A-1>

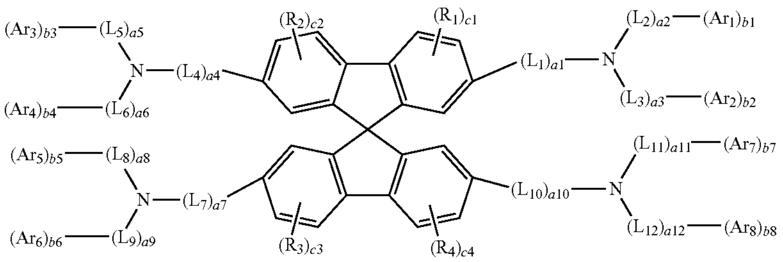

<Formula 1A-2>

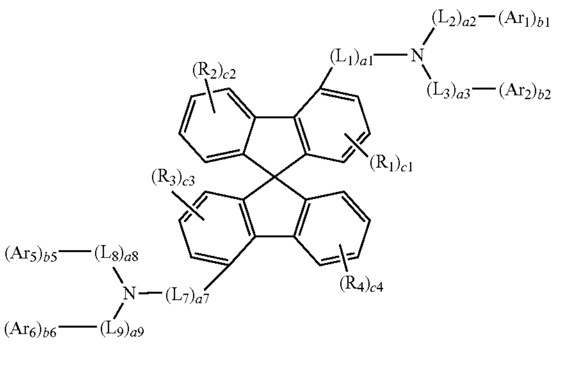

-continued
<Formula 1A-3>
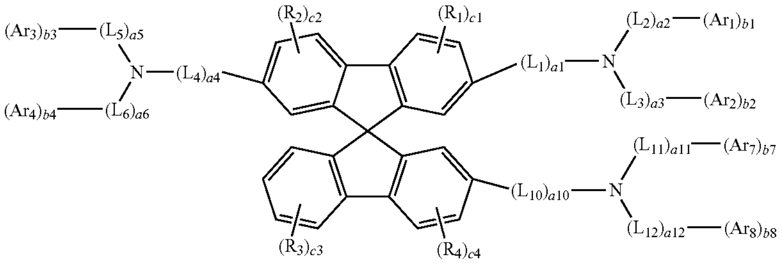
<Formula 1A-4>
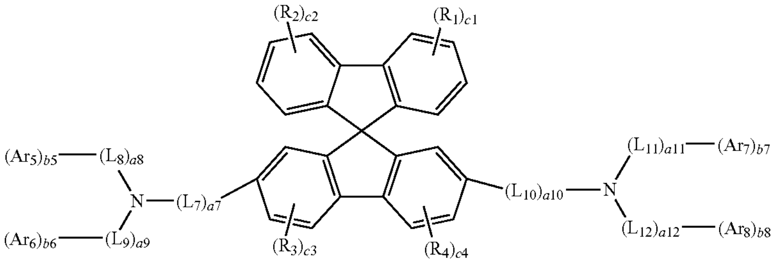
<Formula 1A-5>
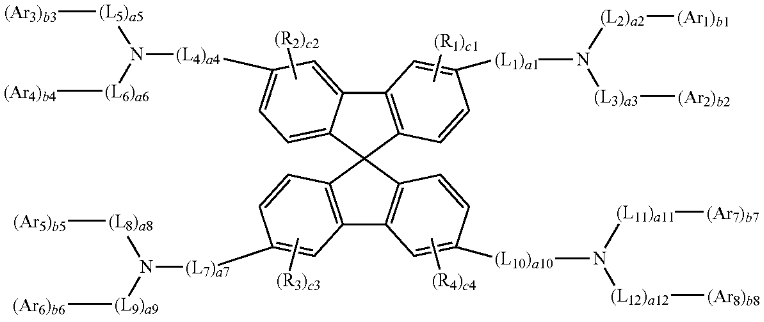
<Formula 1A-6>
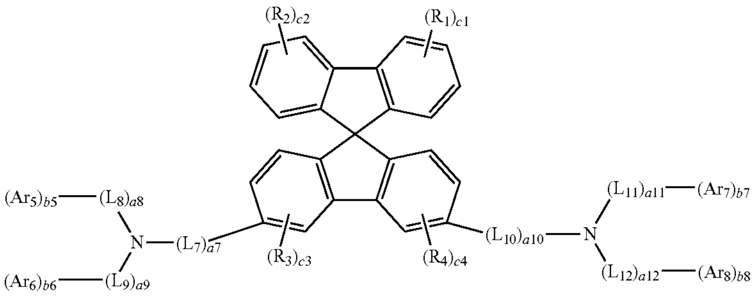
<Formula 1A-7>
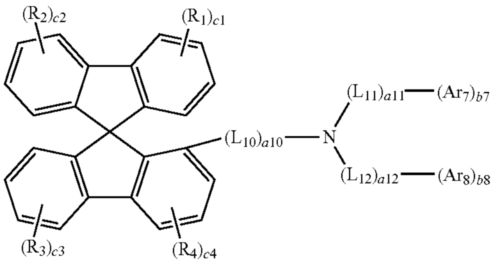
<Formula 1A-8>
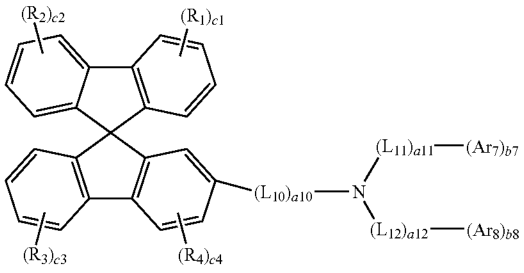

-continued
<Formula 1A-9>
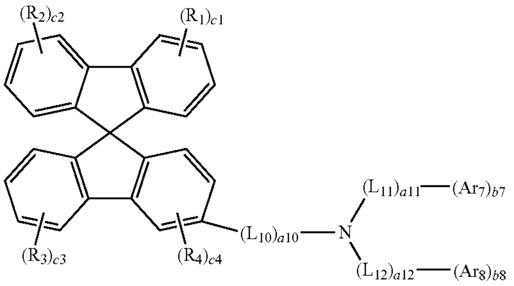
<Formula 1A-10>
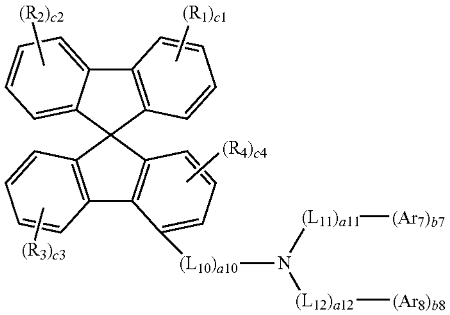
<Formula 1B-1>
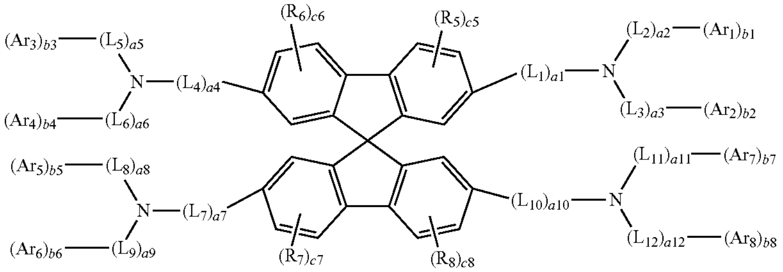
<Formula 1B-2>
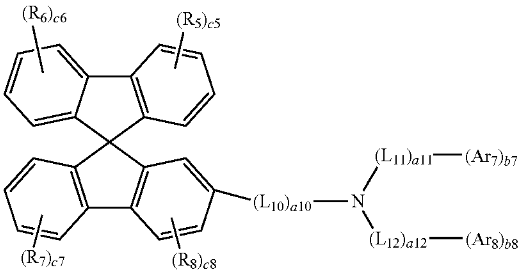
<Formula 1B-3>
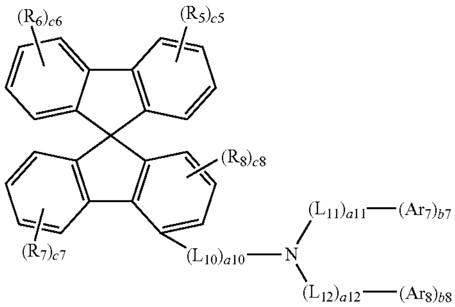
<Formula 1B-4>
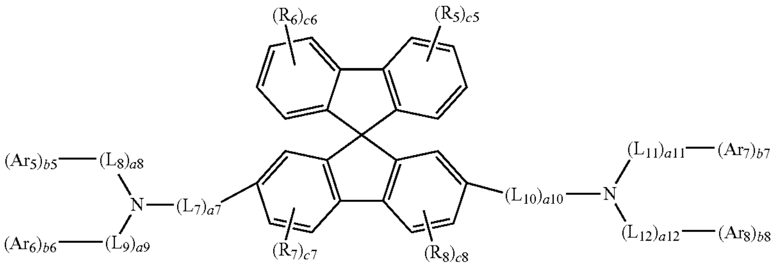
<Formula 1C-1>
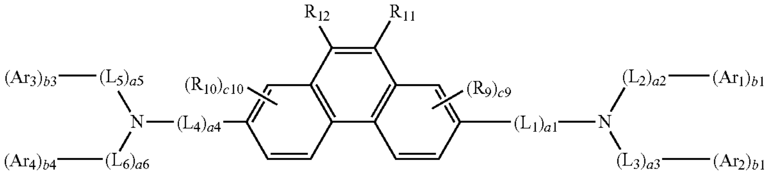
<Formula 40A-1>
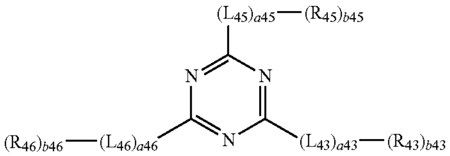
<Formula 40A-2>
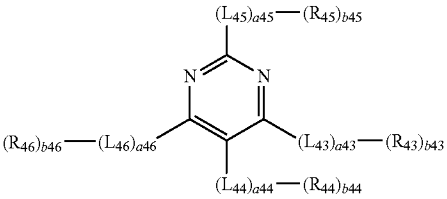

-continued

<Formula 40A-3>

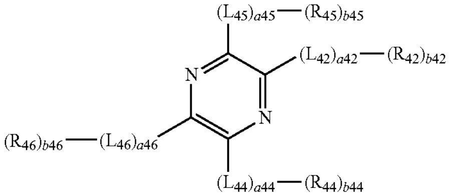

<Formula 40B-1>

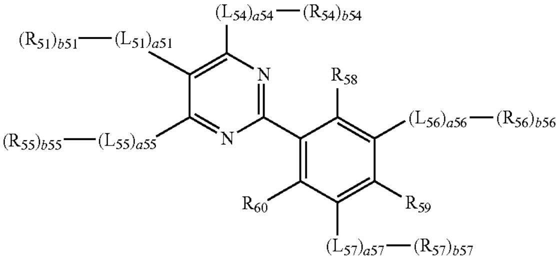

<Formula 40B-2>

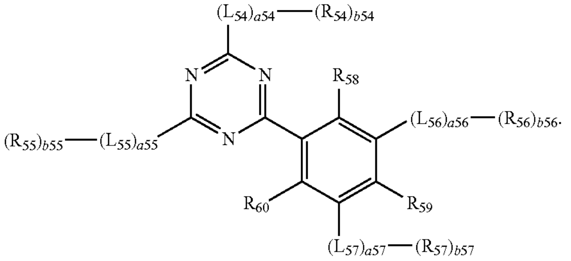

In the Formulae above, descriptions of $L_1$ to $L_{12}$, $L_{41}$ to $L_{46}$, $L_{51}$ to $L_{57}$, a1 to a12, a41 to a46, a51 to a57, $Ar_1$ to $Ar_8$, $R_1$ to $R_{12}$, $R_{42}$ to $R_{46}$, $R_{51}$, $R_{54}$ to $R_{60}$, b1 to b20, b42 to b46, b51 to b57, and c1 to c10 may be understood by referring to the descriptions provided herein.

In some embodiments, the first compound may be represented by one of Formulae 1A-1(1), 1A-2(1), 1A-2(2), 1A-3(1), 1A-4(1), 1A-4(2), 1A-5(1), 1A-6(1), 1A-7(1), 1A-8(1), 1A-8(2), 1A-9(1), 1A-9(2), 1A-9(3), 1A-10(1), 1A-10(2), 1B-(1), 1B-2(1), 1B-3(1), 1B-4(1), 1C-1(1), and 1C-1(2), and the second compound may be represented by one of Formulae 40A-1(1), 40A-1(2), 40A-1(3), 40A-2(1), 40A-3(1), 40B-1(1), 40B-1(2), 40B-2(1), and 40B-2(1) to 40B-2(5):

<Formula 1A-1(1)>

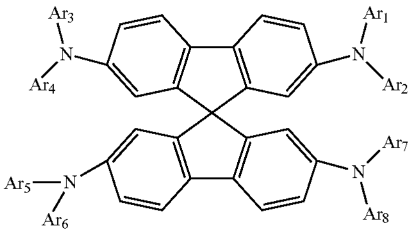

<Formula 1A-2(1)>

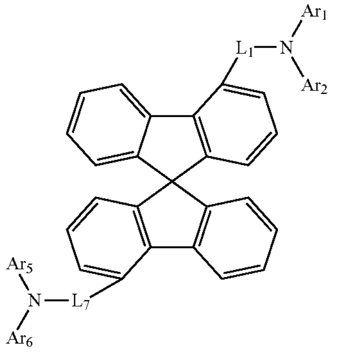

-continued

<Formula 1A-2(2)>

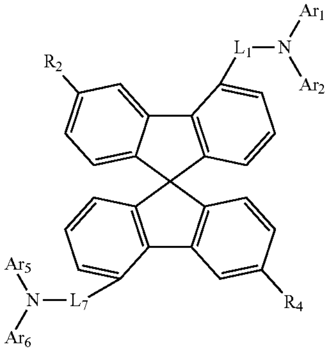

<Formula 1A-3(1)>

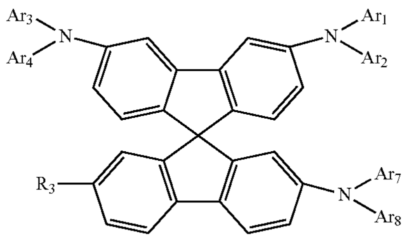

<Formula 1A-4(1)>

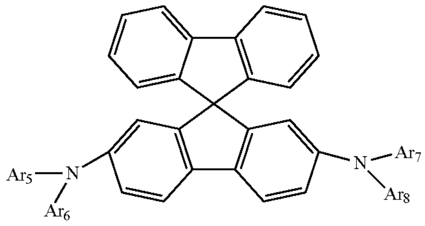

-continued
<Formula 1A-4(2)>
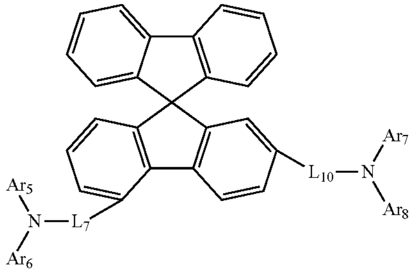
<Formula 1A-5(1)>
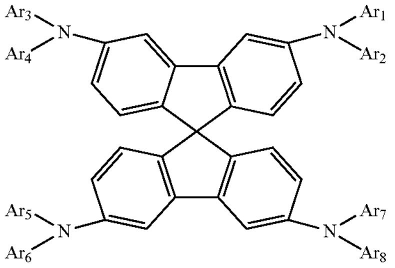
<Formula 1A-6(1)>
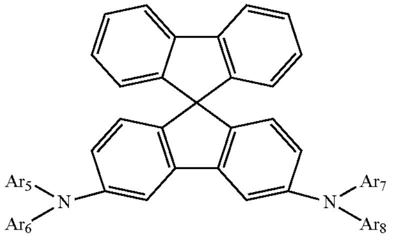
<Formula 1A-7(1)>
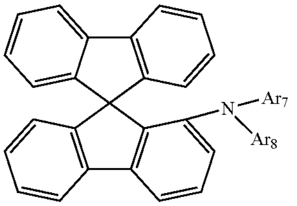
<Formula 1A-8(1)>
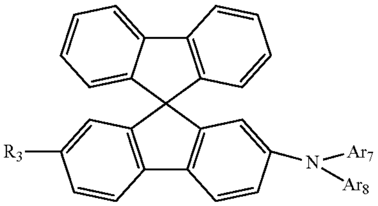
<Formula 1A-8(2)>
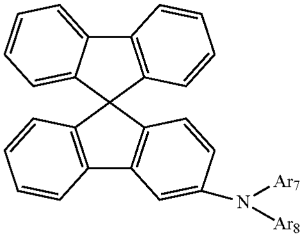
-continued
<Formula 1A-9(1)>
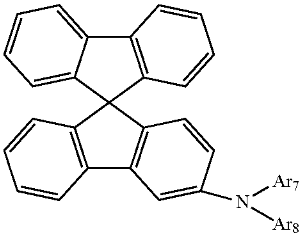
<Formula 1A-9(2)>
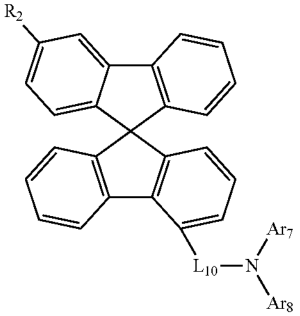
<Formula 1A-9(3)>
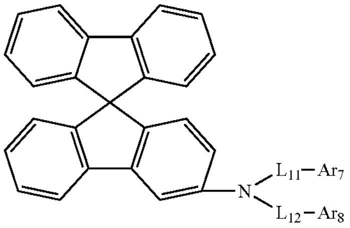
<Formula 1A-10(1)>
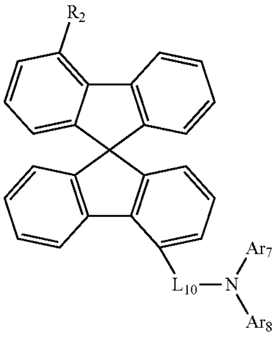
<Formula 1A-10(2)>
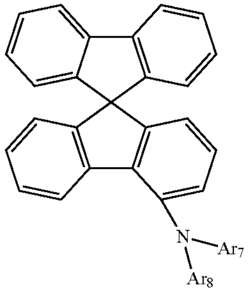

-continued
<Formula 1B-1(1)>
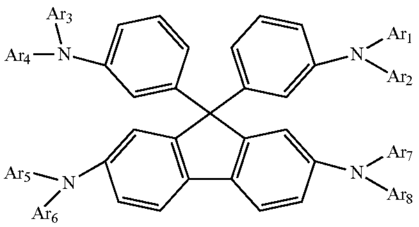
<Formula 1B-2(1)>
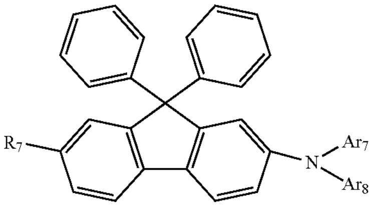
<Formula 1B-3(1)>
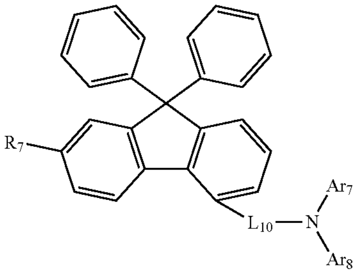
<Formula 1B-4(1)>
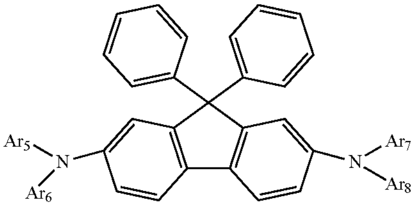
<Formula 1C-1(1)>
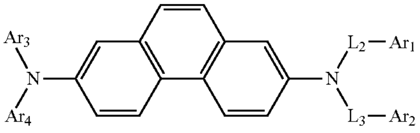
<Formula 1C-1(2)>
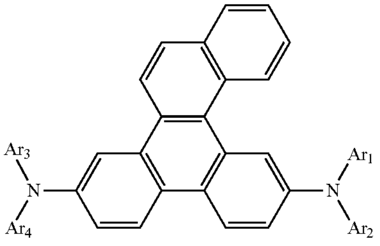
-continued
<Formula 40A-1(1)>
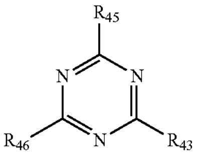
<Formula 40A-1(2)>
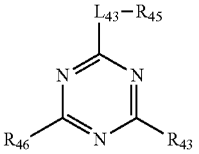
<Formula 40A-1(3)>
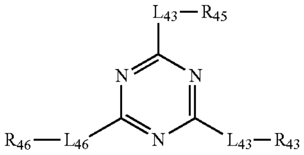
<Formula 40A-2(1)>
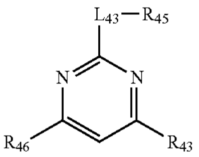
<Formula 40A-3(1)>
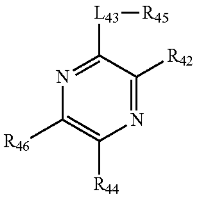
<Formula 40B-1(1)>
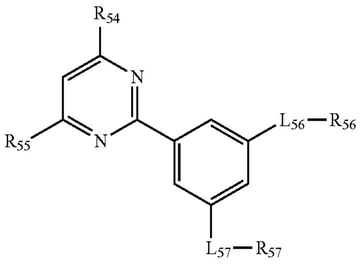
<Formula 40B-1(2)>
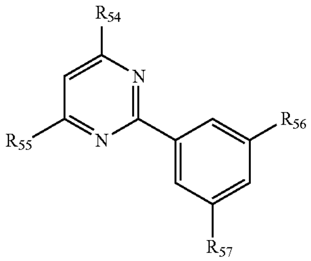

-continued

<Formula 40B-2(1)>

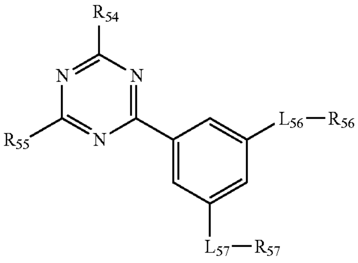

<Formula 40B-2(2)>

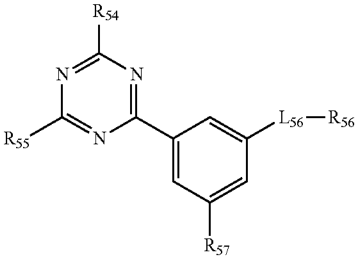

<Formula 40B-2(3)>

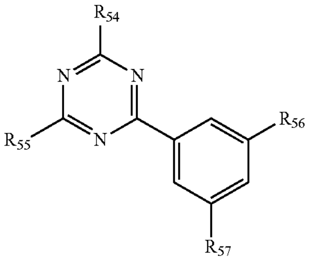

<Formula 40B-2(4)>

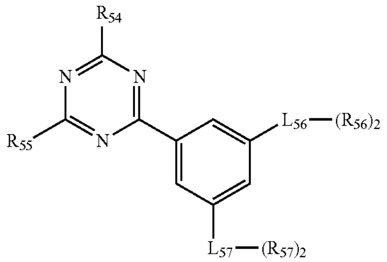

-continued

<Formula 40B-2(5)>

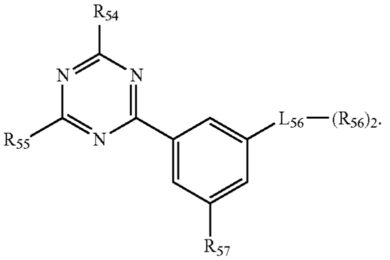

In the Formulae above, descriptions of $L_1$ to $L_3$, $L_7$, $L_{10}$, $L_{12}$, $L_{43}$, $L_{45}$, $L_{46}$, $L_{56}$, $L_{57}$, $Ar_1$ to $Ar_8$, $R_2$, $R_3$, $R_7$, $R_{42}$ to $R_{46}$, and $R_{54}$ to $R_{57}$ may be understood by referring to the descriptions provided herein.

In some embodiments, $L_1$ to $L_3$, $L_7$, $L_{10}$, and $L_{12}$ may be each independently selected from groups represented by Formulae 3-1 to 3-41, $L_{43}$, $L_{45}$, $L_{46}$, $L_{56}$, and $L_{57}$ may be each independently selected from groups represented by Formulae 3-1 to 3-9, 3-25, and 3-33 to 3-41 (provided that $Y_1{=}C(Z_3)(Z_4)$ in Formulae 3-3 and 3-4), $Ar_1$ to $Ar_8$, $R_{42}$ to $R_{44}$, $R_{46}$, $R_{54}$, and $R_{55}$ may be each independently selected from groups represented by Formulae 5-1 to 5-87, $R_{45}$ may be selected from groups represented by Formulae 5-1 to 5-67, at least one of $R_{56}$ and $R_{57}$ may be selected from groups represented by Formulae 5-1 to 5-67, and $R_2$, $R_3$, and $R_7$ may be each independently selected from a hydrogen, a phenyl group, a phenalenyl group, a pyrenyl group, and a dibenzothiophenyl group.

In some embodiments, $L_1$ to $L_3$, $L_7$, $L_{10}$, and $L_{12}$ may be each independently selected from groups represented by Formulae 4-1 to 4-36, and $L_{43}$, $L_{45}$, $L_{46}$, $L_{56}$, and $L_{57}$ may be each independently selected from groups represented by Formulae 4-1, 4-3, 4-5, 4-7 to 4-13, 4-17, and 4-24 to 4-36, $Ar_1$ to $Ar_8$, $R_{42}$ to $R_{44}$, $R_{46}$, $R_{54}$, and $R_{55}$ may be each independently selected from groups represented by Formulae 6-1 to 6-170, $R_{45}$ may be selected from groups represented by Formulae 10-1 to 10-123, and at least one of $R_{56}$ and $R_{57}$ may be selected from groups represented by Formulae 10-1 to 10-123.

The first compound may be a compound represented by one of Compounds 1 to 53, and the second compound may be a compound represented by one of Compounds A1 to A32:

1

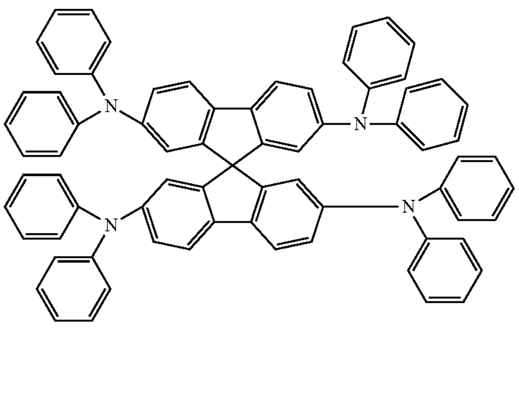

2

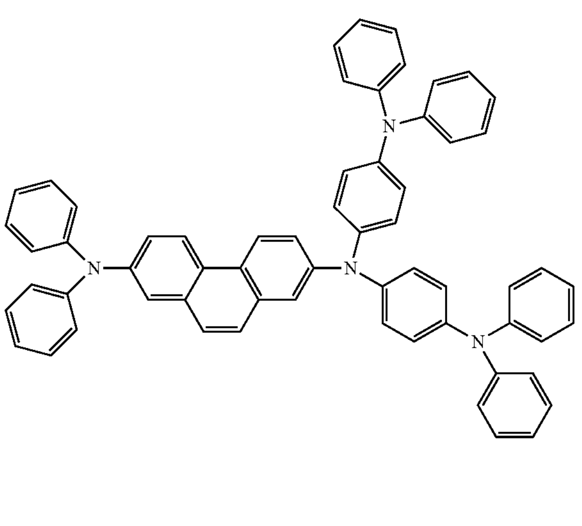

-continued
3
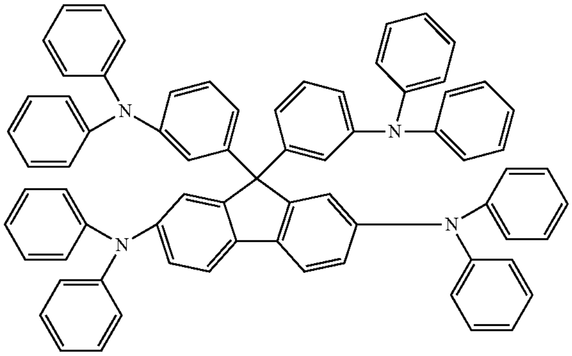
4
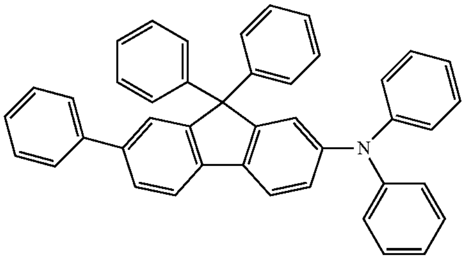
5
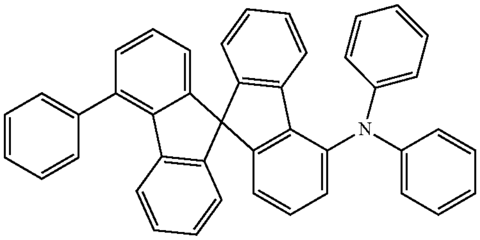
6
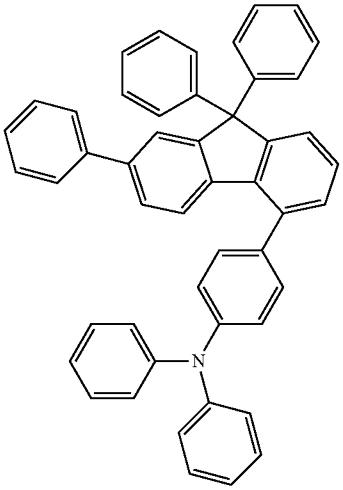
7
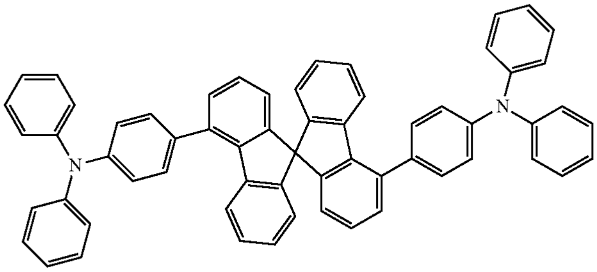
8
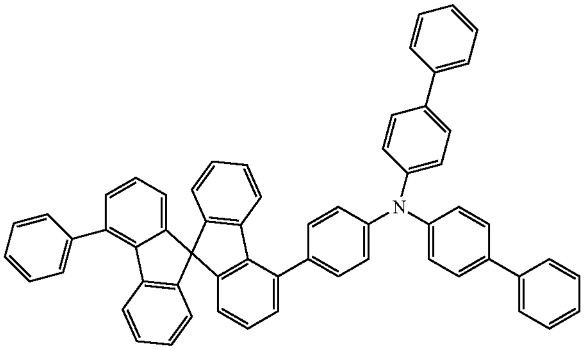

-continued
9
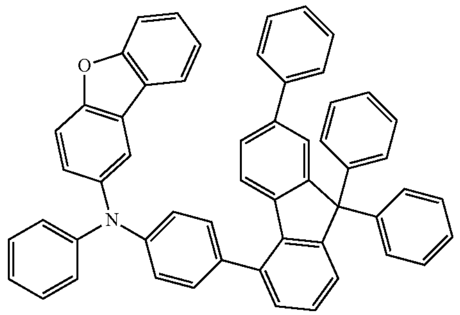
10
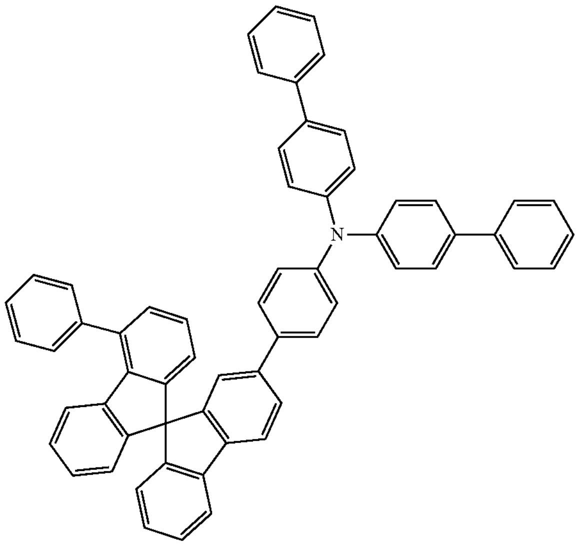
11
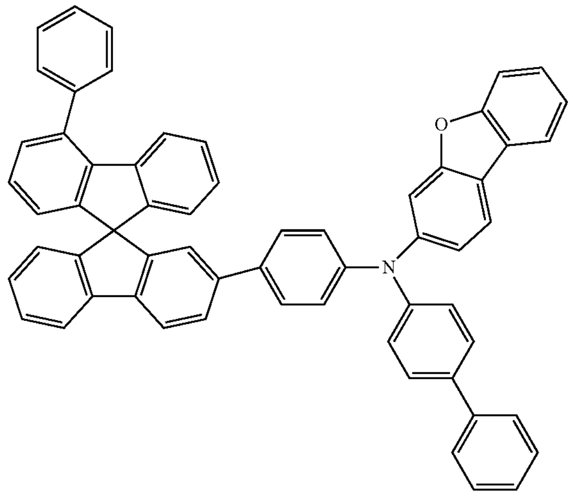
12
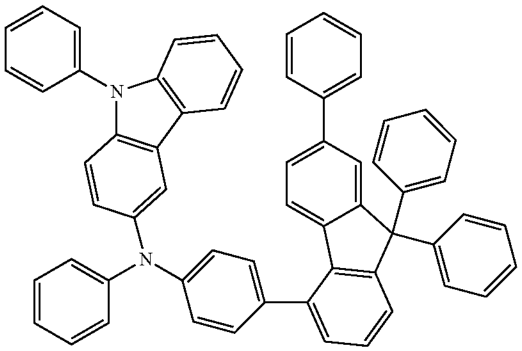
13
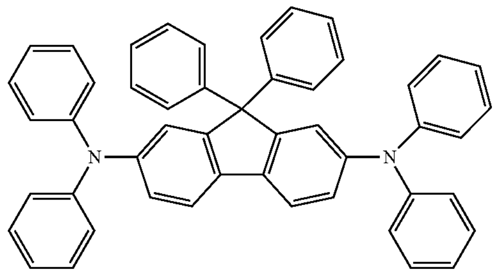
14
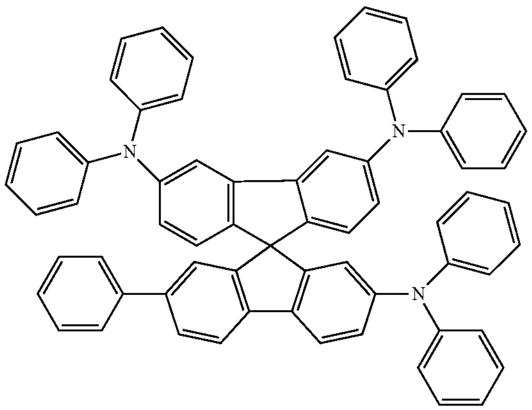

-continued
15
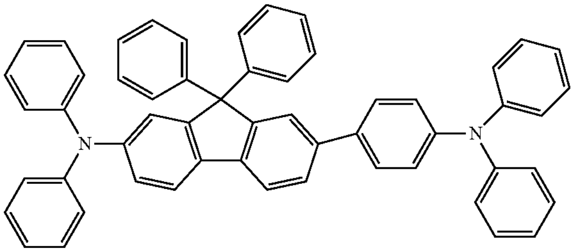
16
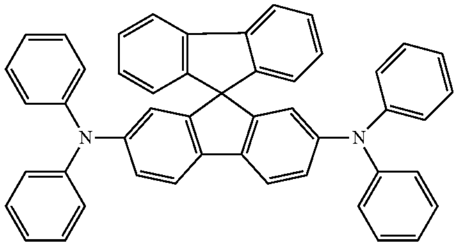
17
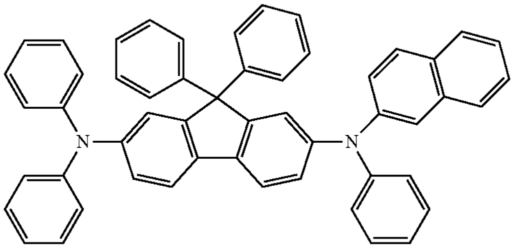
18
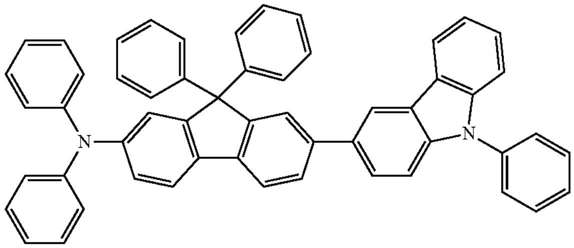
19
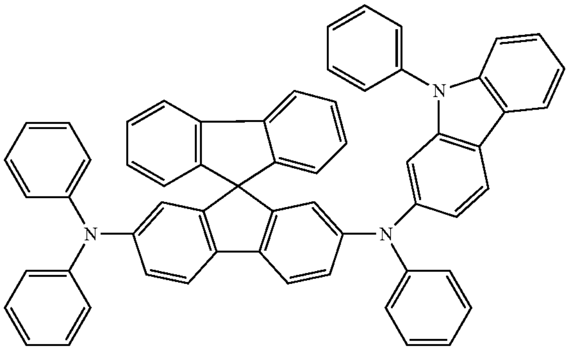
20
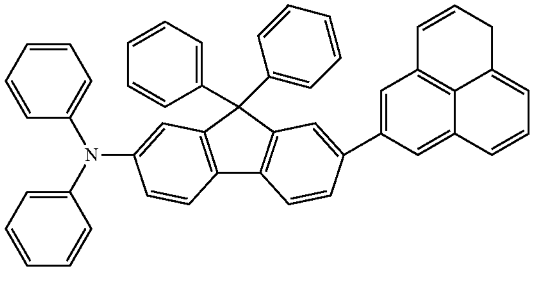
21
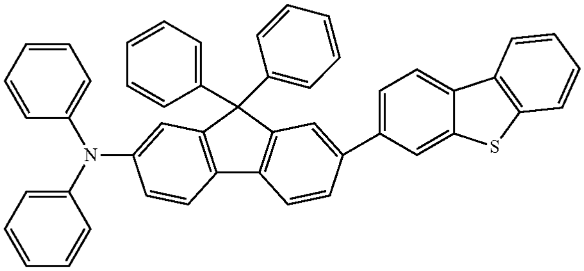
22
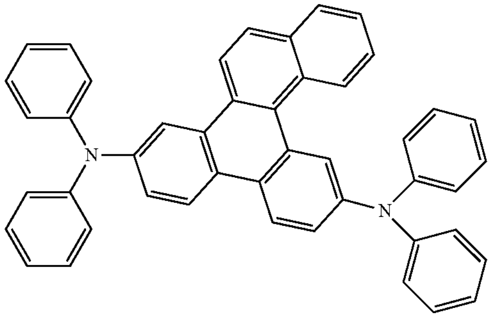

-continued
23
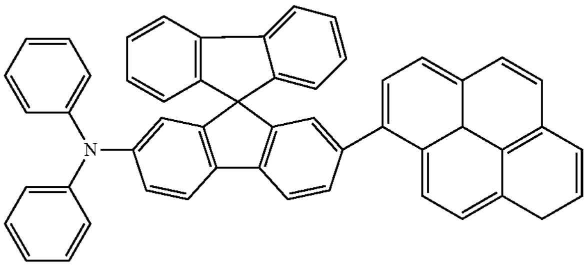
24
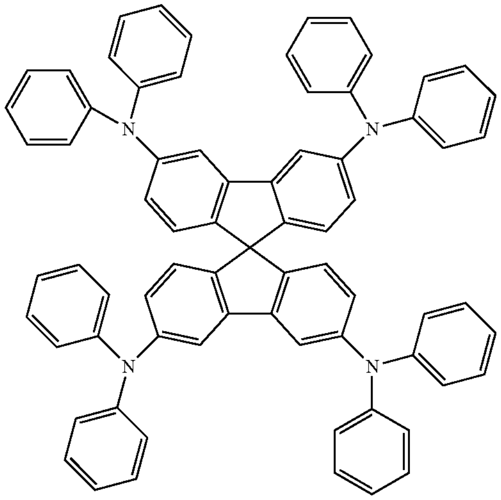
25
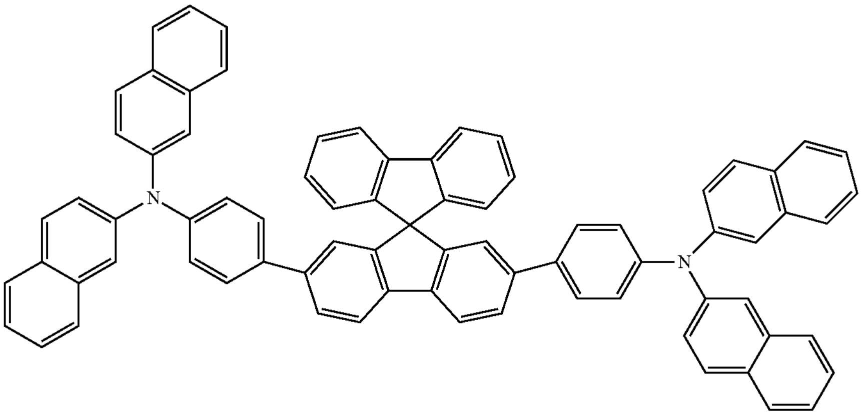
26
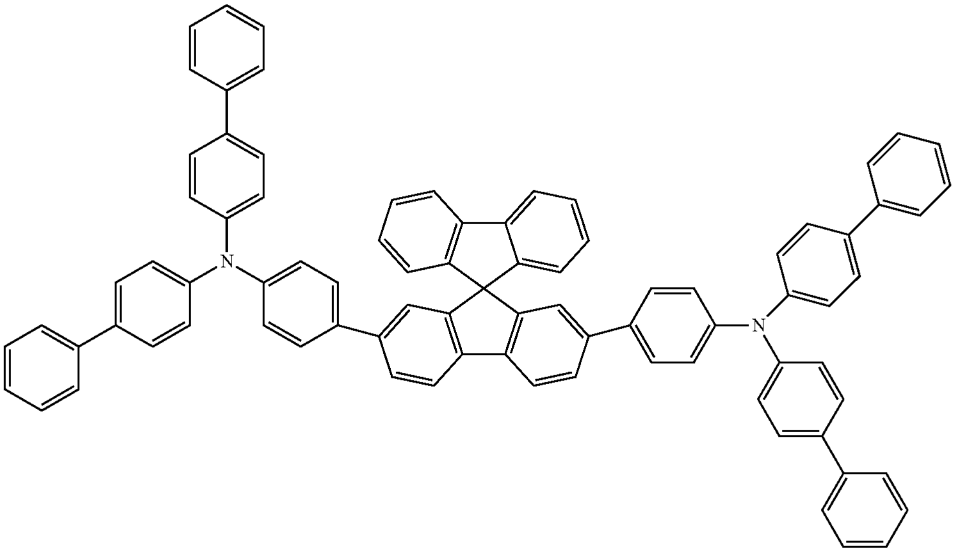

-continued
27
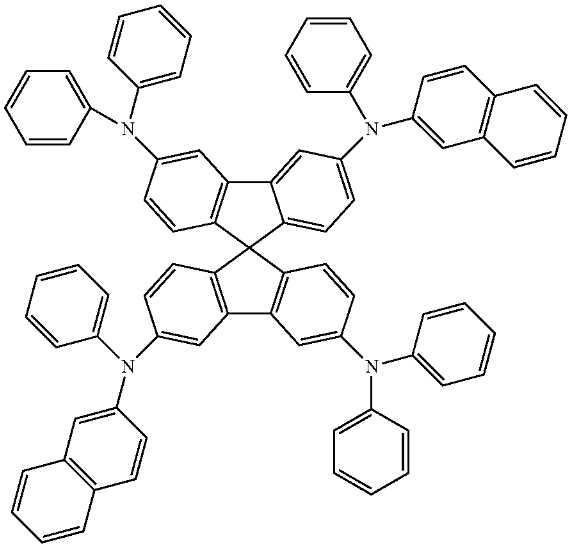
28
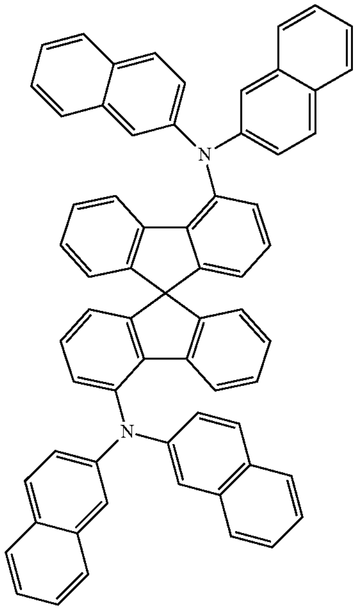
29
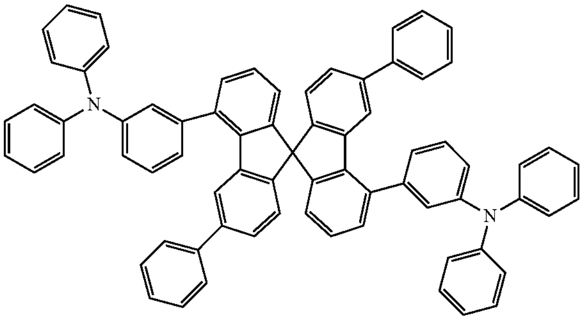
30
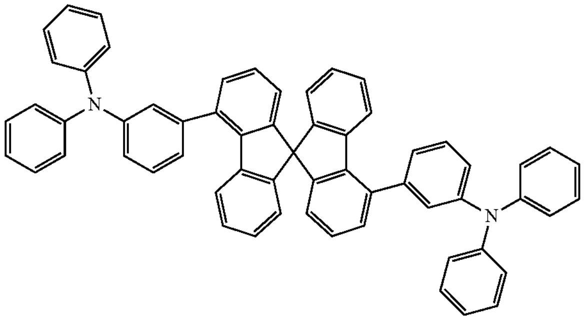
31
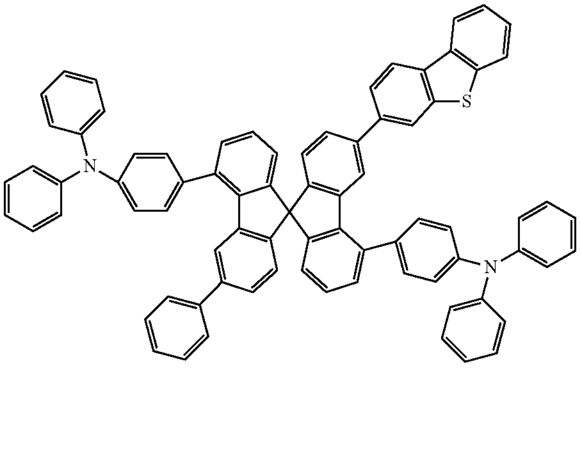
32
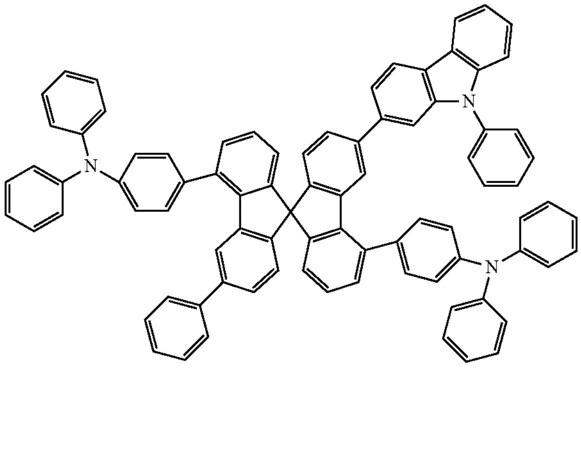

-continued
33
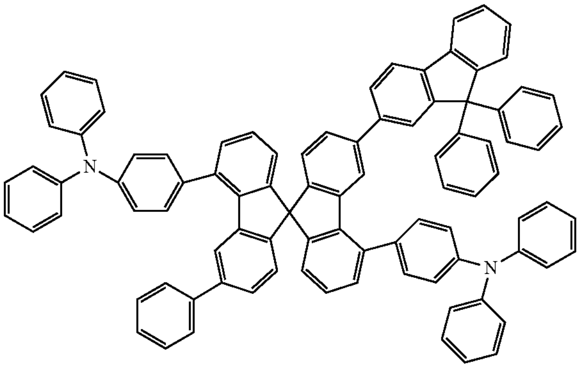
34
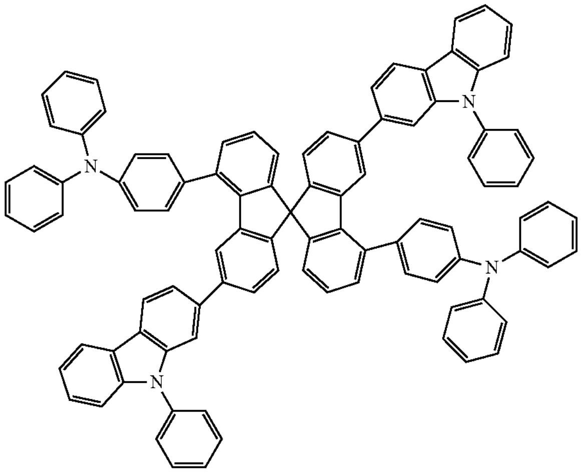
35
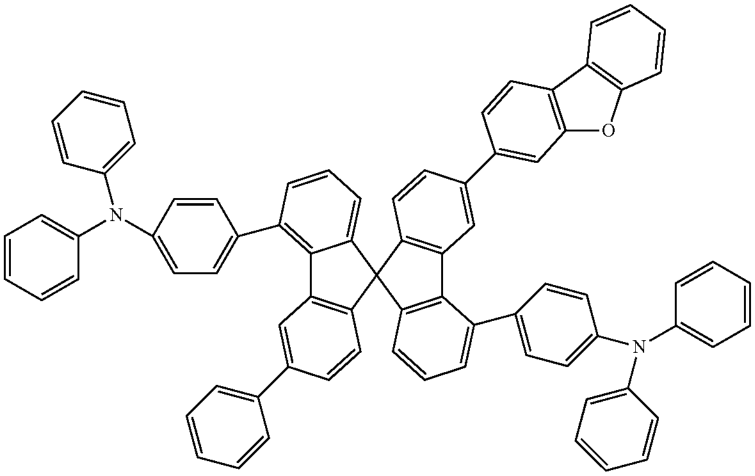
36
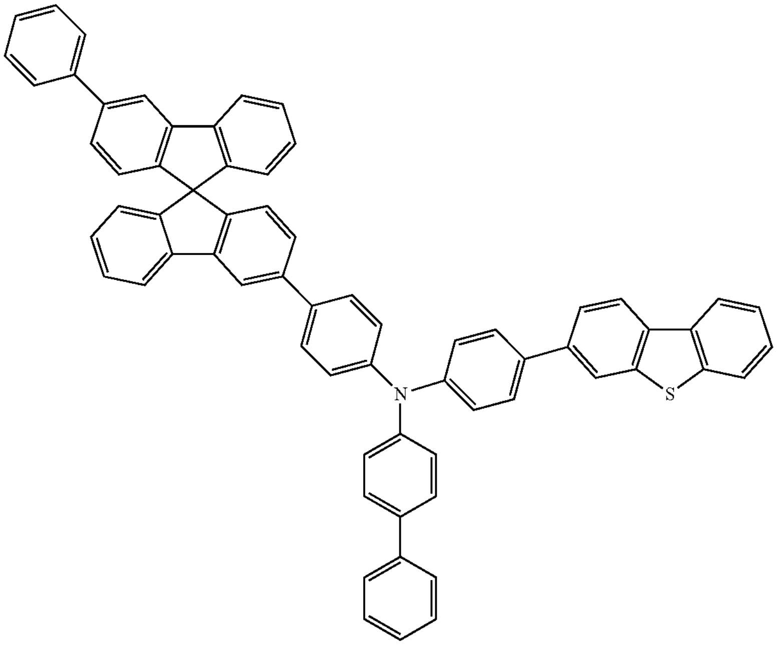

-continued
37
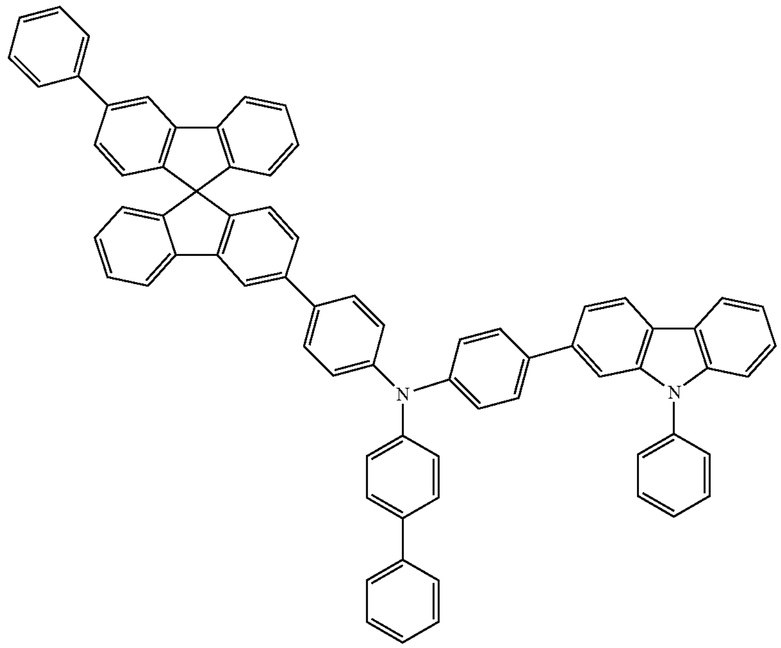
38
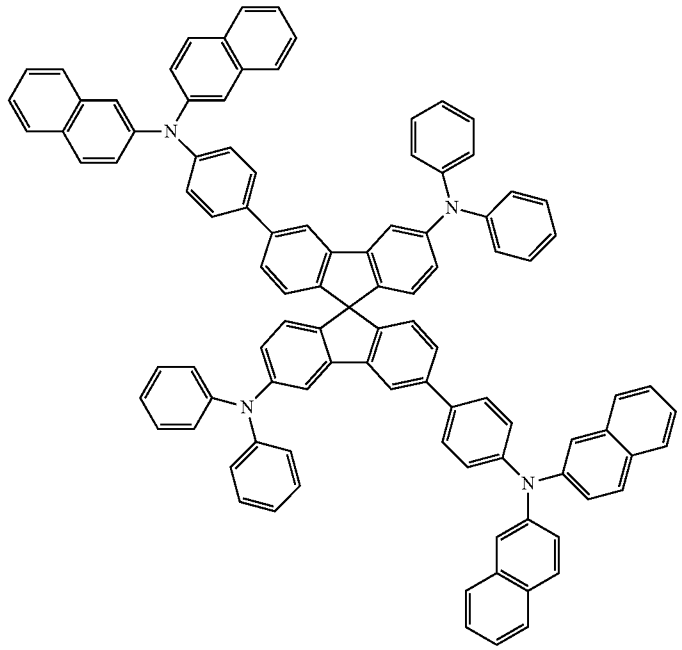

-continued
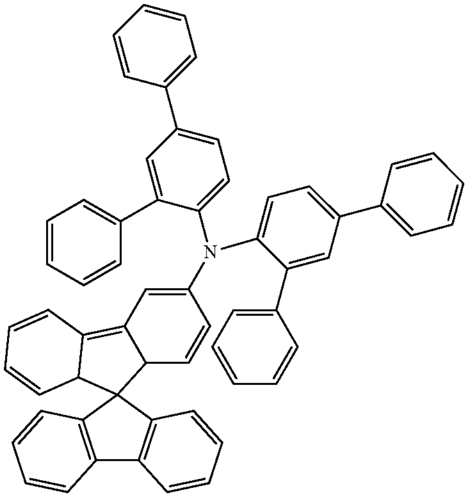
39
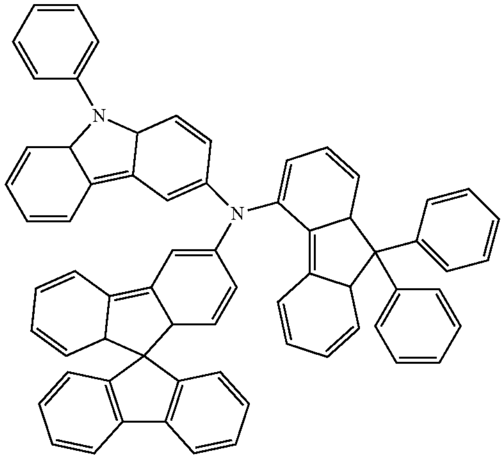
40
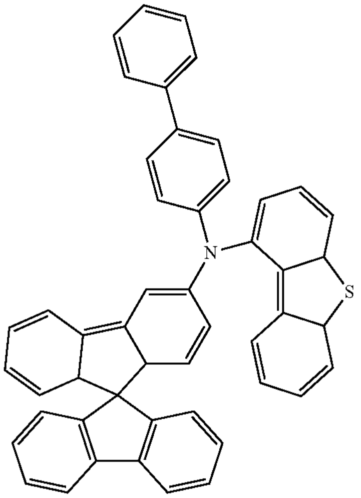
41
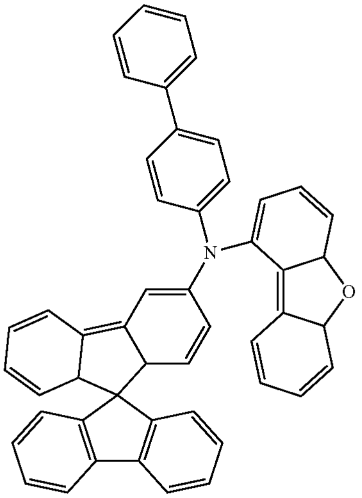
42
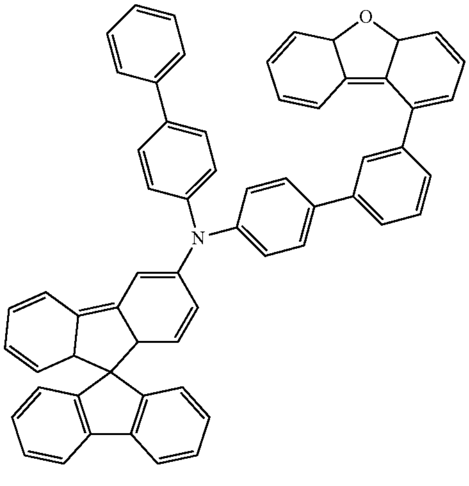
43
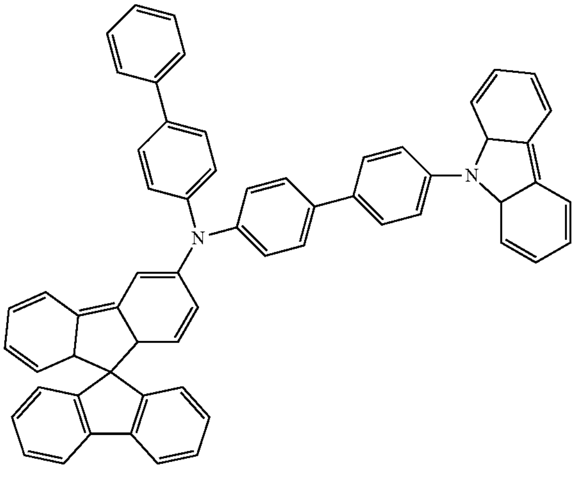
44

-continued
45
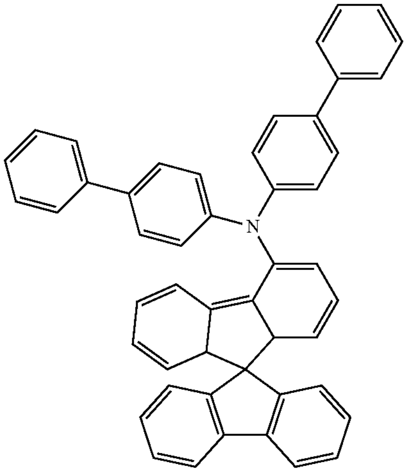
46
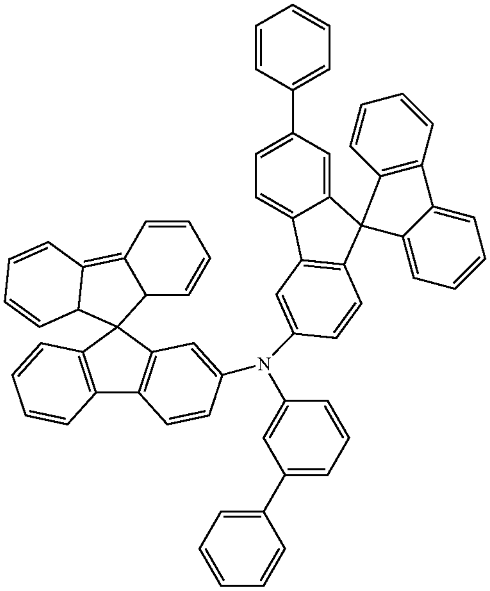
47
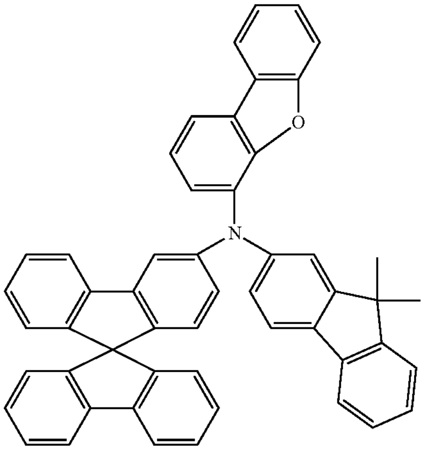
48
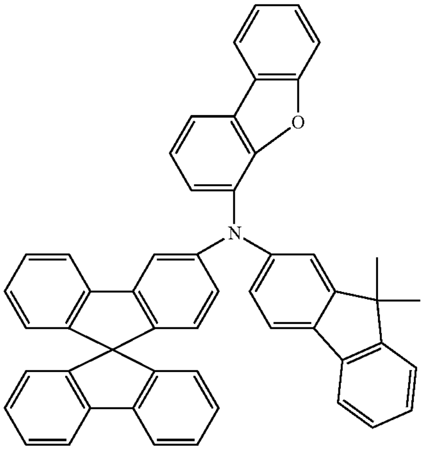
49
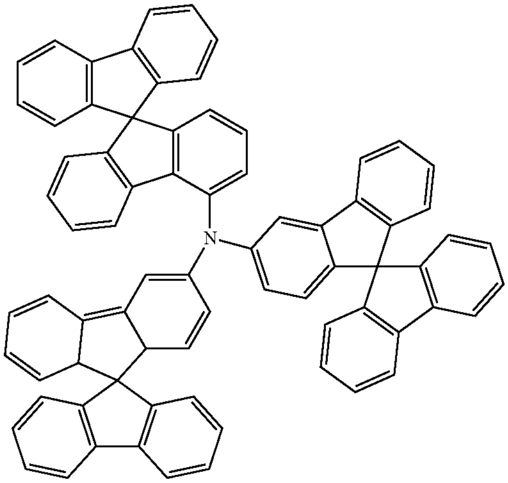
50
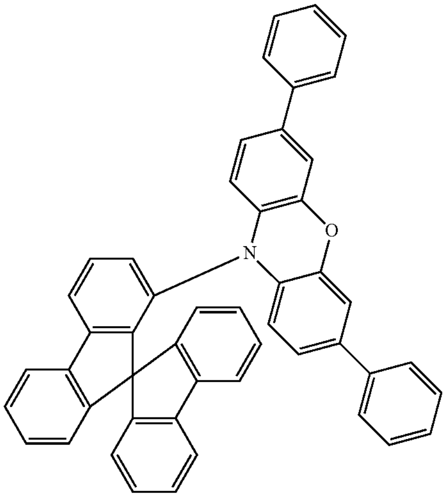

-continued
51
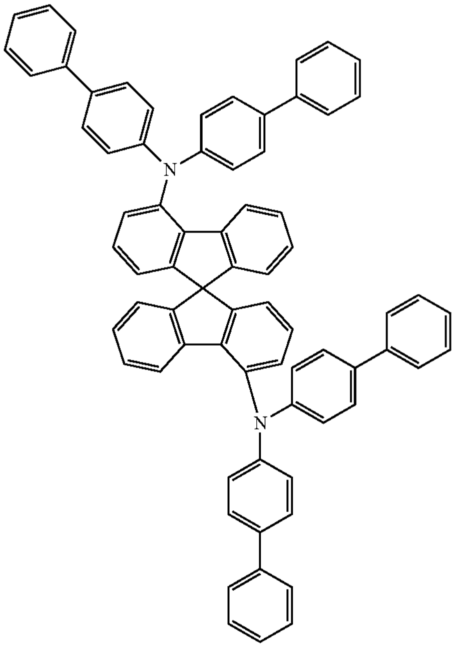
52
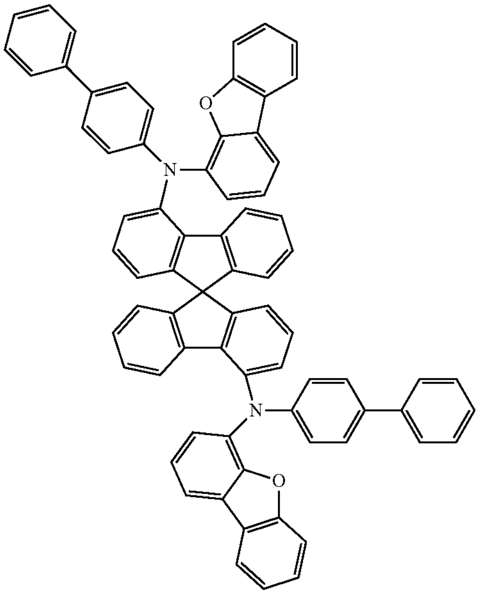
53
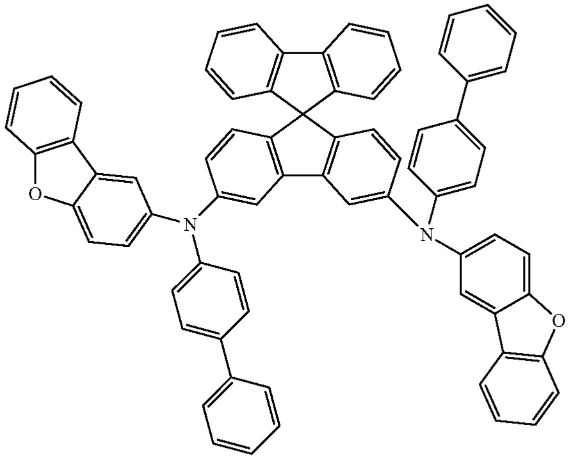
A1
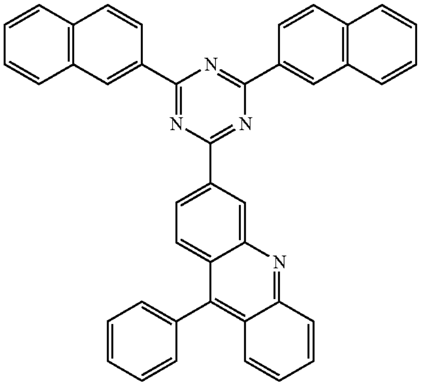
A2
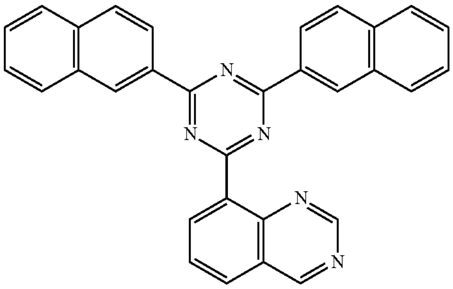
A3
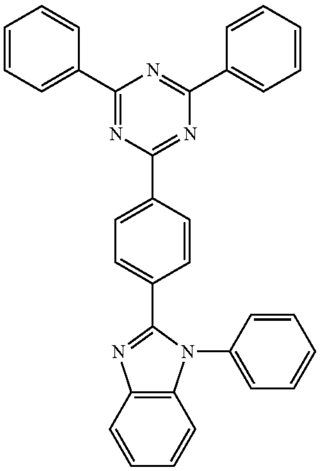

-continued
A4
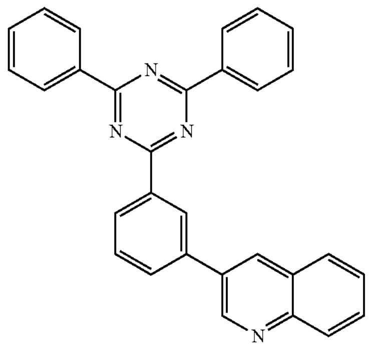
A5
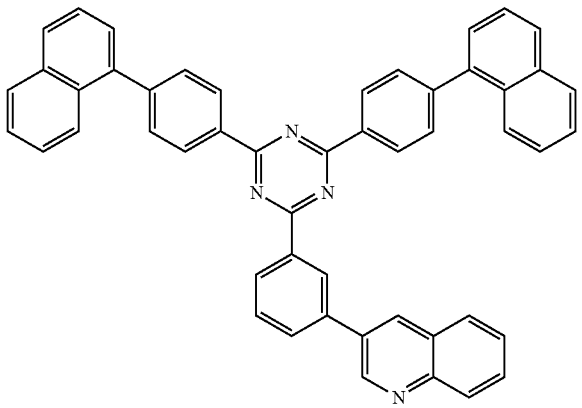
A6
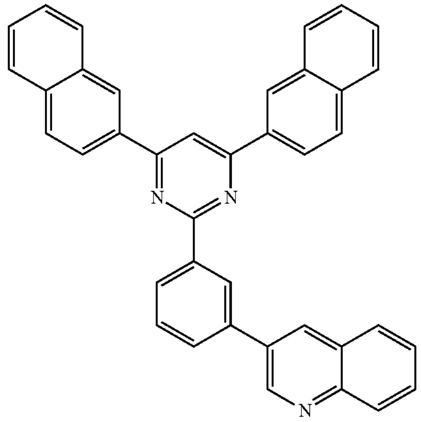
A7
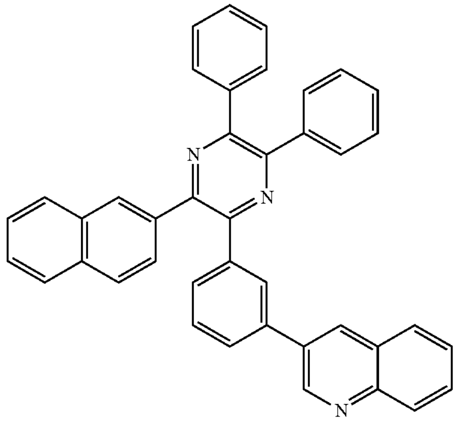
A8
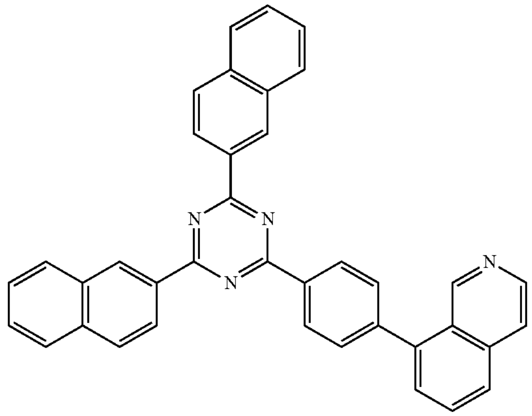
A9
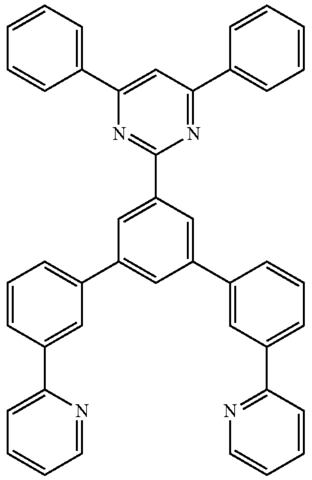

-continued
A10
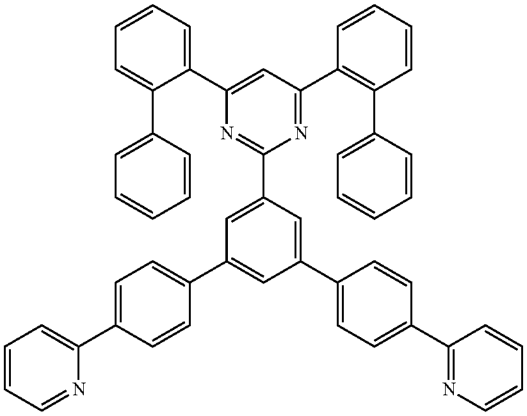
A11
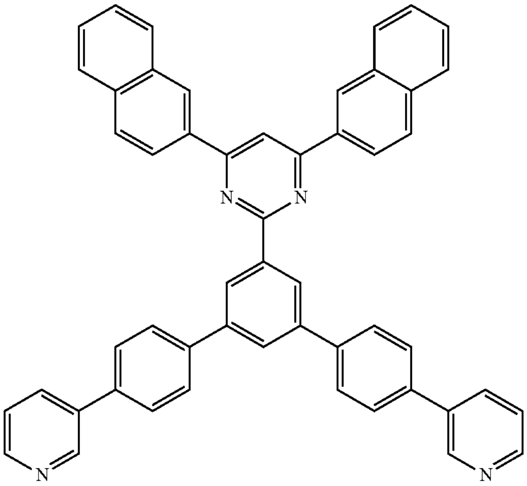
A12
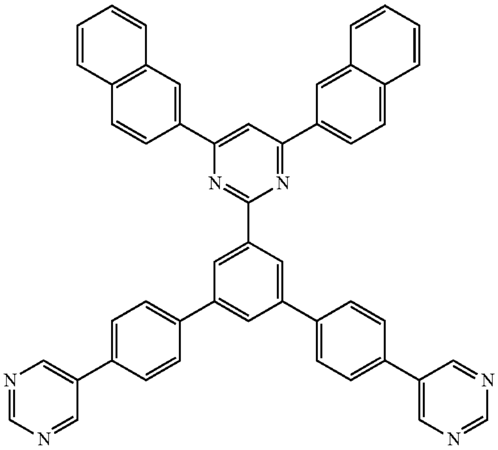
A13
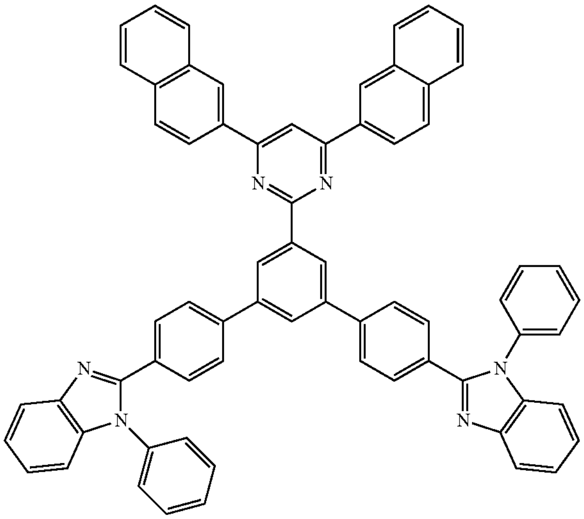
A14
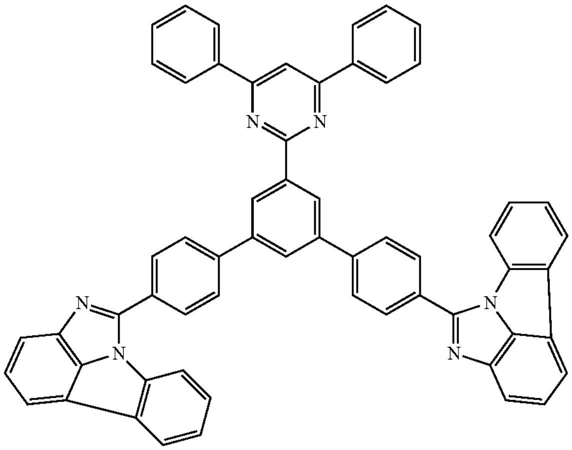
A15
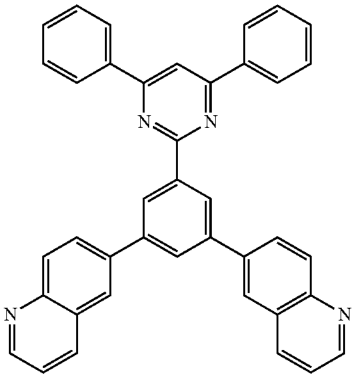

-continued
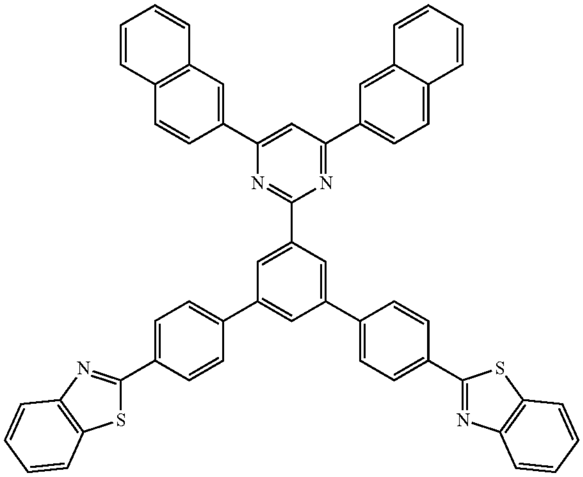
A16
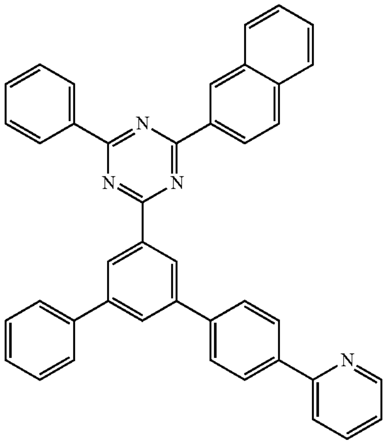
A17
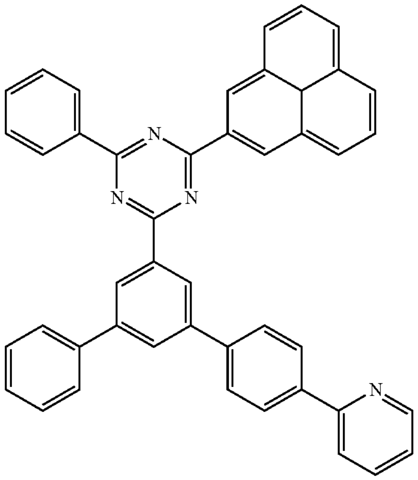
A18
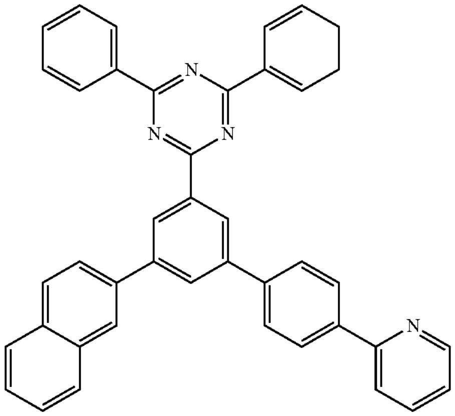
A19
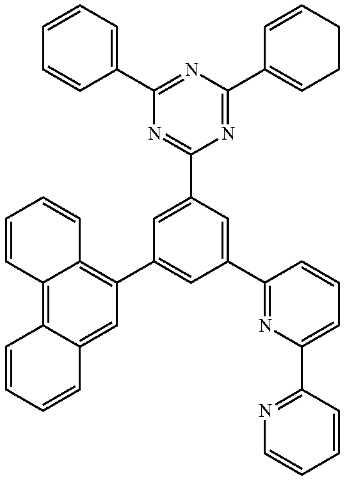
A20
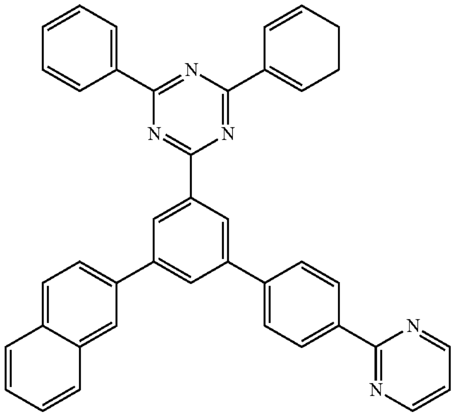
A21

-continued
A22
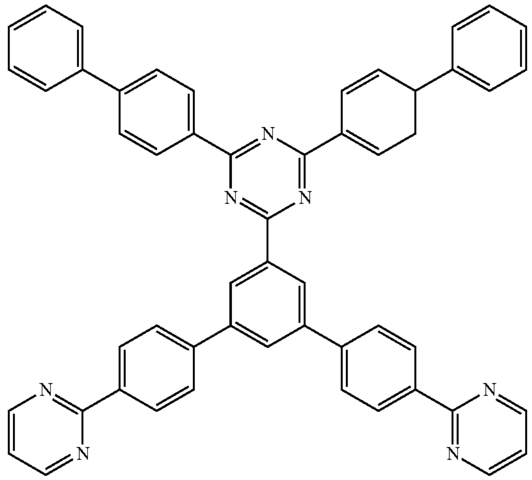
A23
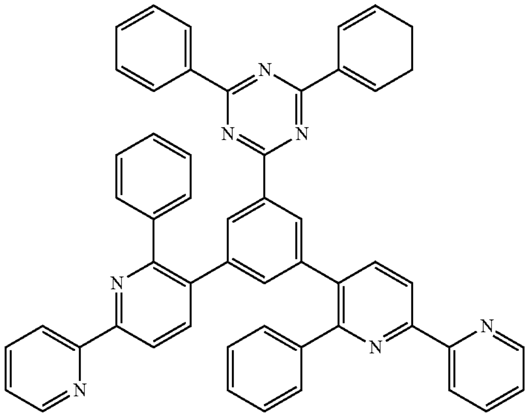
A24
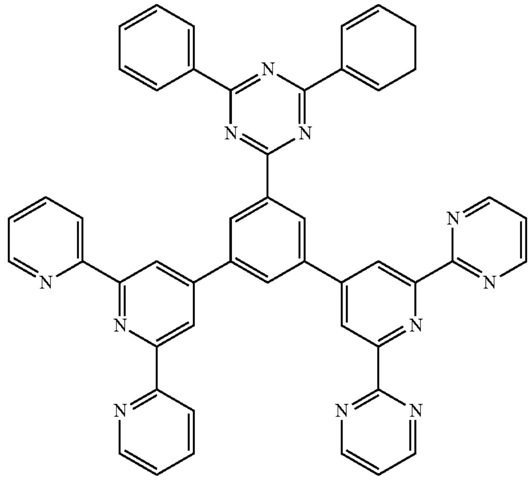
A25
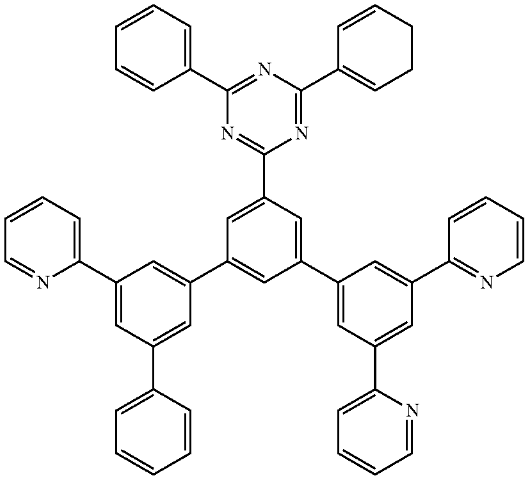
A26
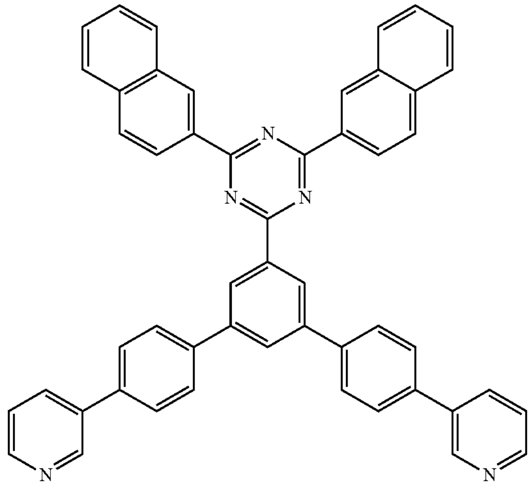
A27
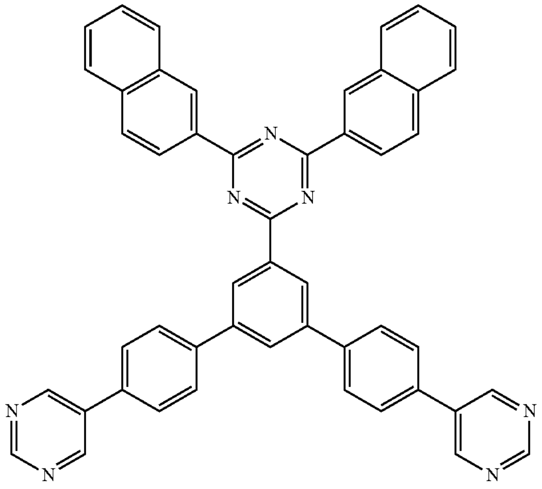

-continued

A28

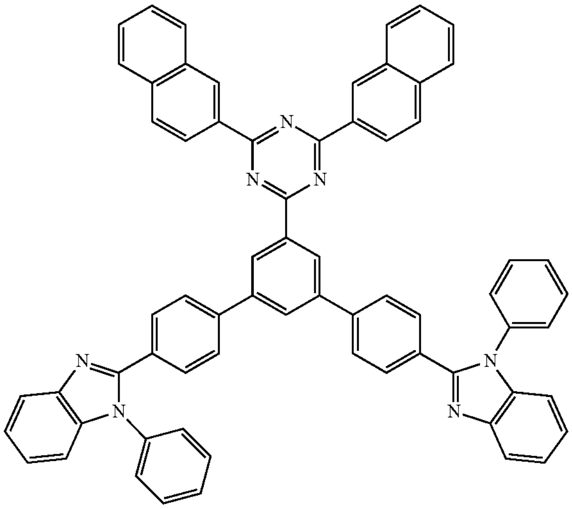

A29

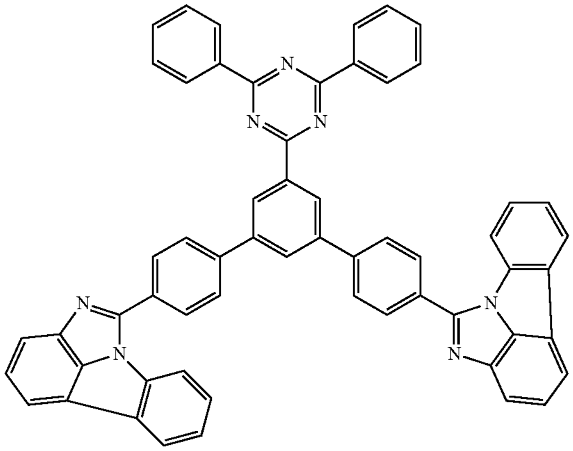

A30

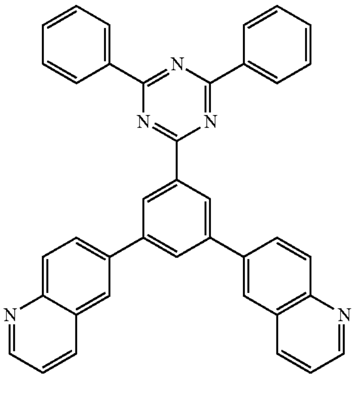

A31

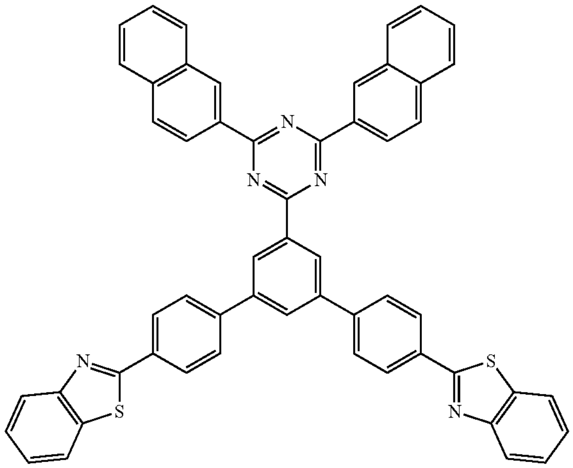

A32

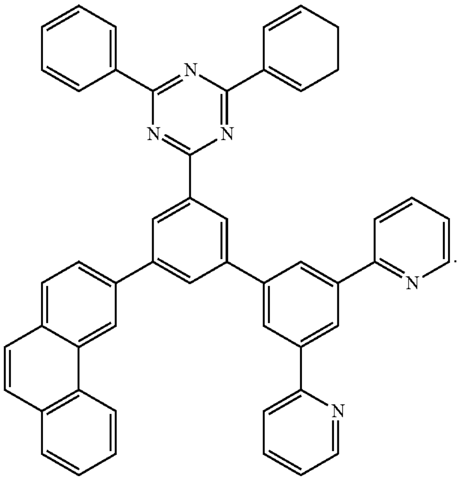

The first compound represented by one of Formulae 1A to 1C may have an excellent hole transporting ability. Thus, controlling the charge balance may be facilitated, and electrical stability may be excellent, improving lifespan characteristics. The second compound represented by one of Formulae 40A and 40B essentially has at least one electron transporting moiety other than a core. The second compound may have an excellent electron transporting ability. The second compound may easily transport electrons, increasing the exciton forming rate and having a relatively high resistance to charges. Accordingly, when an organic light-emitting device includes the first compound represented by one of Formulae 1A to 1C in a hole transport region and a second compound represented by one of Formulae 40A and 40B in a electron transport region, the balance of charges may be maintained, the hole transporting ability and electron transporting ability may be excellent, emission efficiency may be improved, and the electrical stability may be excellent, such that the organic light-emitting device may have long lifespan characteristics. Thus, the organic light-emitting device has a high emission efficiency and long lifespan characteristics even in a low voltage region.

In some embodiments, the hole transport region 130 may include at least one selected from a hole injection layer (HIL), a hole transport layer (HTL), a buffer layer, and an auxiliary emission layer, and the electron transport region 170 may include at least one selected from a hole blocking layer (HBL), an electron transport layer (ETL), and an electron injection layer (EIL).

In some embodiments, the hole transport region 130 may include the hole transport layer and the hole injection layer, and the hole injection layer may be between the first electrode and the hole transport layer. The first compound may be included in the hole injection layer and the hole transport layer. The first compound included in the hole injection layer and the first compound included in the hole transport layer may be identical to or different from each other. The electron transport region 170 may include the electron transport layer and the electron injection layer. The electron injection layer may be between the second electrode and the electron transport layer, and the second compound may be included in the electron transport layer.

The hole transport region may have a single-layered structure formed of a single material, a single-layered structure formed of a plurality of different materials, or a multi-layered structure having a plurality of layers formed of a plurality of different materials.

In some embodiments, the hole transport region 130 may have a structure of hole injection layer/hole transport layer/auxiliary emission layer, a structure of hole injection layer/hole transport layer/buffer layer/auxiliary emission layer, a structure of hole injection layer/auxiliary emission layer, a structure of hole injection layer/buffer layer/auxiliary emission layer, a structure of hole transport layer/hole auxiliary layer, and a structure of hole transport layer/buffer layer/auxiliary emission layer, wherein layers of each structure are sequentially stacked from the first electrode 110 in this stated order.

In some embodiments, the hole transport region 130 may further include an auxiliary emission layer. The auxiliary emission layer may be between the hole transport layer and the emission layer. The auxiliary emission layer may include the first compound, the electron transport region 170 may include the electron transport layer, and the electron transport layer may include the second compound.

When the hole transport region includes a hole injection layer, the hole injection layer may be formed on the first electrode 110 by using a suitable method, such as vacuum-deposition, spin coating, casting, Langmuir-Blodgett (LB) method, ink-jet printing, laser-printing, or laser-induced thermal imaging (LITI).

When the hole injection layer is formed by vacuum-deposition, for example, the vacuum-deposition may be performed at a temperature of a deposition temperature of about 100° C. to about 500° C., at a vacuum degree of about $10^{-8}$ Torr to about $10^{-3}$ Torr, and at a vacuum-deposition rate in a range of about 0.01 Å/sec to about 100 Å/sec in consideration of a compound for the hole injection layer to be deposited, and the structure of the hole injection layer to be formed.

When a hole injection layer is formed by spin coating, the spin coating may be performed at a coating rate of about 2,000 rpm to about 5,000 rpm, and at a temperature of about 80° C. to 200° C. in consideration of a compound for a hole injection layer to be deposited, and the structure of a hole injection layer to be formed.

Methods of forming the hole transport layer, hole auxiliary layer, and buffer layer may be understood by referring to that of the hole injection layer.

The thickness of the hole transport region may be in a range of about 100 Å to about 10,000 Å, or, for example, about 100 Å to about 1,000 Å. When the hole transport region includes a hole injection layer and a hole transport layer, the thickness of the hole injection layer may be in a range of about 100 Å to about 10,000 Å, or, for example, about 100 Å to about 1,000 Å, and the thickness of the hole transport layer may be in a range of about 50 Å to about 2,000 Å, or, for example, about 100 Å to about 1,500 Å. When the thicknesses of the hole transport region, the hole injection layer, and the hole transport layer are within these ranges, excellent hole transport characteristics may be obtained without a substantial increase in driving voltage.

The hole transport region may further include, in addition to the first compound, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound. Examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

<Compound HT-D1>

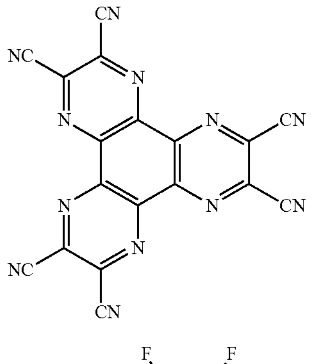

<F4-TCNQ>

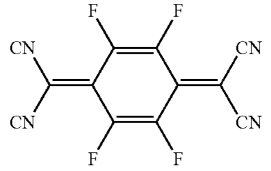

The hole transport region may further include, in addition to the hole injection layer and the hole transport layer, at least one selected from a buffer layer and an electron blocking layer. The buffer layer may compensate for an optical resonance distance according to a wavelength of light emitted from the emission layer. Accordingly, the light-emission efficiency of a formed organic light-emitting device may be improved. As a material included in the buffer layer, materials that are included in the hole transport region may be used. The electron blocking layer may prevent injection of electrons from the electron transport region.

An emission layer may be formed on the first electrode 110 or the hole transport region by using a suitable method, such as vacuum-deposition, spin coating, casting, LB method, ink-jet printing, laser-printing, or LITI. When the emission layer is formed by vacuum-deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In some implementations, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant.

The host may include at least one selected from TPBi, TBADN, ADN (also known as "DNA"), CBP, CDBP, and TCP:

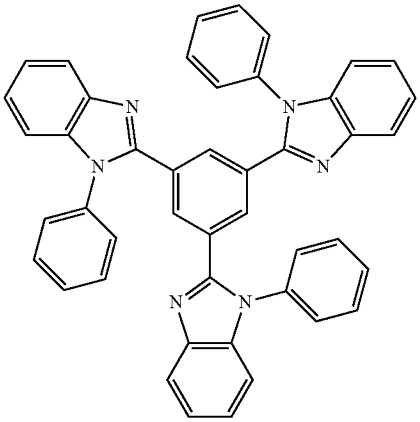

TPBi

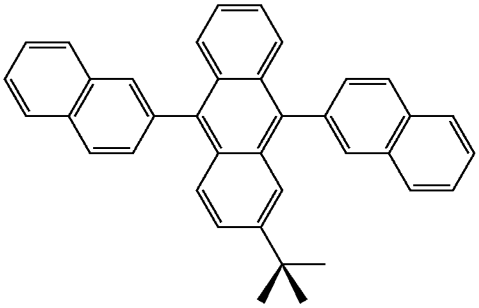

TBADN

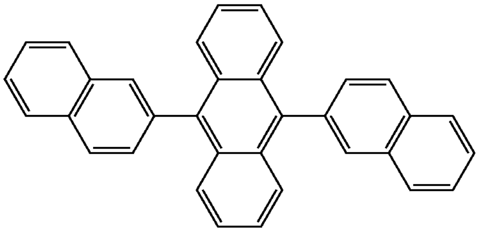

ADN

-continued

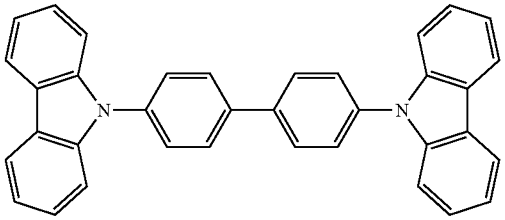

CBP

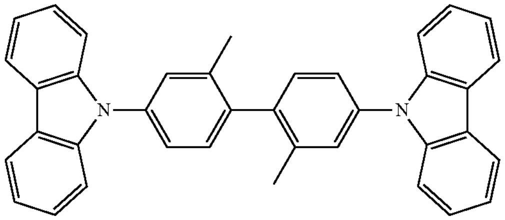

CDBP

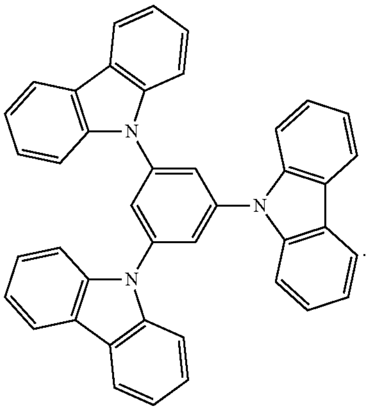

TCP

In some embodiments, the host may include at least one selected from a first host represented by Formula 101, a second host represented by Formula 201, a third host represented by Formula 202, a fourth host represented by Formula 301, and a fifth host represented by Formula 302:

<Formula 101>

$$Ar_{101}—[(L_{101})_{a101}—R_{101}]_{n101}$$

<Formula 201>

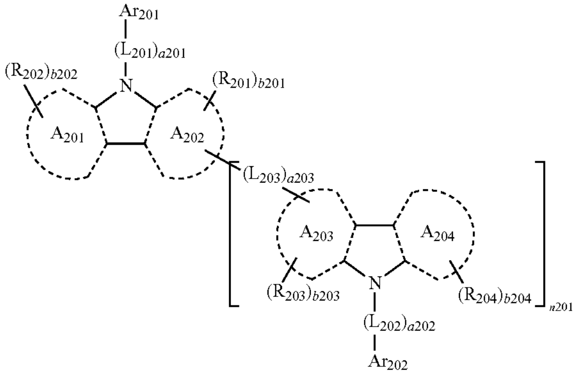

-continued

<Formula 202>

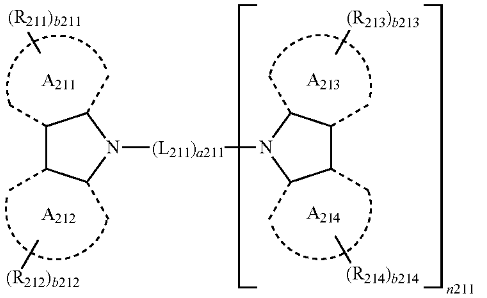

<Formula 301>

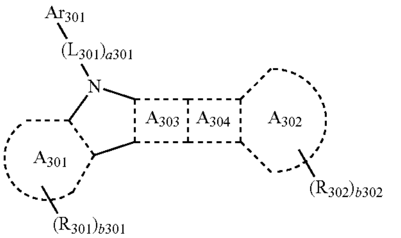

<Formula 302>

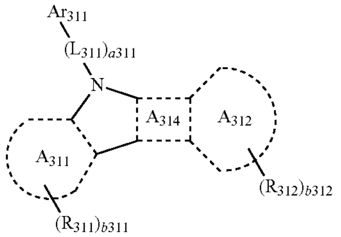

<Formula 303>

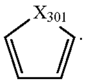

In the Formulae above, $Ar_{101}$, $A_{201}$ to $A_{204}$, $A_{211}$ to $A_{214}$, $A_{301}$ to $A_{303}$, $A_{311}$, and $A_{312}$ may be each independently a substituted or unsubstituted $C_6$-$C_{20}$ aromatic ring;

$A_{304}$ and $A_{314}$ may each independently be a group represented by Formula 303;

$X_{301}$ may be selected from N-$(L_{302})_{a302}$-$Ar_{302}$, O, S, $C(R_{303})(R_{304})$, $Si(R_{303})(R_{304})$, $P(R_{303})$, $B(R_{303})$, and $P(=O)(R_{303})$;

$L_{101}$, $L_{201}$ to $L_{203}$, $L_{211}$, $L_{301}$, $L_{302}$, and $L_{311}$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a101, a201 to a203, a211, a301, a302, and a311 may each independently be an integer selected from 0 to 3;

$R_{101}$, $Ar_{201}$, $Ar_{202}$, $Ar_{301}$, $Ar_{302}$, and $Ar_{311}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$R_{201}$ to $R_{204}$, $R_{211}$ to $R_{214}$, $R_{301}$ to $R_{304}$, $R_{311}$, and $R_{312}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_{101})(Q_{102})$, —$Si(Q_{103})(Q_{104})(Q_{105})$, and —$B(Q_{106})(Q_{107})$;

b201 and b203 may each independently be an integer selected from 0 to 3, b202, b204, b211 to b214, b301, b302, b311, and b312 may each independently be an integer selected from 0 to 4;

n101 may be an integer selected from 0 to 3, n201 and n202 may each independently be an integer selected from 0 to 4, n211 may be an integer selected from 1 and 2;

at least one of substituents of the substituted $C_6$-$C_{20}$ aromatic ring, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{101})(Q_{102})$, —$Si(Q_{103})(Q_{104})(Q_{105})$, and —$B(Q_{106})(Q_{107})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{111})(Q_{112})$, —$Si(Q_{113})(Q_{114})(Q_{115})$, and —$B(Q_{116})(Q_{117})$; and —$N(Q_{121})(Q_{122})$, —$Si(Q_{123})(Q_{124})(Q_{125})$, and —$B(Q_{126})(Q_{127})$;

wherein $Q_{101}$ to $Q_{107}$, $Q_{111}$ to $Q_{117}$, and $Q_{121}$ to $Q_{127}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In some embodiments, $Ar_{101}$, $A_{201}$ to $A_{204}$, $A_{211}$ to $A_{214}$, $A_{301}$ to $A_{303}$, $A_{311}$, and $A_{312}$ may be each independently selected from a benzene, a naphthalene, a pyridine, a pyrimidine, a pyrazine, a quinoline, an isoquinoline, a 2,6-naphthyridine, a 1,8-naphthyridine, a 1,5-naphthyridine, a 1,6-naphthyridine, a 1,7-naphthyridine, a 2,7-naphthyridine, a quinoxaline, a phthalazine, and a quinazoline. In some embodiments, $Ar_{101}$, $A_{201}$ to $A_{204}$, $A_{211}$ to $A_{214}$, $A_{301}$ to $A_{303}$, $A_{311}$, and $A_{312}$ may be each independently selected from a benzene and a naphthalene.

$L_{101}$, $L_{201}$ to $L_{203}$, $L_{211}$, $L_{301}$, $L_{302}$, and $L_{311}$ may be each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a triazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

$R_{101}$, $Ar_{201}$, $Ar_{202}$, $Ar_{301}$, $Ar_{302}$, and $Ar_{311}$ may be each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —$Si(Q_{31})(Q_{32})(Q_{33})$;

wherein $Q_{31}$ to $Q_{33}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

In some embodiments, the first host may be represented by one of Formulae 101A to 101D, the second host may be represented by Formula 201A, the third host may be represented by one of Formulae 202A and 202B, the fourth host may be represented by one of Formulae 301A to 301H, and the fifth host may be represented by one of Formulae 302A and 302B:

<Formula 101A>

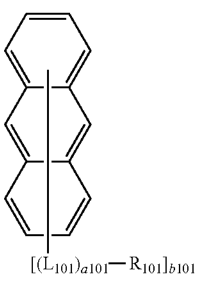

<Formula 101B>

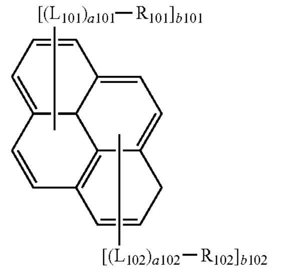

<Formula 101C>

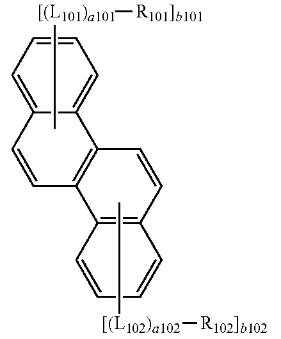

<Formula 101D>

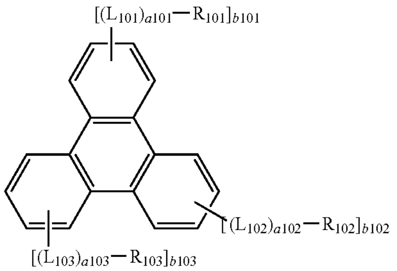

-continued

<Formula 201A>

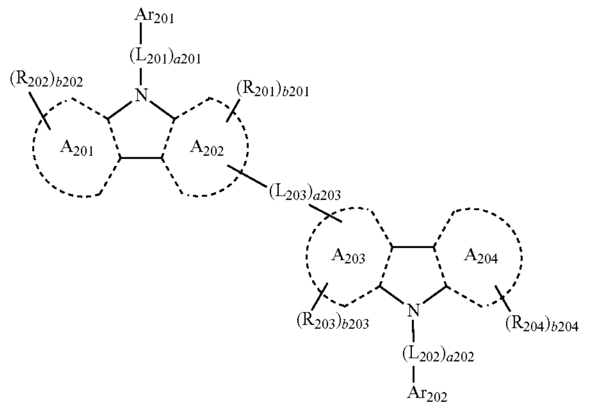

<Formula 202A>

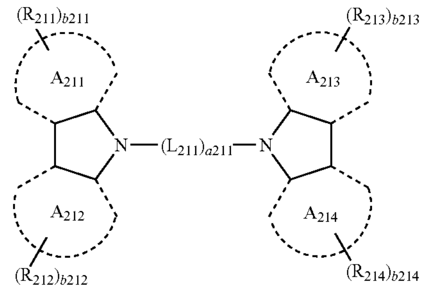

<Formula 202B>

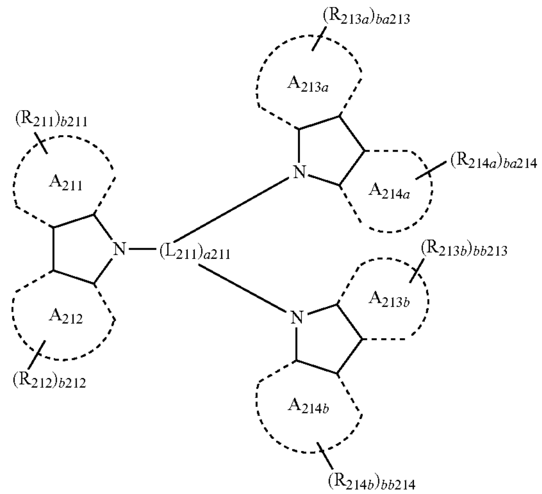

<Formula 301A>

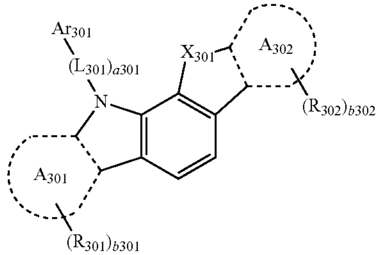

-continued

<Formula 301B>

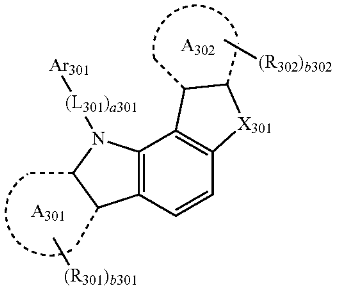

<Formula 301C>

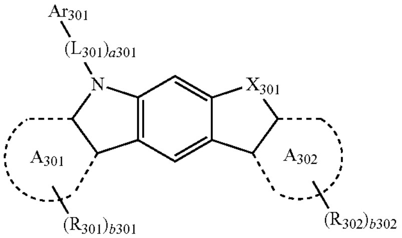

<Formula 301D>

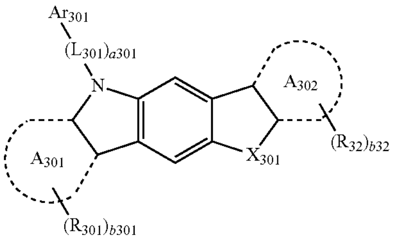

<Formula 301E>

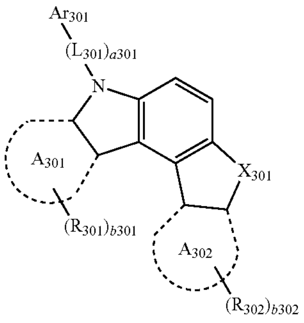

<Formula 301F>

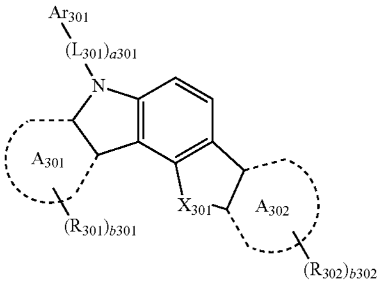

-continued

<Formula 301G>

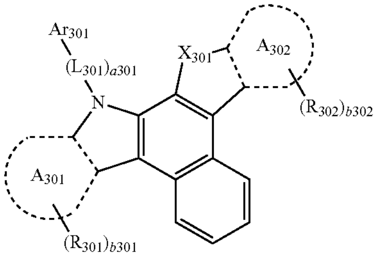

<Formula 301H>

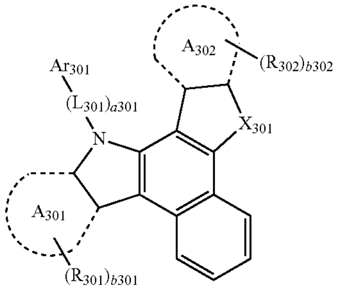

<Formula 302A>

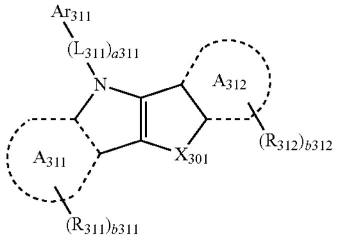

<Formula 302B>

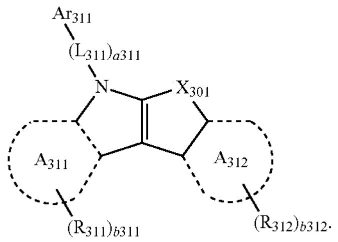

In the Formulae above, descriptions of $Ar_{101}$, $A_{201}$ to $A_{204}$, $A_{211}$ to $A_{214}$, $A_{301}$ to $A_{304}$, $A_{311}$, $A_{312}$, $A_{314}$, $X_{301}$, $L_{101}$, $L_{201}$ to $L_{203}$, $L_{301}$, $L_{302}$, $L_{311}$, a101, a201 to a203, a301, a302, a311, $Ar_{201}$, $Ar_{202}$, $Ar_{301}$, $Ar_{302}$, $Ar_{311}$, $R_{101}$, $R_{201}$ to $R_{204}$, $R_{211}$ to $R_{214}$, $R_{301}$, $R_{302}$, $R_{311}$, $R_{312}$, b101, b201 to b204, b211 to b214, b301, b302, b311, and b312 may be understood by referring to the descriptions thereof provided herein, descriptions of $L_{102}$ and $L_{103}$ may each be the same as defined in connection with descriptions of $L_{101}$, descriptions of a102 and a103 may each be the same as defined in connection with a101, descriptions of b102 and b103 may each be the same as defined in connection with $R_{101}$, and descriptions of b102 and b103 may each be the same as defined in connection with b101, and descriptions of $A_{213a}$ and $A_{213b}$ may each be the same as defined in connection with $A_{213}$, descriptions of $A_{214a}$ and $A_{214b}$ may each be the same as defined in connection with $A_{214}$, descriptions of $R_{213a}$ and $R_{213b}$ may each be the same as defined in connection with $R_{213}$, descriptions of $R_{214b}$ and $R_{214b}$ may each be the same as defined in connection with $R_{214}$, descriptions of ba213 and bb213 may each be the same as defined in connection with b213, and descriptions of ba214 and bb214 may each be the same as defined in connection with b214.

The compound represented by Formula 101 may be one of Compounds H-1a to H-188a, the compound represented by Formula 201 may be one of Compounds H-1b to H-74b, the compound represented by Formula 301 may be one of Compounds H-1c to H-141c, as examples:

H-1a

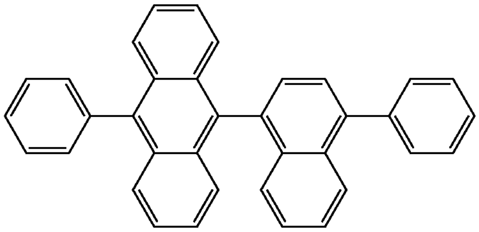

H-2a

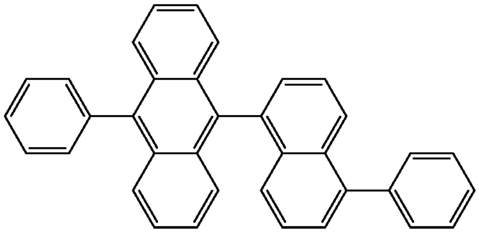

H-3a

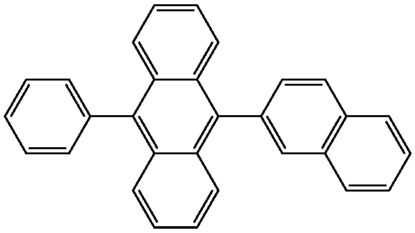

H-4a

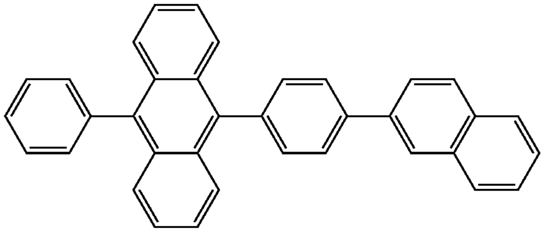

H-5a

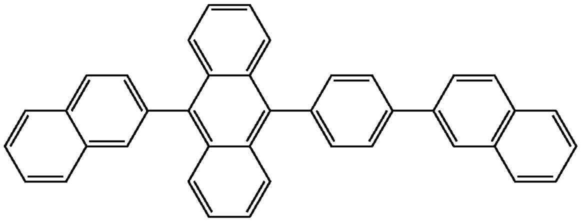

-continued

H-6a

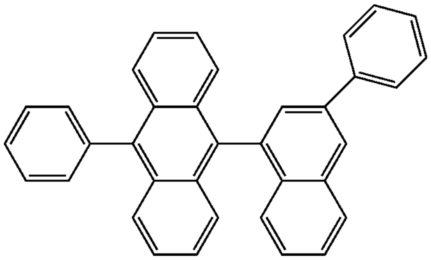

H-7a

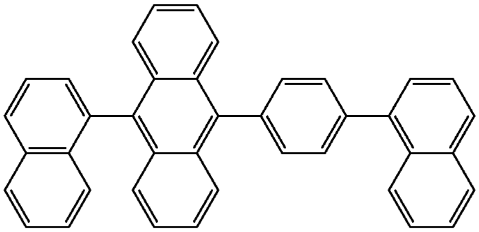

H-8a

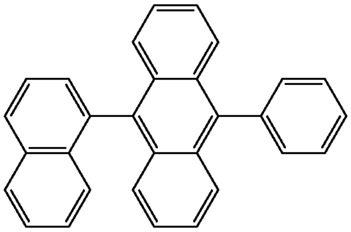

H-9a

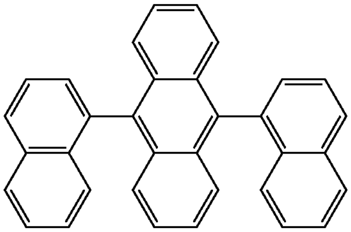

H-10a

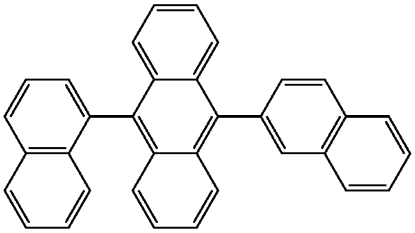

H-11a

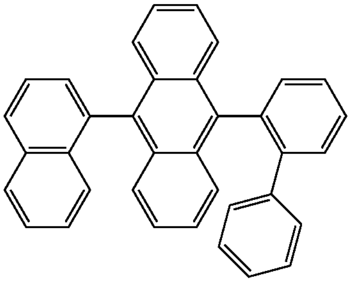

-continued
H-12a
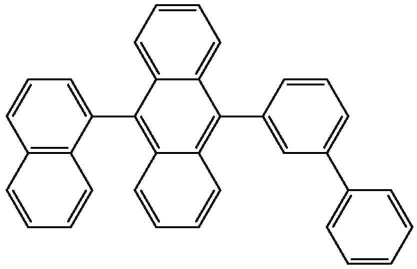
H-13a
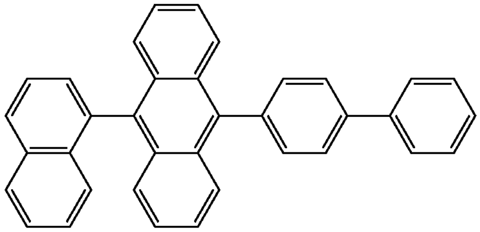
H-14a
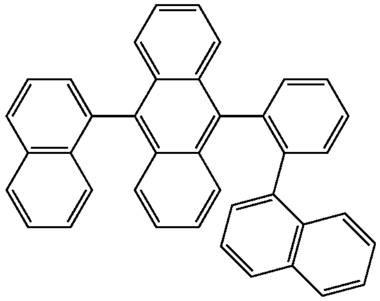
H-15a
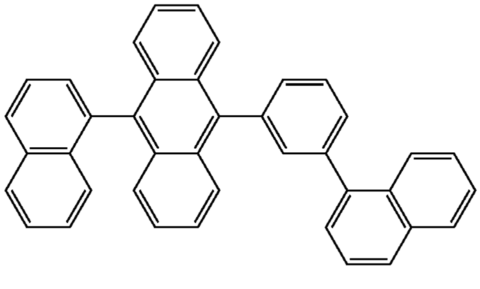
H-16a
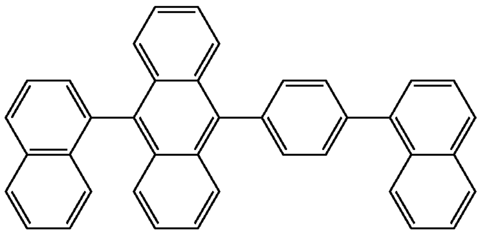
-continued
H-17a
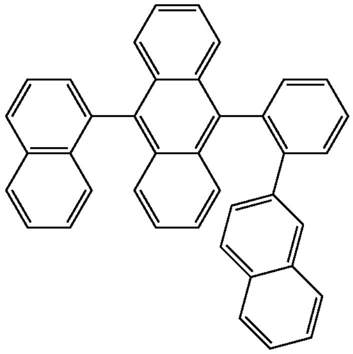
H-18a
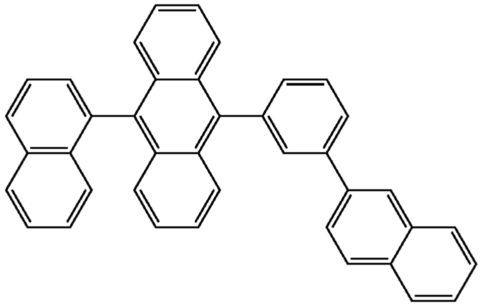
H-19a
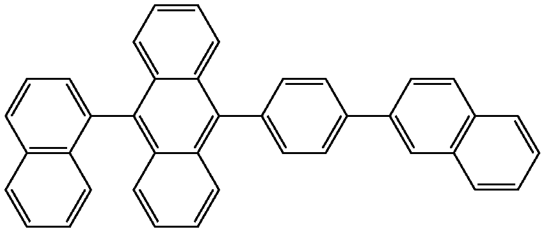
H-20a
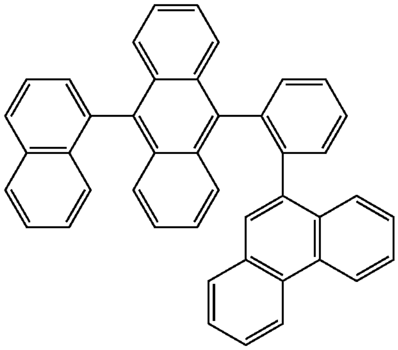
H-21a
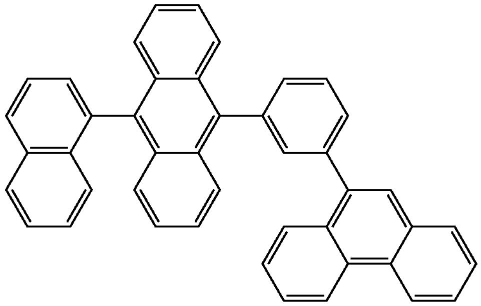

-continued
H-22a
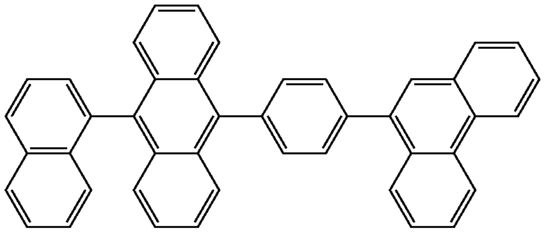
H-23a
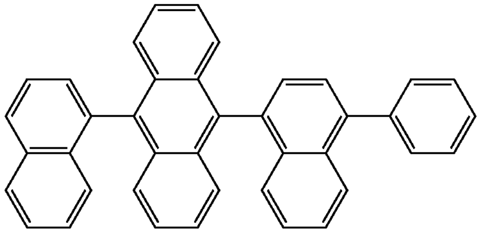
H-24a
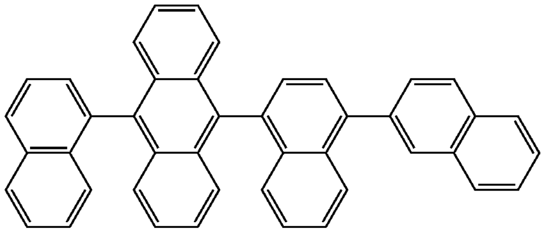
H-25a
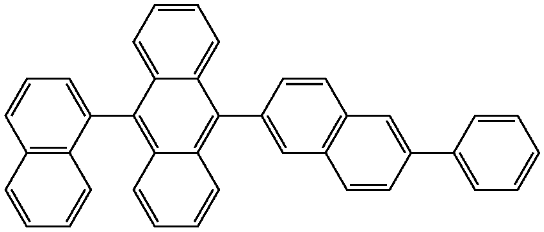
H-26a
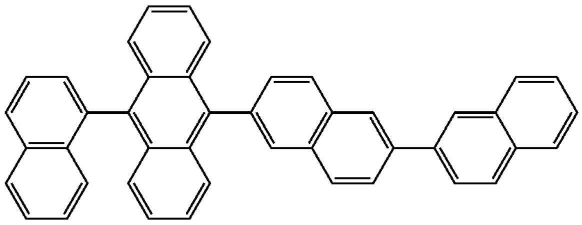
H-27a
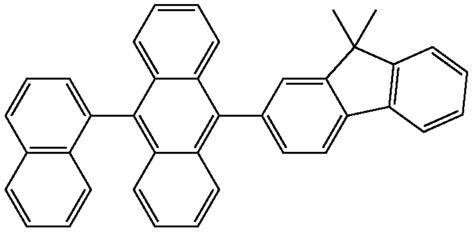
-continued
H-28a
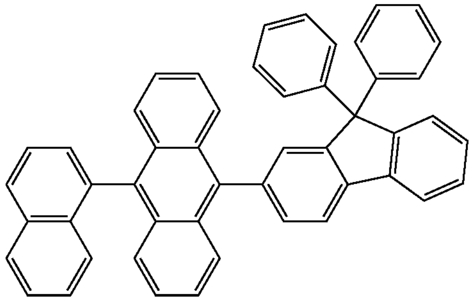
H-29a
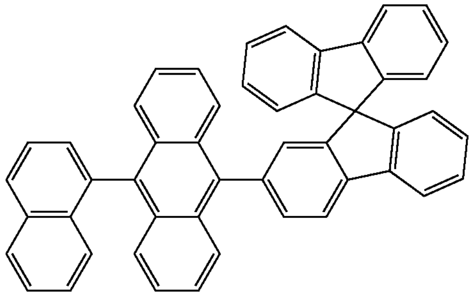
H-30a
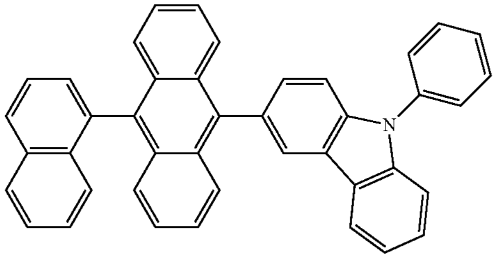
H-31a
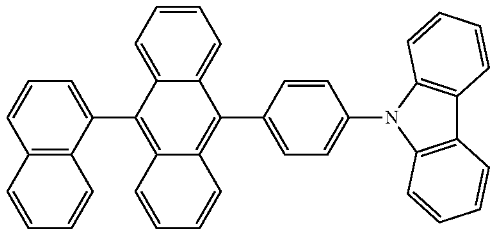
H-32a
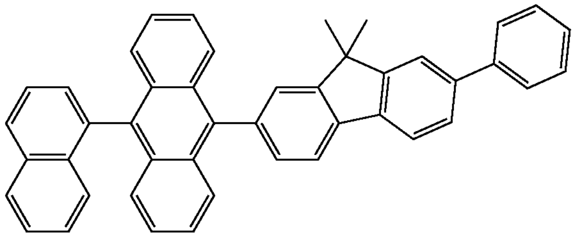

-continued
H-33a
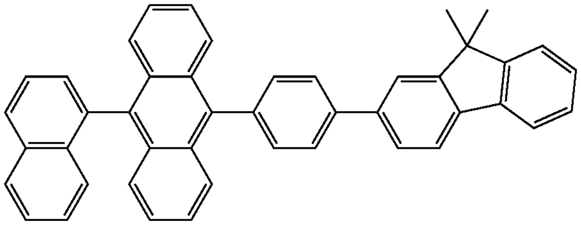
H-34a
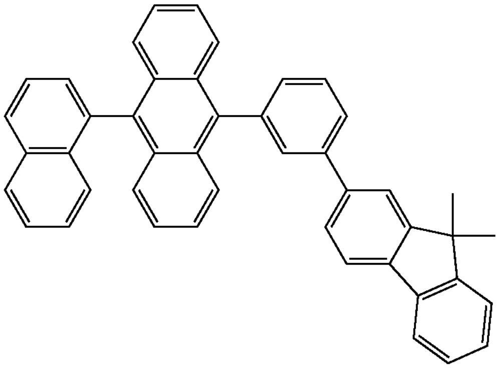
H-35a
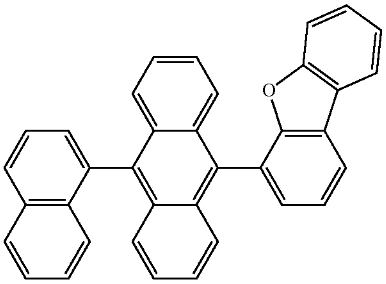
H-36a
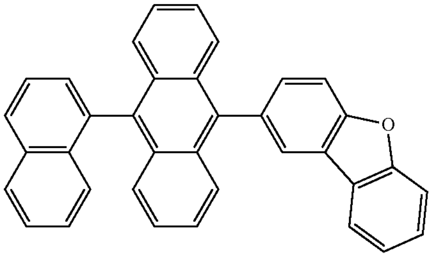
H-37a
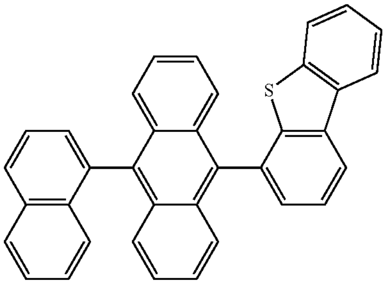
-continued
H-38a
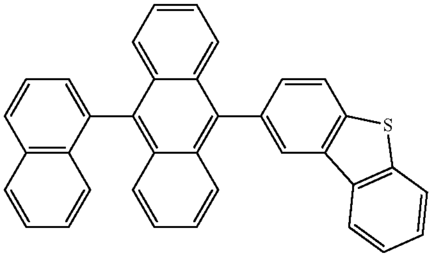
H-39a
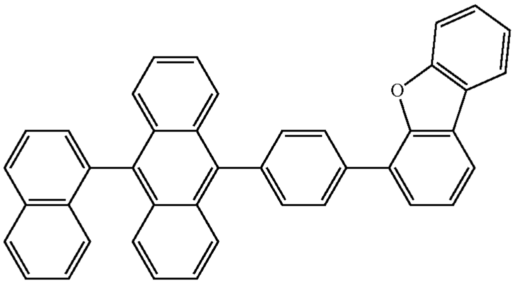
H-40a
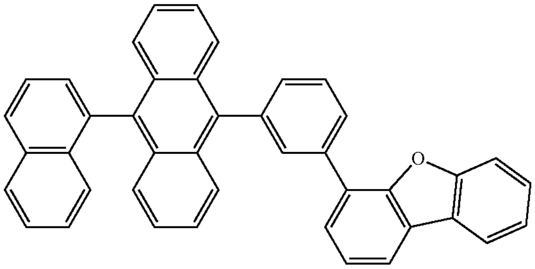
H-41a
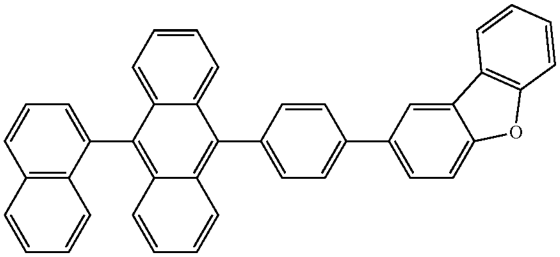
H-42a
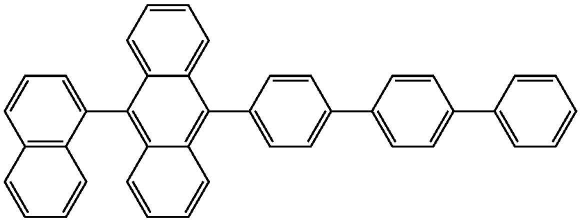

-continued
H-43a
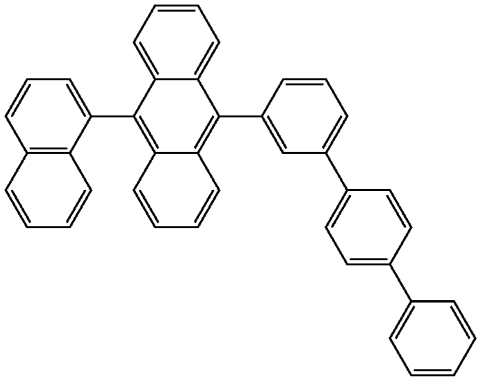
H-44a
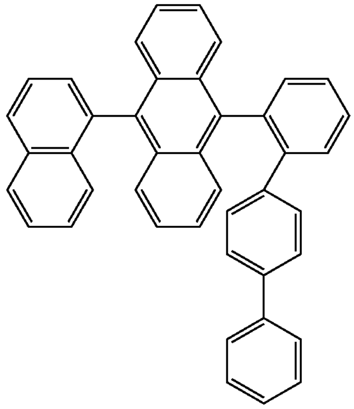
H-45a
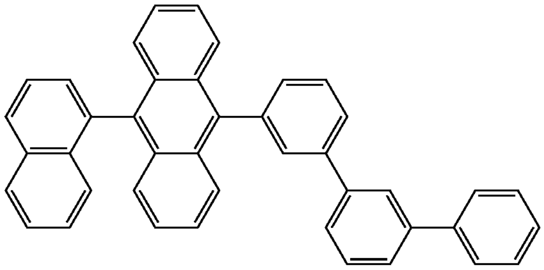
H-46a
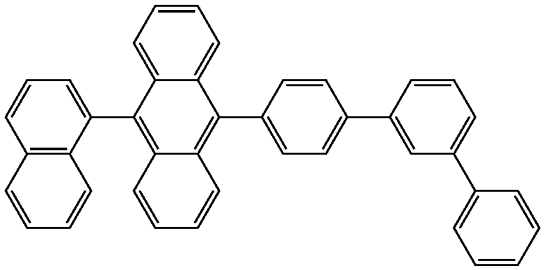
H-47a
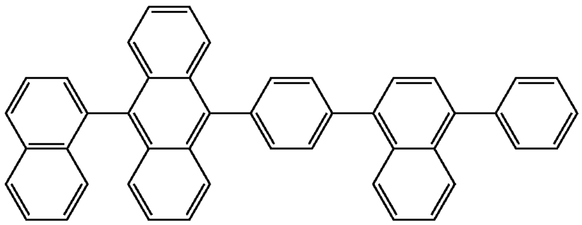
-continued
H-48a
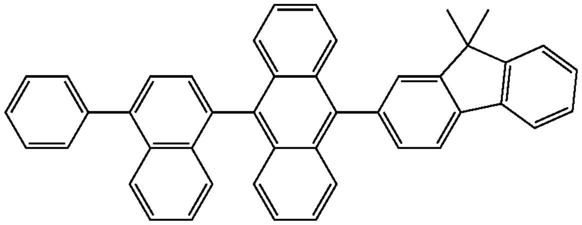
H-49a
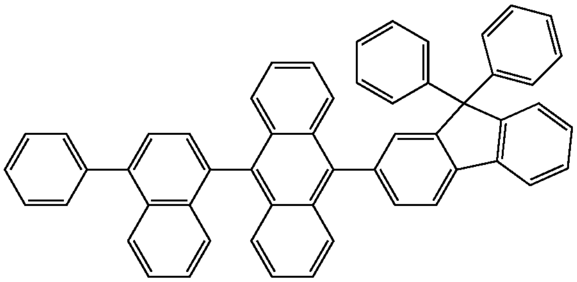
H-50a
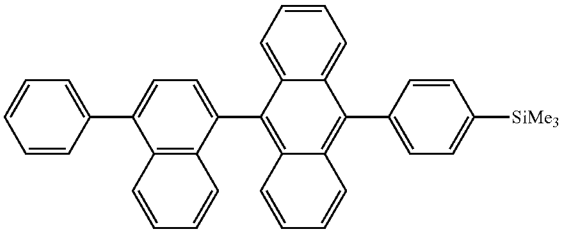
H-51a
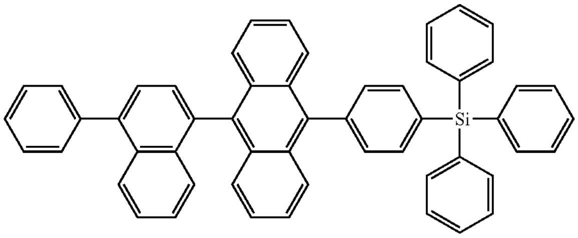
H-52a
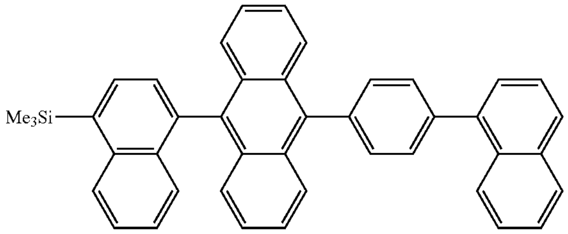

-continued
H-53a
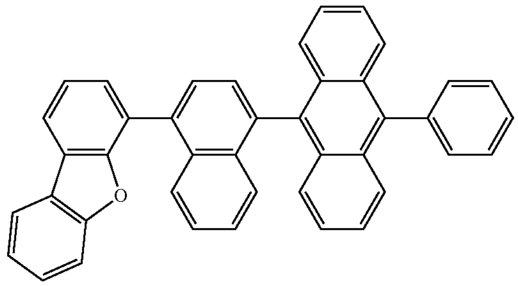
H-54a
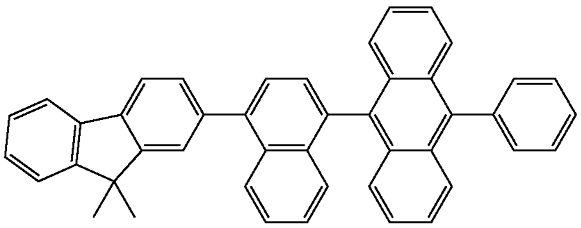
H-55a
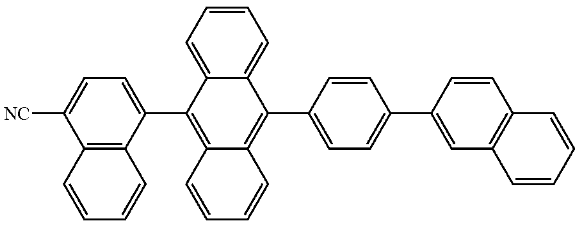
H-56a
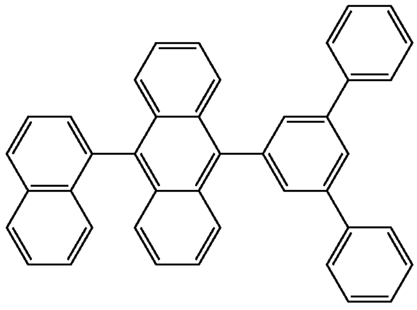
H-57a
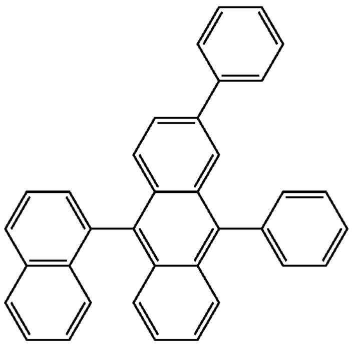
-continued
H-58a
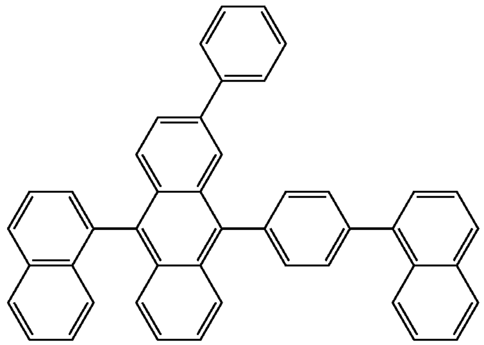
H-59a
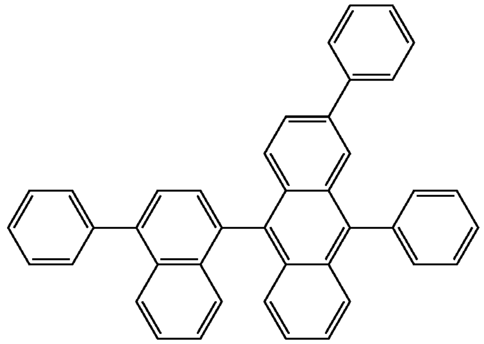
H-60a
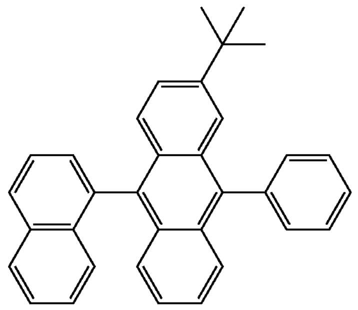
H-61a
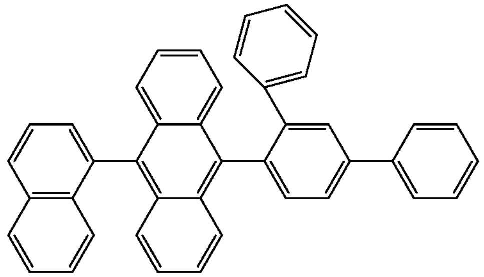
H-62a
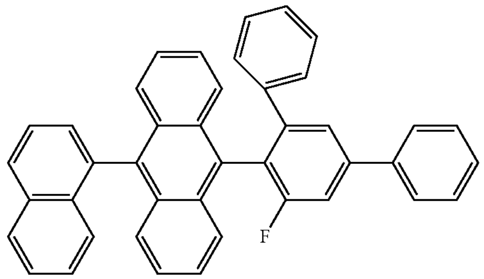

H-63a
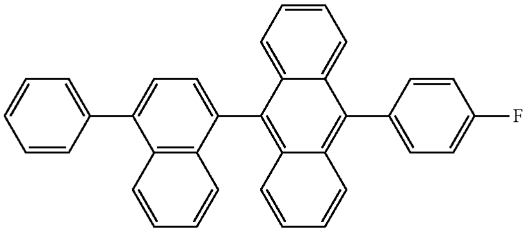
H-64a
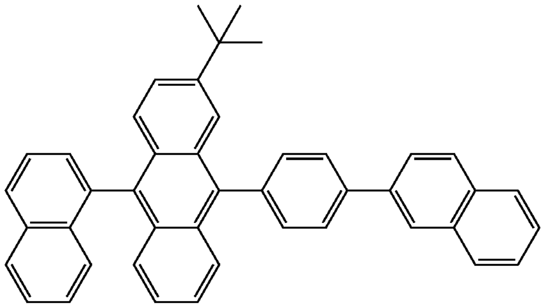
H-65a
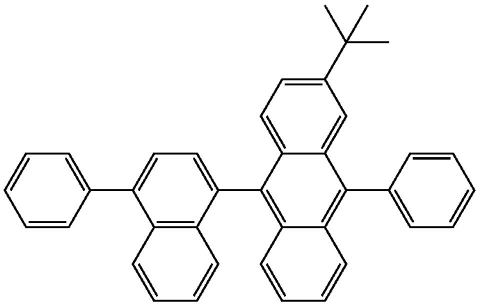
H-66a
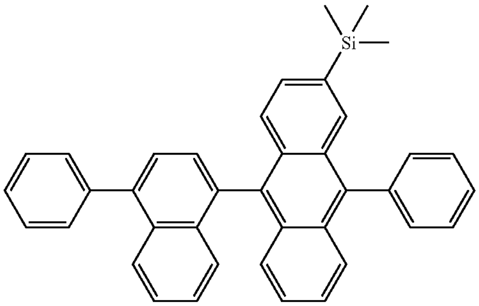
H-67a
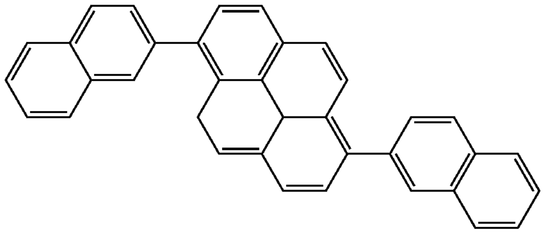
H-68a
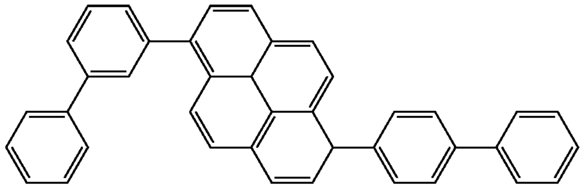
H-69a
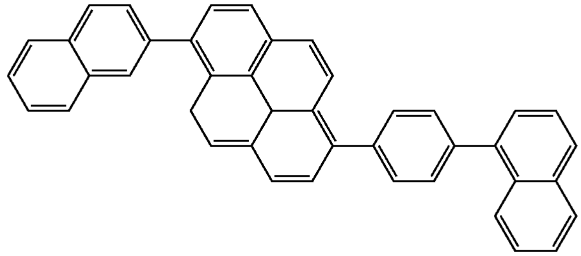
H-70a
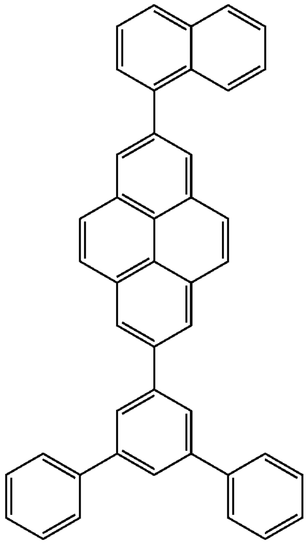
H-71a
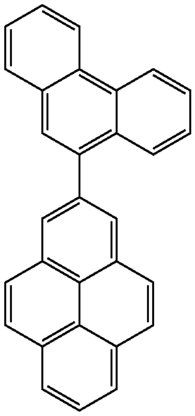

-continued
H-72a
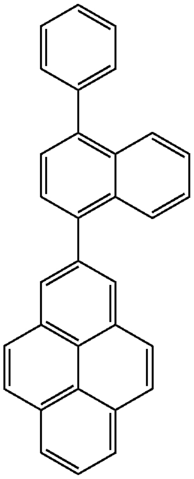
H-73a
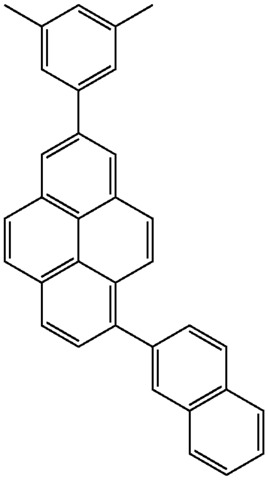
H-74a
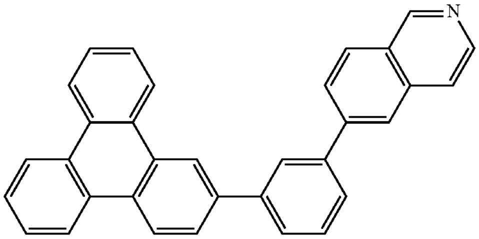
H-75a
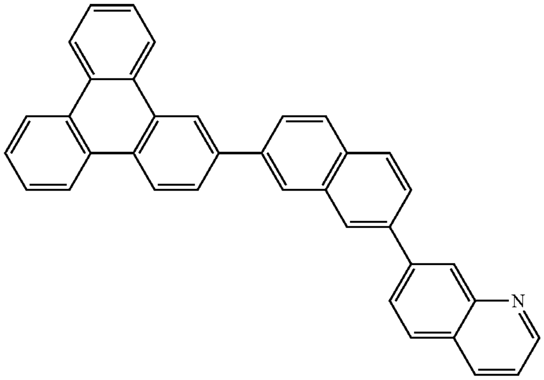
-continued
H-76a
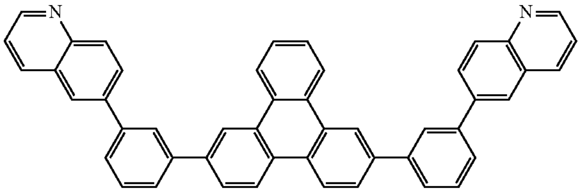
H-77a
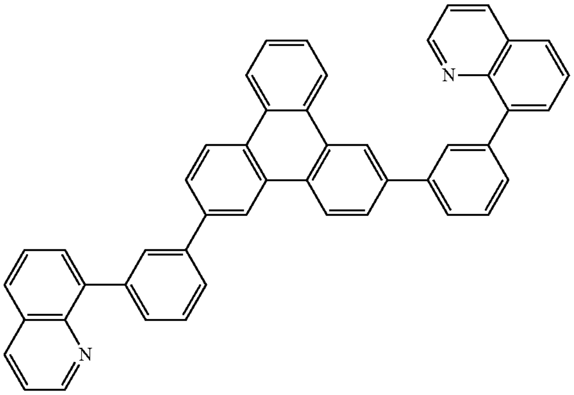
H-78a
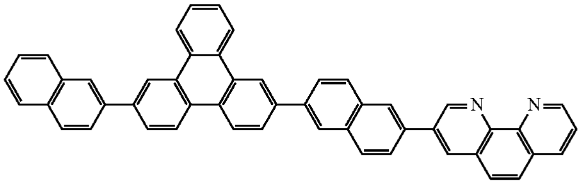
H-79a
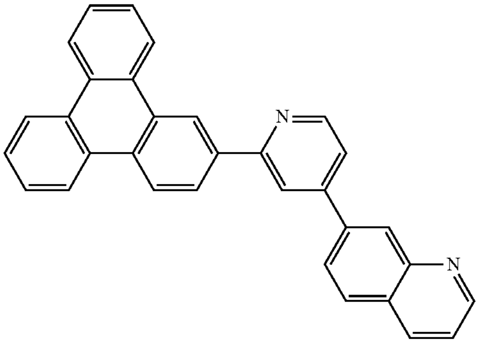
H-80a
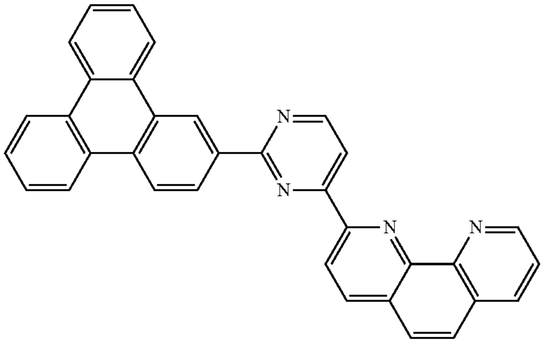

H-81a
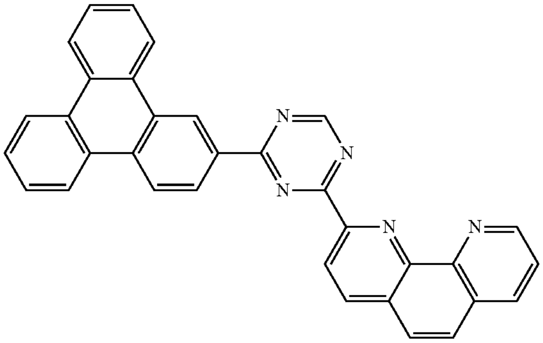
H-82a
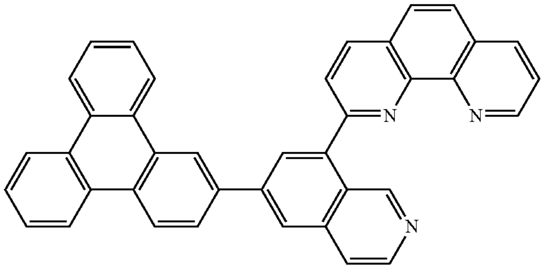
H-83a
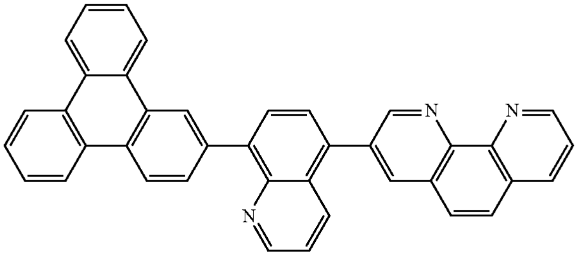
H-84a
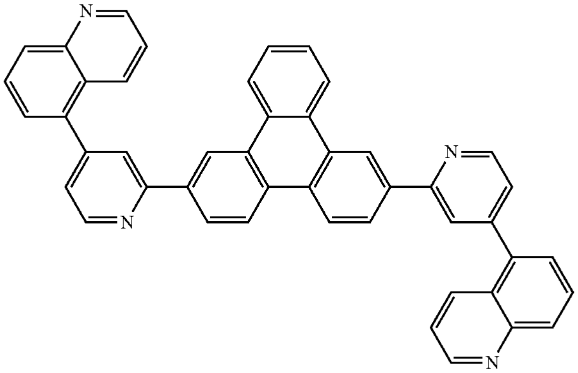
H-85a
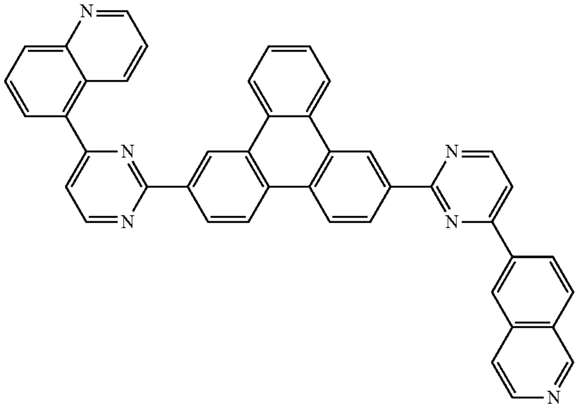
H-86a
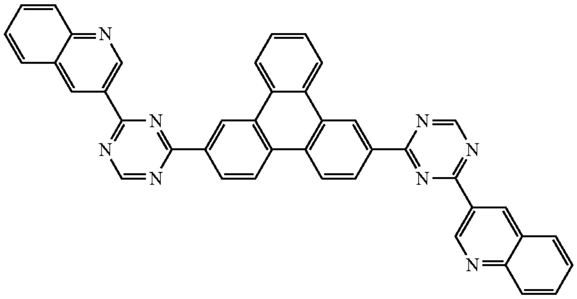
H-87a
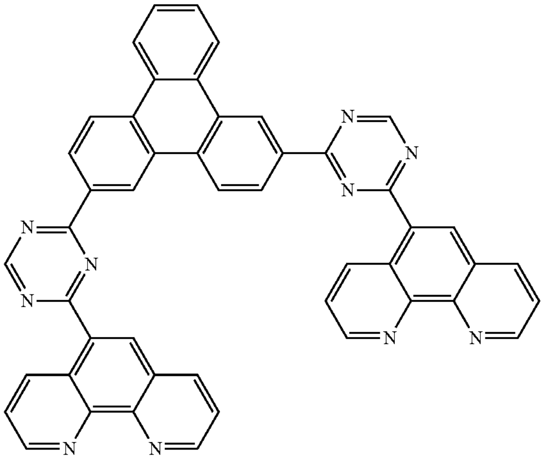

-continued
H-88a
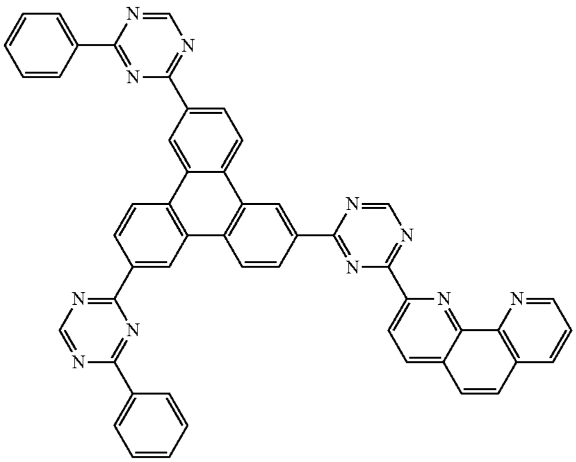
H-89a
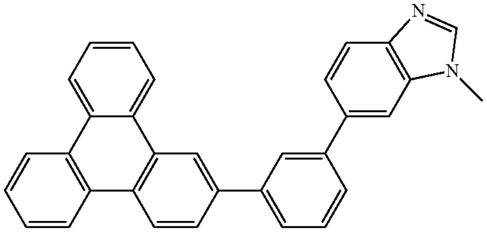
H-90a
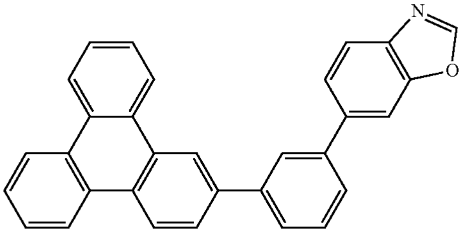
H-91a
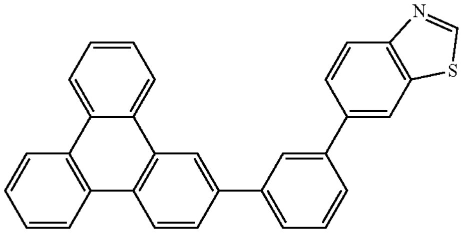
H-92a
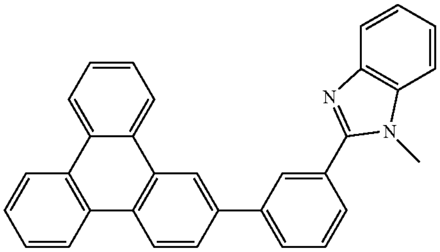
-continued
H-93a
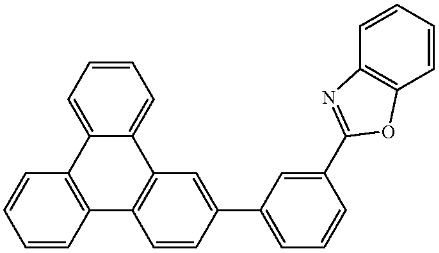
H-94a
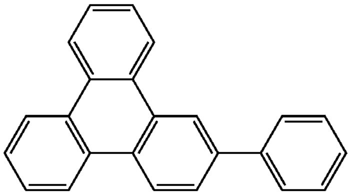
H-95a
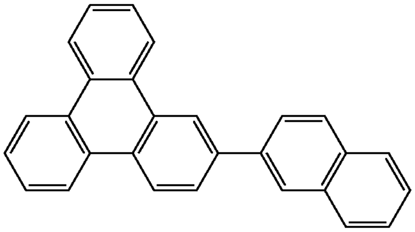
H-96a
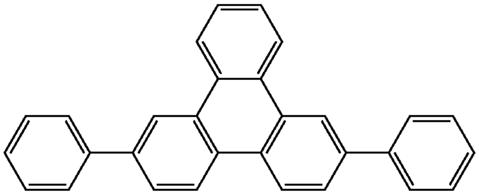
H-97a
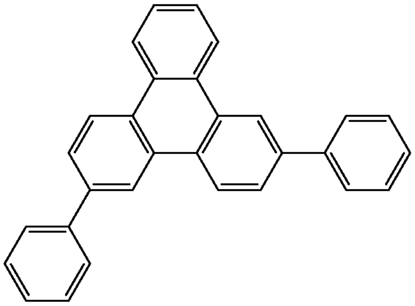
H-98a
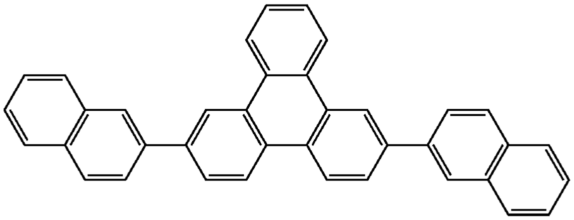

-continued
H-99a
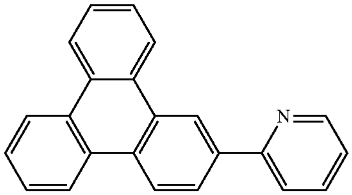
H-100a
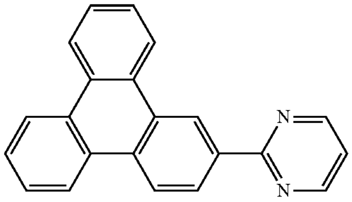
H-101a
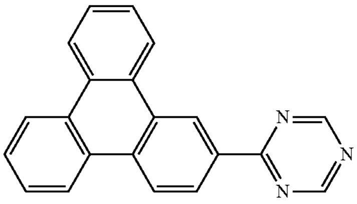
H-102a
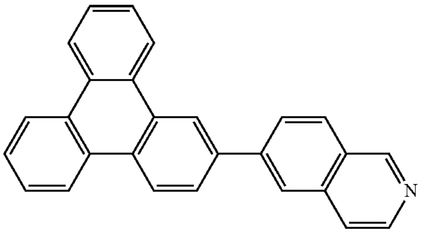
H-103a
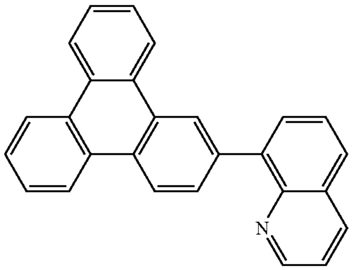
H-104a
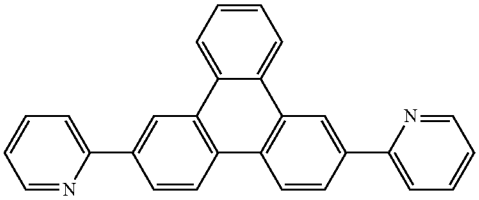
H-105a
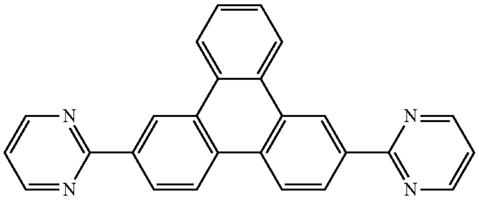
-continued
H-106a
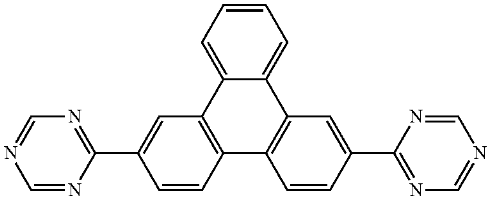
H-107a
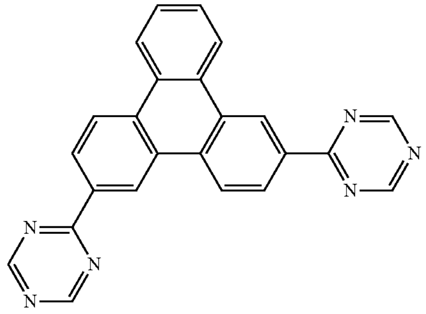
H-108a
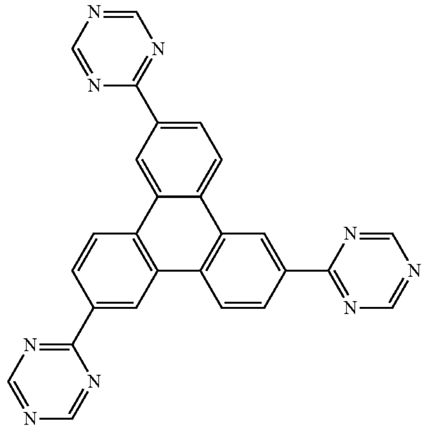
H-109a
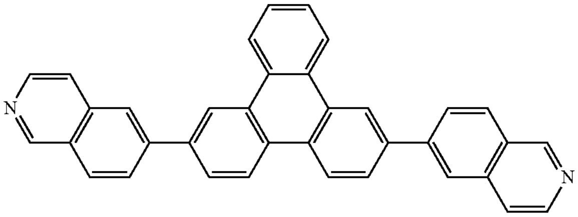
H-110a
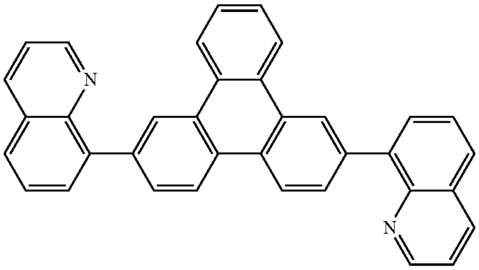

-continued
H-111a
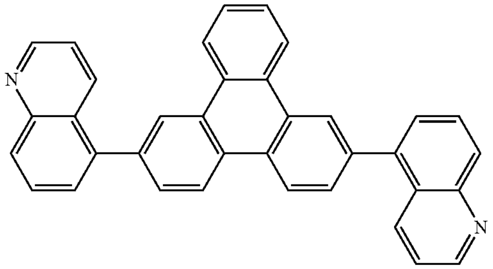
H-112a
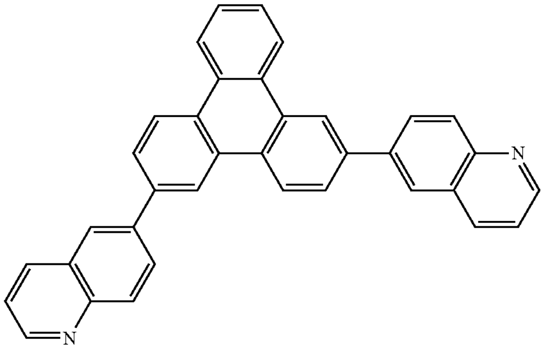
H-113a
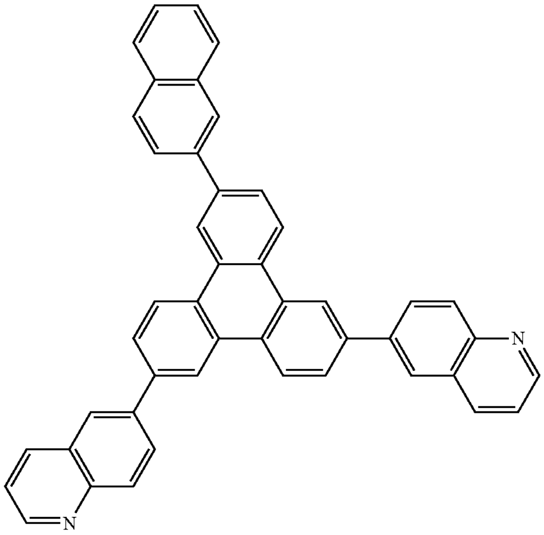
H-114a
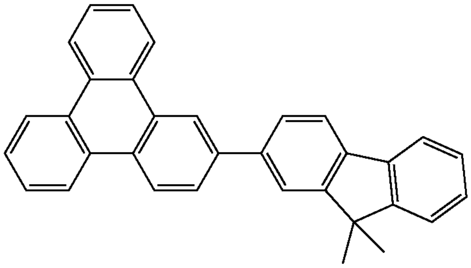
-continued
H-115a
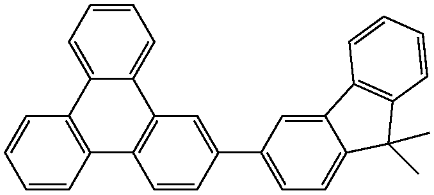
H-116a
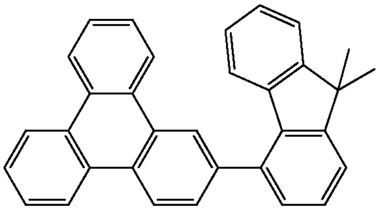
H-117a
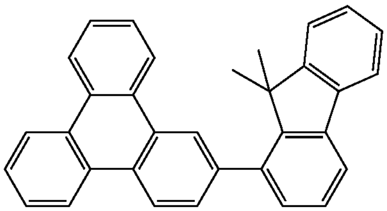
H-118a
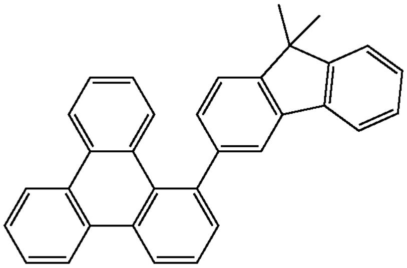
H-119a
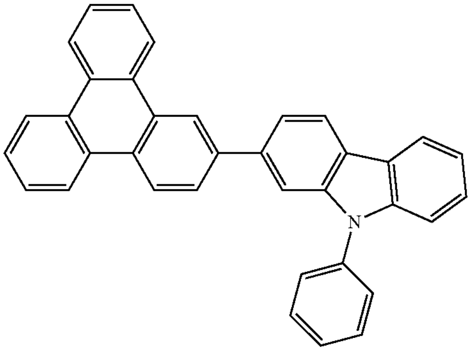
H-120a
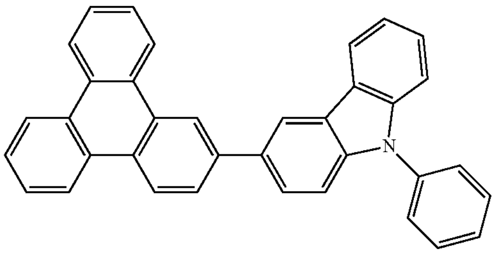

-continued
H-121a
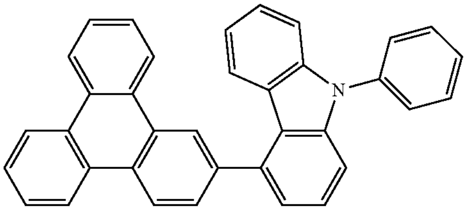
H-122a
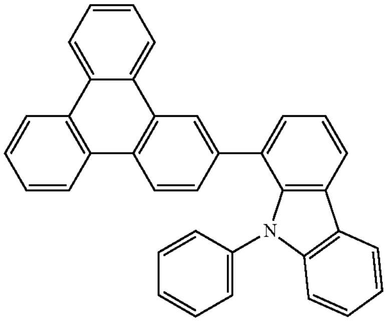
H-123a
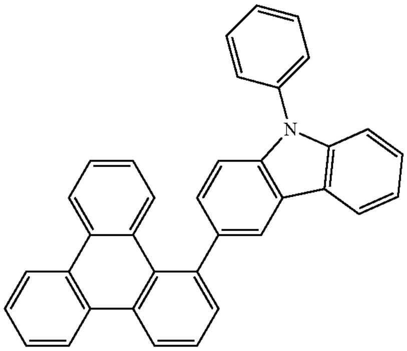
H-124a
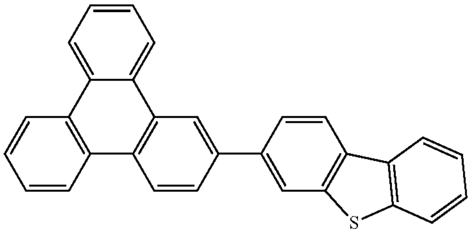
H-125a
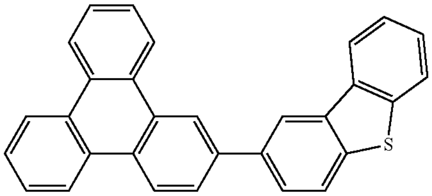
H-126a
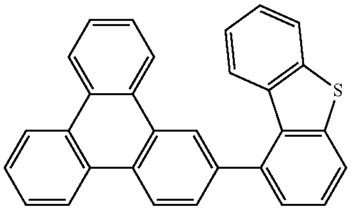
-continued
H-127a
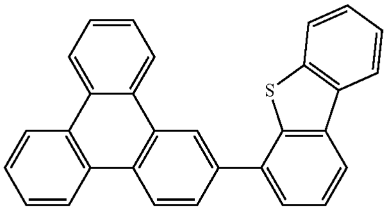
H-128a
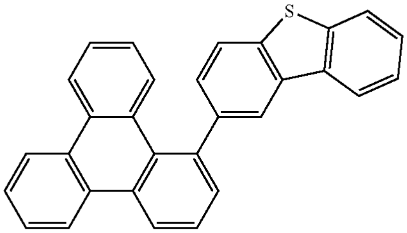
H-129a
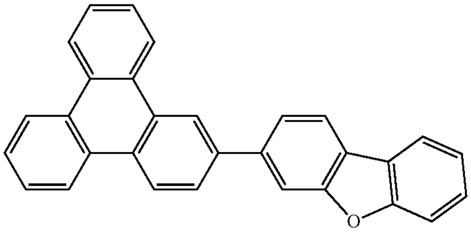
H-130a
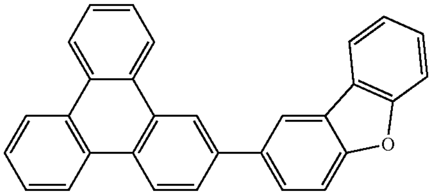
H-131a
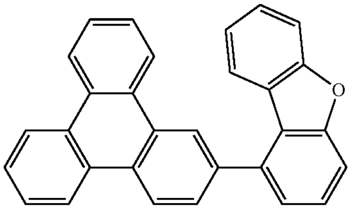
H-132a
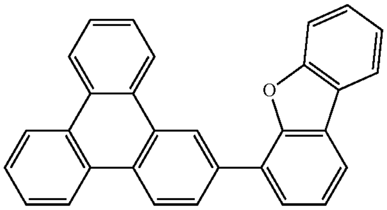
H-133a
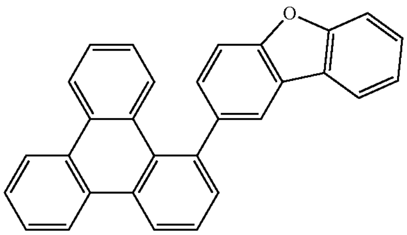

-continued
H-134a
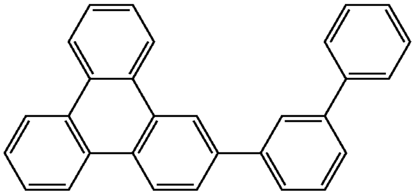
H-135a
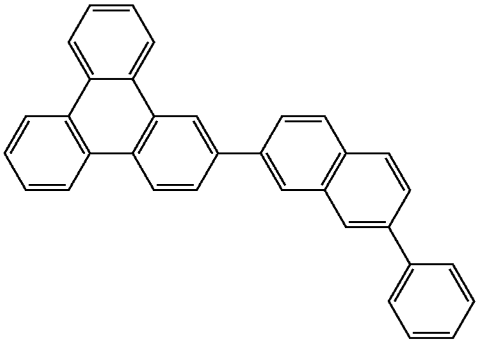
H-136a
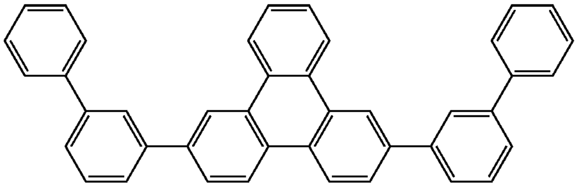
H-137a
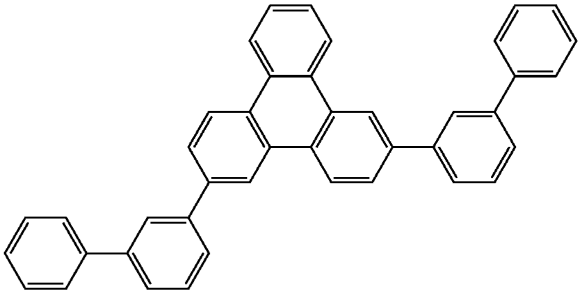
H-138a
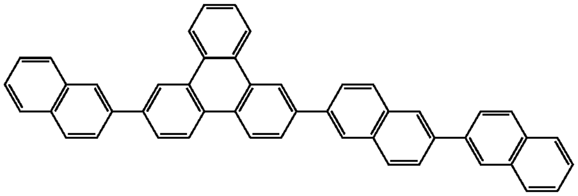
H-139a
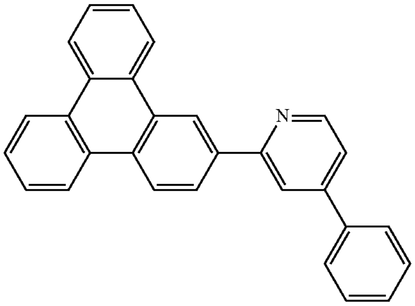
-continued
H-140a
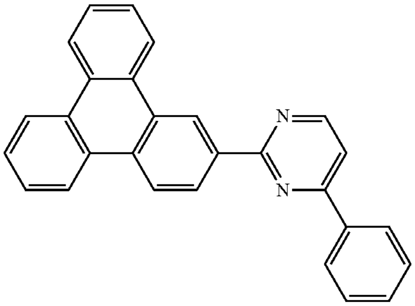
H-141a
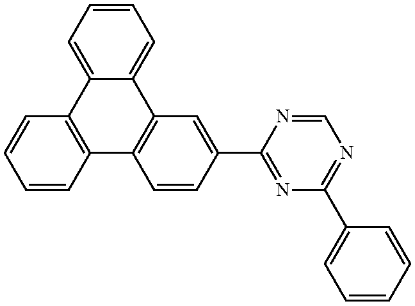
H-142a
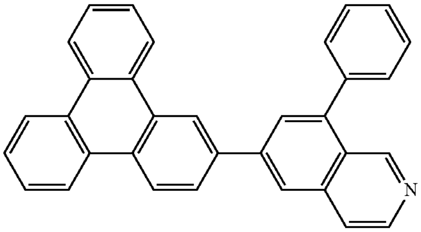
H-143a
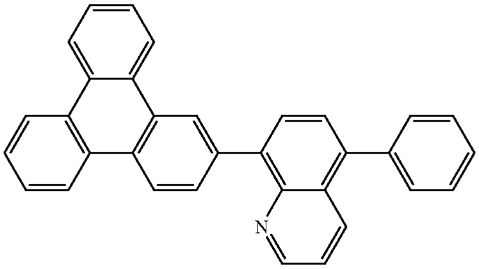
H-144a
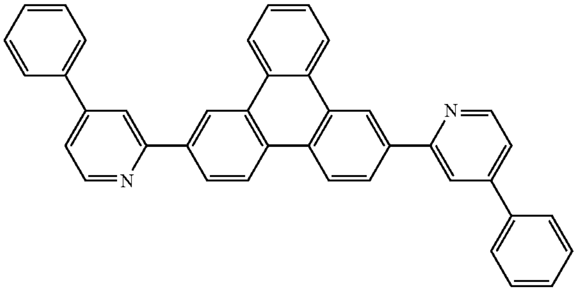

-continued
H-145a
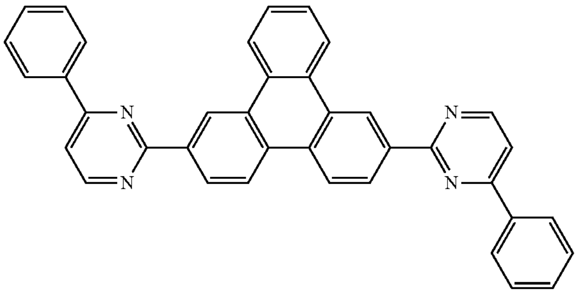
H-146a
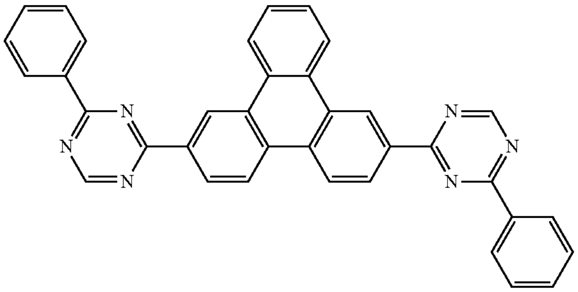
H-147a
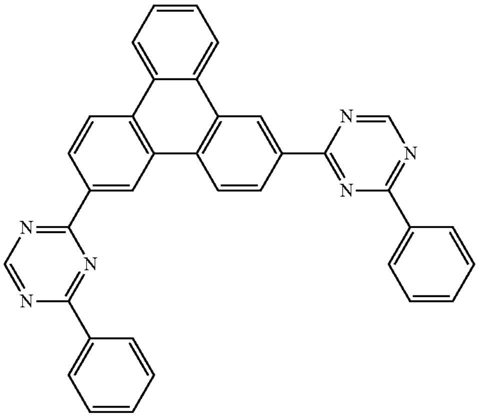
H-148a
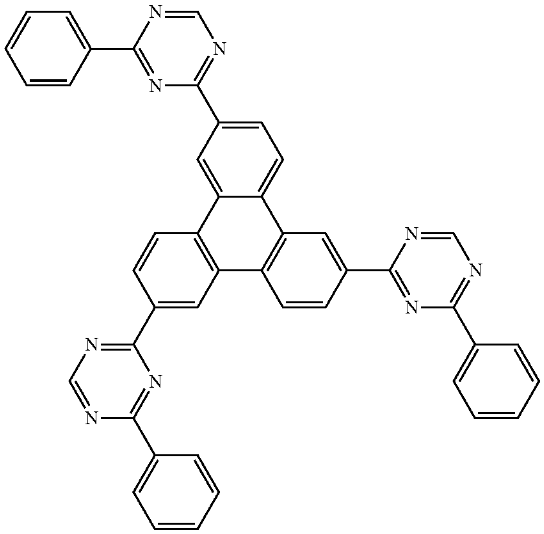
-continued
H-149a
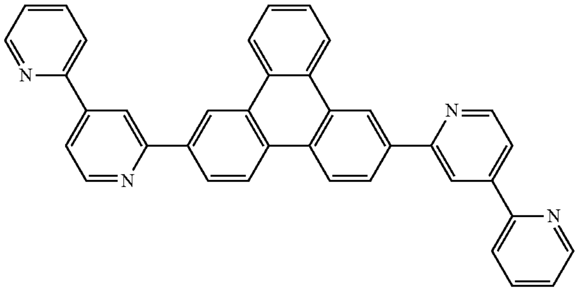
H-150a
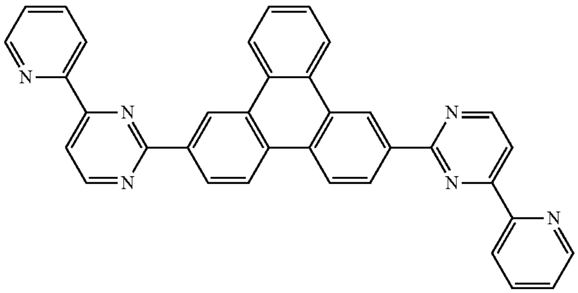
H-151a
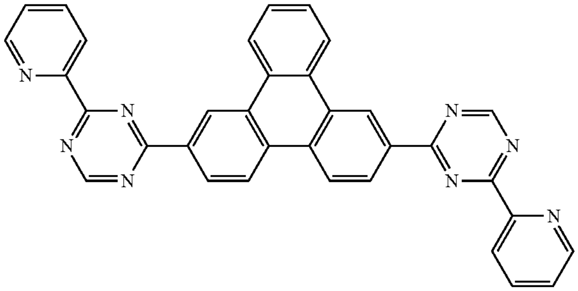
H-152a
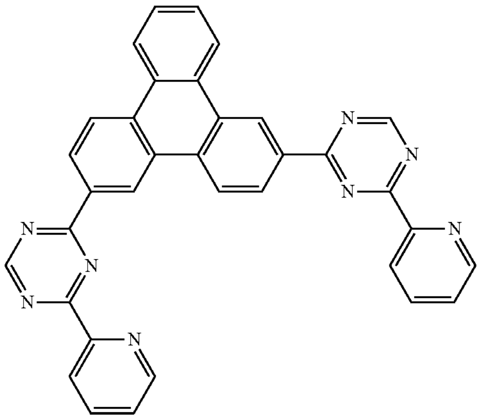

-continued
H-153a
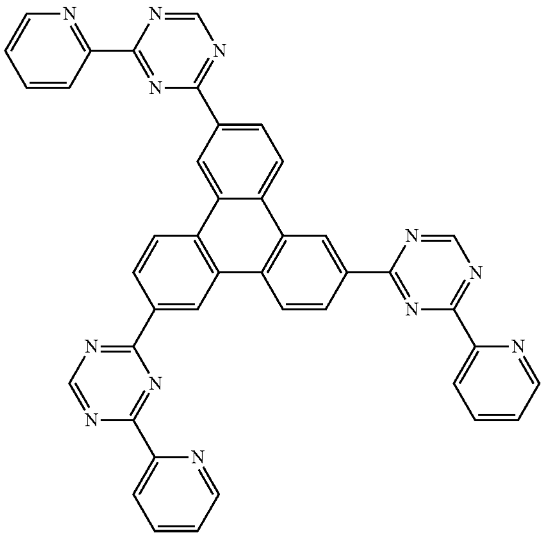
H-164a
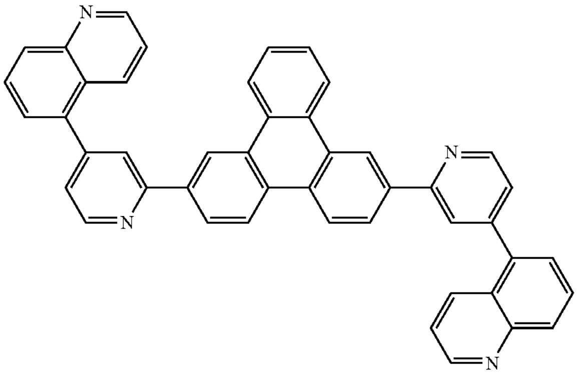
H-165a
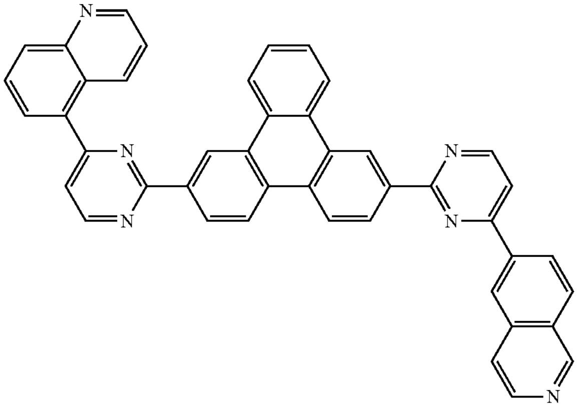
-continued
H-166a
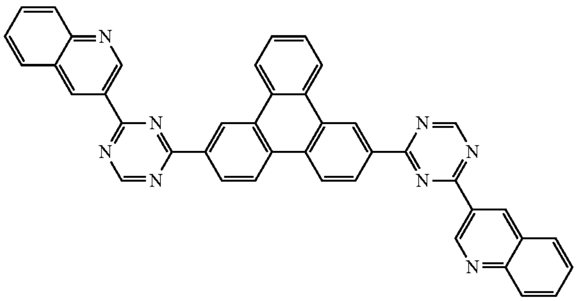
H-167a
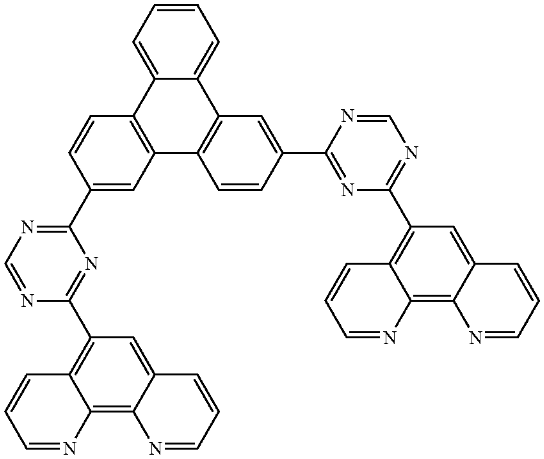
H-168a
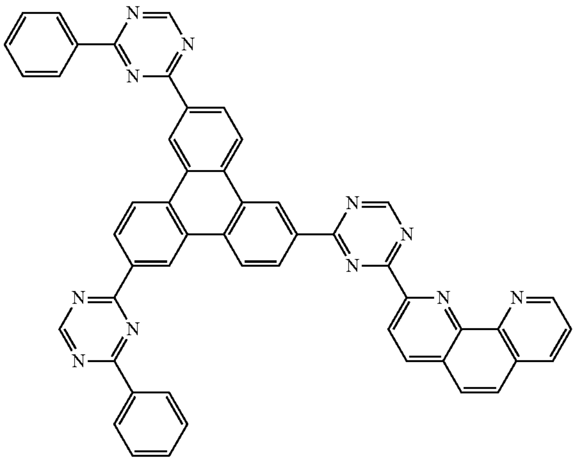
H-169a
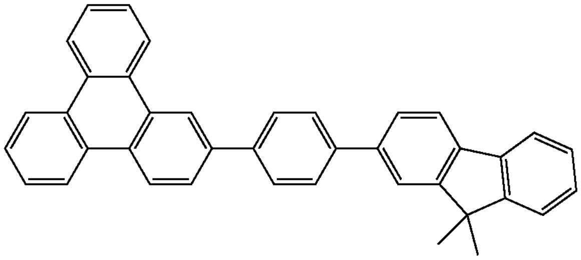

-continued
H-170a
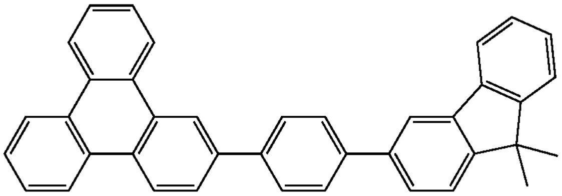
H-171a
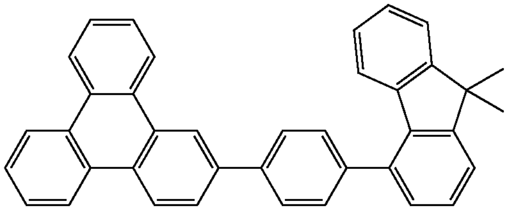
H-172a
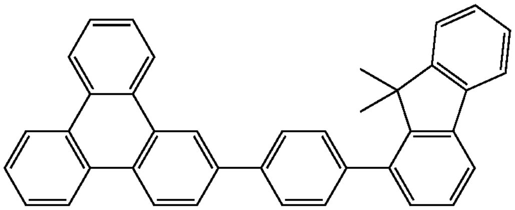
H-173a
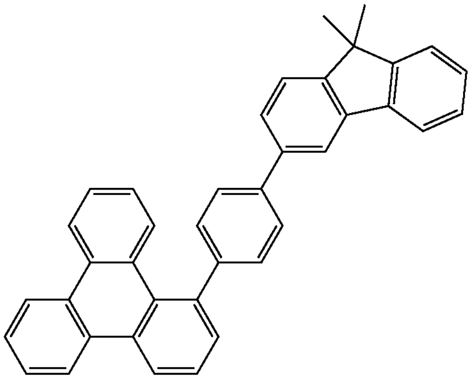
H-174a
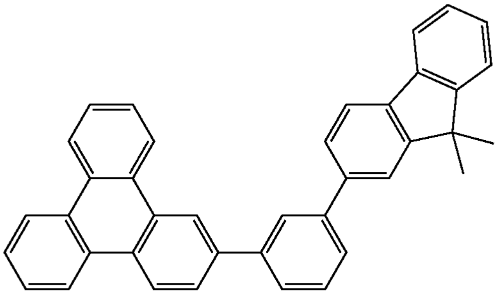
-continued
H-175a
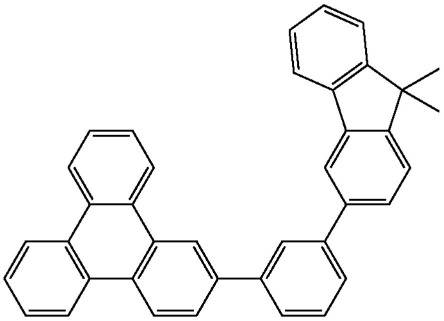
H-176a
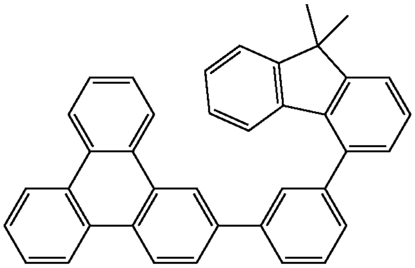
H-177a
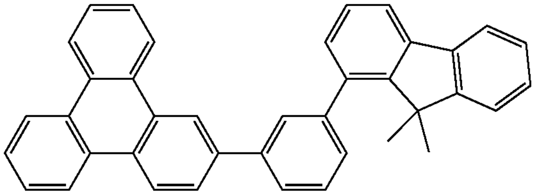
H-178a
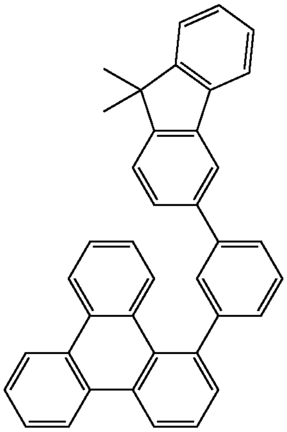
H-179a
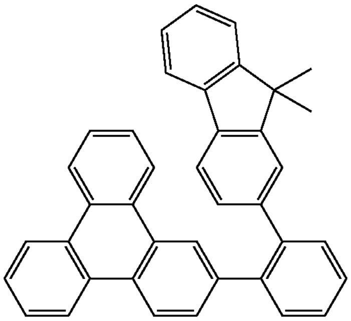

-continued
H-180a
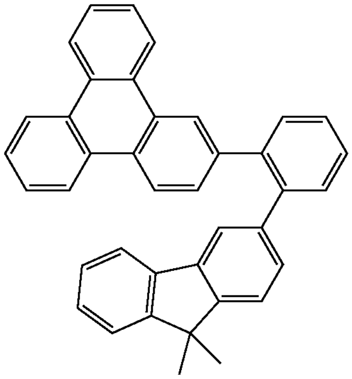
H-181a
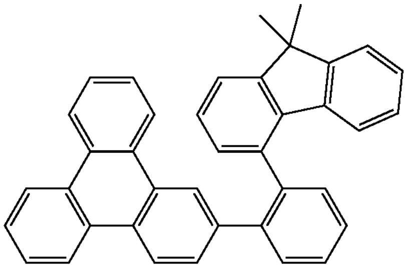
H-182a
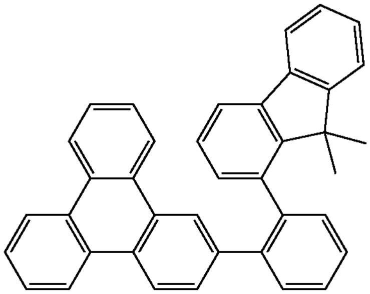
H-183a
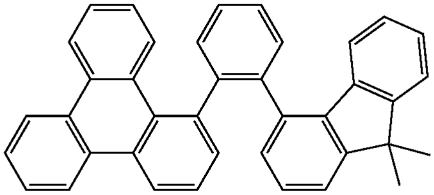
H-184a
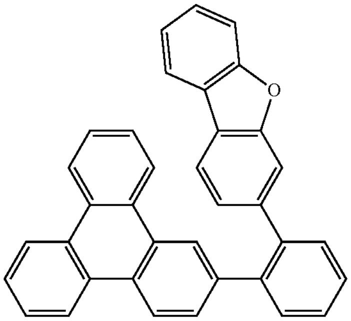
-continued
H-185a
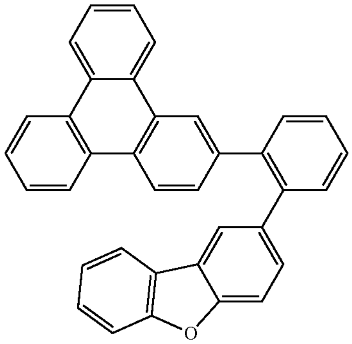
H-186a
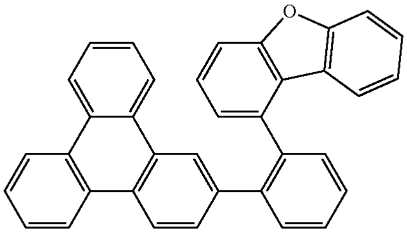
H-187a
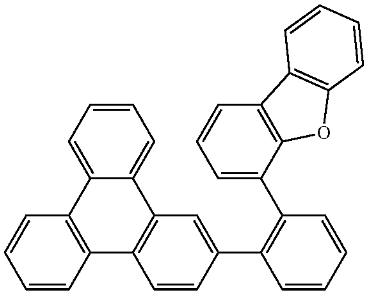
H-188a
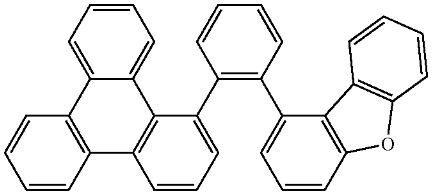
H-1b
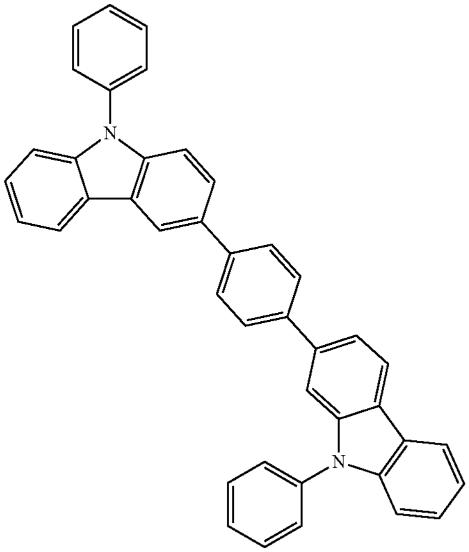

-continued
H-2b
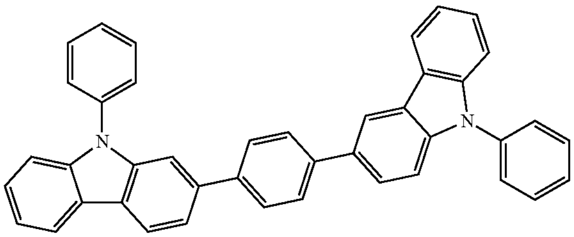
H-3b
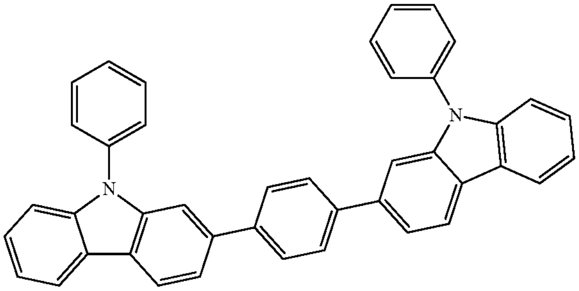
H-4b
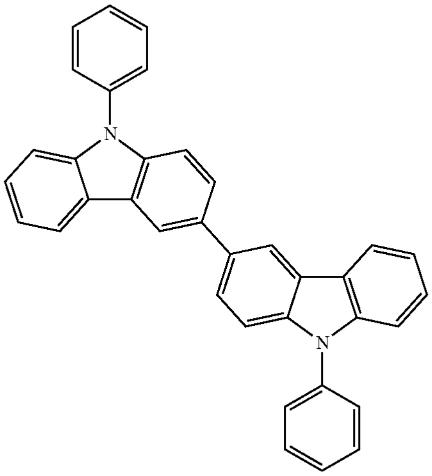
H-5b
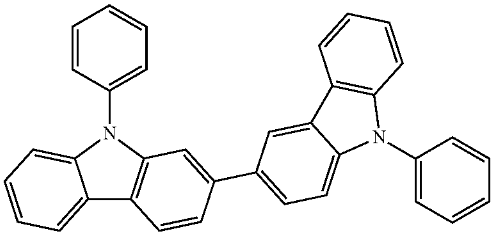
H-6b
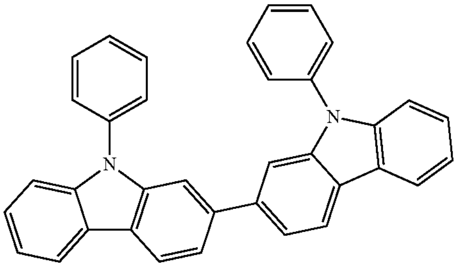
-continued
H-7b
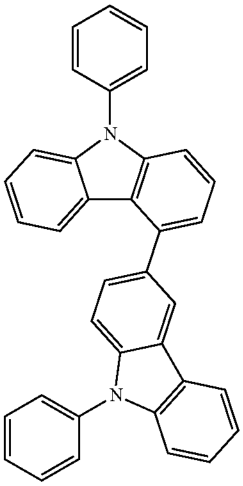
H-8b
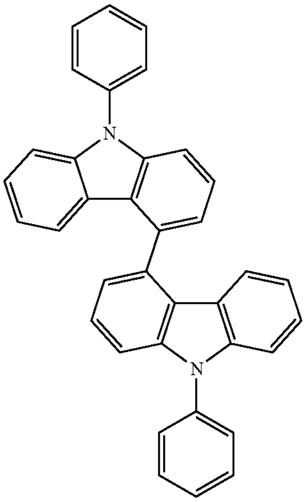
H-9b
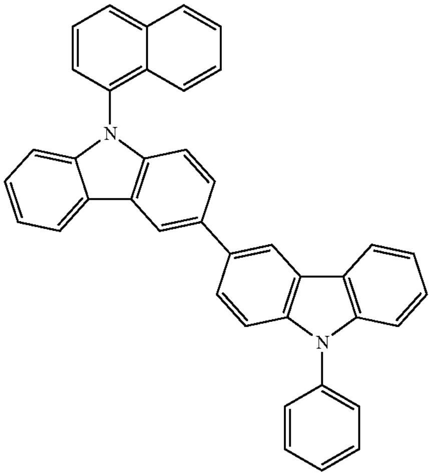

-continued
H-10b
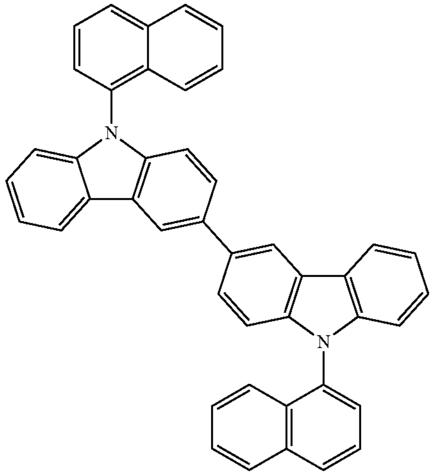
H-11b
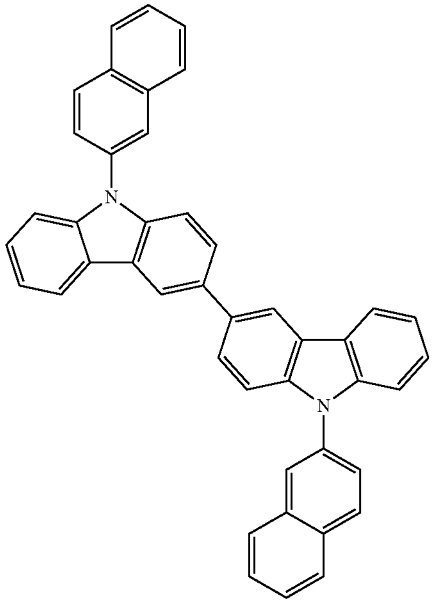
H-12b
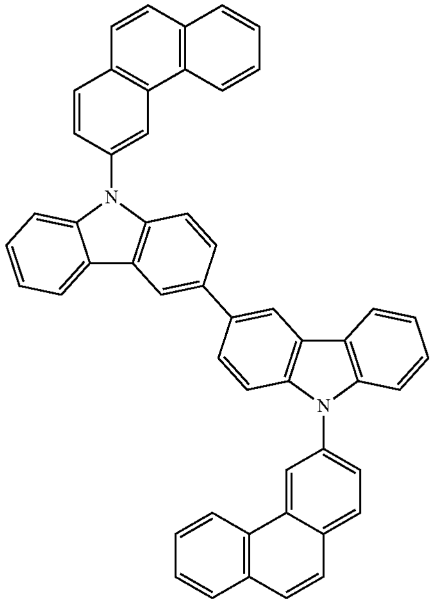
-continued
H-13b
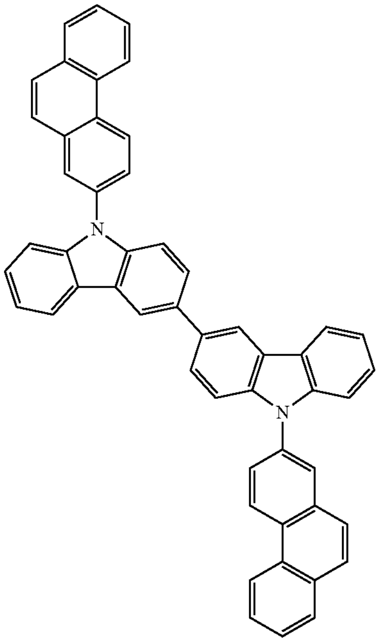
H-14b
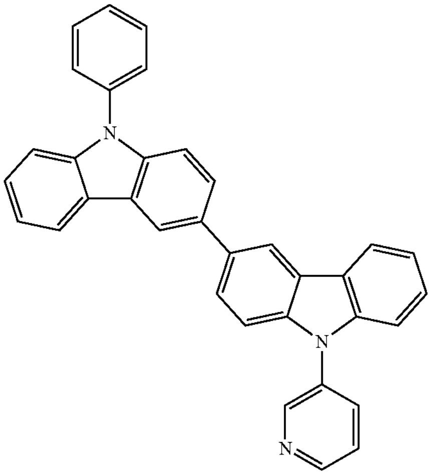
H-15b
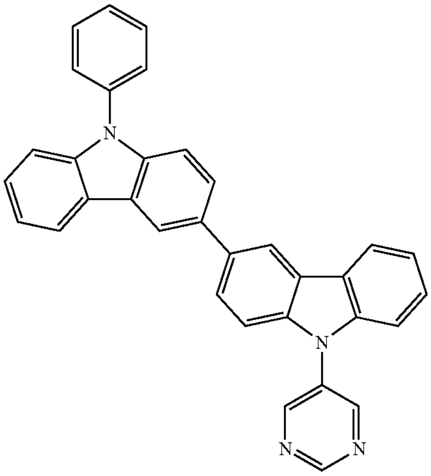

-continued
H-16b
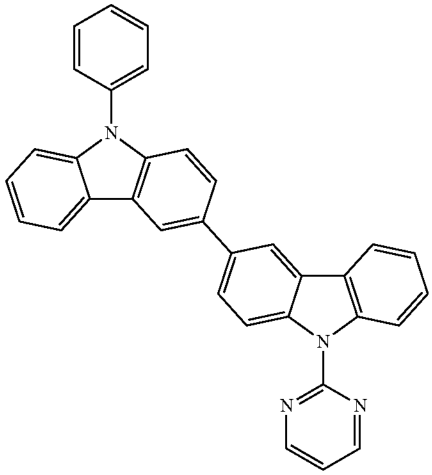
H-17b
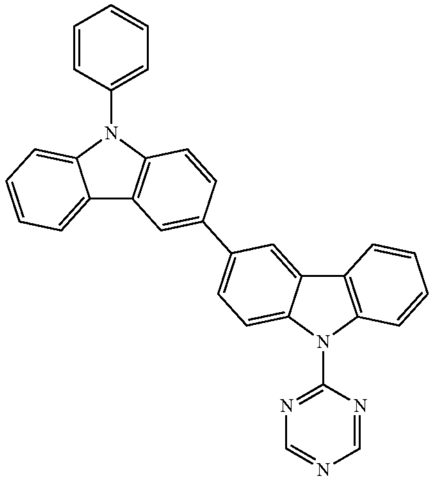
H-18b
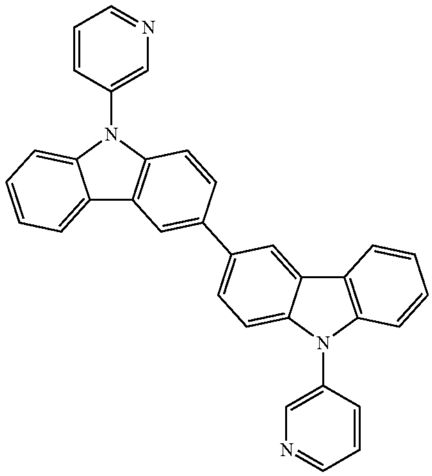
-continued
H-19b
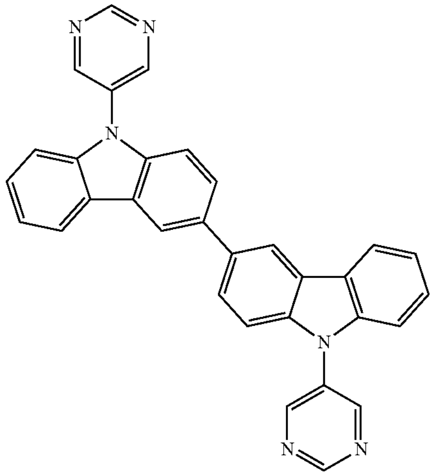
H-20b
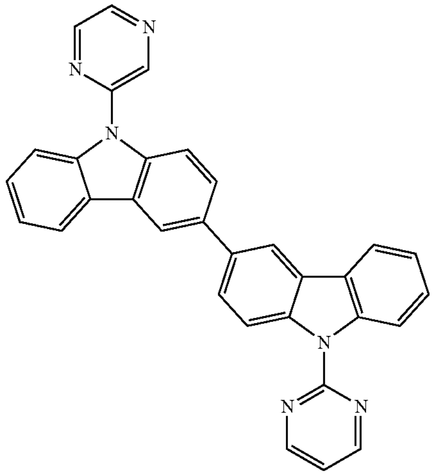
H-21b
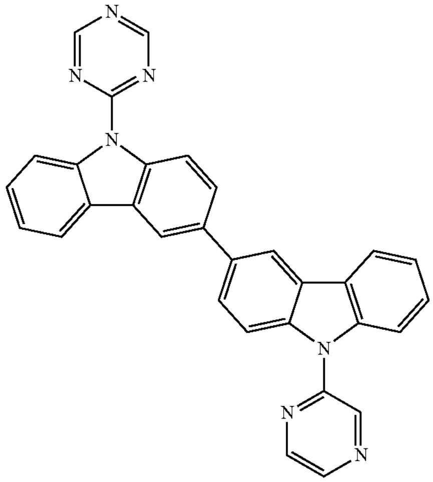

-continued
H-22b
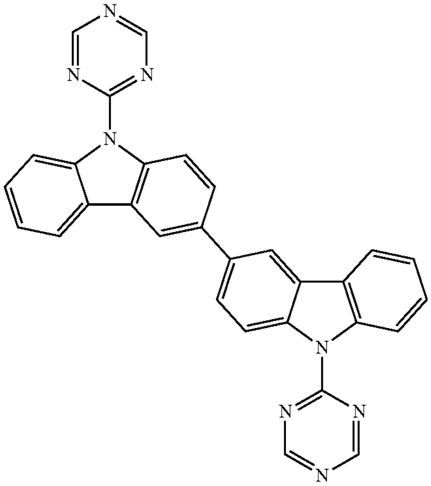
H-23b
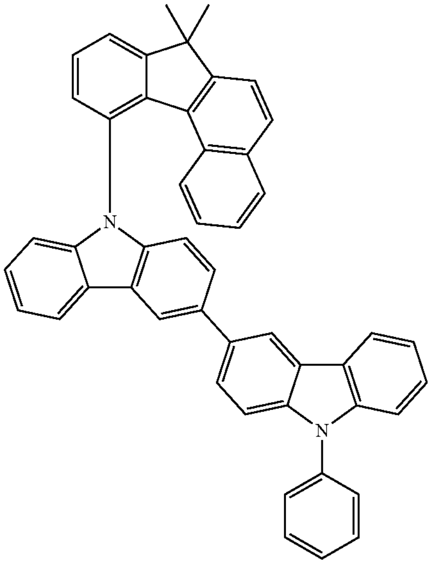
H-24b
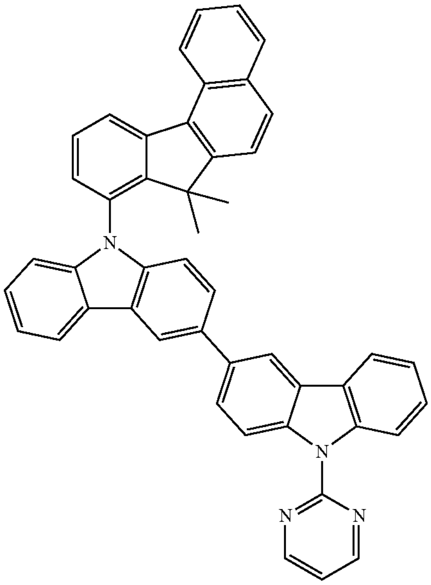
-continued
H-25b
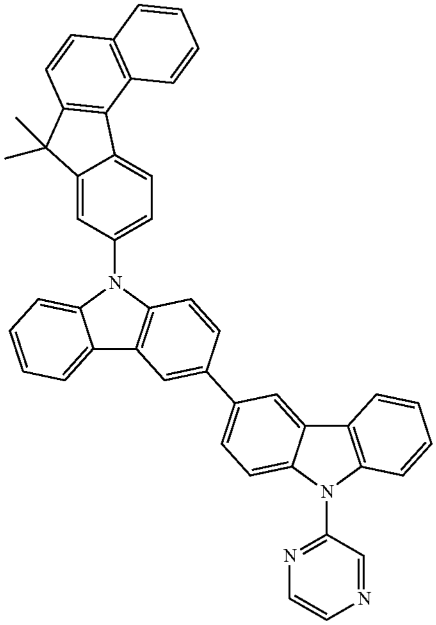
H-26b
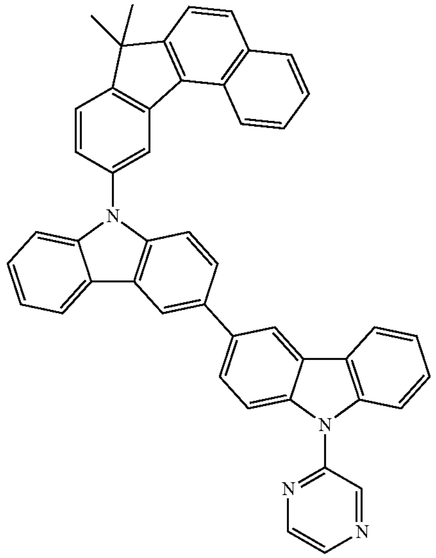

-continued
H-27b
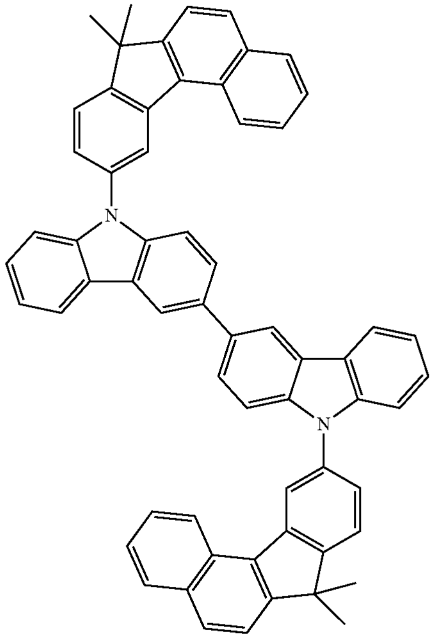
H-28b
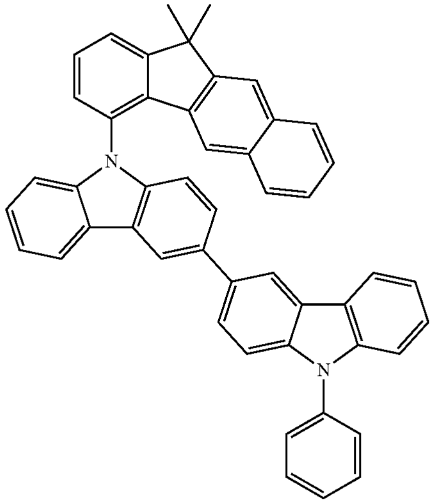
-continued
H-29b
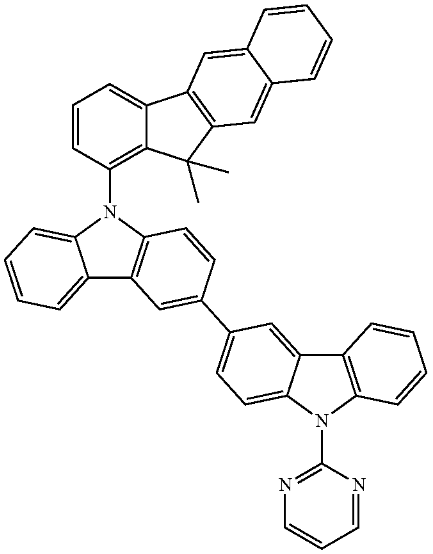
H-30b
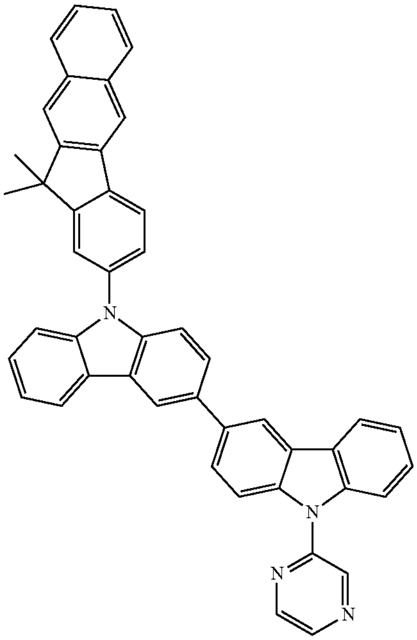

-continued
H-31b
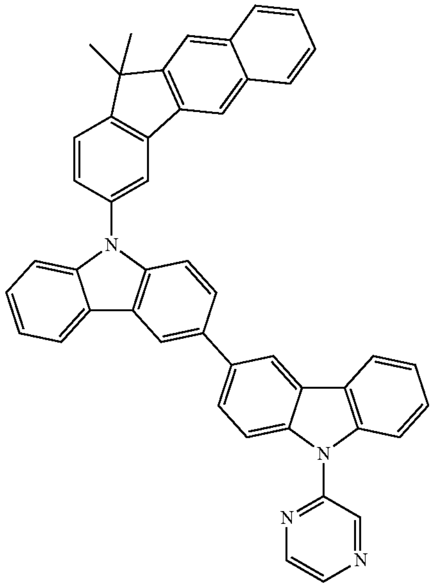
H-32b
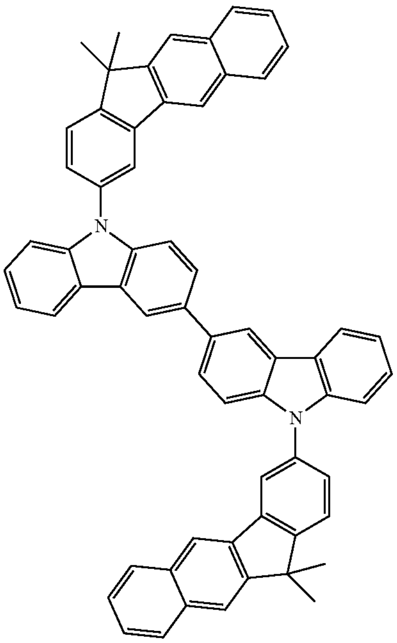
-continued
H-33b
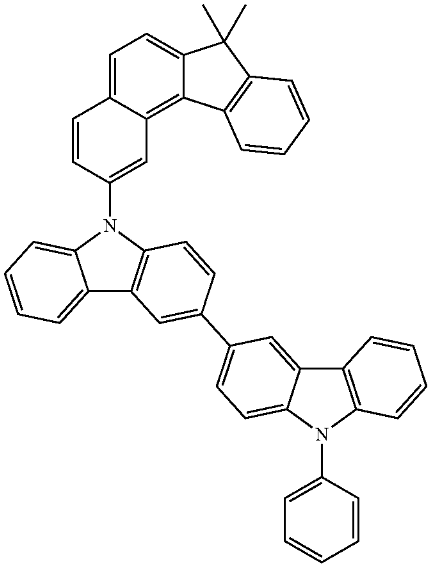
H-34b
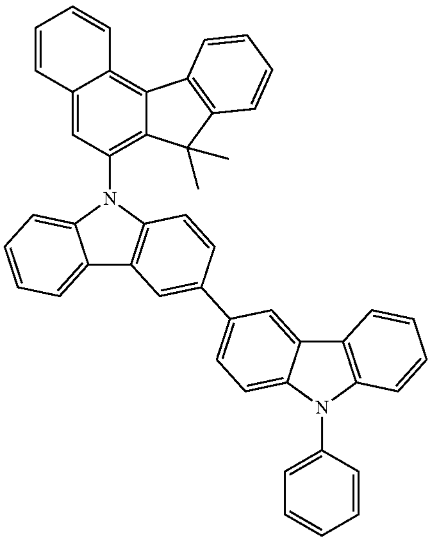
H-35b
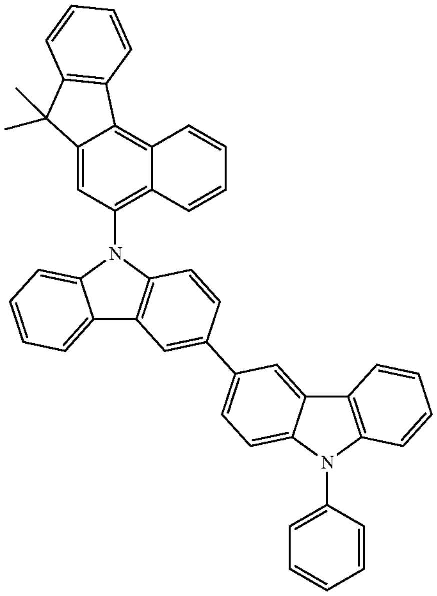

-continued
H-36b
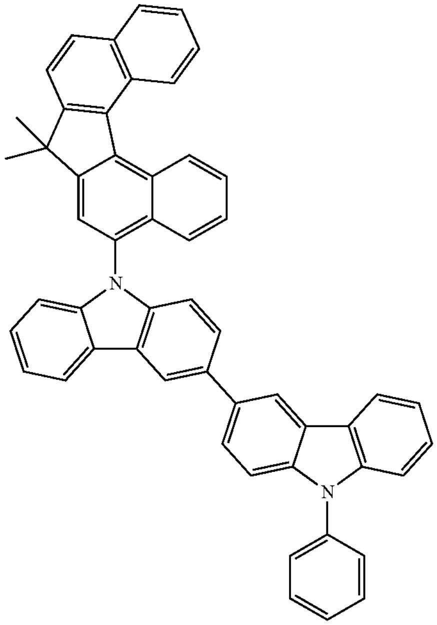
H-37b
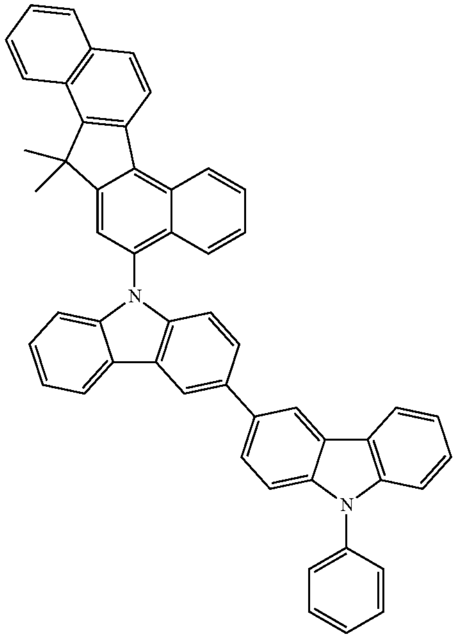
-continued
H-38b
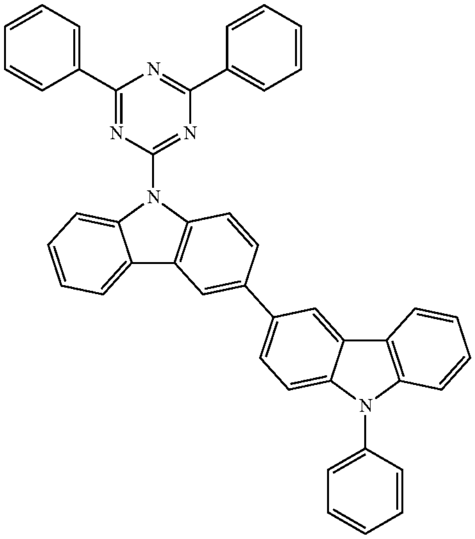
H-39b
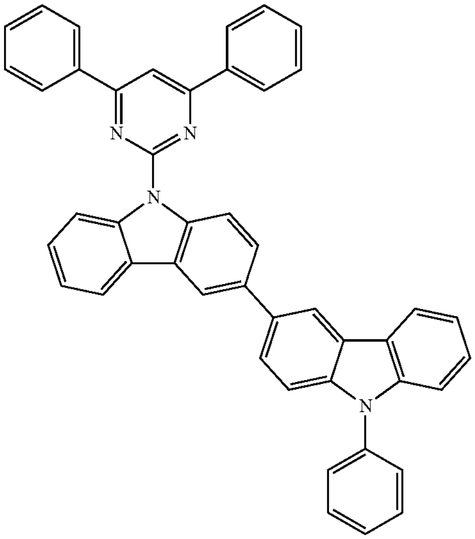
H-40b
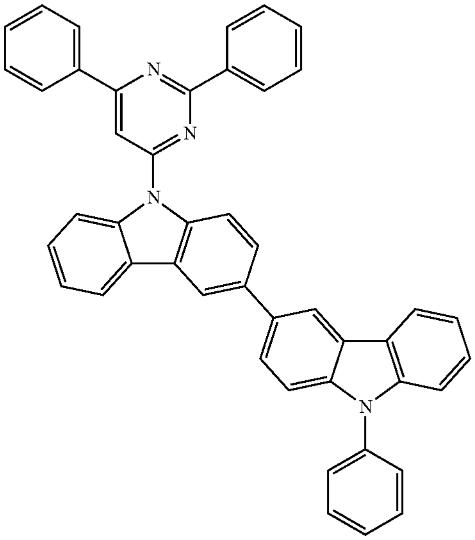

-continued
H-41b
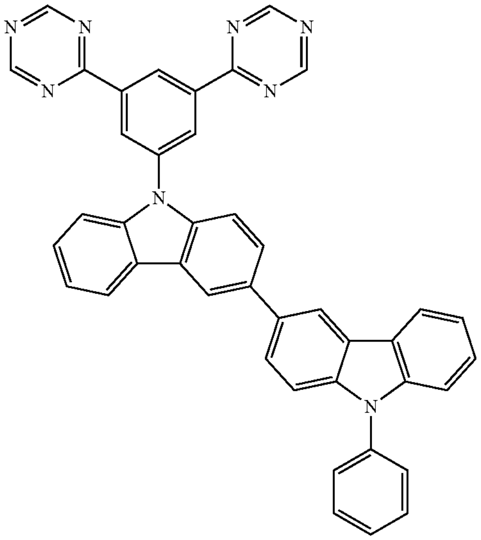
H-42b
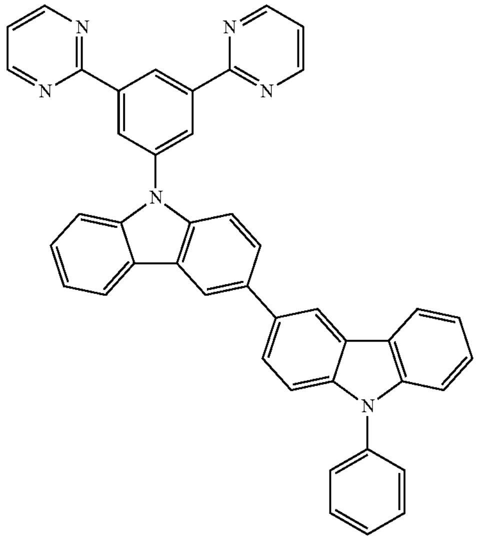
-continued
H-43b
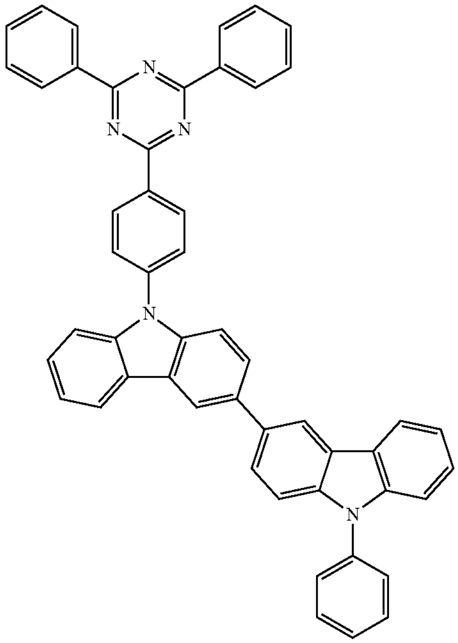
H-44b
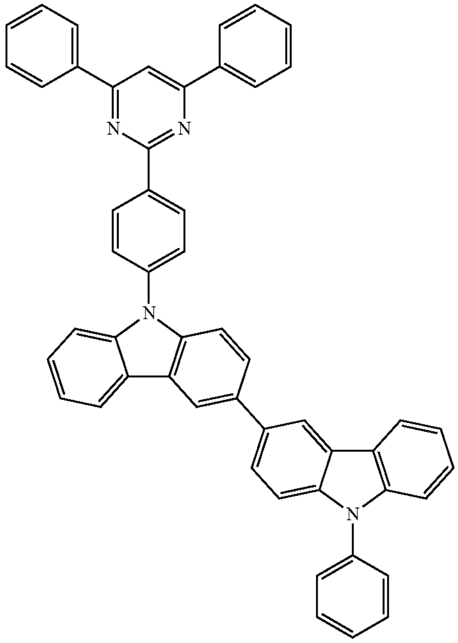

-continued
H-45b
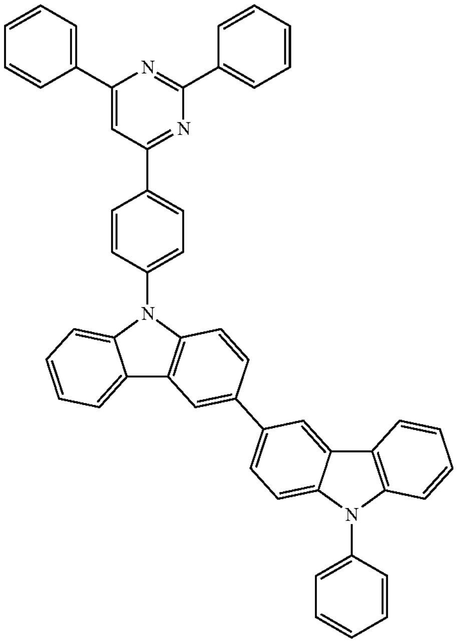
H-46b
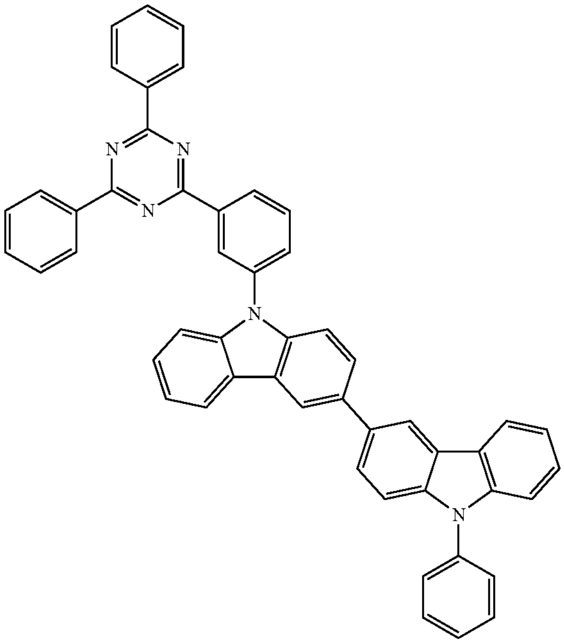
-continued
H-47b
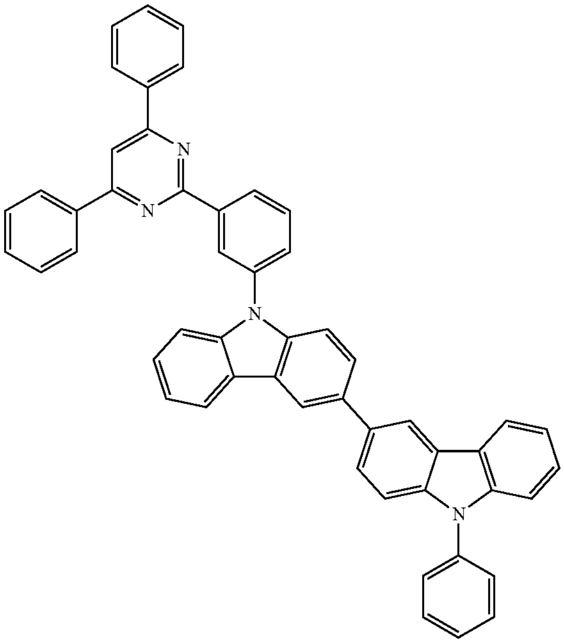
H-48b
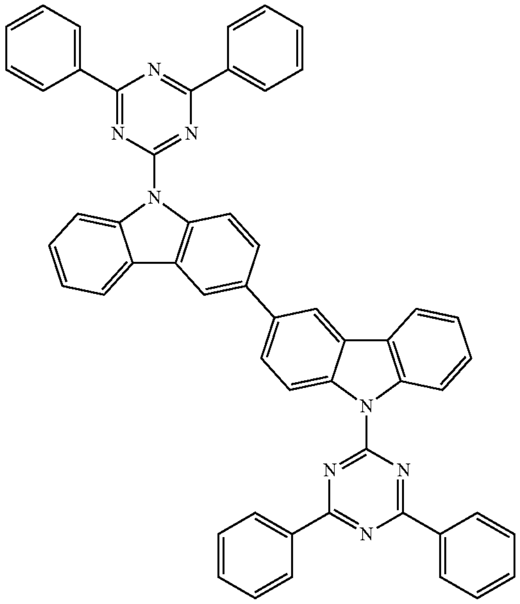

-continued
H-49b
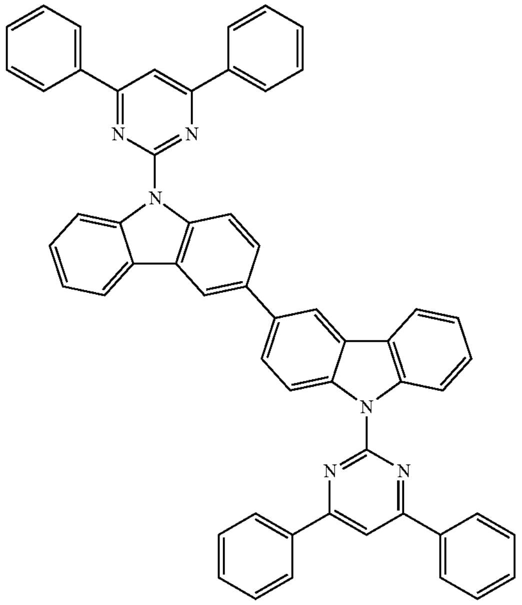
H-50b
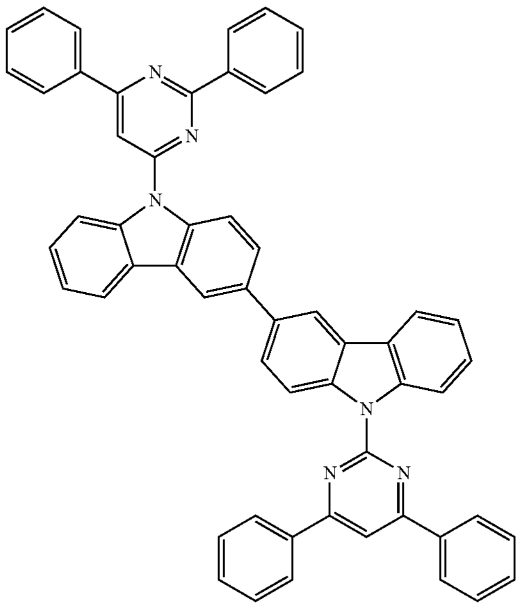
-continued
H-51b
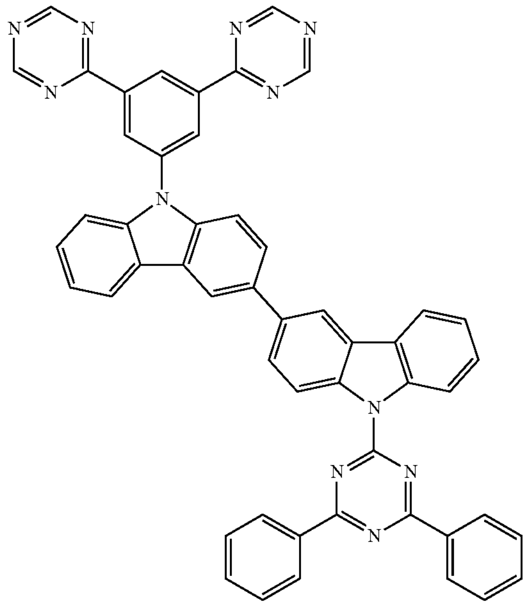
H-52b
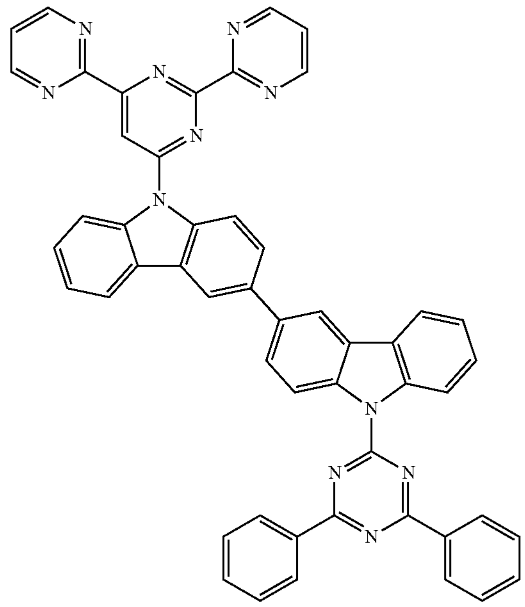

-continued
H-53b
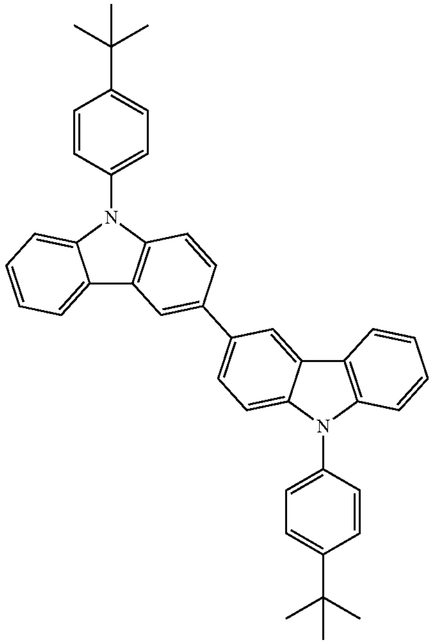
H-54b
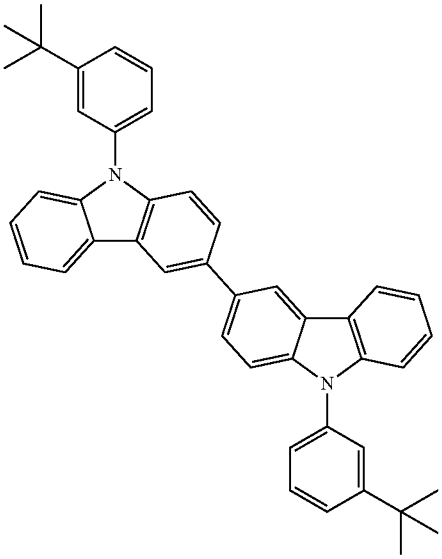
-continued
H-55b
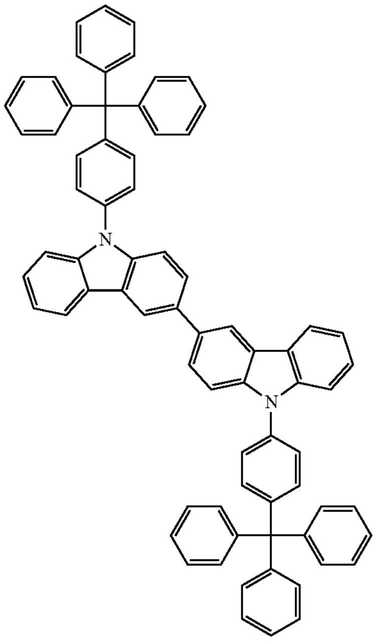
H-56b
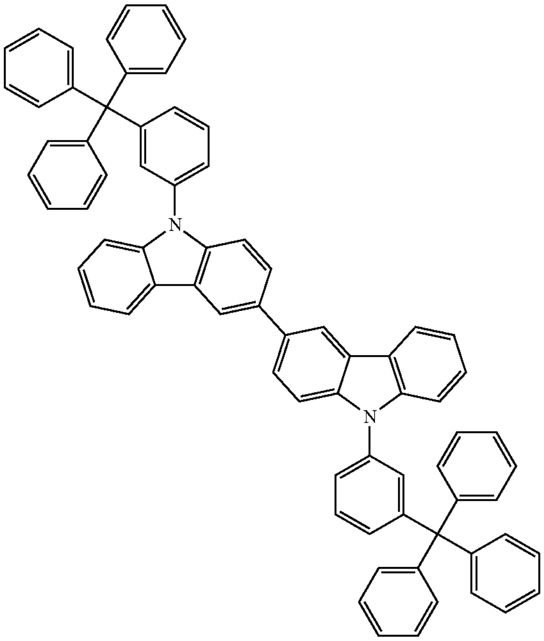

-continued
H-57b
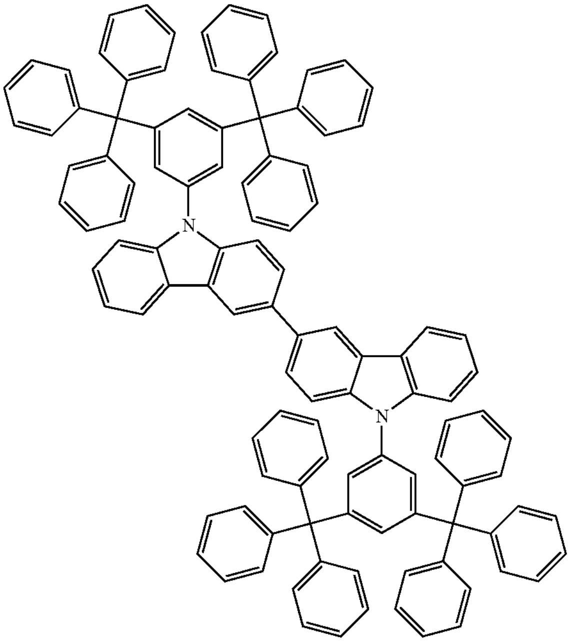
H-58b
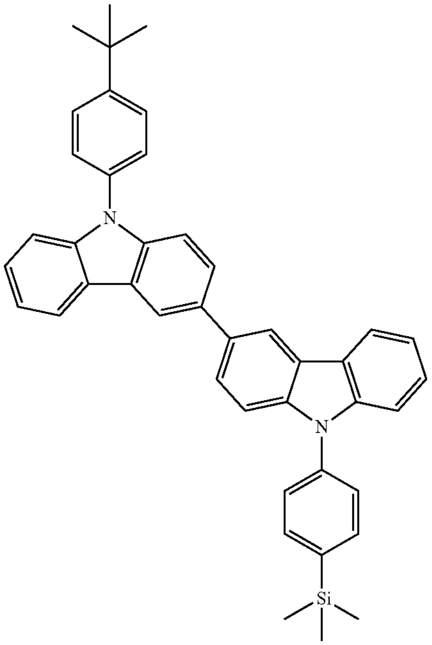
-continued
H-59b
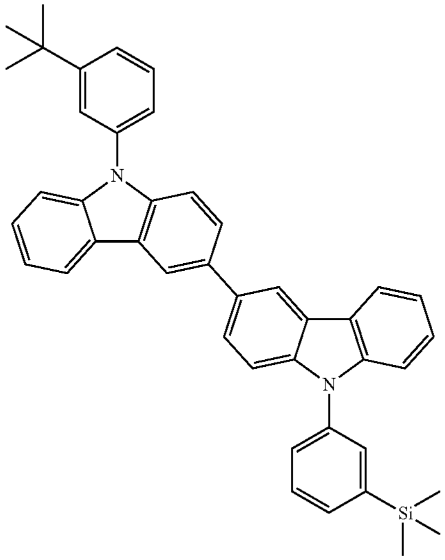
H-60b
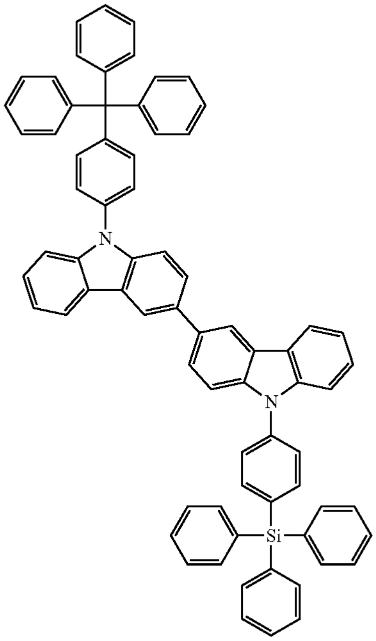

-continued
H-61b
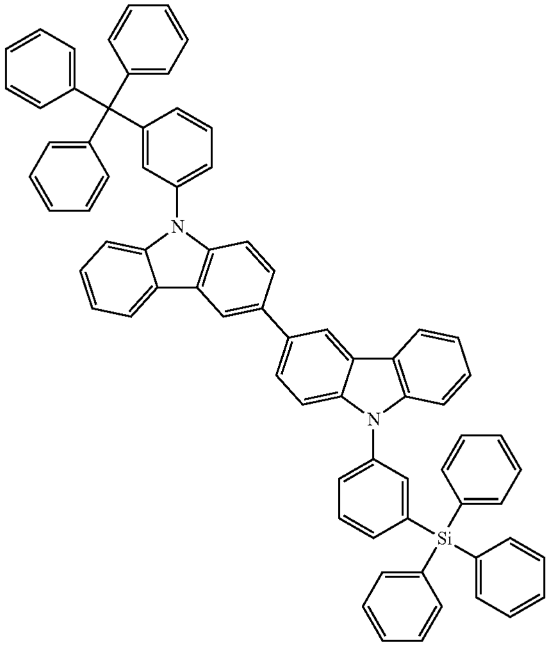
H-62b
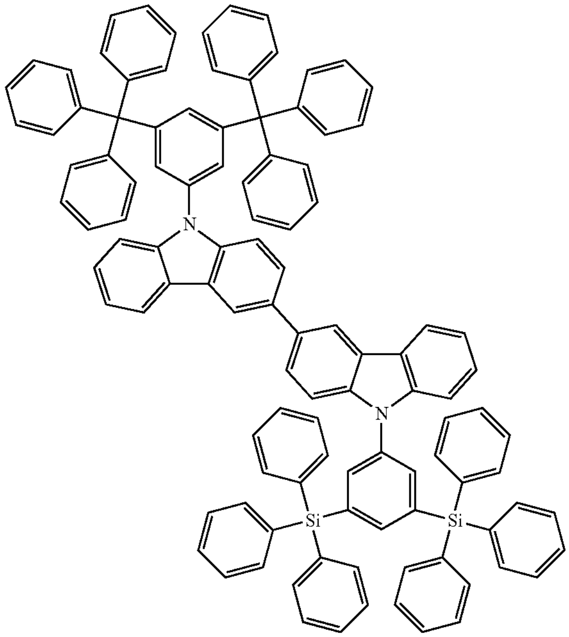
-continued
H-63b
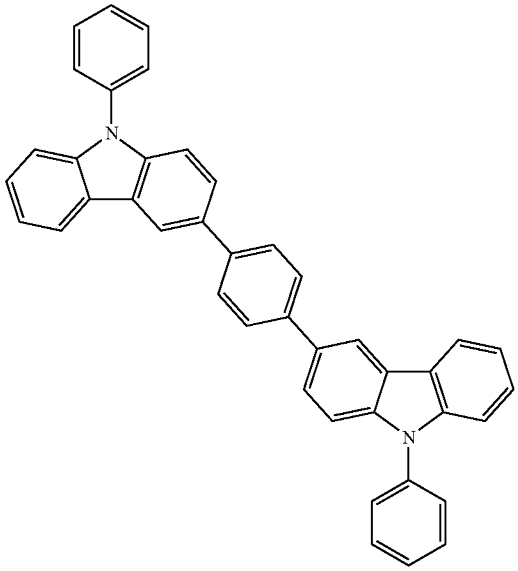
H-64b
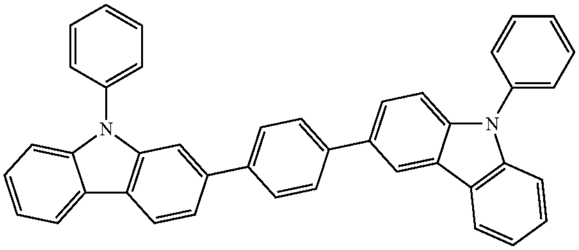
H-65b
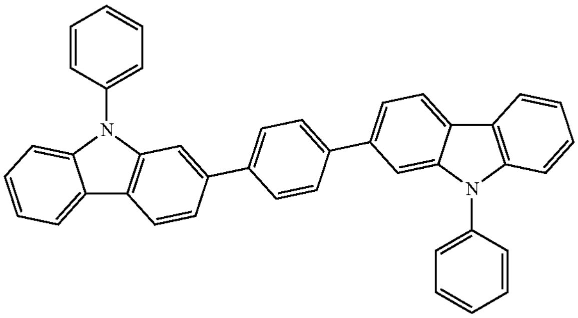

-continued
H-66b
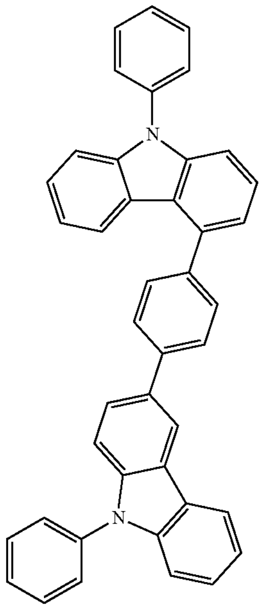
H-67b
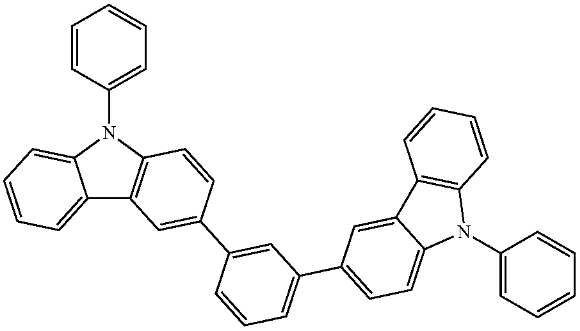
H-68b
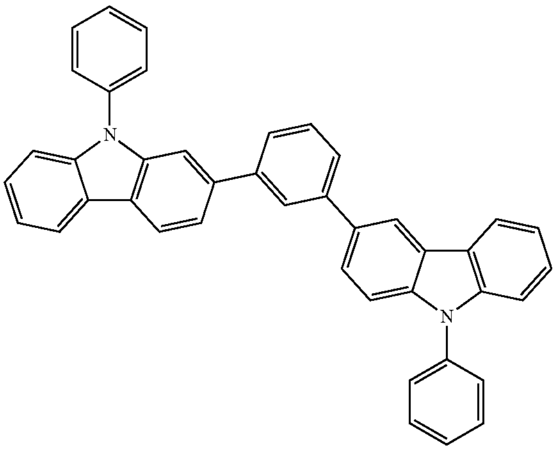
-continued
H-69b
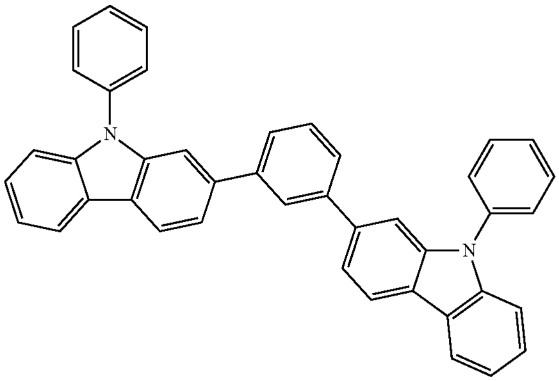
H-70b
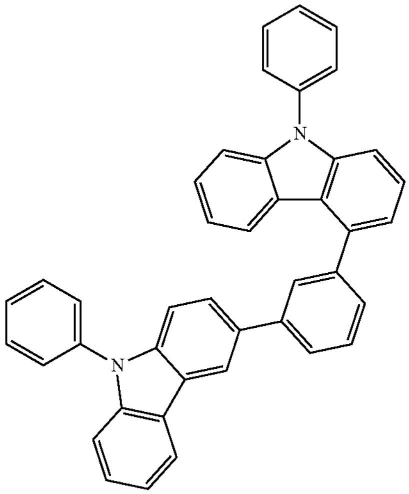
H-71b
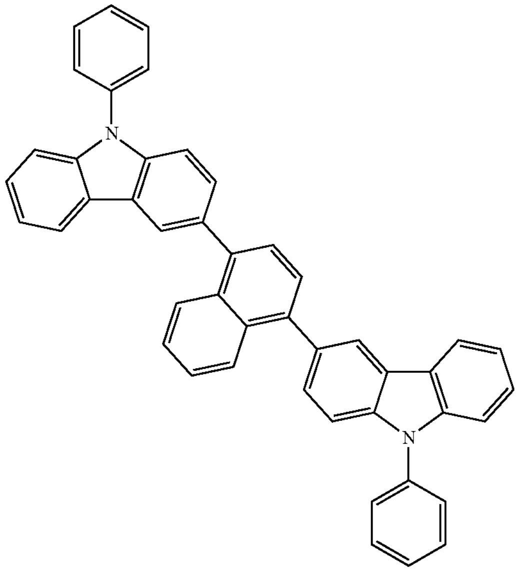

-continued
H-72b
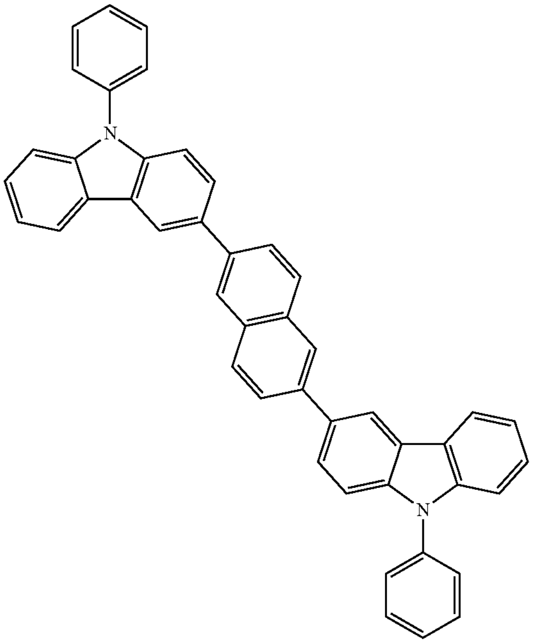
H-73b
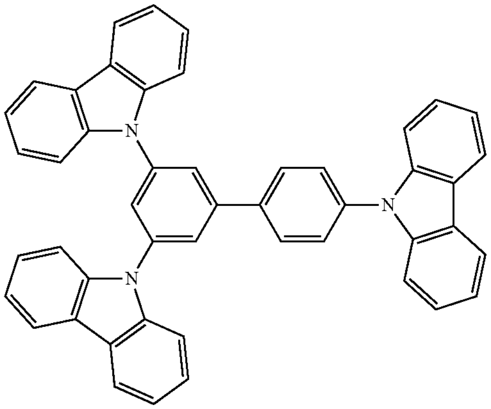
H-74b
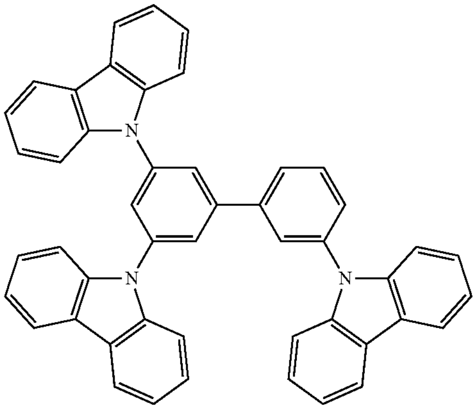
-continued
H-1c
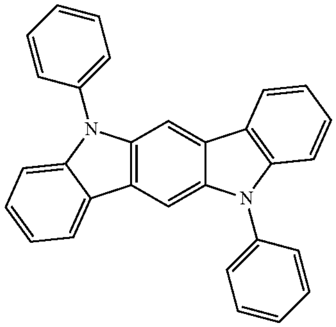
H-2c
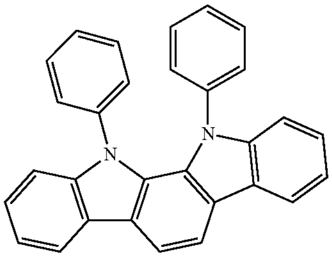
H-3c
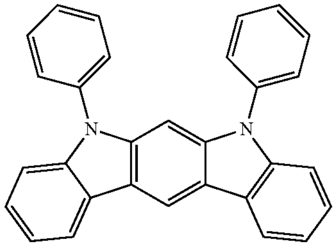
H-4c
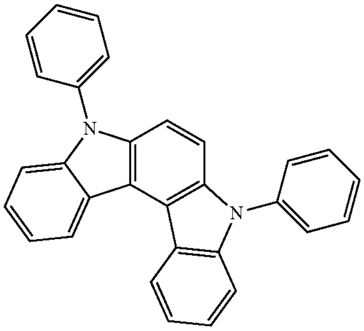
H-5c
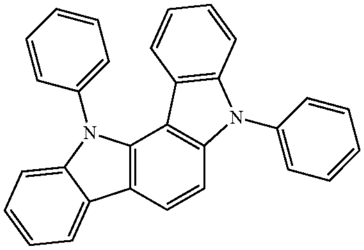

-continued
H-6c
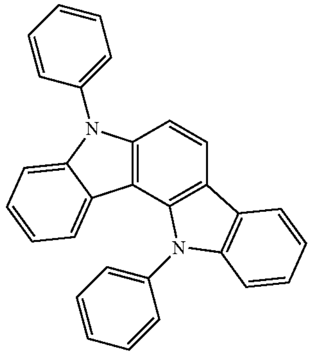
H-7c
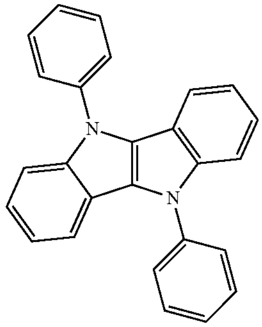
H-8c
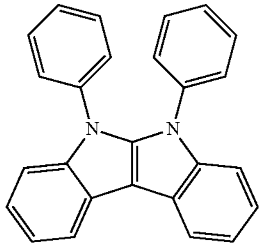
H-9c
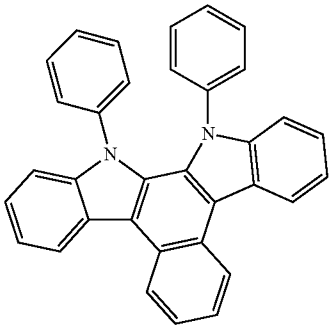
H-10c
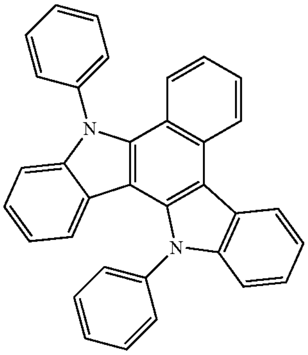
-continued
H-11c
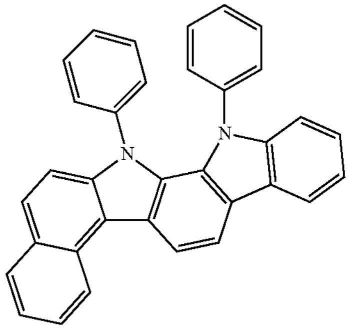
H-12c
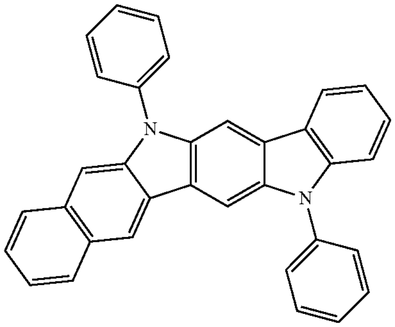
H-13c
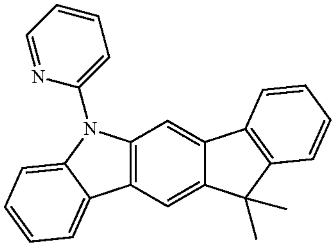
H-14c
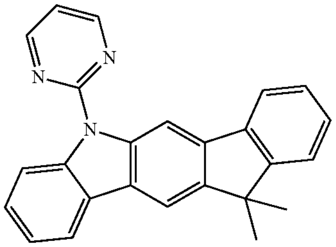
H-15c
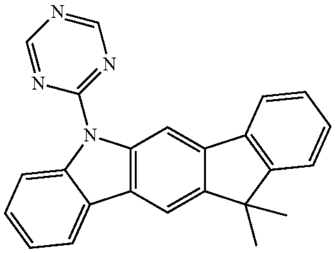

-continued
H-16c
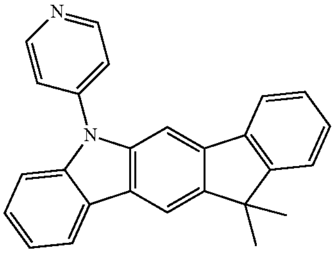
H-17c
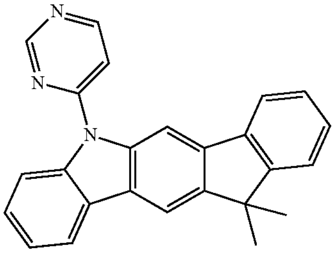
H-18c
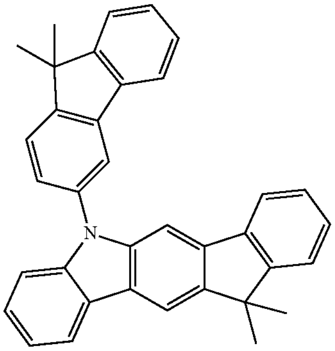
H-19c
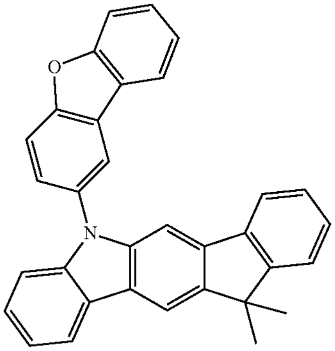
H-20c
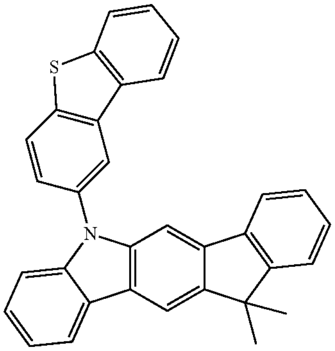
-continued
H-21c
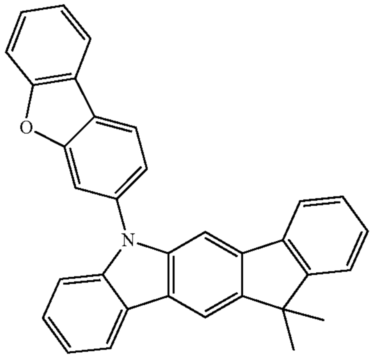
H-22c
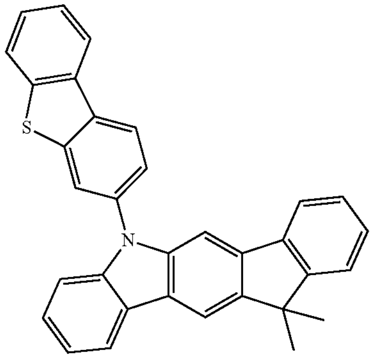
H-23c
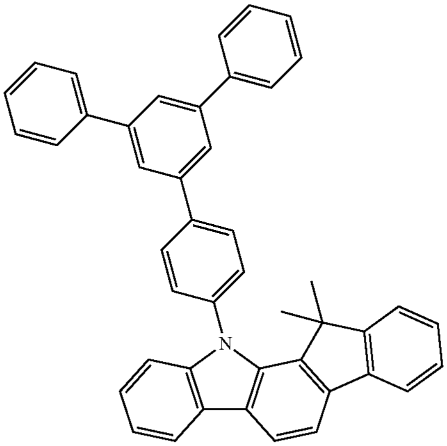
H-24c
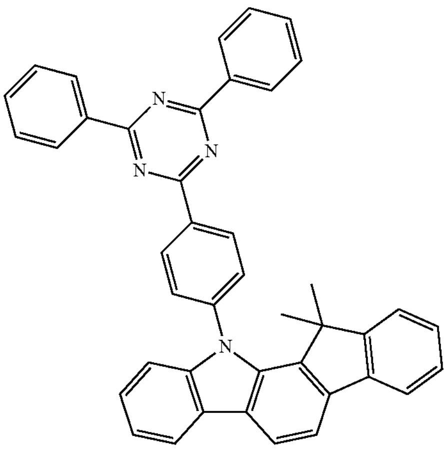

-continued
H-25c
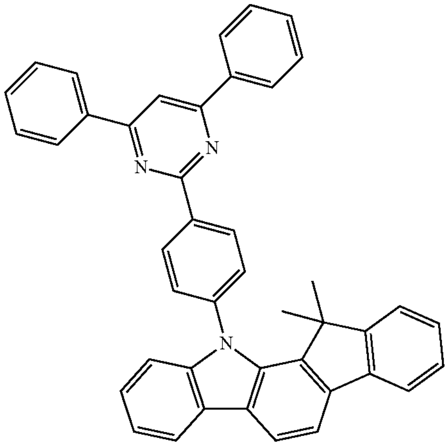
H-26c
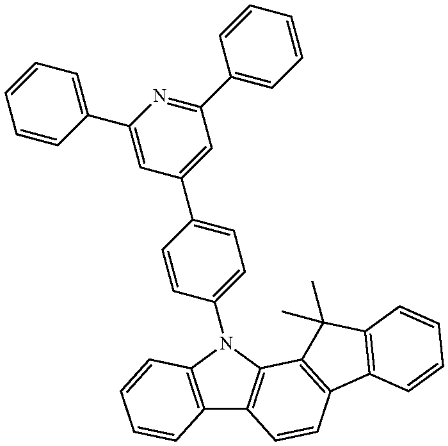
H-27c
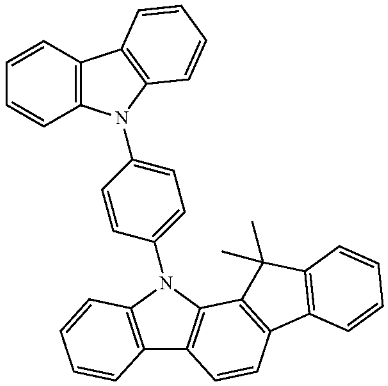
H-28c
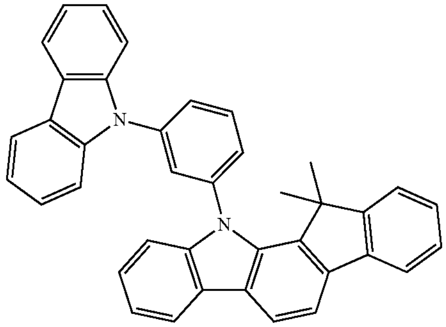
-continued
H-29c
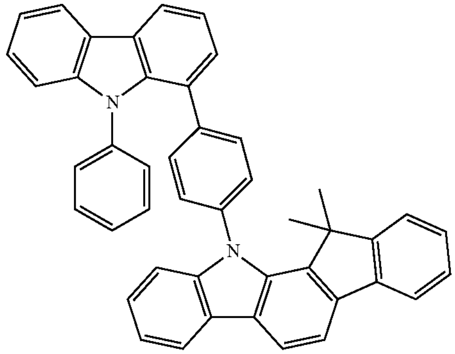
H-30c
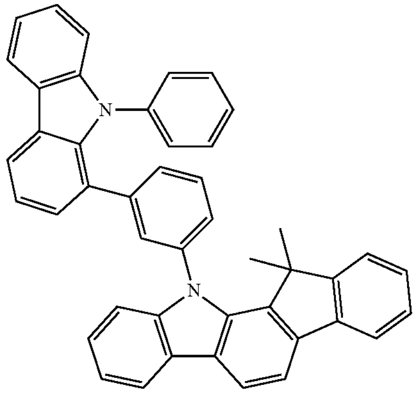
H-31c
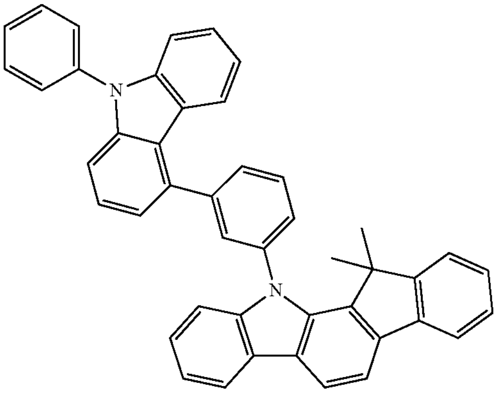
H-32c
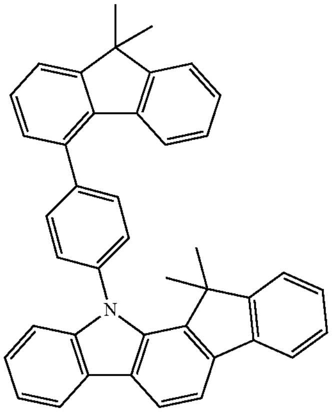

-continued
H-33c
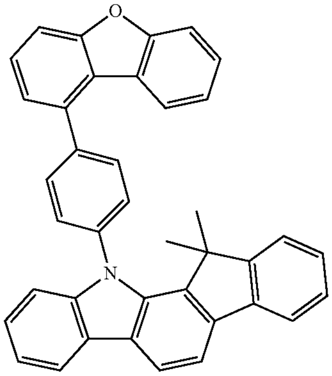
H-34c
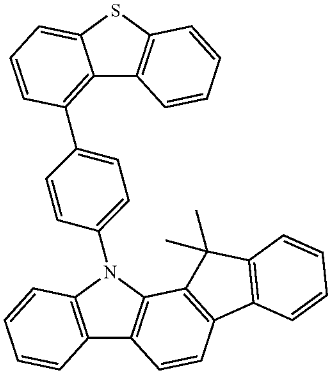
H-35c
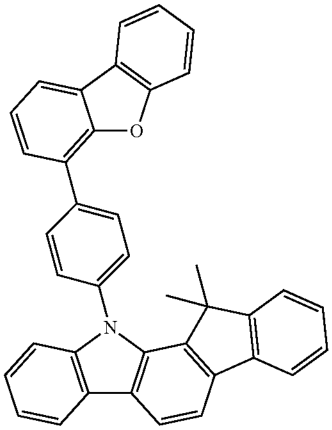
H-36c
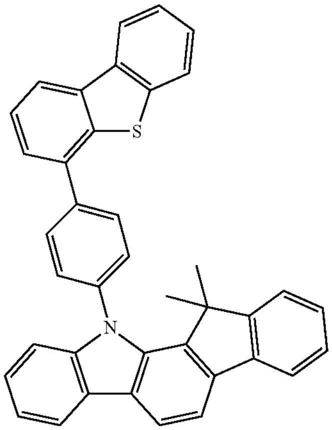
-continued
H-37c
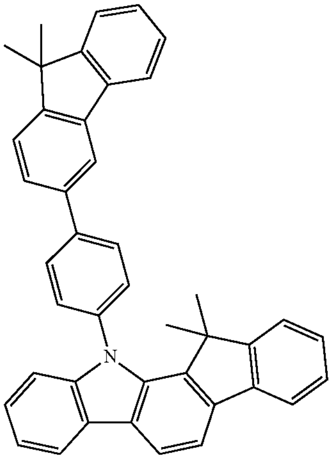
H-38c
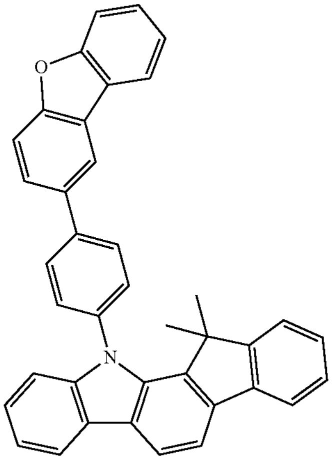
H-39c
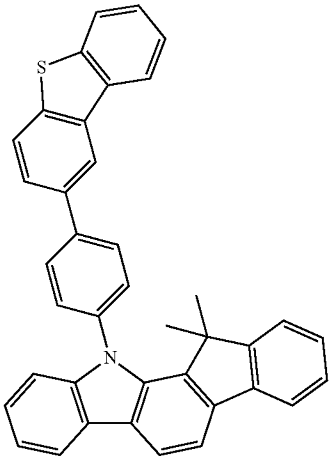

-continued
H-40c
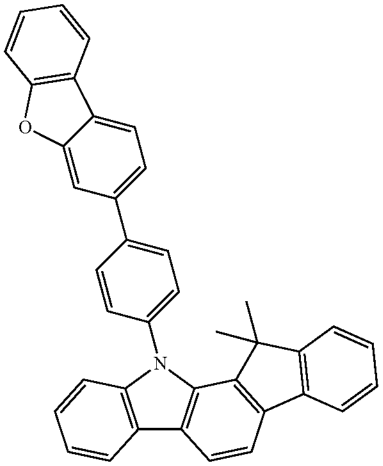
H-41c
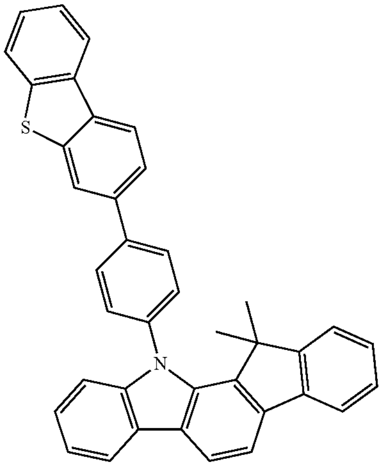
H-42c
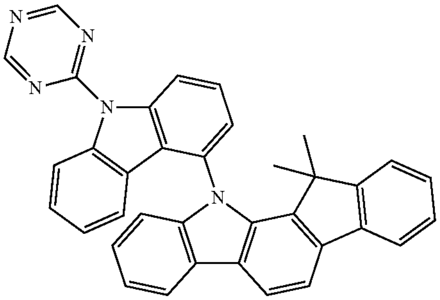
H-43c
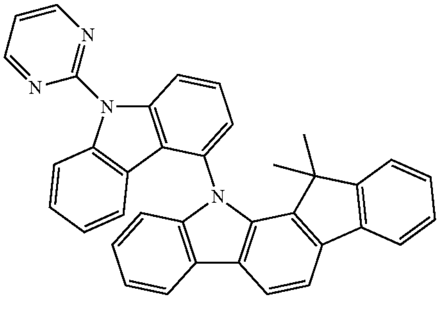
-continued
H-44c
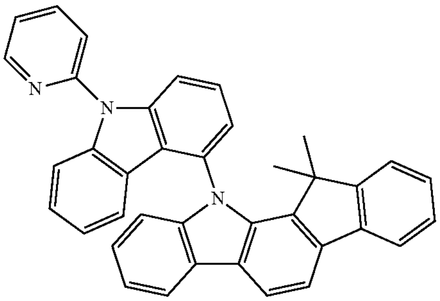
H-45c
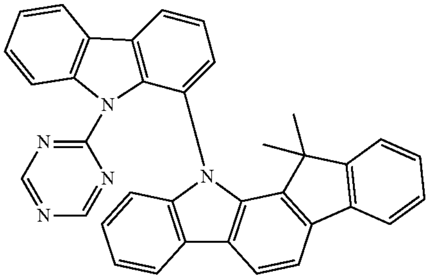
H-46c
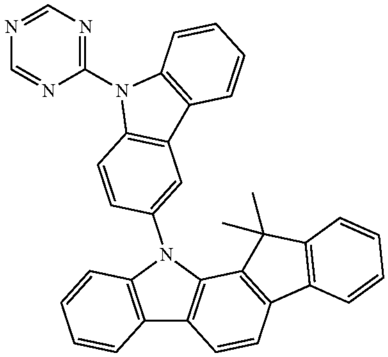
H-47b
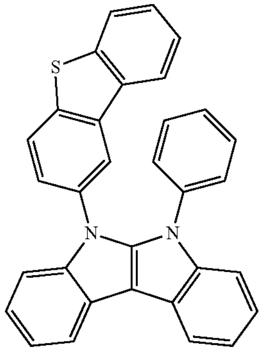

-continued
H-48c
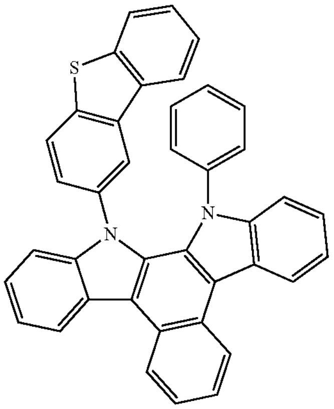
H-49c
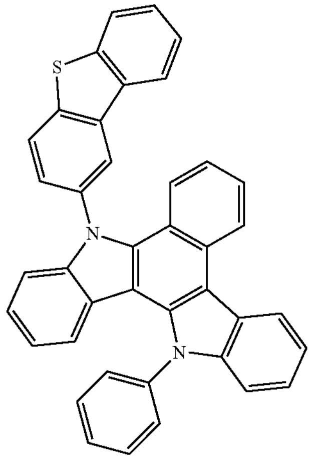
H-50c
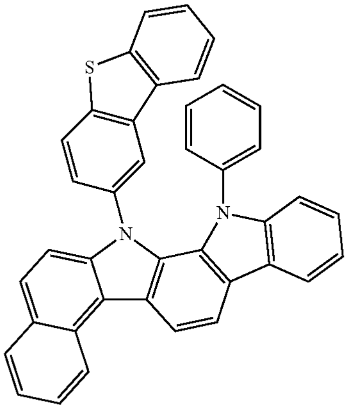
-continued
H-51c
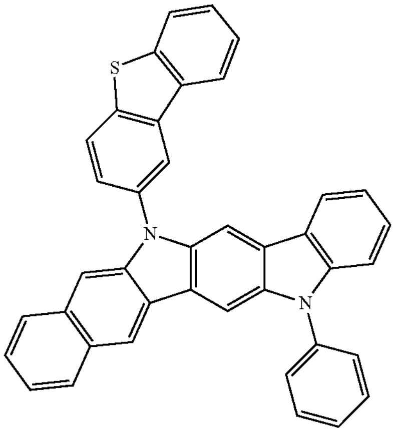
H-52c
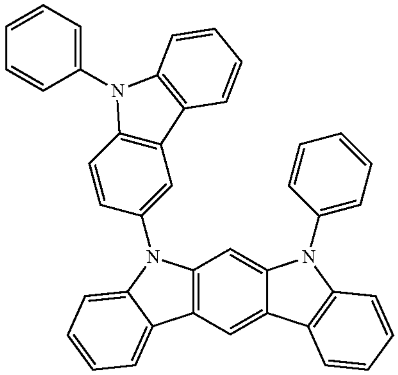
H-53c
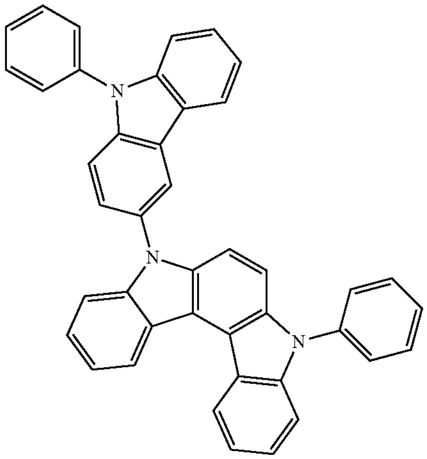

-continued
H-54c
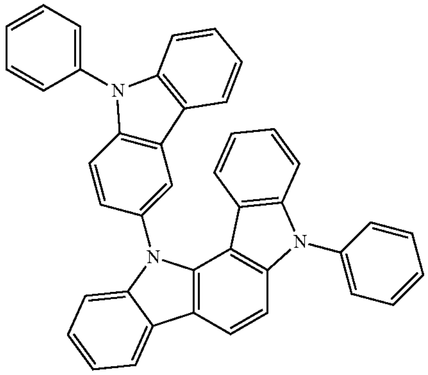
H-55c
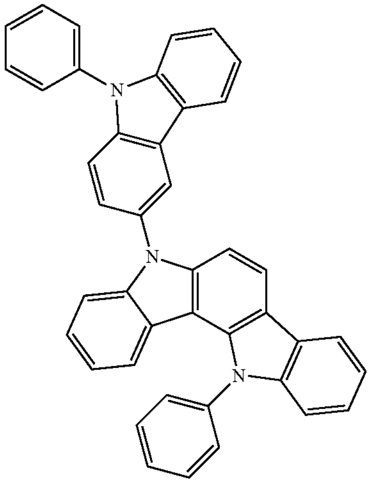
H-56c
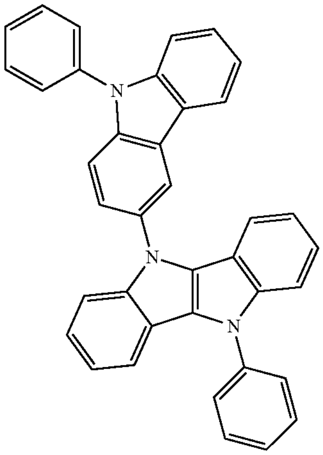
-continued
H-57c
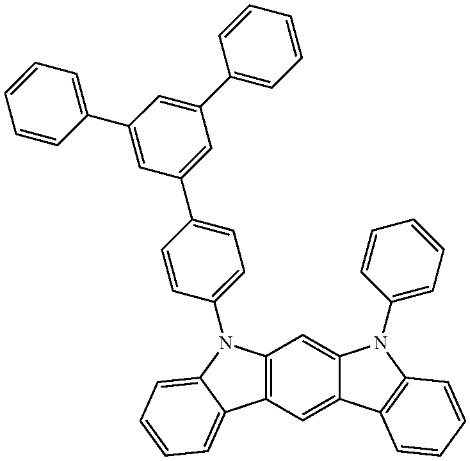
H-58c
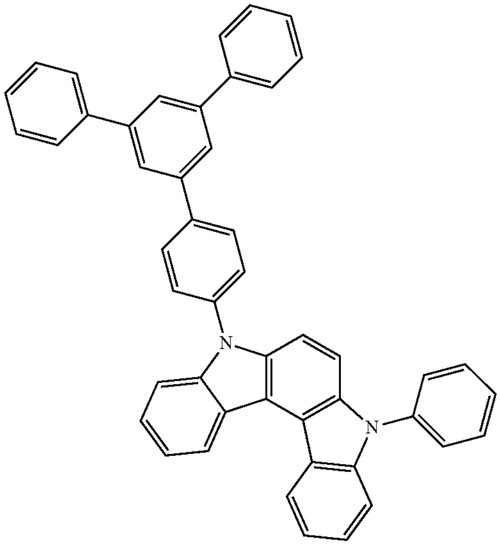
H-59c
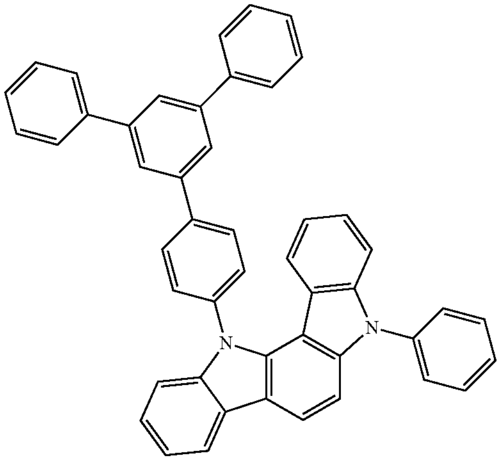

-continued
H-60c
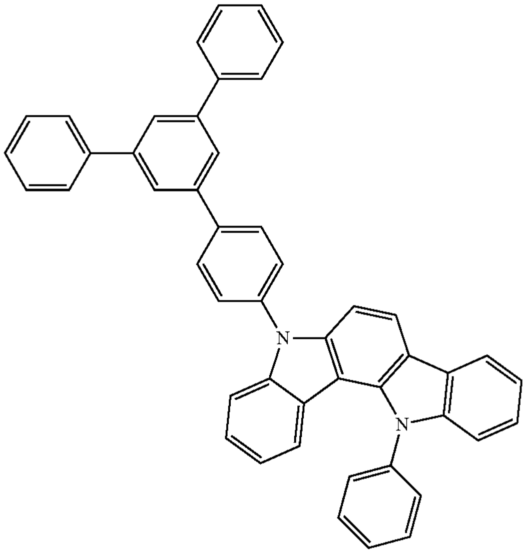
H-61c
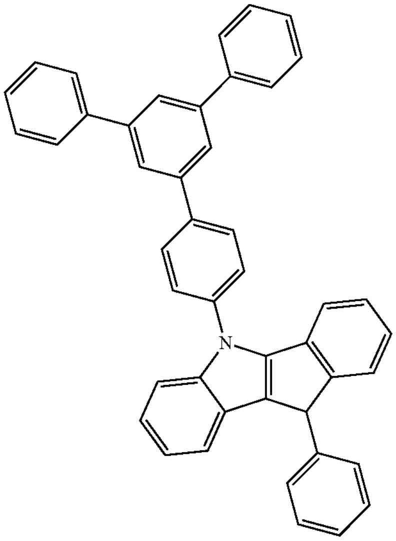
H-62c
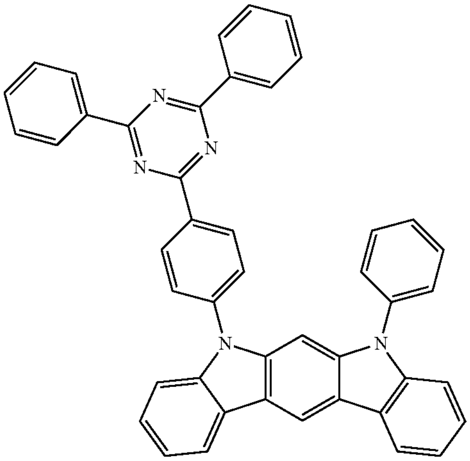
-continued
H-63c
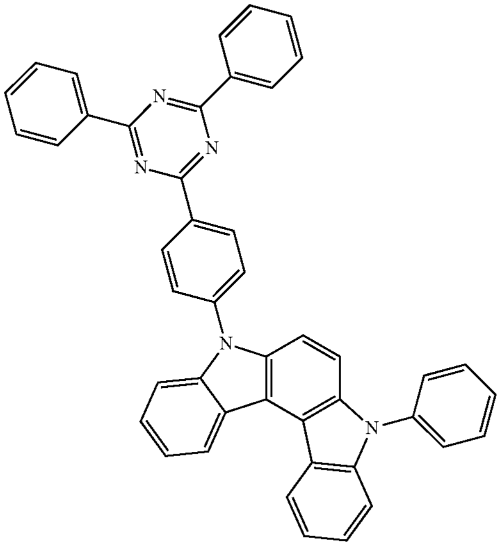
H-64c
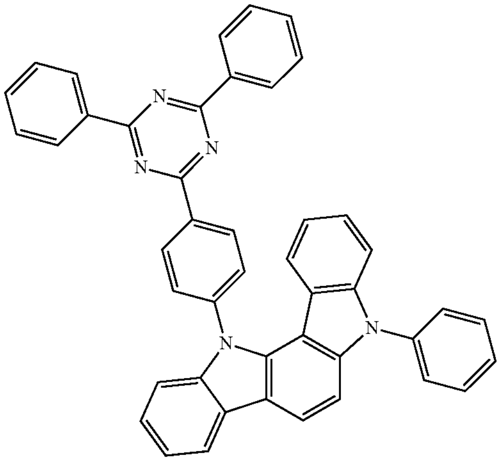
H-65c
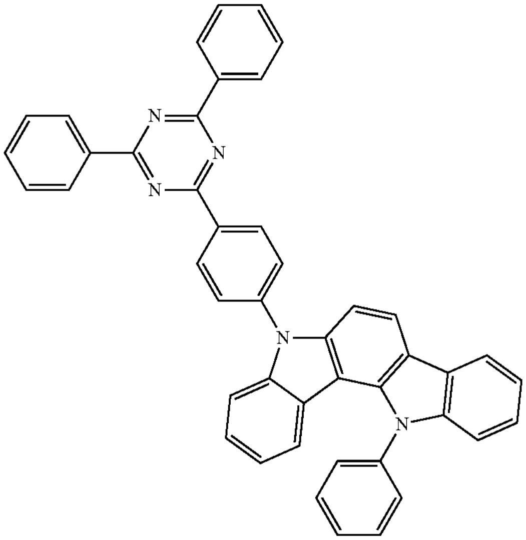

-continued
H-66c
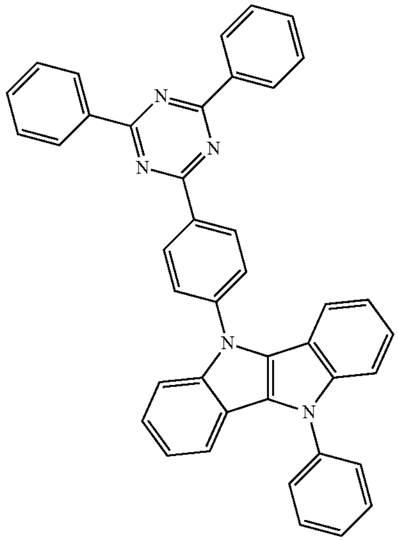
H-67c
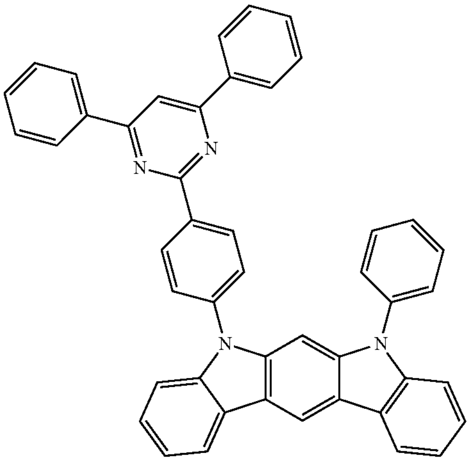
H-68c
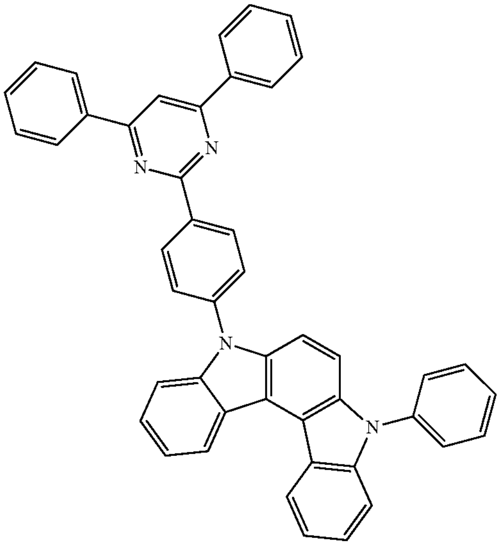
-continued
H-69c
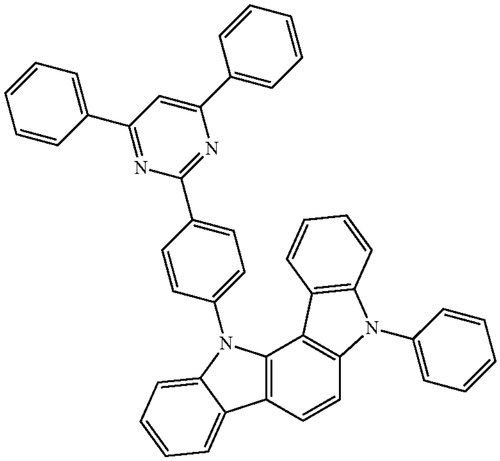
H-70c
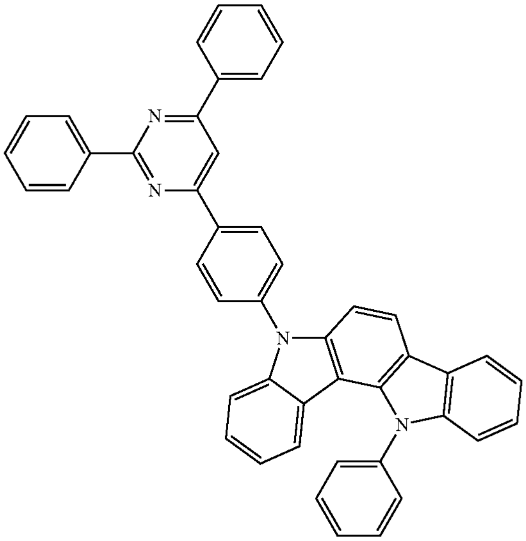
H-71c
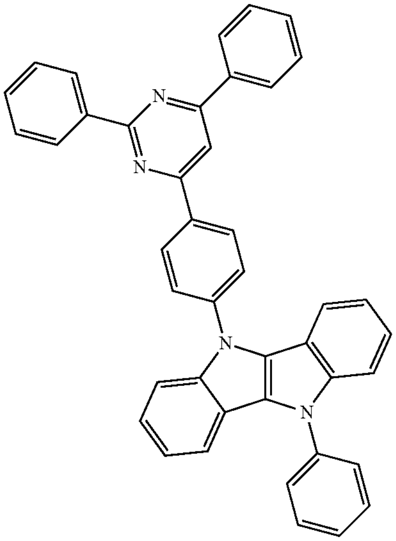

-continued
H-72c
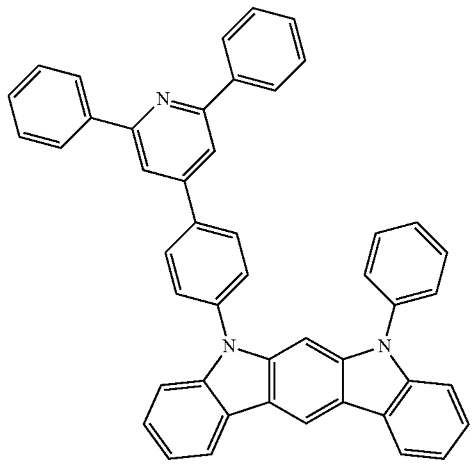
H-73c
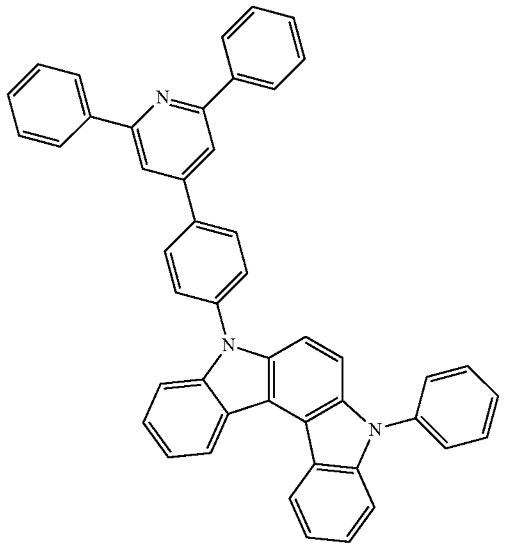
H-74c
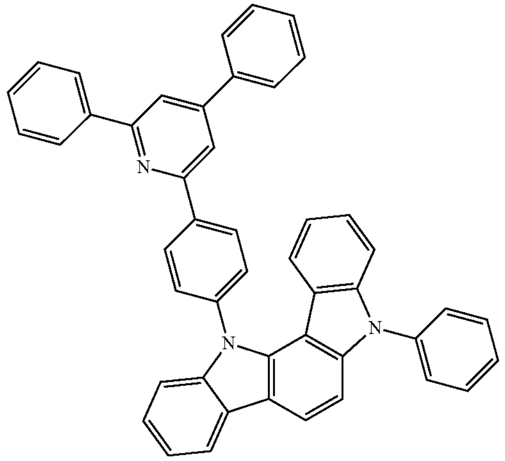
-continued
H-75c
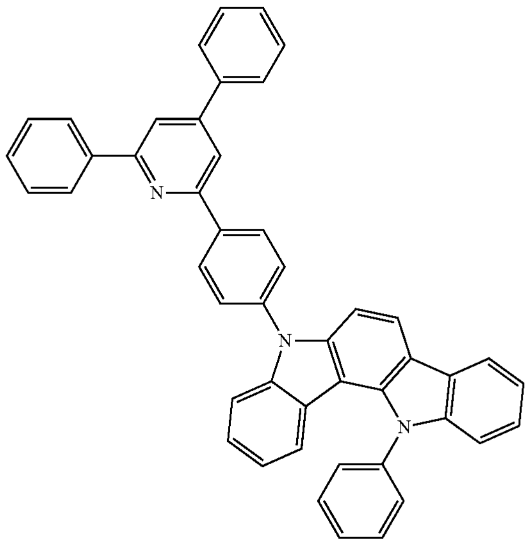
H-76c
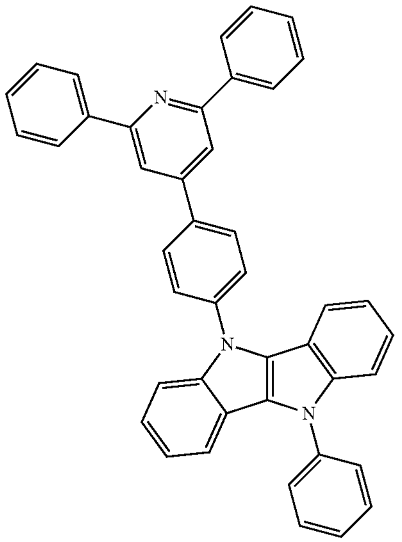
H-77c
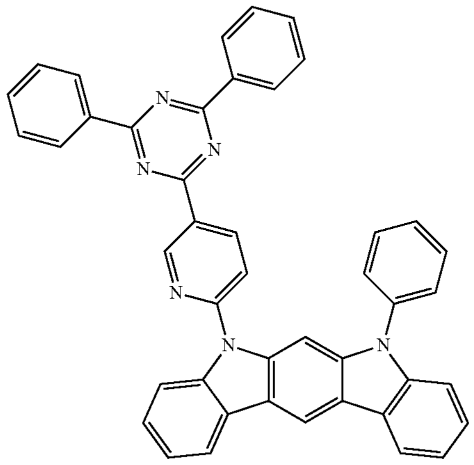

-continued
H-78c
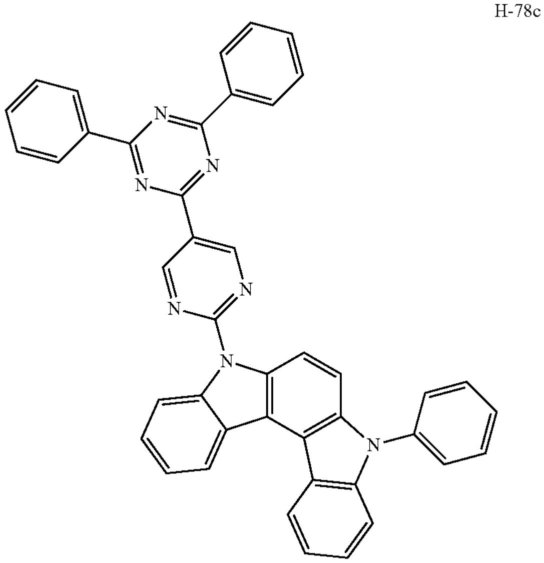
H-79c
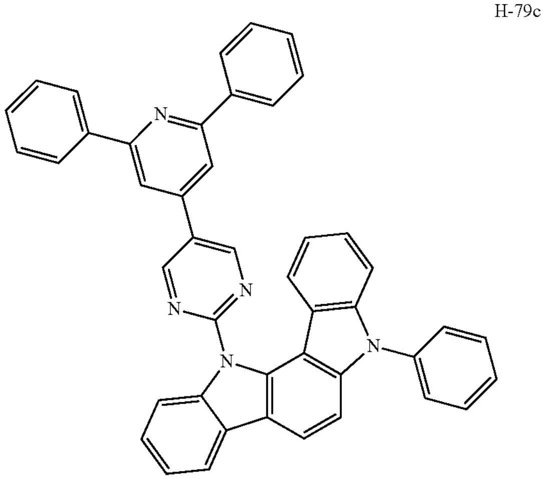
H-80c
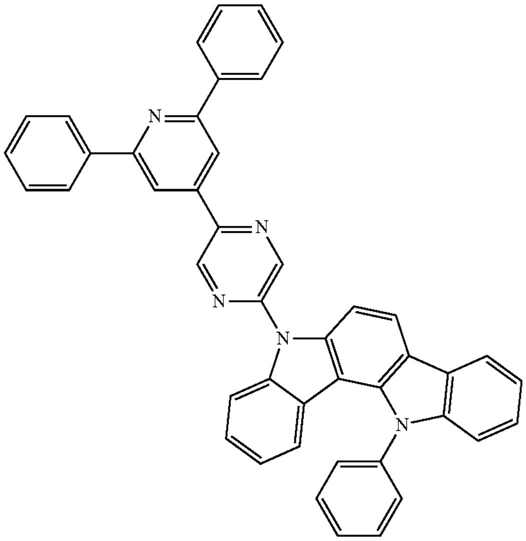
-continued
H-81c
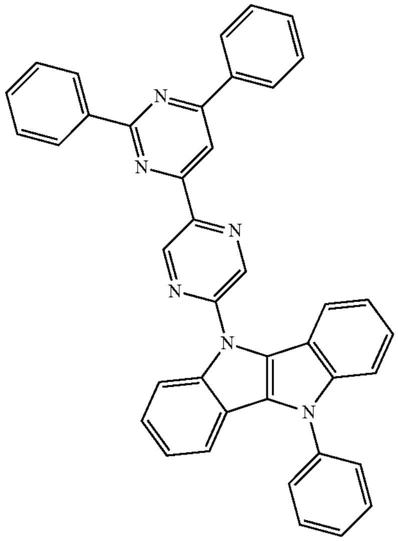
H-82c
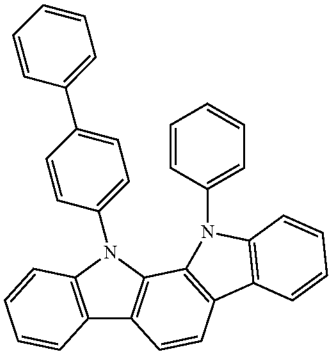
H-83c
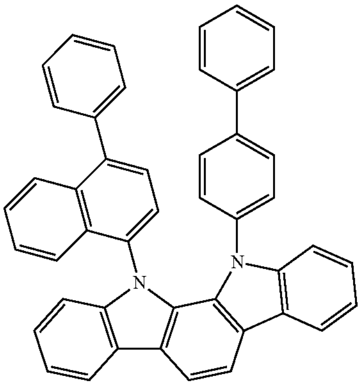
H-84c
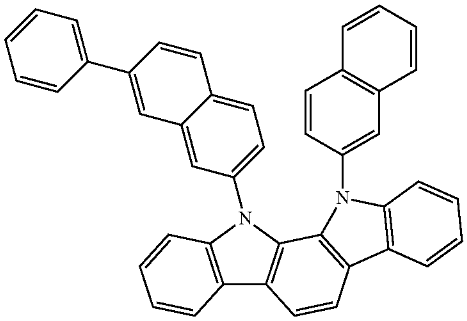

-continued
H-85c
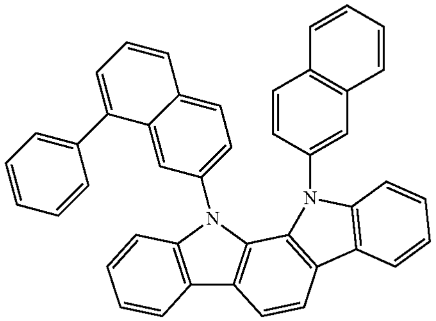
H-86c
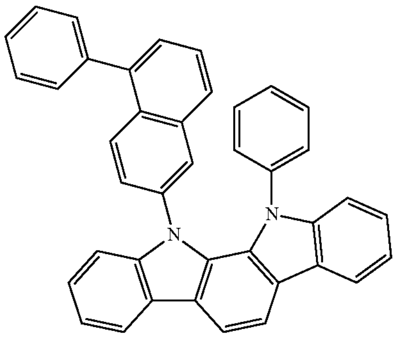
H-87c
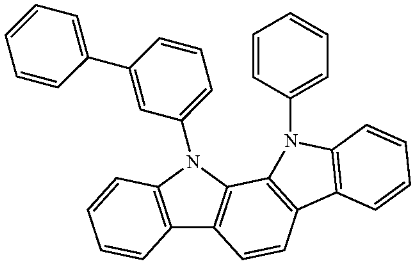
H-88c
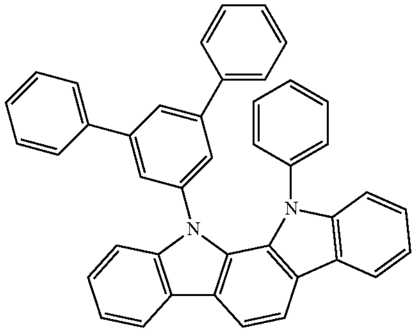
H-89c
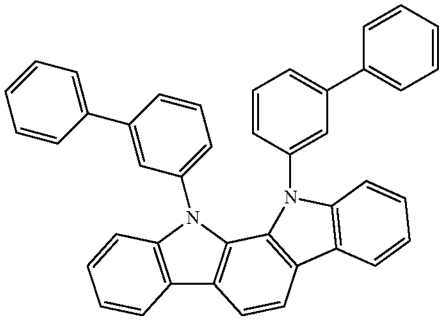
-continued
H-90c
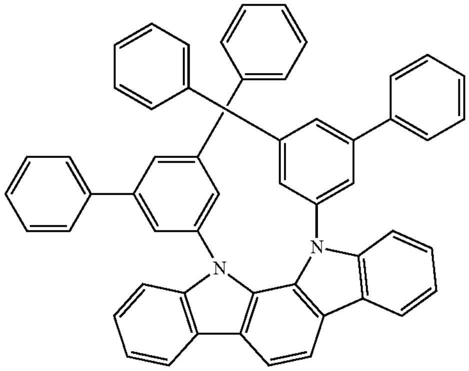
H-91c
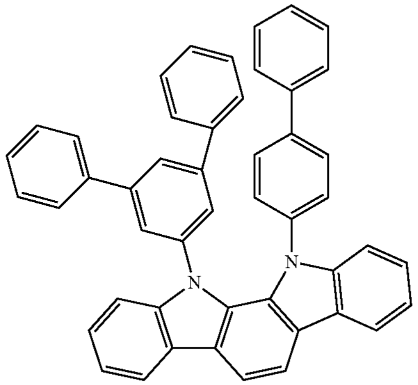
H-92c
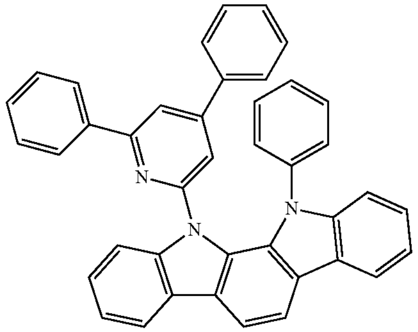
H-93c
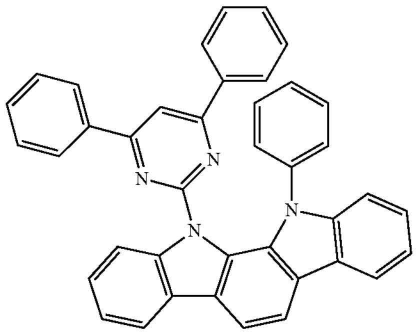

-continued
H-94c
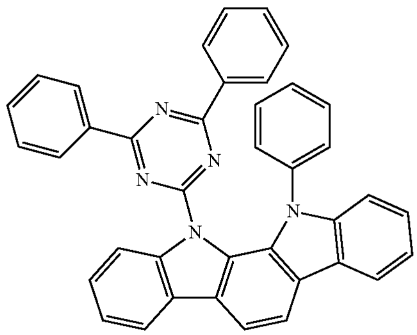
H-95c
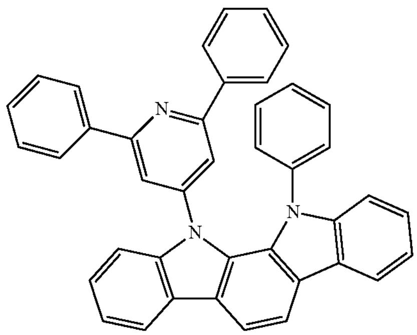
H-96c
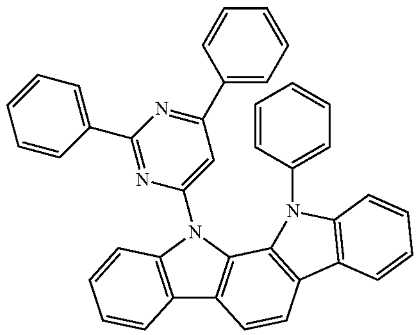
H-97c
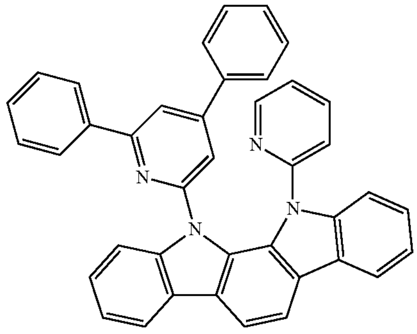
-continued
H-96c
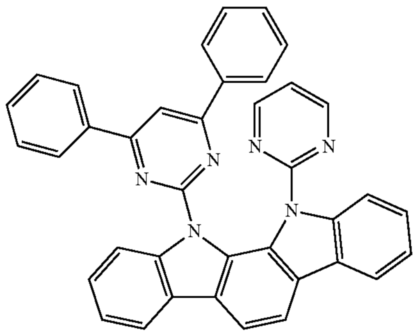
H-99c
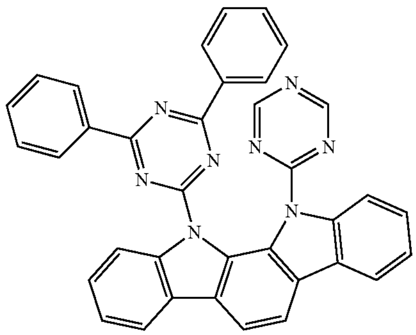
H-100c
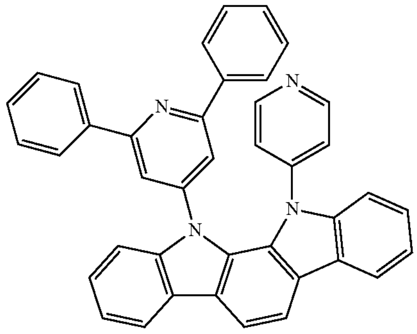
H-101c
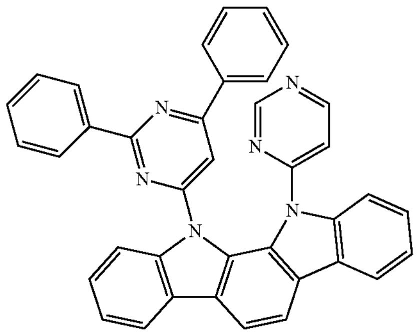

-continued
H-102c
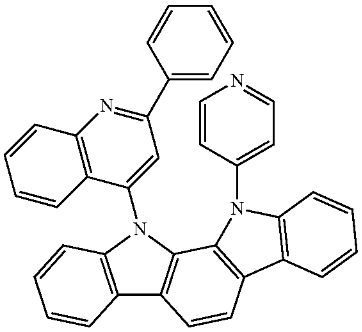
H-103c
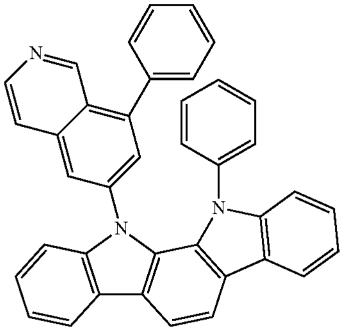
H-104c
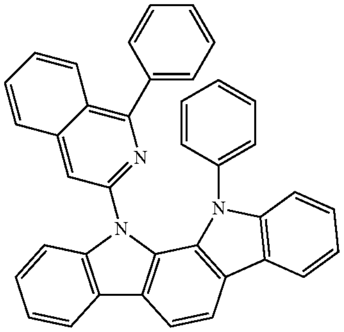
H-105c
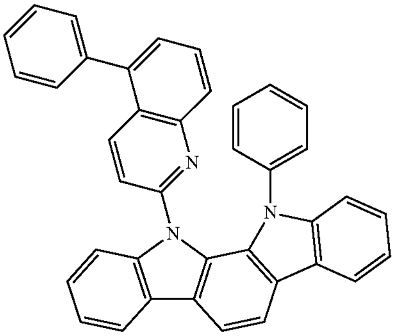
-continued
H-106c
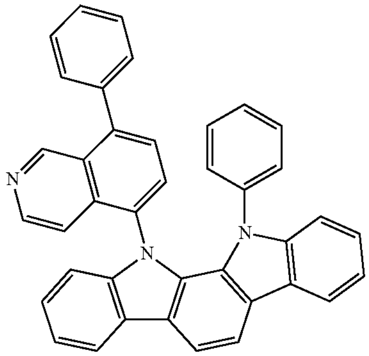
H-107c
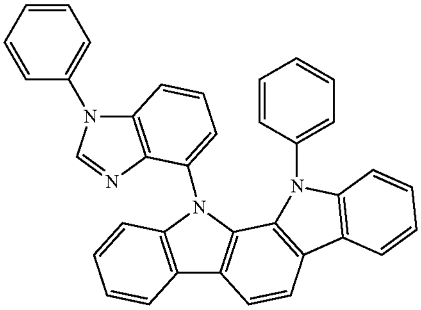
H-108c
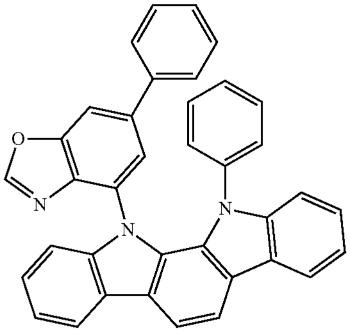
H-109c
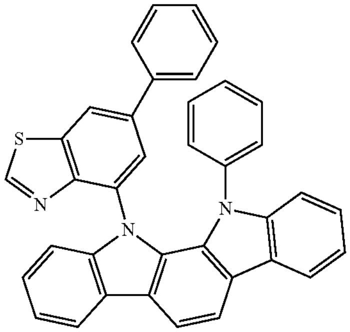

-continued
H-110c
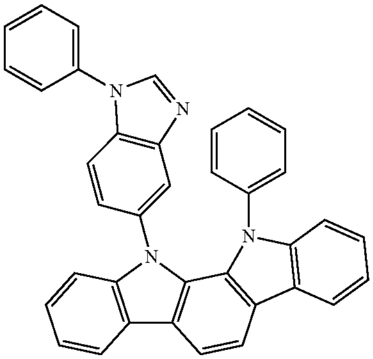
H-111c
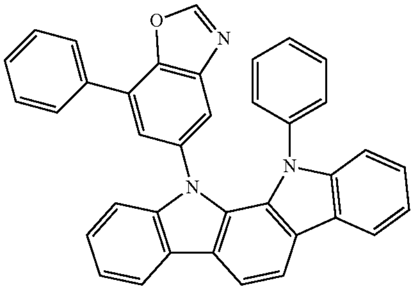
H-112c
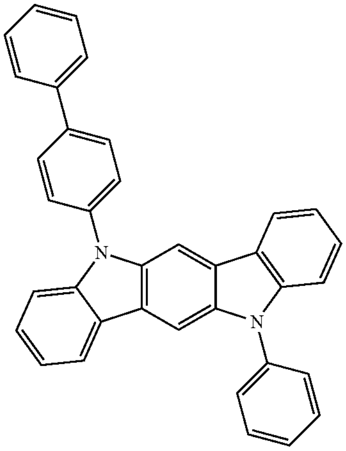
H-113c
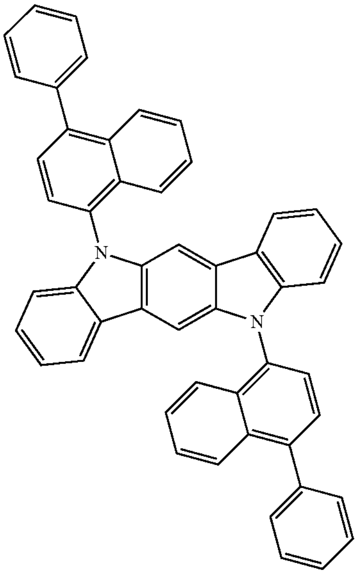
-continued
H-114c
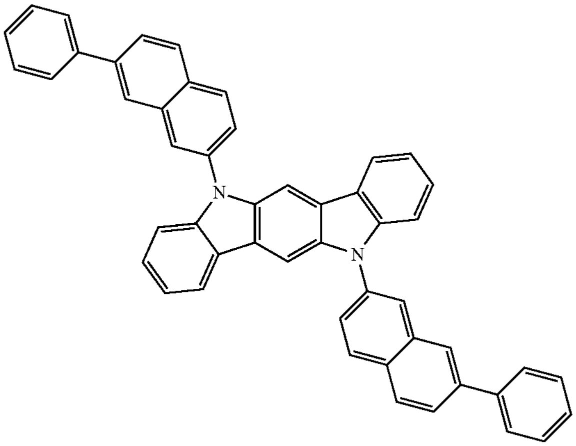
H-115c
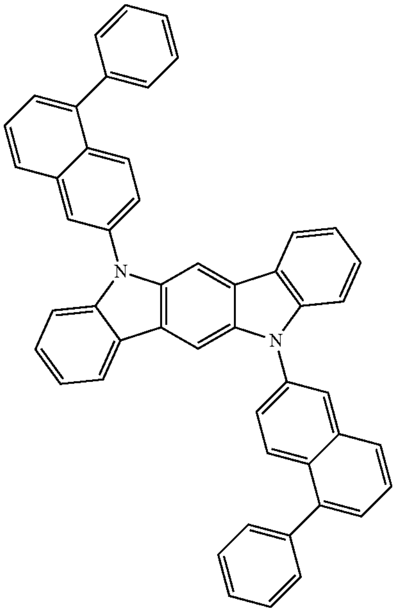
H-116c
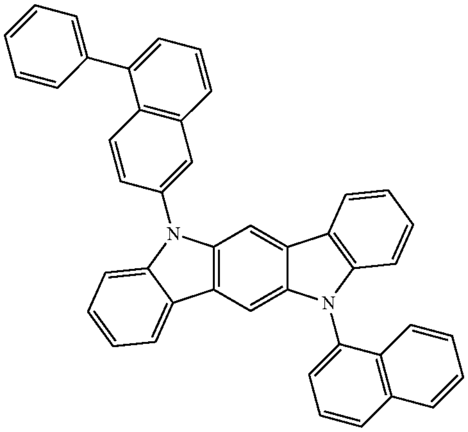

-continued
H-117c
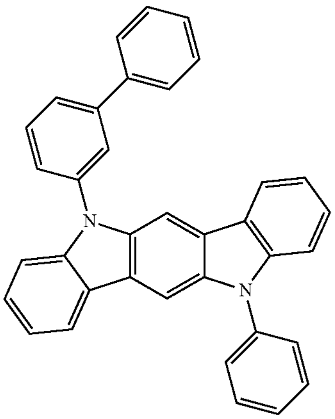
H-118c
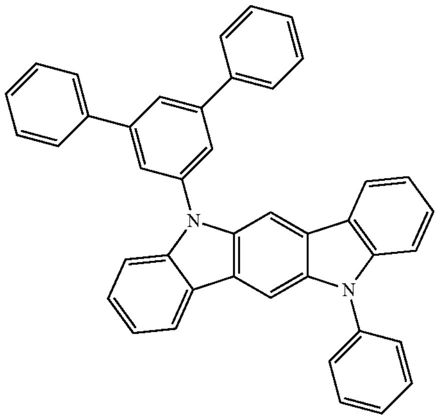
H-119c
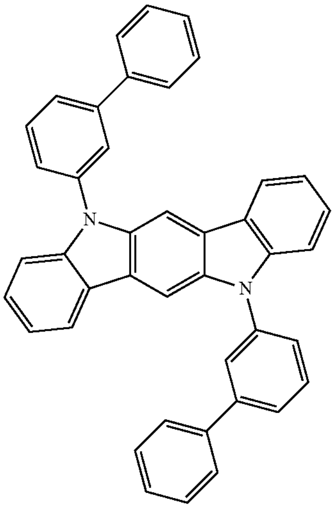
-continued
H-120c
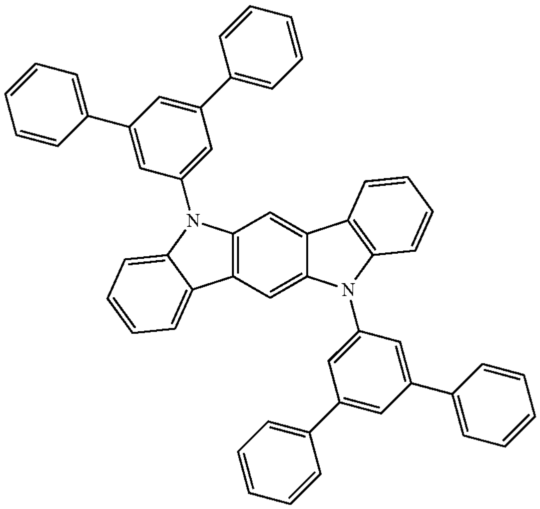
H-121c
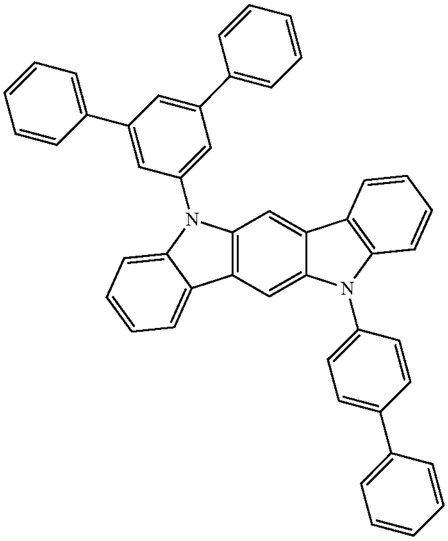
H-122c
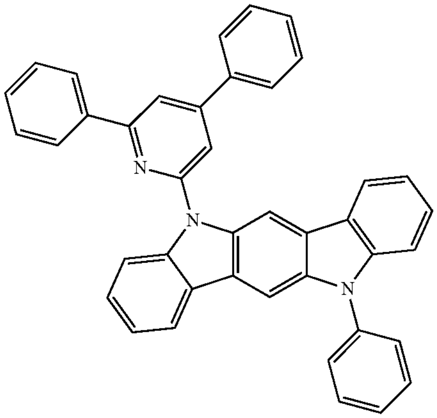

-continued
H-123c
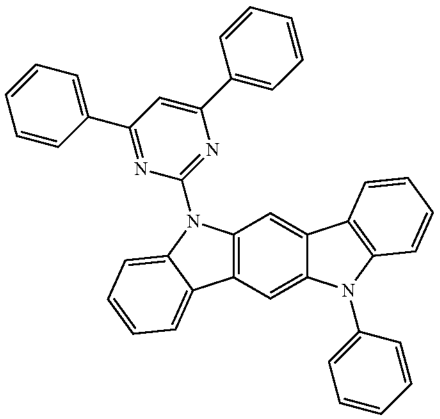
H-124c
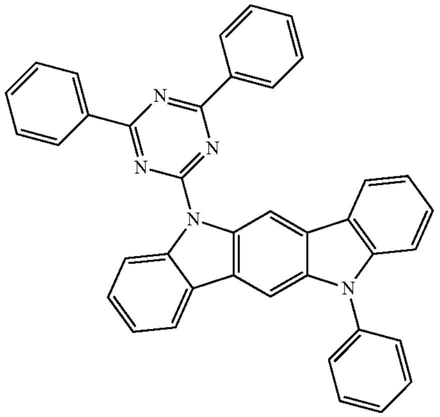
H-125c
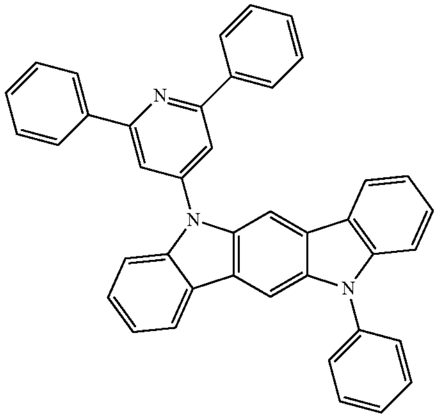
-continued
H-126c
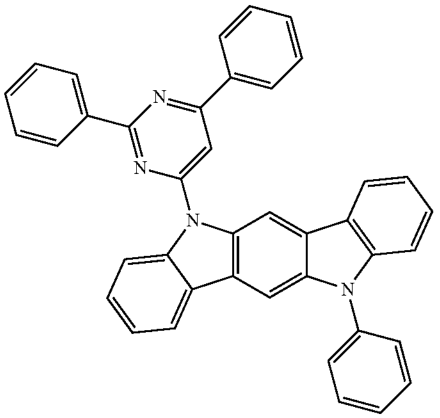
H-127c
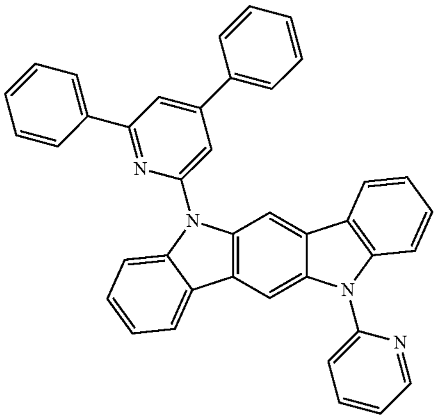
H-128c
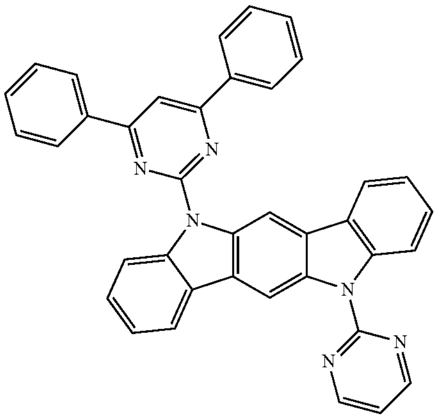

-continued
H-129c
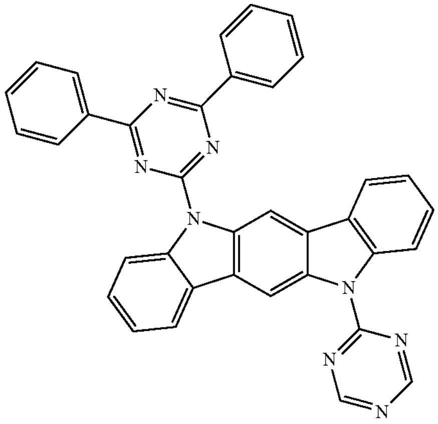
H-130c
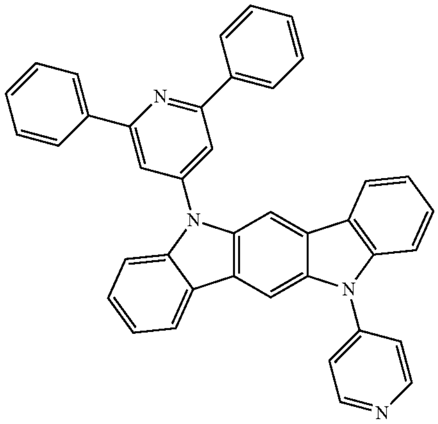
H-131c
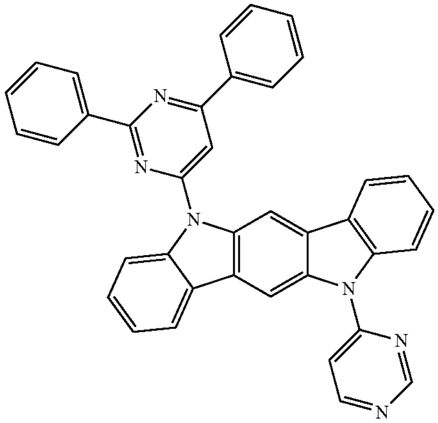
H-132c
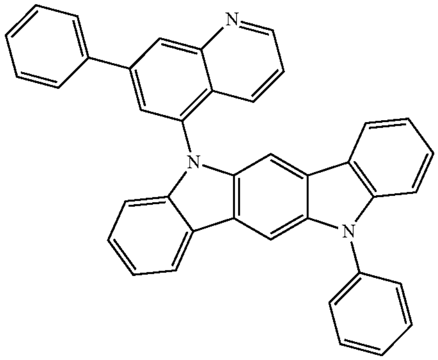
-continued
H-133c
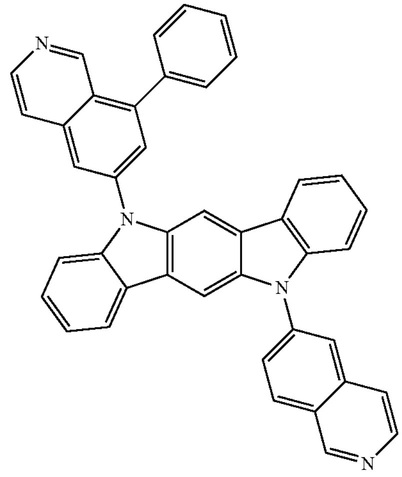
H-134c
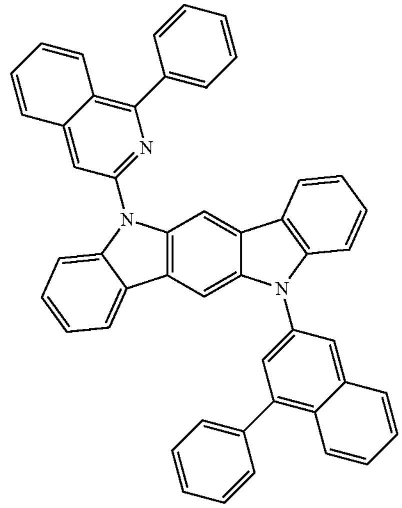
H-135c
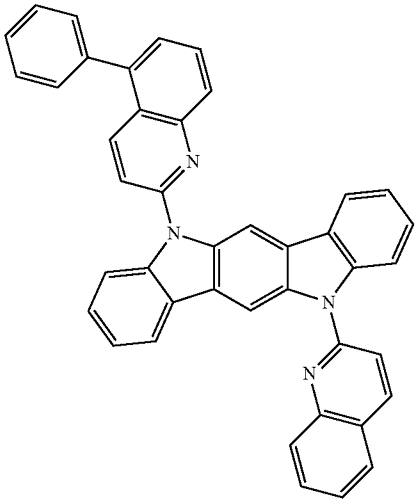

-continued

H-136c

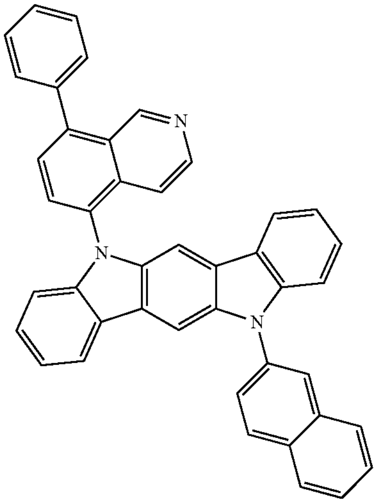

H-137c

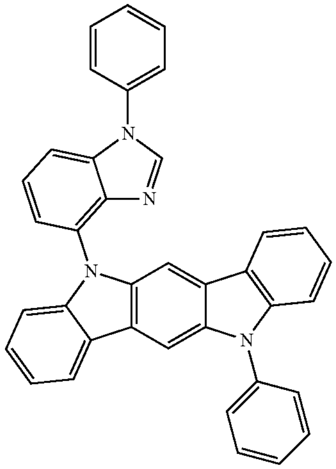

H-138c

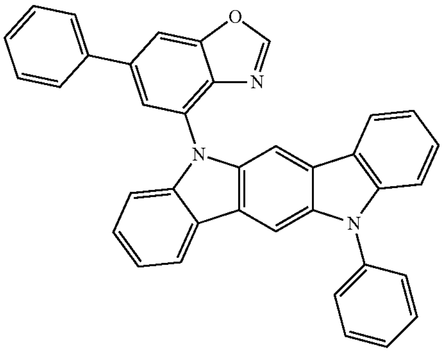

-continued

H-139c

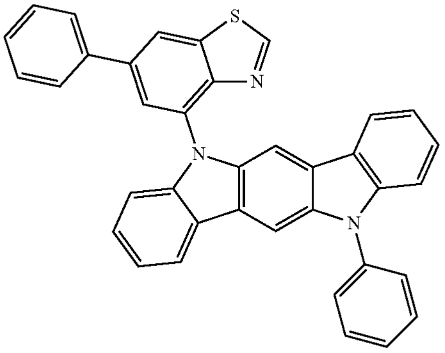

H-140c

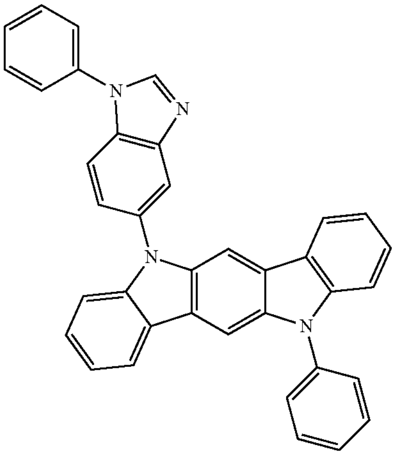

H-141c

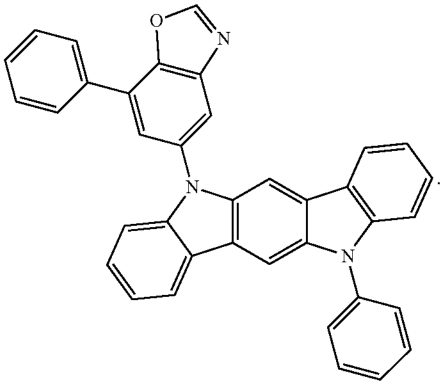

The dopant may include at least one selected from a fluorescent dopant and a phosphorescent dopant.

The phosphorescent dopant may include an organometallic complex represented by Formula 401 below:

<Formula 401>

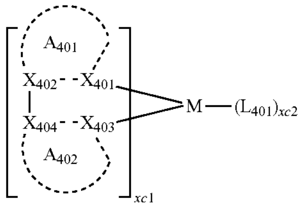

wherein in Formula 401,

M may be selected from iridium (Ir), platinum (Pt), osmium (Os), titanium (Ti), zirconium (Zr), hafnium (Hf), europium (Eu), terbium (Tb), and thulium (Tm);

$X_{401}$ to $X_{404}$ may each independently be nitrogen or carbon;

$A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isoxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzoxazole, a substituted or unsubstituted isobenzoxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene;

at least one of substituents of the substituted benzene, substituted naphthalene, substituted fluorene, substituted spiro-fluorene, substituted indene, substituted pyrrole, substituted thiophene, substituted furan, substituted imidazole, substituted pyrazole, substituted thiazole, substituted isothiazole, substituted oxazole, substituted isoxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted carbazole, substituted benzoimidazole, substituted benzofuran, substituted benzothiophene, substituted isobenzothiophene, substituted benzoxazole, substituted isobenzoxazole, substituted triazole, substituted oxadiazole, substituted triazine, substituted dibenzofuran, and substituted dibenzothiophene may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_1$-$C_{60}$ alkenyl group, a $C_1$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;

xc1 may be selected from 1, 2, and 3; and xc2 may be selected from 0, 1, 2, and 3.

Descriptions of $Q_{401}$ to $Q_{407}$, $Q_{411}$ to $Q_{417}$, and $Q_{421}$ to $Q_{427}$ may be understood by referring to the description of $Q_1$.

$L_{401}$ may be any suitable monovalent, divalent, or trivalent organic ligand. For example, $L_{401}$ may be selected from a halogen ligand (for example, Cl or F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazolecarboxylate, or benzoate), a carbon monoxide ligand, an isonitrile ligand, a cyano ligand, and a phosphorous ligand (for example, phosphine, or phosphite), as examples.

When $A_{401}$ in Formula 401 has a plurality of substituents, the plurality of substituents of $A_{401}$ may bind to each other to form a saturated or unsaturated ring.

When $A_{402}$ in Formula 401 has a plurality of substituents, the plurality of substituents of $A_{402}$ may bind to each other to form a saturated or unsaturated ring.

When xc1 in Formula 401 is two or more, a plurality of ligands

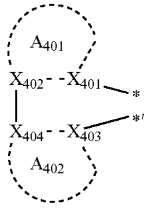

in Formula 401 may be identical to or different from each other. When xc1 in Formula 401 is two or more, $A_{401}$ and $A_{402}$ of one ligand may be respectively linked to $A_{401}$ and $A_{402}$ of an adjacent ligand, directly or connected via a linking group (for example, a $C_1$-$C_5$ alkylene group, —N(R')— (wherein, R' indicates a $C_1$-$C_{10}$ alkyl group or a $C_6$-$C_{20}$ aryl group), or —C(=O)—).
The phosphorescent dopant may include at least one selected from Compounds PD1 to PD74 below.
PD1
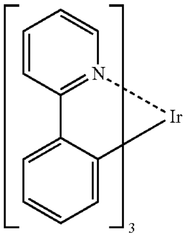
PD2
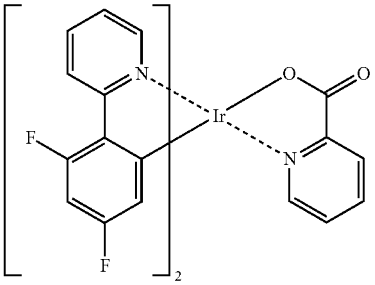
PD3
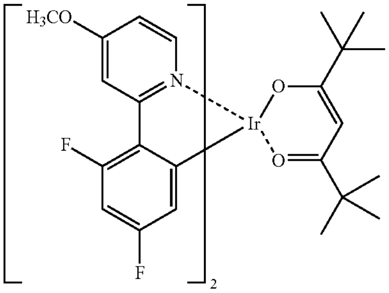
PD4
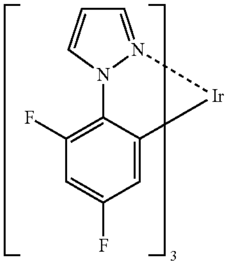
PD5
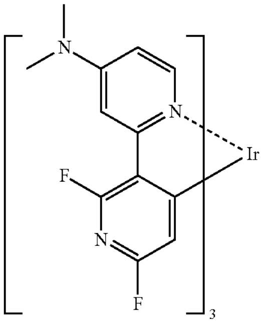
-continued
PD6
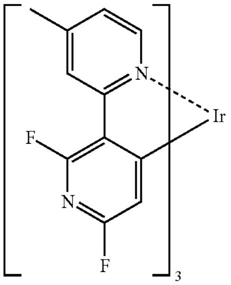
PD7
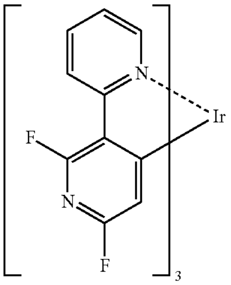
PD8
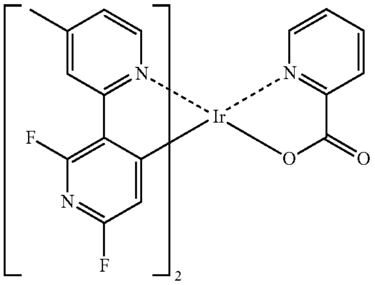
PD9
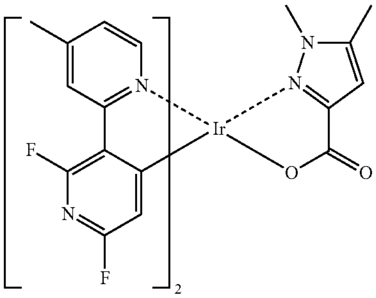
PD10
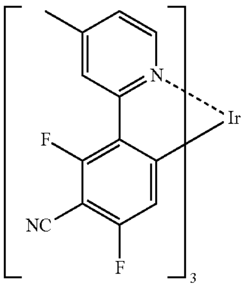

-continued
PD11
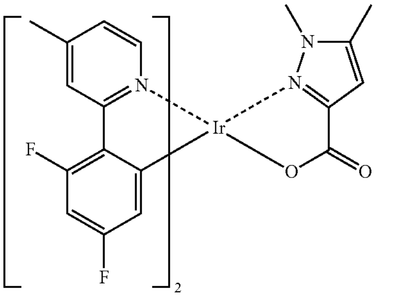
PD12
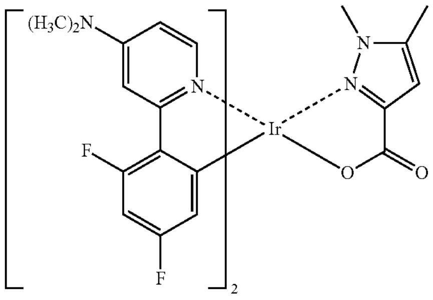
PD13
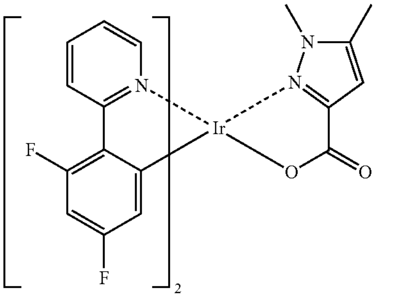
PD14
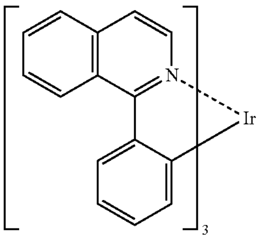
PD15
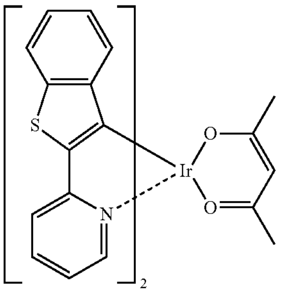
-continued
PD16
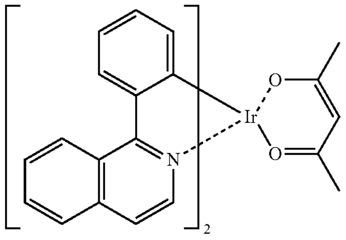
PD17
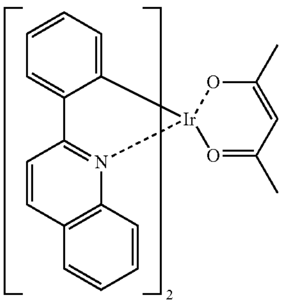
PD18
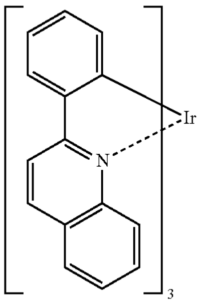
PD19
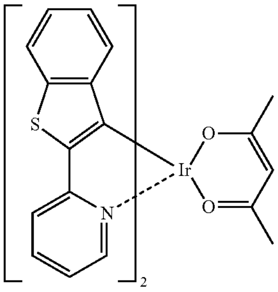
PD20
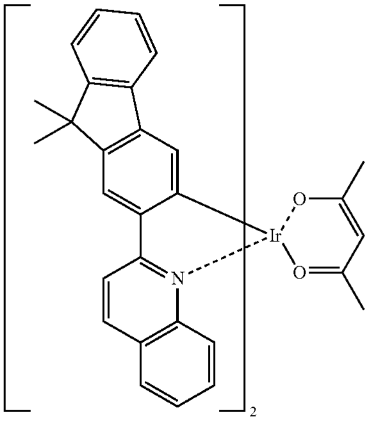

-continued
PD21
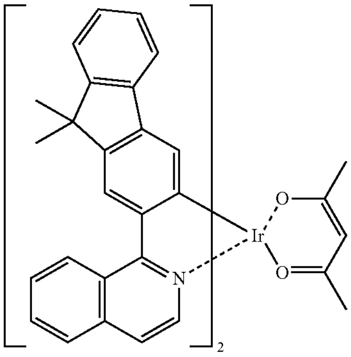
PD22
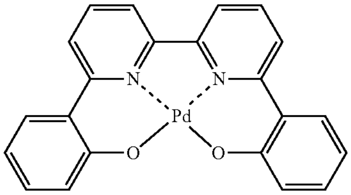
PD23
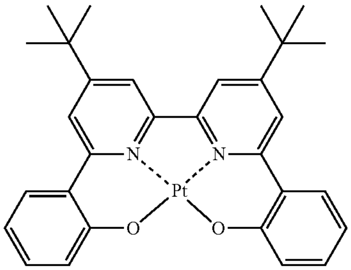
PD24
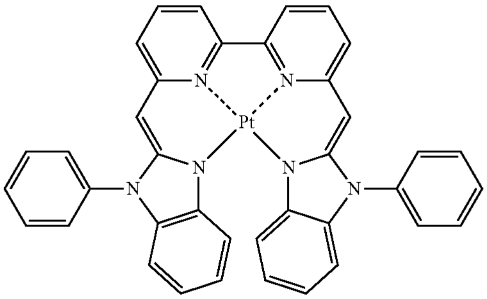
PD25
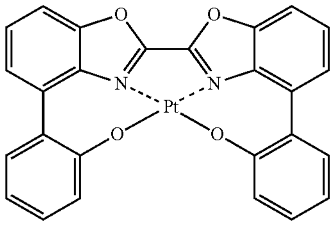
PD26
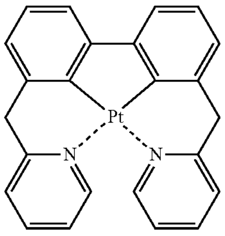
-continued
PD27
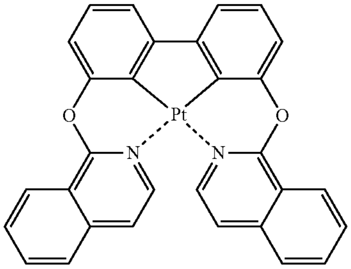
PD28
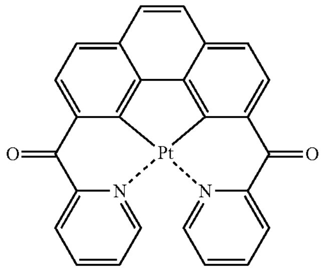
PD29
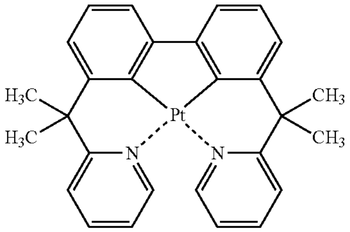
PD30
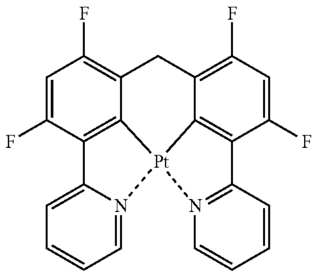
PD31
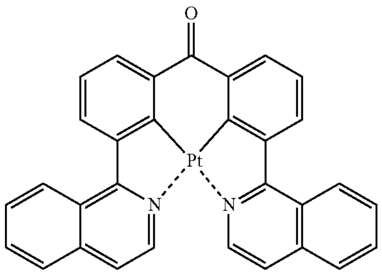
PD32
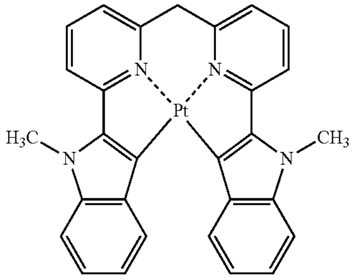

-continued
PD33
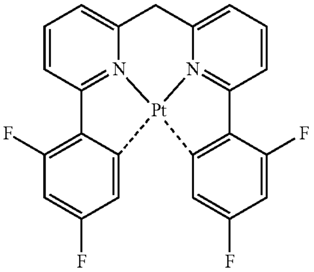
PD34
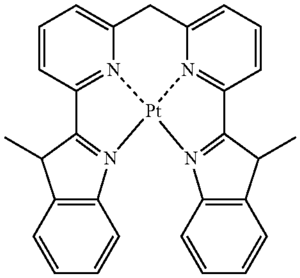
PD35
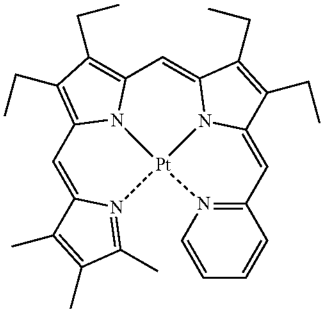
PD36
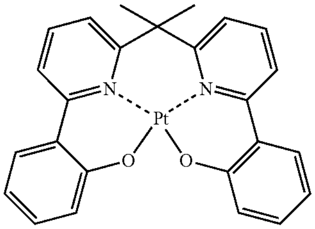
PD37
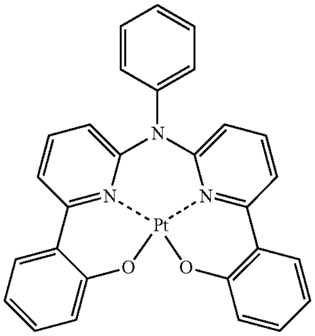
-continued
PD38
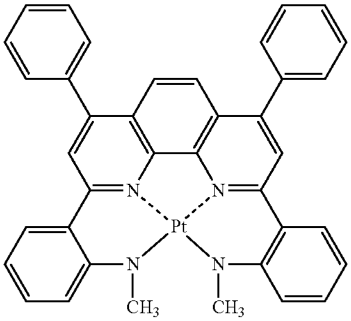
PD39
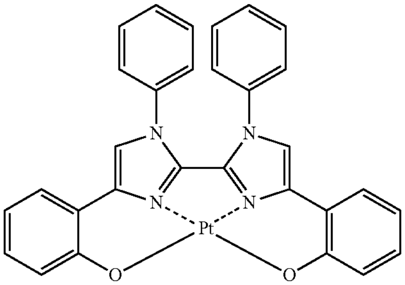
PD40
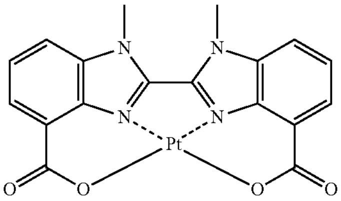
PD41
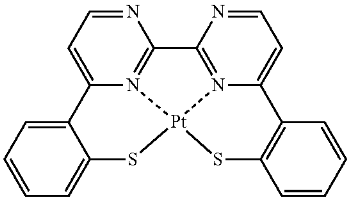
PD42
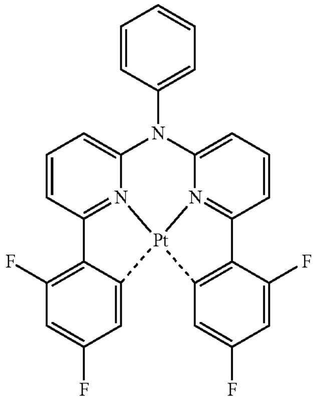

-continued
PD43
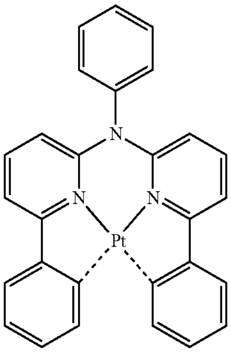
PD44
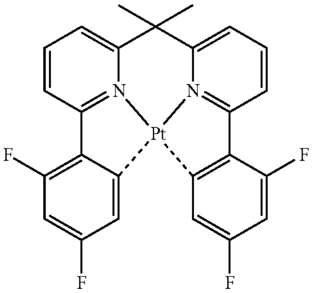
PD45
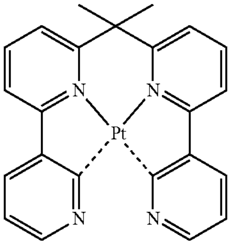
PD46
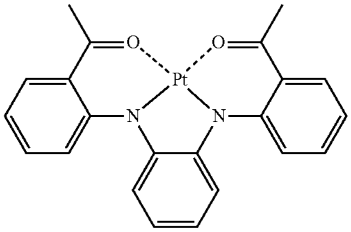
PD47
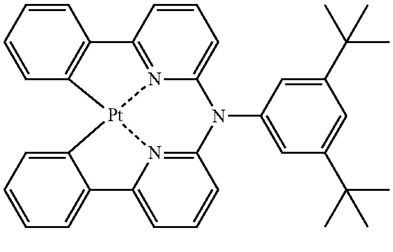
PD48
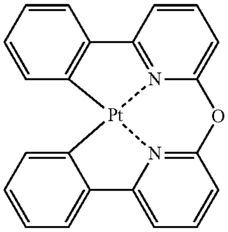
-continued
PD49
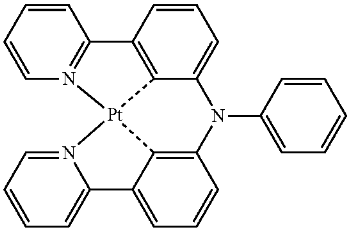
PD50
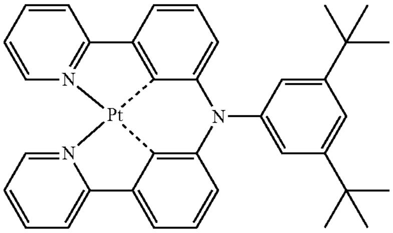
PD51
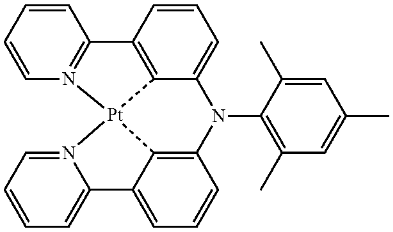
PD52
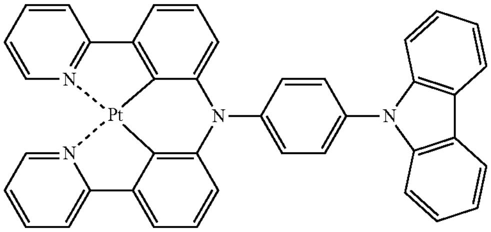
PD53
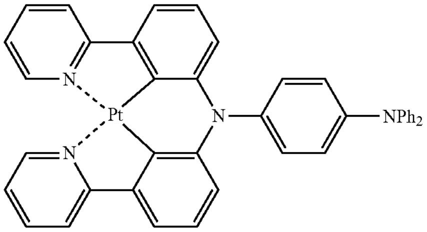
PD54
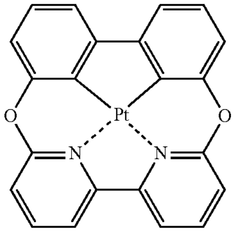

-continued
PD55
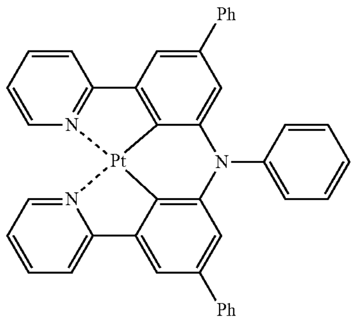
PD56
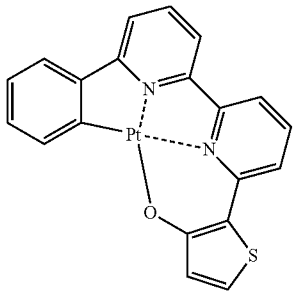
PD57
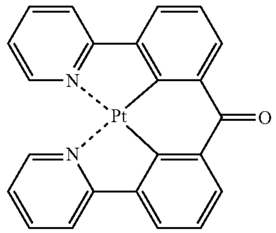
PD58
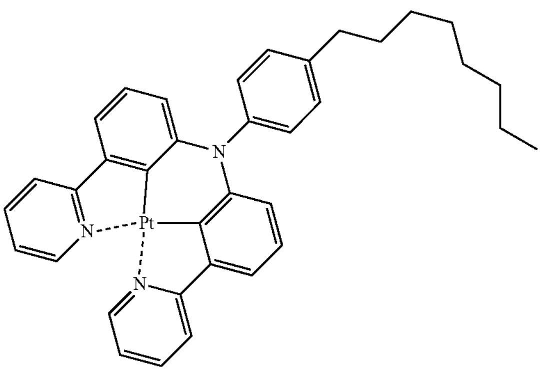
PD59
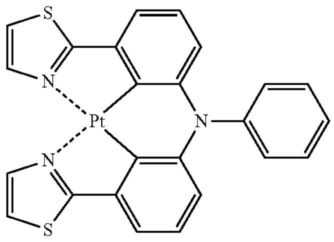
-continued
PD60
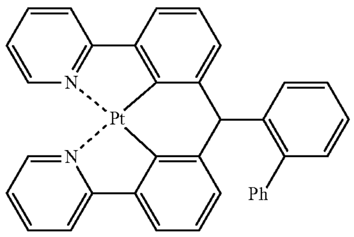
PD61
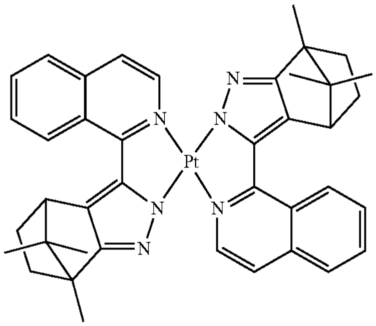
PD62
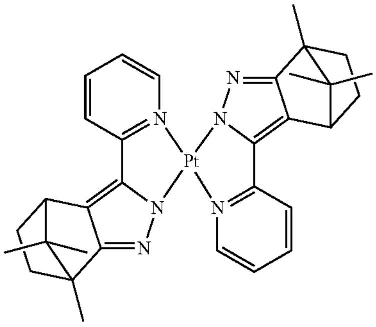
PD63
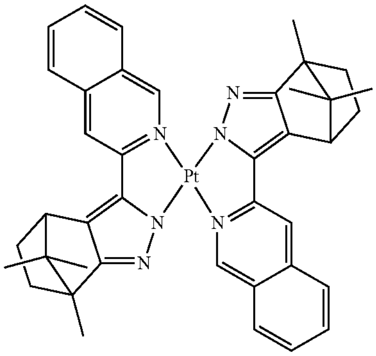
PD64
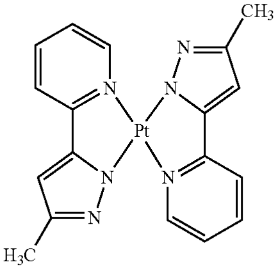

-continued
PD65
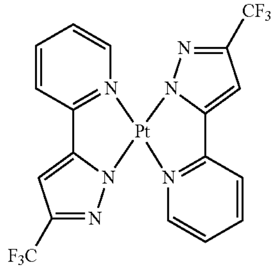
PD66
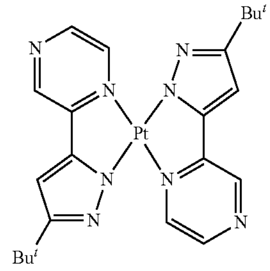
PD67
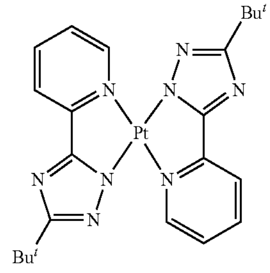
PD68
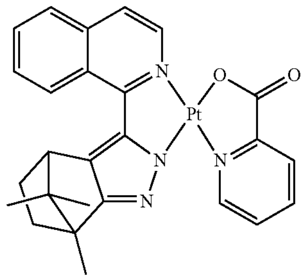
PD69
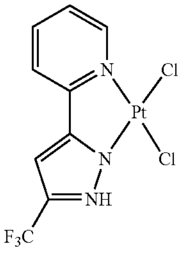
-continued
PD70
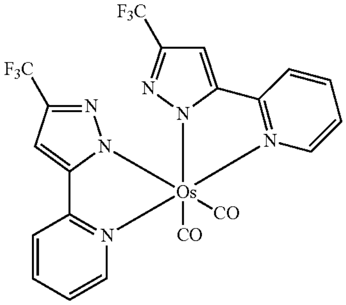
PD71
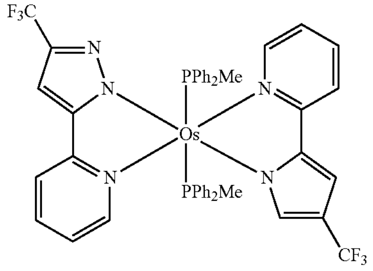
PD72
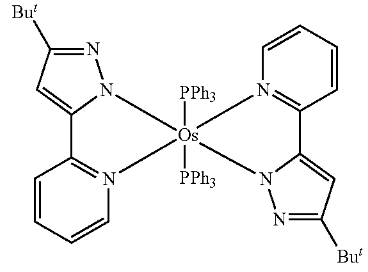
PD73
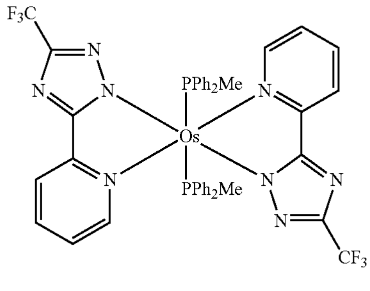
PD74
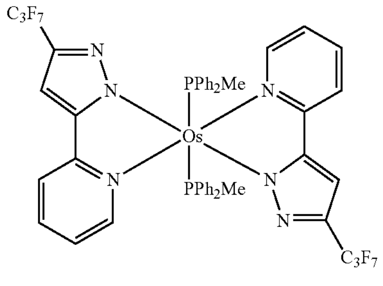
In some embodiments, the phosphorescent dopant may include PtOEP below:

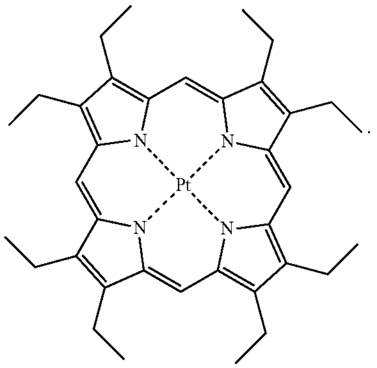

PtOEP

In some embodiments, the fluorescent dopant may include a compound represented by Formula 501:

<Formula 501>

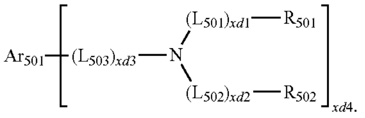

In Formula 501, $Ar_{501}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

$L_{501}$ to $L_{503}$ may be the same as defined in connection with $L_1$ provided herein;

$R_{501}$ and $R_{502}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_{603}$)($Q_{604}$)($Q_{605}$);

xd1 to xd3 may be each independently selected from 0, 1, 2, and 3; and xd4 may be selected from 1, 2, 3, and 4;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_1$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{501}$)($Q_{502}$). —Si($Q_{503}$)($Q_{504}$)($Q_{505}$), and —B($Q_{506}$)($Q_{507}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{511}$)($Q_{512}$), —Si($Q_{513}$)($Q_{514}$)($Q_{515}$), and —B($Q_{516}$)($Q_{517}$); and —N($Q_{521}$)($Q_{522}$), —Si($Q_{523}$)($Q_{524}$)($Q_{525}$), and —B($Q_{526}$)($Q_{527}$);

wherein $Q_{501}$ to $Q_{507}$, $Q_{511}$ to $Q_{517}$, and $Q_{521}$ to $Q_{527}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

In some embodiments, $Ar_{501}$ may be selected from a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, N($Q_{601}$)($Q_{602}$), and —Si($Q_{603}$)($Q_{604}$)($Q_{605}$);

$L_{501}$ to $L_{503}$ may be each independently selected from:

a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

$R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

wherein $Q_{501}$ to $Q_{505}$ may be each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group.

The fluorescent dopant may include at least one selected from Compounds FD1 to FD16 below:

-continued
FD1
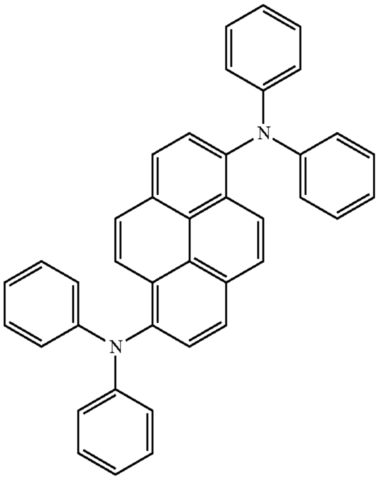
FD2
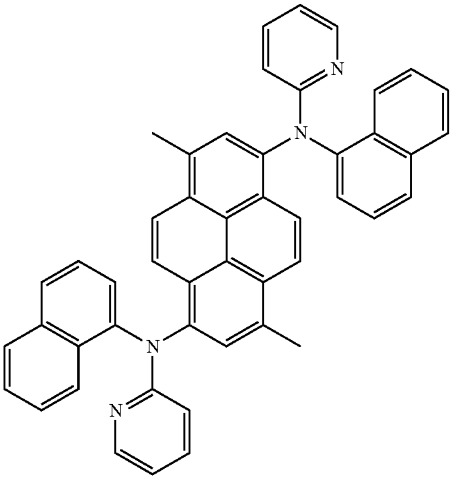
FD3
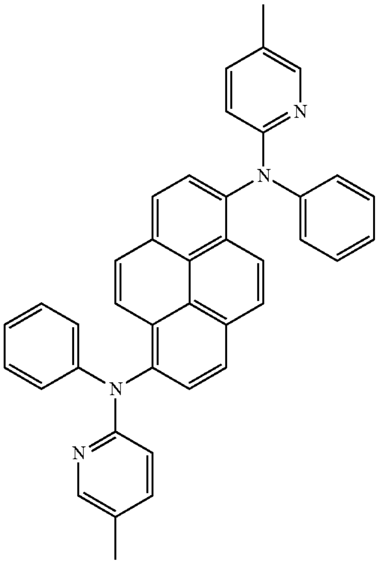
FD4
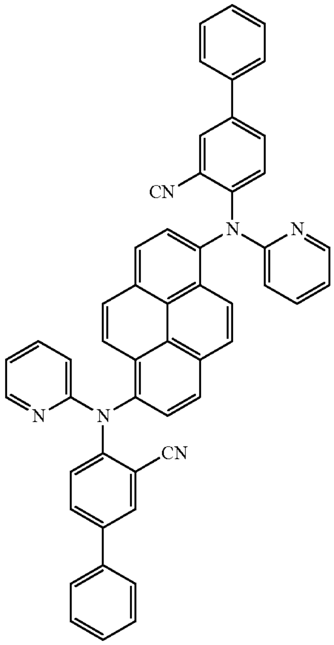
FD5
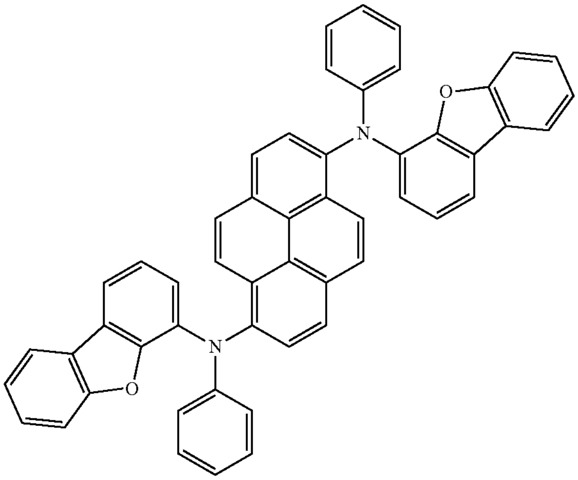
FD6
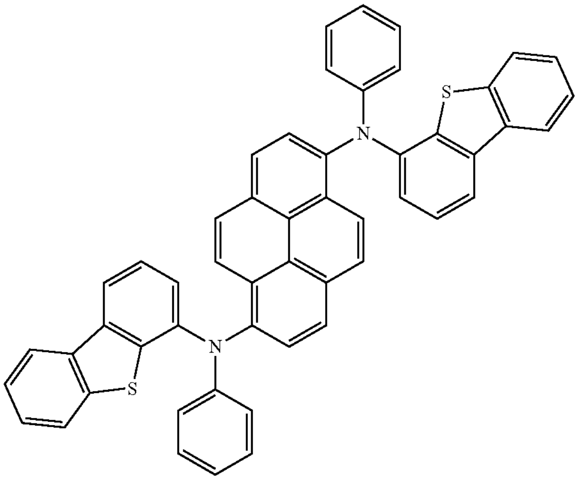

-continued
FD7
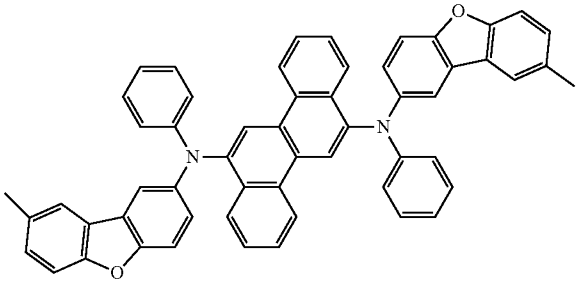
FD8
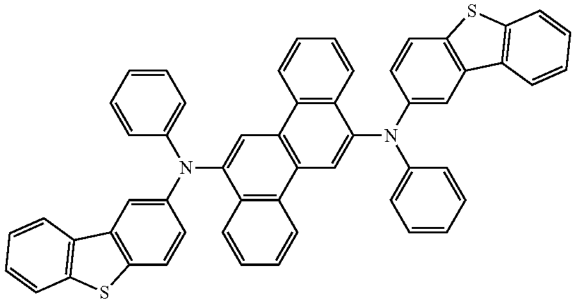
FD9
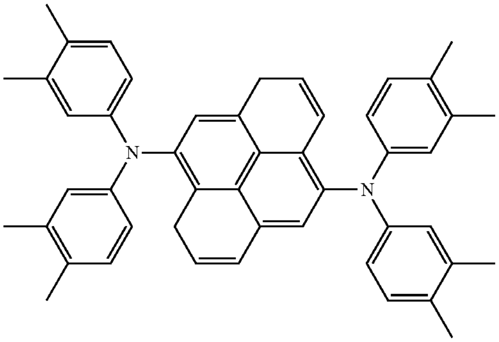
FD11
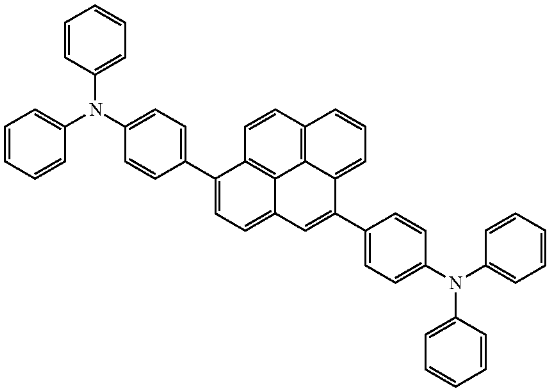
-continued
FD12
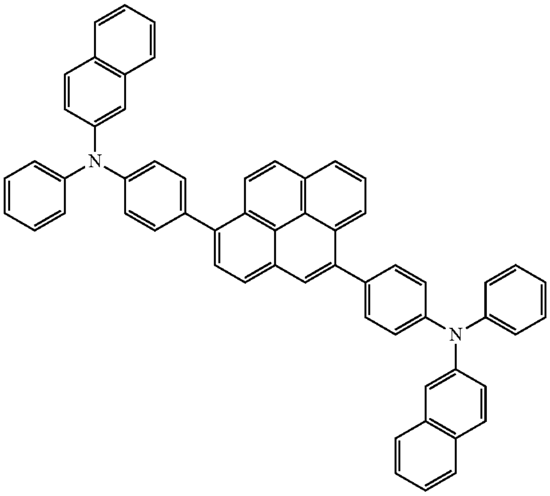
FD13
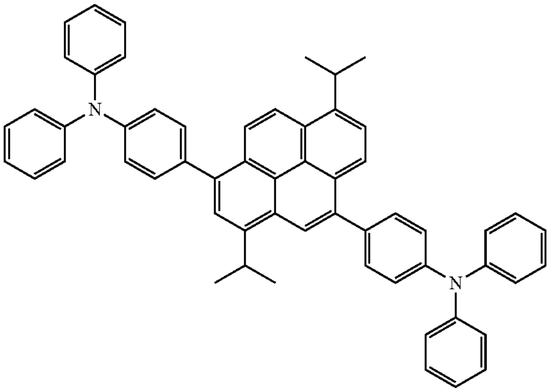
FD14
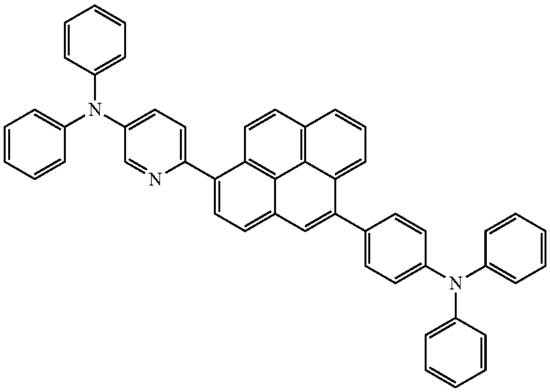

-continued

FD15

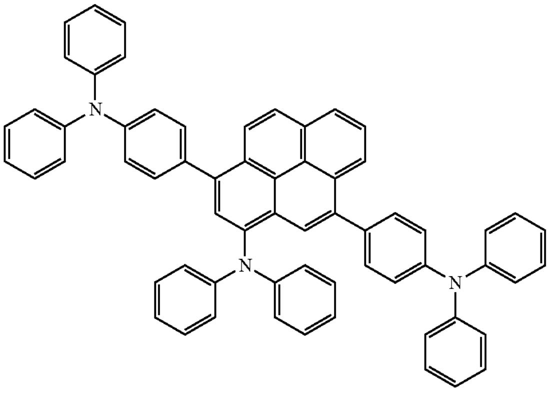

FD16

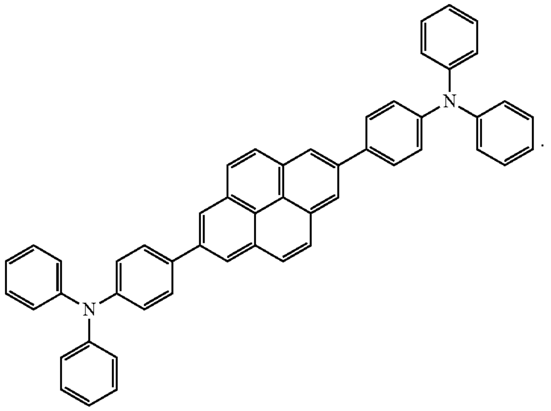

The amount of the dopant in the emission layer may be, in general, in a range of about 0.01 part by weight to about 15 parts by weight based on 100 parts by weight of the host.

The thickness of the emission layer may be in a range of about 100 Å to about 1,000 Å, or, for example, about 200 Å to about 600 Å. When the thickness of the emission layer is within this range, excellent light-emission characteristics may be obtained without a substantial increase in driving voltage.

An electron transport region may be on the emission layer 150.

The electron transport region 170 may include at least one selected from a hole blocking layer, an electron transport layer (ETL), and an electron injection layer.

In some embodiments, the electron transport region may have a structure of electron transport layer/electron injection layer or a structure of hole blocking layer/electron transport layer/electron injection layer, wherein layers of each structure are sequentially stacked from the emission layer in the stated order.

The electron transport region may include a hole blocking layer. The hole blocking layer may be formed, when the emission layer includes a phosphorescent dopant, to prevent diffusion of excitons or holes into an electron transport layer.

When the electron transport region includes a hole blocking layer, the hole blocking layer may be formed on the emission layer by using various methods, such as vacuum-deposition, spin coating, casting, LB method, ink-jet printing, laser-printing, or LITI. When the hole blocking layer is formed by vacuum-deposition or spin coating, deposition and coating conditions for the hole blocking layer may be determined by referring to the deposition and coating conditions for the hole injection layer.

The hole blocking layer may include, for example, at least one selected from BCP and Bphen:

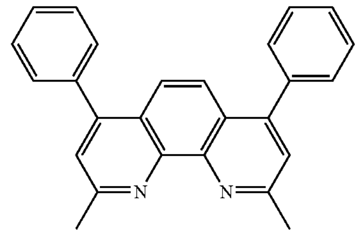

BCP

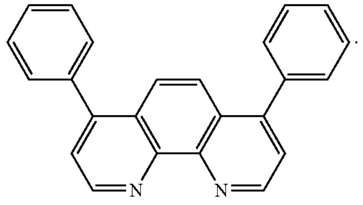

Bphen

A thickness of the hole blocking layer may be in a range of about 20 Å to about 1,000 Å, for example, about 30 Å to about 300 Å. When the thickness of the hole blocking layer is within this range, excellent hole blocking characteristics may be obtained without a substantial increase in driving voltage.

The electron transport region may include an electron transport layer. The electron transport layer may be formed on the emission layer or the hole blocking layer by using a suitable method, such as vacuum deposition, spin coating, casting, LB method, ink-jet printing, laser-printing, or LITI. When the electron transport layer is formed by using vacuum deposition or spin coating, vacuum deposition and coating conditions for the electron transport layer may be determined by referring to the vacuum deposition and coating conditions for the hole injection layer.

In some embodiments, the organic layer 150 of the organic light-emitting device may include an electron transport region disposed between the emission layer and the second electrode 190. The electron transport region may include, for example, at least one selected from an electron transport layer and an electron injection layer.

The thickness of the electron transport layer may be in a range of about 100 Å to about 1,000 Å, for example, about 150 Å to about 500 Å. When the thickness of the electron transport layer is within this range, excellent electron transport characteristics may be obtained without a substantial increase in driving voltage.

The electron transport layer may further include a metal-containing material, in addition to the second compound.

The metal-containing material may include a Li complex. The Li complex may include, for example, Compound ET-D1 (lithium quinolate, LiQ) or ET-D2:

ET-D1

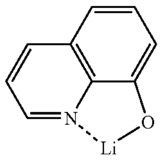

-continued

ET-D2

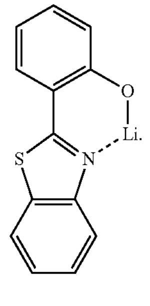

The electron transport region may include an electron injection layer that facilitates electron injection from the second electrode 190.

The electron injection layer may be formed on the electron transport layer by a suitable method, such as vacuum-deposition, spin coating, casting, LB method, ink-jet printing, laser-printing, or LITI. When the electron injection layer is formed by vacuum-deposition or spin coating, vacuum-deposition and coating conditions for the electron injection layer may be determined by referring to the vacuum-deposition and coating conditions for the hole injection layer.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. When the thickness of the electron injection layer is within this range, excellent electron injection characteristics may be obtained without a substantial increase in driving voltage.

The second electrode 190 may be on the electron transport region 170. The second electrode 190 may be a cathode that is an electron injection electrode, and in this regard, a material for forming the second electrode 190 may be a material having a low work function, and such a material may be metal, alloy, an electrically conductive compound, or a mixture thereof. Examples of the second electrode 190 include lithium (Li), magnesium (Mg), aluminum (Al), aluminum-lithium (Al—Li), calcium (Ca), magnesium-indium (Mg—In), and magnesium-silver (Mg—Ag). In some embodiments, the material for forming the second electrode 190 may be ITO or IZO. The second electrode 190 may be a reflective electrode, a semi-transmissive electrode, or a transmissive electrode.

The term "$C_1$-$C_{60}$ alkyl group" used herein refers to a linear or branched aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" used herein refers to a divalent group having the same structure as a $C_1$-$C_{60}$ alkyl group.

The term "$C_1$-$C_{60}$ alkoxy group" used herein refers to a monovalent group represented by —$OA_{101}$ (wherein $A_{101}$ is the $C_1$-$C_{60}$ alkyl group). Examples thereof include a methoxy group, an ethoxy group, and an isopropyloxy group.

The term "$C_2$-$C_{60}$ alkenyl group" used herein refers to a hydrocarbon group formed by substituting at least one carbon double bond in the middle or at the terminal of the $C_2$-$C_{60}$ alkyl group. Examples thereof include an ethenyl group, a propenyl group, and a butenyl group. The term "$C_2$-$C_{60}$ alkenylene group" used herein refers to a divalent group having the same structure as a $C_2$-$C_{60}$ alkenyl group.

The term "$C_2$-$C_{60}$ alkynyl group" used herein refers to a hydrocarbon group formed by substituting at least one carbon triple bond in the middle or at the terminal of the $C_2$-$C_{60}$ alkyl group. Examples thereof include an ethynyl group and a propynyl group. The term "$C_2$-$C_{60}$ alkynylene group" used herein refers to a divalent group having the same structure as a $C_2$-$C_{60}$ alkynyl group.

The term "$C_3$-$C_{10}$ cycloalkyl group" used herein refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" used herein refers to a divalent group having the same structure as a $C_3$-$C_{10}$ cycloalkyl group.

The term "$C_1$-$C_{10}$ heterocycloalkyl group" used herein refers to a monovalent monocyclic group including at least one heteroatom selected from N, O, P, and S as a ring-forming atom and 1 to 10 carbon atoms. Examples thereof include a tetrahydrofuranyl group and a tetrahydrothiophenyl group. The term "$C_1$-$C_{10}$ heterocycloalkylene group" used herein refers to a divalent group having the same structure as a $C_1$-$C_{10}$ heterocycloalkyl group.

The term "$C_3$-$C_{10}$ cycloalkenyl group" used herein refers to a monovalent monocyclic group that has 3 to 10 carbon atoms and at least one double bond in its ring, and which is not aromatic. Examples thereof include a cyclopentenyl group, a cyclohexenyl group, and a cycloheptenyl group. The term "$C_3$-$C_{10}$ cycloalkenylene group" used herein refers to a divalent group having the same structure as a $C_3$-$C_{10}$ cycloalkenyl group.

The term "$C_1$-$C_{10}$ heterocycloalkenyl group" used herein refers to a monovalent monocyclic group including at least one heteroatom selected from N, O, P, and S as a ring-forming atom, 1 to 10 carbon atoms, and at least one double bond in its ring. Examples of the $C_1$-$C_{10}$ heterocycloalkenyl group include a 2,3-hydrofuranyl group and a 2,3-hydrothiophenyl group. The term "$C_1$-$C_{10}$ heterocycloalkenylene group" used herein refers to a divalent group having the same structure as a $C_1$-$C_{10}$ heterocycloalkenyl group.

The term "$C_6$-$C_{60}$ aryl group" used herein refers to a monovalent group including a carbocyclic aromatic system having 6 to 60 carbon atoms. The term "$C_6$-$C_{60}$ arylene group" used herein refers to a divalent group including a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group or the $C_6$-$C_{60}$ arylene group include a plurality of rings, the rings may be fused to each other.

The term "$C_1$-$C_{60}$ heteroaryl group" used herein refers to a monovalent group having a carbocyclic aromatic system including at least one hetero atom selected from N, O, P, and S as a ring-forming atom and 1 to 60 carbon atoms. The term "$C_1$-$C_{60}$ heteroarylene group" used herein refers to a divalent group having a carbocyclic aromatic system including at least one hetero atom selected from N, O, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group or the $C_1$-$C_{60}$ heteroarylene group include a plurality of rings, the rings may be fused to each other.

The term "$C_6$-$C_{60}$ aryloxy group" used herein indicates —$OA_{102}$ (wherein $A_{102}$ is the $C_6$-$C_{60}$ aryl group). The term "$C_6$-$C_{60}$ arylthio group" used herein indicates —$SA_{103}$ (wherein $A_{103}$ is the $C_6$-$C_{60}$ aryl group).

The term "monovalent non-aromatic condensed polycyclic group" used herein refers to a monovalent group that has two or more rings condensed to each other, and has only carbon atoms (for example, the number of carbon atoms may be in a range of 8 to 60) as ring forming atoms, wherein the molecular structure as a whole is non-aromatic in the entire molecular structure. An example of the monovalent non-aromatic condensed polycyclic group is a fluorenyl group. The term "divalent non-aromatic condensed polycyclic group" used herein refers to a divalent group having the same structure as the monovalent non-aromatic condensed polycyclic group.

The term "monovalent non-aromatic condensed heteropolycyclic group" used herein refers to a monovalent group that has two or more rings condensed to each other, and has a heteroatom selected from N, O, P, and S, other than carbon atoms (for example, the number of carbon atoms may be in a range of 2 to 60), as ring-forming atoms, wherein the molecular structure as a whole is non-aromatic in the entire molecular structure. An example of a monovalent non-aromatic condensed heteropolycyclic group is a carbazolyl group. The term "divalent non-aromatic condensed hetero-polycyclic group" used herein refers to a divalent group having the same structure as the monovalent non-aromatic condensed hetero-polycyclic group.

In the present specification, at least one of the substituents of the substituted $C_6$-$C_{20}$ aromatic ring, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group (arylthio), a $C_1$-$C_{60}$ heteroaryl group, a monovalent non-aromatic condensed polycyclic group, a monovalent non-aromatic condensed heteropolycyclic group, and —$Si(Q_{11})(Q_{12})(Q_{13})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{21})(Q_{22})(Q_{23})$, and —$Si(Q_{31})(Q_{32})(Q_{33})$, wherein $Q_1$ to $Q_3$, $Q_{11}$ to $Q_{13}$, $Q_{21}$ to $Q_{23}$ and $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In some embodiments, at least one of the substituents of the substituted $C_6$-$C_{20}$ aromatic ring, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{11}$)($Q_{12}$)($Q_{13}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a Spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{21}$)($Q_{22}$)($Q_{23}$); and —Si($Q_{31}$)($Q_{32}$)($Q_{33}$);

wherein $Q_{11}$ to $Q_{13}$, $Q_{21}$ to $Q_{23}$, and $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

Hereinafter, an organic light-emitting device according to an embodiment will be described in detail with reference to Synthesis Examples and Examples. The wording "B was used instead of A" used in describing Synthesis Examples means that a molar equivalent of A was identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Example 1

For an anode, an ITO glass substrate (a product of Corning Co., Ltd) with an ITO layer having a thickness of 15 Ω/$cm^2$ (1,200 Å) thereon was cut to a size of 50 mm×50 mm×0.7 mm. Then, the substrate was sonicated using isopropyl alcohol and pure water each for 5 minutes, and cleaned by exposure to ultraviolet rays for 30 minutes, and then ozone. Then, the ITO glass substrate was mounted on a vacuum deposition apparatus.

Compound 1 and F4-TCNQ were co-vacuum-deposited on the ITO anode to form a hole injection layer having a thickness of about 200 Å. Then, Compound 1 was vacuum-deposited on the hole injection layer to form a hole transport layer having a thickness of about 1,000 Å Then, Compound H1-a (host) and FD9 (fluorescent dopant) were co-vacuum-deposited on the hole transport layer in a weight ratio of about 95:5 to form an emission layer having a thickness of about 200 Å.

Thereafter, Compound A4 and Liq were co-vacuum-deposited on the emission layer to form an electron transport layer having a thickness of 300 Å. Then, LiF was vacuum-deposited on the electron transport layer to form an electron injection layer having a thickness of 10 Å. Then, Al was vacuum-deposited on the electron injection layer to form a cathode having a thickness of 1,000 Å, thereby completing the manufacture of an organic light-emitting device.

Example 2

An organic light-emitting device was manufactured in the same manner as in Example 1, except that in forming a hole injection layer and a hole transport layer, Compound 2 was used instead of Compound 1.

Example 3

An organic light-emitting device was manufactured in the same manner as in Example 1, except that in forming a hole injection layer and a hole transport layer, Compound 3 was used instead of Compound 1.

Example 4

For an anode, an ITO glass substrate (a product of Corning Co., Ltd) with an ITO layer having a thickness of 15 Ω/$cm^2$ (1,200 Å) thereon was cut to a size of 50 mm×50 mm×0.7 mm. Then, the substrate was sonicated using isopropyl alcohol and pure water each for 5 minutes, and cleaned by exposure to ultraviolet rays for 30 minutes, and then ozone. Then, the ITO glass substrate was mounted on a vacuum deposition apparatus.

Compound HT-2 and F4-TCNQ were co-vacuum-deposited on the ITO anode to form a hole injection layer having a thickness of about 200 Å. Then, Compound HT-2 was vacuum-deposited on the hole injection layer to form a hole transport layer having a thickness of about 1000 Å.

Compound 24 was vacuum-deposited on the hole transport layer to form an auxiliary emission layer having a thickness of about 100 Å.

Compound H1-a (host) and FD9 (fluorescent dopant) were co-vacuum-deposited on the auxiliary emission layer in a weight ratio of about 95:5 to form an emission layer having a thickness of about 200 Å.

Thereafter, Compound A4 and Liq were co-vacuum-deposited on the emission layer to form an electron transport layer having a thickness of 300 Å. Then, LiF was vacuum-deposited on the electron transport layer to form an electron injection layer having a thickness of 10 Å. Then, Al was vacuum-deposited on the electron injection layer to form a cathode having a thickness of 1,000 Å, thereby completing the manufacture of an organic light-emitting device.

HT2

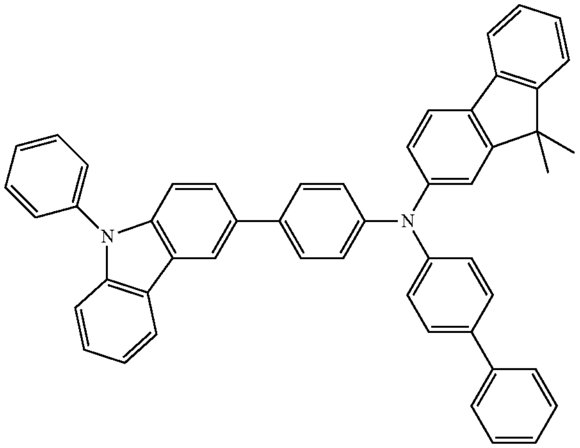

Example 5

An organic light-emitting device was manufactured in the same manner as in Example 4, except that in forming an emission layer, Compound H-11b, Compound H-141a, and PD14 (phosphorescent dopant) were co-vacuum-deposited, instead of Compound H1-a and FD9, in a weight ratio of about 45:45:10.

Example 6

An organic light-emitting device was manufactured in the same manner as in Example 4, except that in forming an emission layer, Compound H-124c, Compound H-128a, and PD18 (phosphorescent dopant) were co-vacuum-deposited, instead of Compound H1-a and FD9, in a weight ratio of about 45:45:10.

Example 7

An organic light-emitting device was manufactured in the same manner as in Example 4, except that in forming an emission layer, Compound H-124c, Compound H-128a, and PD19 (phosphorescent dopant) were co-vacuum-deposited, instead of Compound H1-a and FD9, in a weight ratio of about 45:45:10.

Example 8

An organic light-emitting device was manufactured in the same manner as in Example 4, except that in forming an auxiliary emission layer, Compound 7 was used instead of Compound 24.

Example 9

An organic light-emitting device was manufactured in the same manner as in Example 4, except that in forming an auxiliary emission layer, Compound 25 was used instead of Compound 24.

Example 10

An organic light-emitting device was manufactured in the same manner as in Example 4, except that in forming an auxiliary emission layer, Compound 29 was used instead of Compound 24.

Example 11

An organic light-emitting device was manufactured in the same manner as in Example 4, except that in forming an electron transport layer, Compound A8 was used instead of Compound A4.

Example 12

An organic light-emitting device was manufactured in the same manner as in Example 4, except that in forming an electron transport layer, Compound A12 was used instead of Compound A4.

Example 13

An organic light-emitting device was manufactured in the same manner as in Example 4, except that in forming an electron transport layer, Compound A14 was used instead of Compound A4.

Example 14

An organic light-emitting device was manufactured in the same manner as in Example 4, except that in forming an electron transport layer, Compound A18 was used instead of Compound A4.

Example 15

An organic light-emitting device was manufactured in the same manner as in Example 4, except that in forming an electron transport layer, Compound A19 was used instead of Compound A4.

Example 16

An organic light-emitting device was manufactured in the same manner as in Example 4, except that in forming an electron transport layer, Compound A26 was used instead of Compound A4.

Comparative Example 1

An organic light-emitting device was manufactured in the same manner as in Example 4, except that in forming an auxiliary emission layer, Compound X1 was used instead of Compound 24, and in forming an electron transport layer, Compound Y1 was used instead of Compound A4.

Comparative Example 2

An organic light-emitting device was manufactured in the same manner as in Example 4, except that in forming an auxiliary emission layer, Compound X2 was used instead of Compound 24, and in forming an electron transport layer, Compound Y2 was used instead of Compound A4.

Comparative Example 3

An organic light-emitting device was manufactured in the same manner as in Example 4, except that in forming an auxiliary emission layer, Compound X3 was used instead of Compound 24, and in forming an electron transport layer, Compound Y2 was used instead of Compound A4.

Comparative Example 4

An organic light-emitting device was manufactured in the same manner as in Example 4, except that in forming an auxiliary emission layer, Compound X4 was used instead of Compound 24.

Evaluation Example 1

The driving voltage, efficiency, and lifespan (800 nit) of the organic light-emitting devices manufactured according to Examples 1 to 16 and Comparative Examples 1 to 4 were evaluated. The results thereof are shown in Table 1. A Keithley 2400 current voltmeter and a PR650 Spectroscan Source Measurement Unit luminance meter (available from PhotoResearch) were used in evaluation. The term "lifespan" used herein indicates a period of time required for the luminance of the organic light-emitting device to reach 95% with respect to an initial luminance. Here, the efficiency and lifespan of the organic light-emitting devices manufactured according to Examples 2 to 16 and Comparative Examples 1 to 4 were described as a comparison, based on the value of efficiency and lifespan of the organic light-emitting device according to Example 1, which was determined as 1.

TABLE 1

| | Hole transport layer | Emission auxiliary layer | Electron transport layer | Emission layer | | Driving voltage (V) | Efficiency | Lifetime |
|---|---|---|---|---|---|---|---|---|
| | | | | Host | Dopant | | | |
| Example 1 | Compound 1 | Compound 1 | Compound A4 | Compound H-1a | FD9 | 4.5 | 1 | 1 |
| Example 2 | Compound 2 | Compound 2 | Compound A4 | Compound H-1a | FD9 | 4.3 | 1.1 | 1 |
| Example 3 | Compound 3 | Compound 3 | Compound A4 | Compound H-1a | FD9 | 4.3 | 1.1 | 1.1 |
| Example 4 | Compound HT-2 | Compound 24 | Compound A4 | Compound H-1a | FD9 | 4.1 | 1.2 | 1 |
| Example 5 | Compound HT-2 | Compound 24 | Compound A4 | Compound H-11b + Compound H-141a | PD14 | 4.7 | 1 | 1 |
| Example 6 | Compound HT-2 | Compound 24 | Compound A4 | Compound H-124c + Compound H-128a | PD18 | 4.6 | 1.2 | 1 |
| Example 7 | Compound HT-2 | Compound 24 | Compound A4 | Compound H-124c + Compound H-128a | PD19 | 4.6 | 1.1 | 1 |
| Example 8 | Compound HT-2 | Compound 7 | Compound A4 | Compound H-1a | FD9 | 4.8 | 1.1 | 1.1 |
| Example 9 | Compound HT-2 | Compound 25 | Compound A4 | Compound H-1a | FD9 | 4.1 | 1.3 | 1.1 |
| Example 10 | Compound HT-2 | Compound 29 | Compound A4 | Compound H-1a | FD9 | 4.2 | 1.2 | 1.1 |
| Example 11 | Compound HT-2 | Compound 24 | Compound A8 | Compound H-1a | FD9 | 4.2 | 1.1 | 1 |
| Example 12 | Compound HT-2 | Compound 24 | Compound A12 | Compound H-1a | FD9 | 4.3 | 1 | 1.1 |
| Example 13 | Compound HT-2 | Compound 24 | Compound A14 | Compound H-1a | FD9 | 4.3 | 1.2 | 1.1 |
| Example 14 | Compound HT-2 | Compound 24 | Compound A18 | Compound H-1a | FD9 | 4.0 | 1.3 | 1 |
| Example 15 | Compound HT-2 | Compound 24 | Compound A19 | Compound H-1a | FD9 | 4.1 | 1.2 | 1.1 |
| Example 16 | Compound HT-2 | Compound 24 | Compound A26 | Compound H-1a | FD9 | 4.1 | 1.2 | 1.2 |
| Comparative Example 1 | Compound HT-2 | Compound X1 | Compound Y1 | Compound H-1a | FD9 | 5.2 | 0.9 | 0.8 |
| Comparative Example 2 | Compound HT-2 | Compound X2 | Compound Y2 | Compound H-1a | FD9 | 5.4 | 0.8 | 0.7 |
| Comparative Example 3 | Compound HT-2 | Compound X3 | Compound Y2 | Compound H-1a | FD9 | 5.4 | 0.8 | 0.8 |
| Comparative Example 4 | Compound HT-2 | Compound X4 | Compound A4 | Compound H-1a | FD9 | 5.3 | 0.9 | 0.8 |

1

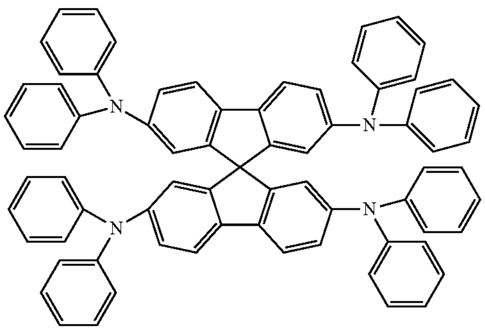

2

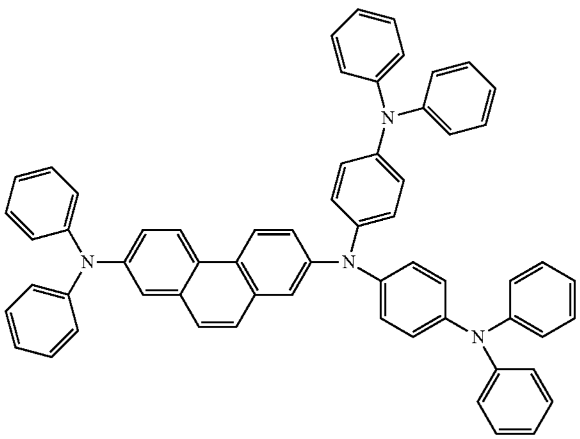

-continued
3
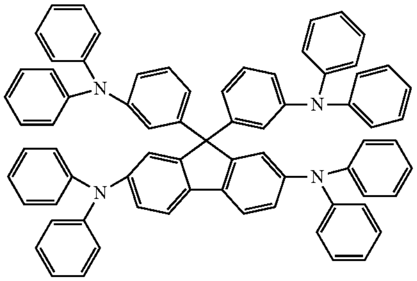
7
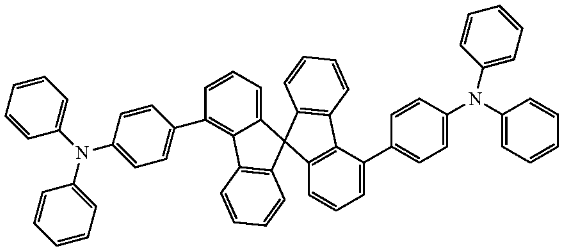
24
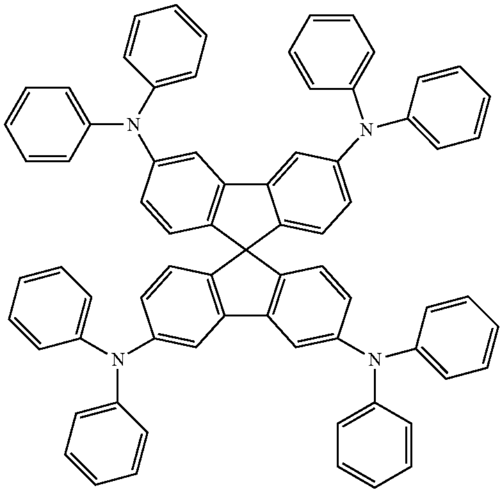
25
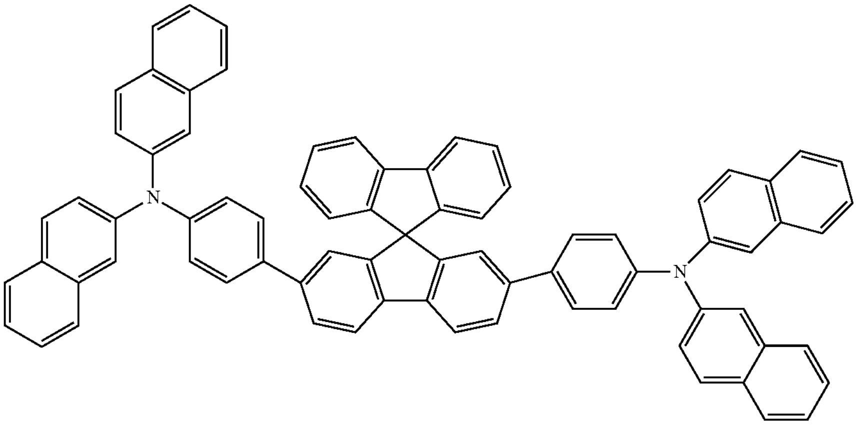
29
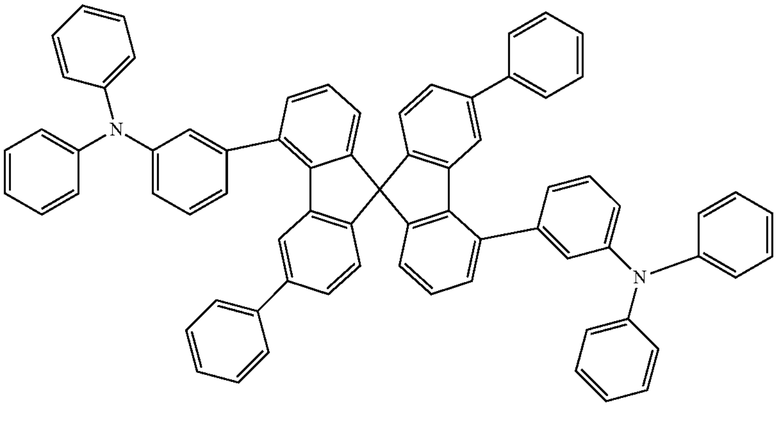

-continued
A4
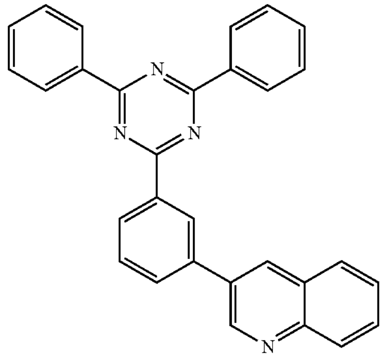
A8
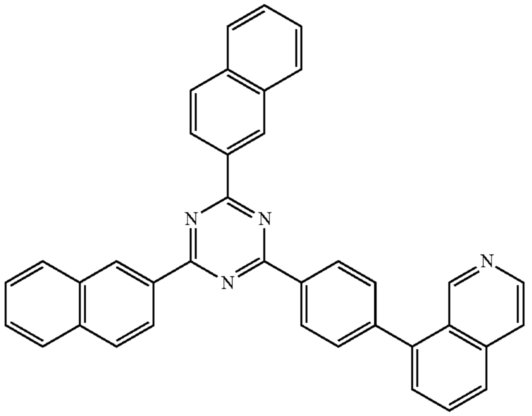
A12
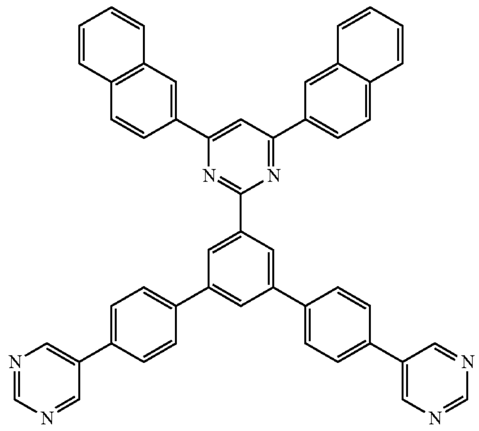
A14
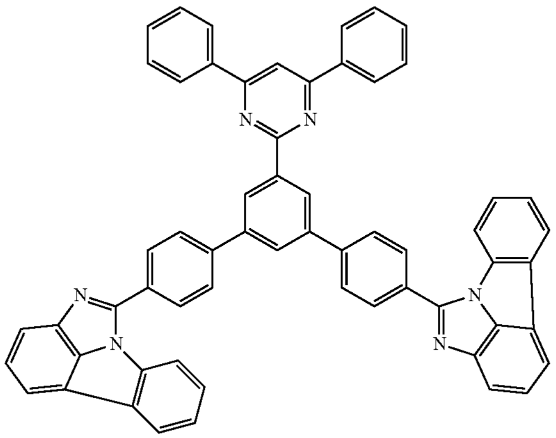
A18
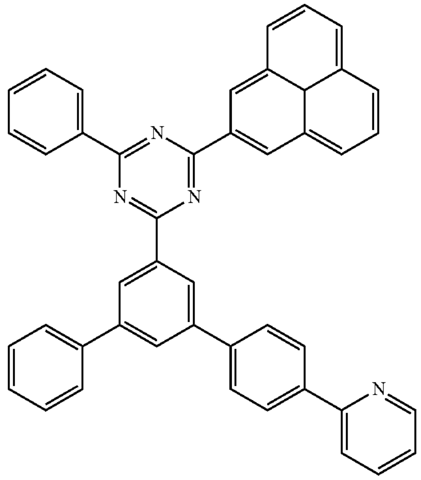
A19
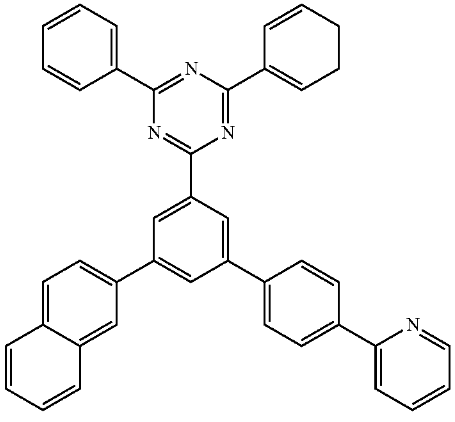

-continued
A26
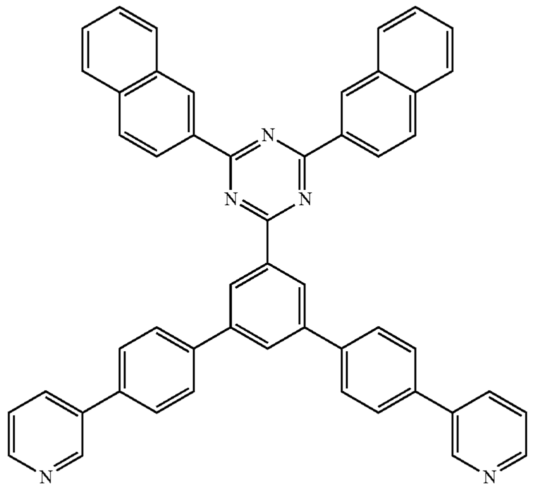
H-1a
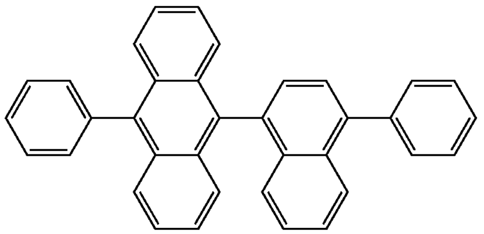
H-128a
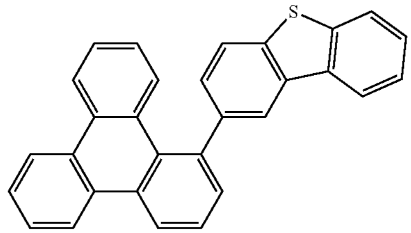
H-141a
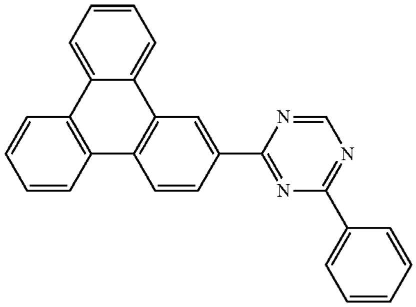
H-11b
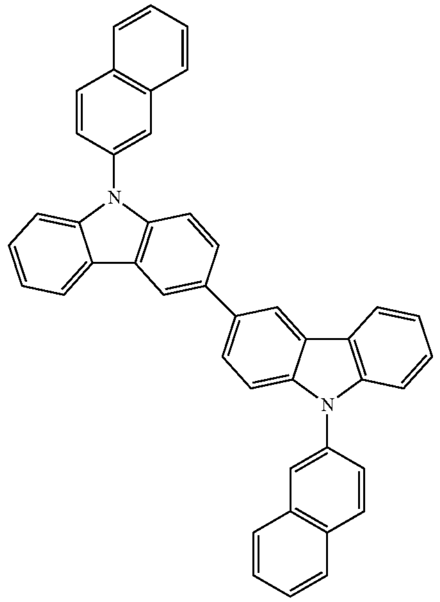
H-124c
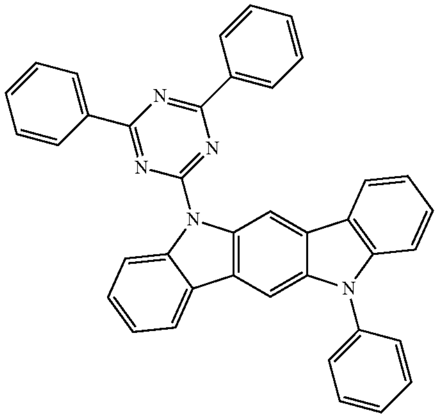

-continued

Compound X1

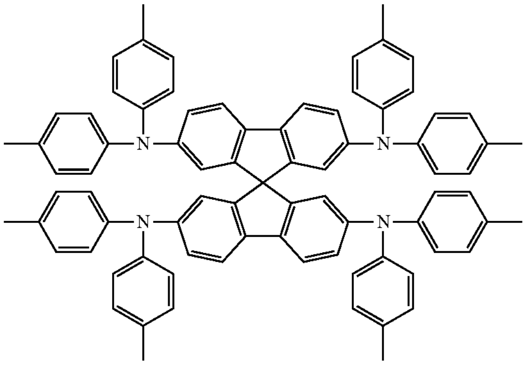

Compound X2

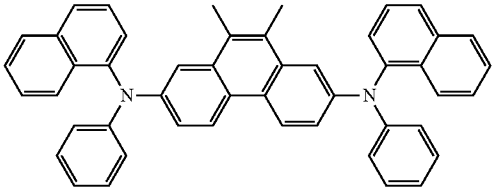

Compound X3

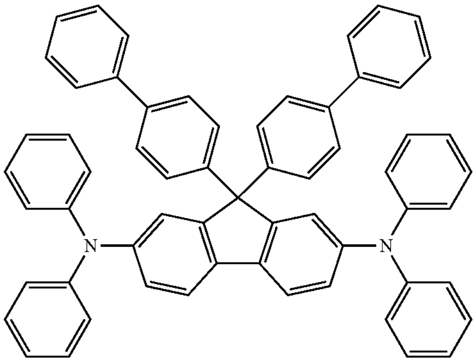

Compound X4

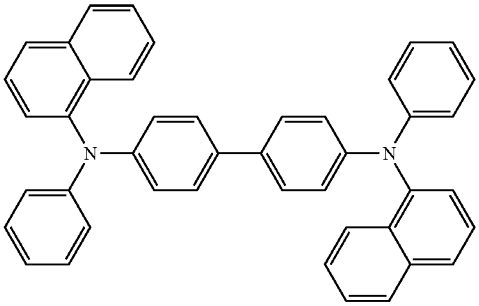

Compound Y1

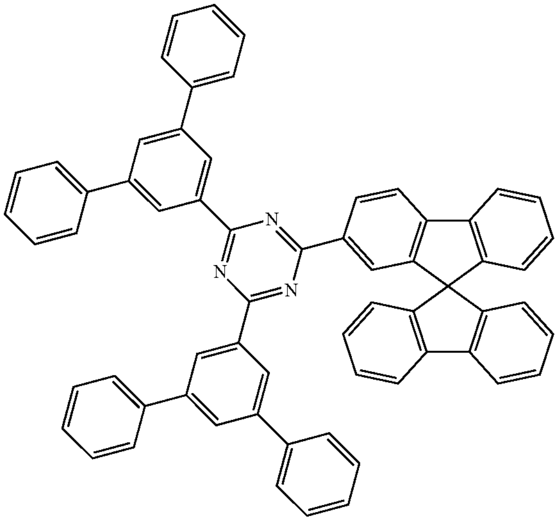

Compound Y2

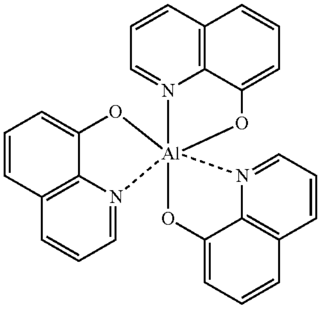

Example 17

An organic light-emitting device was manufactured in the same manner as in Example 4, except that in forming an auxiliary emission layer, Compound 7 was used instead of Compound 24, and in forming an emission layer, FD19 was used instead of FD9 as a dopant.

Comparative Example 5

An organic light-emitting device was manufactured in the same manner as in Example 4, except that in forming an auxiliary emission layer, Compound X4 was used instead of Compound 24, and in forming an emission layer, PD14 was used instead of FD9 as a dopant.

Evaluation Example 2

The efficiency at a voltage of 4V of the organic light-emitting devices according to Examples 5 to 7 and 17 and Comparative Example 5 were evaluated by using a PR650 Spectroscan Source Measurement Unit. (available from PhotoResearch) luminance meter. The results thereof are shown in Table 2. Here, the efficiency of the organic light-emitting devices according to Example 6 to 7 and 17 and Comparative Example 5 were described as a comparison, based on the value of the efficiency of the organic light-emitting device according to Example 5, which was determined as 1.

TABLE 2

| | Hole transport layer | Emission auxiliary layer | electron transport layer | Emission layer Host | Emission layer Dopant | Efficiency |
|---|---|---|---|---|---|---|
| Example 5 | Compound HT-2 | Compound 24 | Compound A4 | Compound H-11b + Compound H-141a | PD14 | 1 |
| Example 6 | Compound HT-2 | Compound 24 | Compound A4 | Compound H-124c + Compound H-128a | PD18 | 1 |
| Example 7 | Compound HT-2 | Compound 24 | Compound A4 | Compound H-124c + Compound H-128a | PD19 | 1 |
| Example 17 | Compound HT-2 | Compound 7 | Compound A4 | Compound H-1a | PD19 | 1 |
| Comparative Example 5 | Compound HT-2 | Compound X4 | Compound A4 | Compound H-1a | PD14 | 0.8 |

Referring to Tables 1 and 2, it was found that the organic light-emitting devices according to Examples 1 to 17 exhibited low driving voltage, improved emission efficiency compared to the organic light-emitting devices according to Comparative Examples 1 to 5. The organic light-emitting devices according to Examples 1 to 17 exhibited low driving voltage, even at a low voltage.

As described above, according to the one or more of the above exemplary embodiments, the organic light-emitting device may have low driving voltage, improved efficiency, improved luminance, and long lifespan characteristics.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the FIGURES, it will be understood by those of ordinary skill in the art that various changes in form and details may be made therein without departing from the spirit and scope as defined by the following claims.

What is claimed is:

1. An organic light-emitting device, comprising:

a first electrode;

a second electrode facing the first electrode;

an emission layer between the first electrode and the second electrode;

a hole transport region between the first electrode and the emission layer; and an electron transport region between the second electrode and the emission layer, wherein the hole transport region includes a first compound represented by one of Formulae 1A, 1B, and 1C, and the electron transport region includes a second compound represented by one of Formulae 40A and 40B:

<Formula 1A>

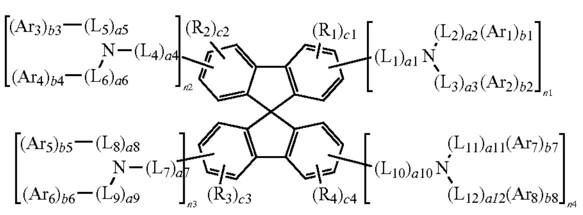

-continued

<Formula 1B>

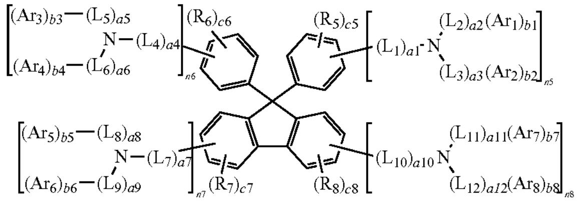

<Formula 1C>

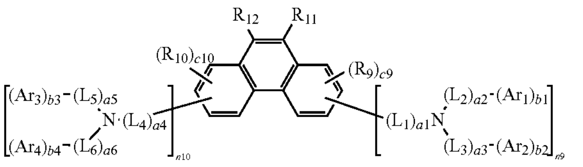

<Formula 40A>

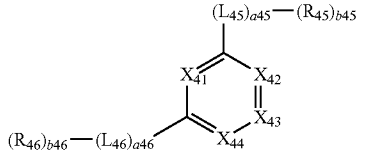

<Formula 40B>

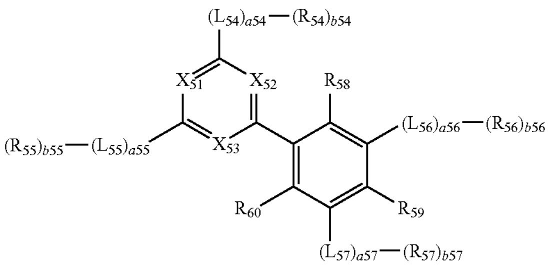

wherein, in Formulae 1A, 1B, 1C, 40A, and 40B, $X_{41}$ is N or C-$(L_{41})_{a41}$-$(R_{41})_{b41}$, $X_{42}$ is N or C-$(L_{42})_{a42}$-$(R_{42})_{b42}$, $X_{43}$ is N or C-$(L_{43})_{a43}$-$(R_{43})_{b43}$, $X_{44}$ is N or C-$(L_{44})_{a44}$-$(R_{44})_{b44}$, and at least one selected from $X_{41}$ to $X_{44}$ is N;

$X_{51}$ is N or C-$(L_{51})_{a51}$-$(R_{51})_{b51}$, $X_{52}$ is N or C-$(L_{52})_{a52}$-$(R_{52})_{b52}$, $X_{53}$ is N or C-$(L_{53})_{a53}$-$(R_{53})_{b53}$, and at least one selected from $X_{51}$ to $X_{53}$ is N;

$L_1$ to $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

$L_{41}$ to $L_{46}$ and $L_{51}$ to $L_{57}$ are each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent non-aromatic condensed polycyclic group;

a1 to a12, a41 to a46, and a51 to a57 are each independently an integer selected from 0 to 3;

$Ar_1$ to $Ar_8$, $R_{41}$ to $R_{46}$, and $R_{51}$ to $R_{57}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$Ar_1$ and $Ar_2$ are optionally linked to each other to form a saturated or unsaturated ring, $Ar_3$ and $Ar_4$ are optionally linked to each other to form a saturated or unsaturated ring, $Ar_5$ and $Ar_6$ are optionally linked to each other to form a saturated or unsaturated ring, and $Ar_7$ and $Ar_8$ are optionally linked to each other to form a saturated or unsaturated ring;

at least one of $R_{41}$ to $R_{46}$ or at least one of $R_{51}$ to $R_{57}$ is selected from a substituted or unsubstituted $C_1$-$C_{10}$ heterocycloalkyl group, a substituted or unsubstituted $C_1$-$C_{10}$ heterocycloalkenyl group, a substituted or unsubstituted $C_1$-$C_{60}$ heteroaryl group, and a substituted or unsubstituted monovalent non-aromatic condensed heteropolycyclic group;

b1 to b8, b41 to b46, and b51 to b57 are each independently an integer selected from 1 to 4;

$R_1$ to $R_{12}$ and $R_{58}$ to $R_{60}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —$Si(Q_1)(Q_2)(Q_3)$;

$R_{11}$ and $R_{12}$ are optionally linked to each other to form a saturated or unsaturated ring;

c1 to c10 are each independently an integer selected from 0 to 4;

n1 to n4 and n7 to n10 are each independently an integer selected from 0 to 4, and n5 and n6 are each independently an integer selected from 0 to 5, provided that n1+n2+n3+n4 is 1 or more, n5+n6+n7+n8 is 1 or more, and n9+n10 is 1 or more;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group(arylthio), a $C_1$-$C_{60}$ heteroaryl group, a monovalent non-aromatic condensed polycyclic group, a monovalent non-aromatic condensed heteropolycyclic group, and —$Si(Q_{11})(Q_{12})(Q_{13})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{21})(Q_{22})(Q_{23})$; and —$Si(Q_{31})(Q_{32})(Q_{33})$, wherein $Q_1$ to $Q_3$, $Q_{11}$ to $Q_{13}$, $Q_{21}$ to $Q_{23}$, and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The organic light-emitting device as claimed in claim 1, wherein:

the second compound is represented by Formula 40A, and in Formula 40A, $X_{41}$, $X_{42}$, and $X_{44}$ are N, and $X_{43}$ is $C(R_{43})$;

$X_{41}$ and $X_{44}$ are N, $X_{42}$ is $C(R_{42})$, and $X_{43}$ is $C(R_{43})$; or $X_{41}$ and $X_{43}$ are N, $X_{42}$ is $C(R_{42})$, and $X_{44}$ is $C(R_{44})$; or the second compound is represented by Formula 40B and in Formula 40B, $X_{51}$, $X_{52}$, and $X_{53}$ are N; or $X_{52}$ and $X_{53}$ are N, and $X_{51}$ is $C(R_{51})$.

3. The organic light-emitting device as claimed in claim 1, wherein $L_1$ to $L_{12}$, $L_{41}$ to $L_{46}$, and $L_{51}$ to $L_{57}$ are each independently selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dihenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

4. The organic light-emitting device as claimed in claim 1, wherein $L_1$ to $L_{12}$ are each independently selected from groups represented by Formulae 3-1 to 3-41, and $L_{41}$ to $L_{46}$ and $L_{51}$ to $L_{57}$ are each independently selected from groups represented by Formulae 3-1 to 3-9, 3-25, and 3-33 to 3-41:

Formula 3-1

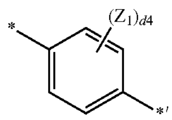

Formula 3-2

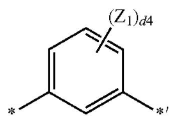

Formula 3-3

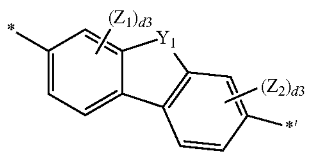

-continued

Formula 3-4

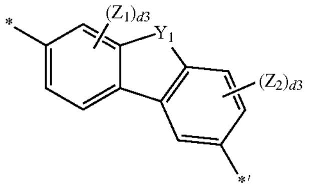

Formula 3-5

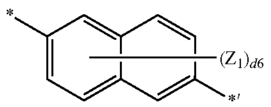

Formula 3-6

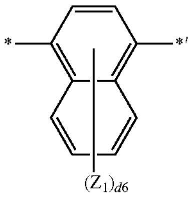

Formula 3-7

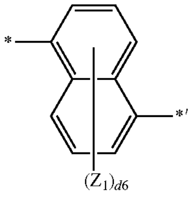

Formula 3-8

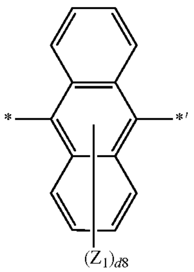

Formula 3-9

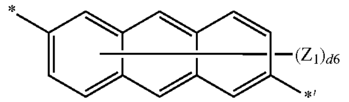

Formula 3-10

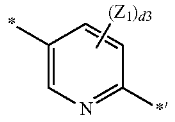

Formula 3-11

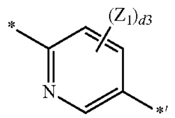

Formula 3-12

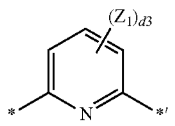

Formula 3-13

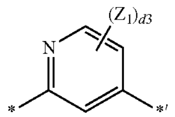

-continued
Formula 3-14
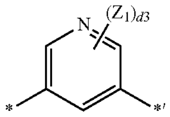
Formula 3-15
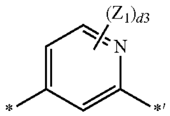
Formula 3-16
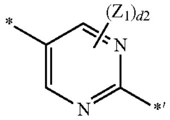
Formula 3-17
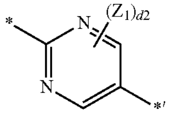
Formula 3-18
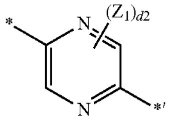
Formula 3-19
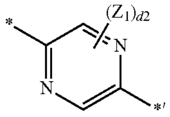
Formula 3-20
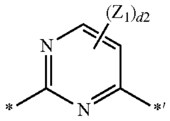
Formula 3-21
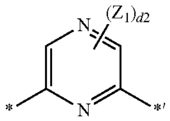
Formula 3-22
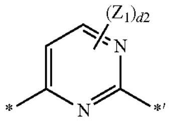
Formula 3-23
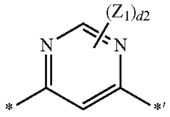
Formula 3-24
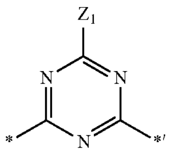
-continued
Formula 3-25
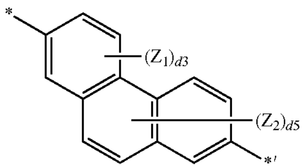
Formula 3-26
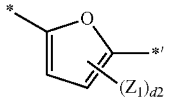
Formula 3-27
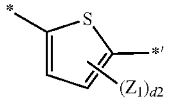
Formula 3-28
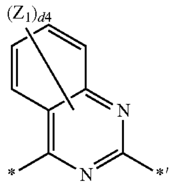
Formula 3-29
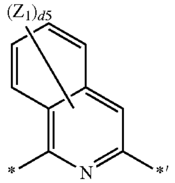
Formula 3-30
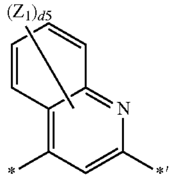
Formula 3-31
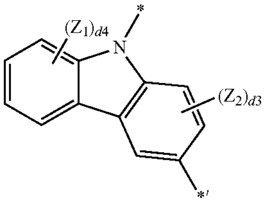
Formula 3-32
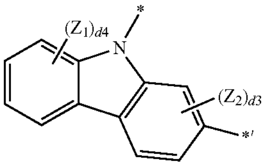
Formula 3-33
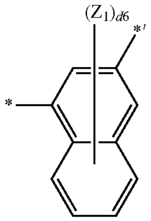

-continued

Formula 3-34

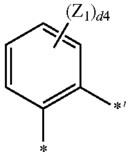

Formula 3-35

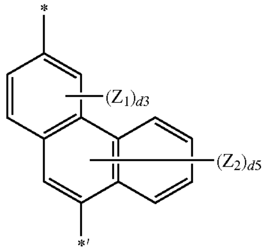

Formula 3-36

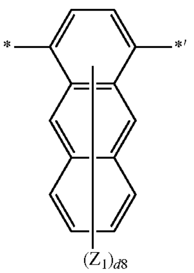

Formula 3-37

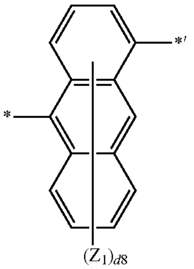

Formula 3-38

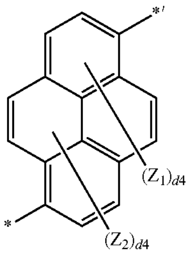

Formula 3-39

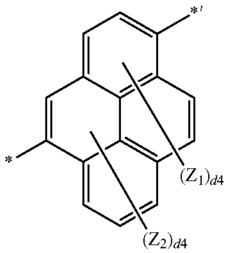

-continued

Formula 3-40

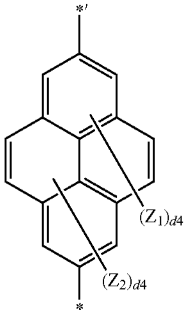

Formula 3-41

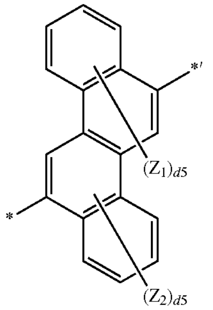

wherein, in Formulae 3-1 to 3-41, $Y_1$ is O, S, $C(Z_3)(Z_4)$, $N(Z_5)$, or $Si(Z_6)(Z_7)$, provided that in Formulae 3-3 and 3-4, $Y_1$=$C(Z_3)(Z_4)$;

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group; and —$Si(Q_{31})(Q_{32})(Q_{33})$, wherein $Q_1$ to $Q_3$ and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group;

d2 is an integer selected from 1 and 2;

d3 is an integer selected from 1 to 3;

d4 is an integer selected from 1 to 4;

d5 is an integer selected from 1 to 5;

d6 is an integer selected from 1 to 6;

d8 is an integer selected from 1 to 8; and

* and *' each indicate a binding site to an adjacent atom.

5. The organic light-emitting device as claimed in claim 1, wherein $L_1$ to $L_{12}$ are each independently selected from groups represented by Formulae 4-1 to 4-36, and $L_{41}$ to $L_{46}$ and $L_{51}$ to $L_{57}$ are each independently selected from groups represented by Formulae 4-1, 4-3, 4-5, 4-7 to 4-13, 4-17, and 4-24 to 4-36:

Formula 4-1

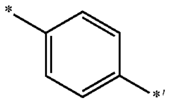

Formula 4-2

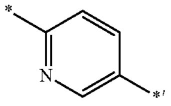

Formula 4-3

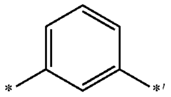

Formula 4-4

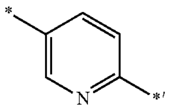

Formula 4-5

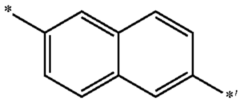

Formula 4-6

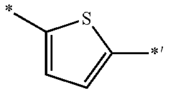

Formula 4-7

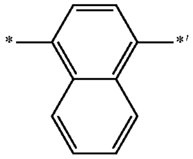

-continued

Formula 4-8

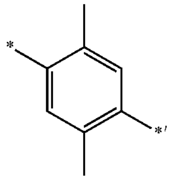

Formula 4-9

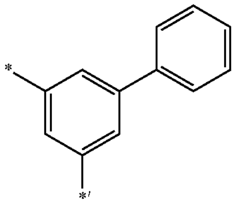

Formula 4-10

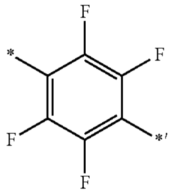

Formula 4-11

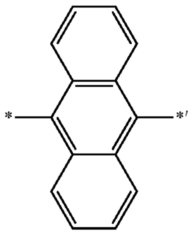

Formula 4-12

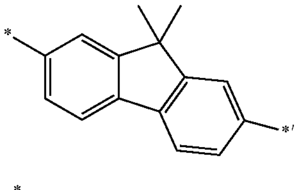

Formula 4-13

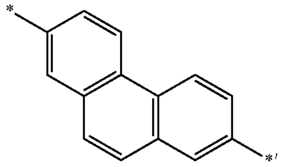

Formula 4-14

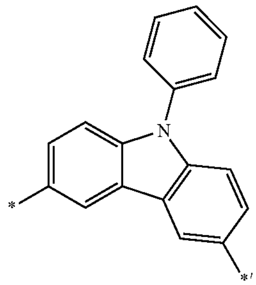

Formula 4-15

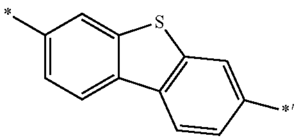

-continued
Formula 4-16
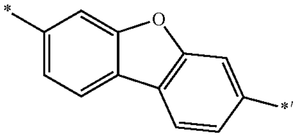
Formula 4-17
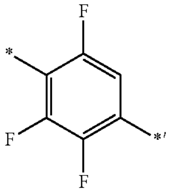
Formula 4-18
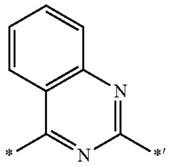
Formula 4-19
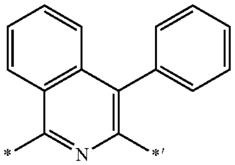
Formula 4-20
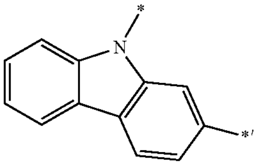
Formula 4-21
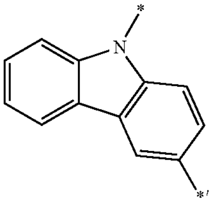
Formula 4-22
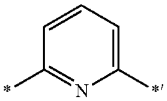
Formula 4-23
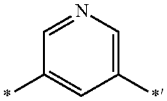
Formula 4-24
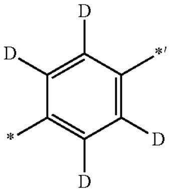
-continued
Formula 4-25
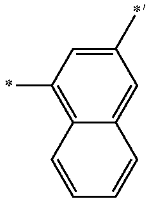
Formula 4-26
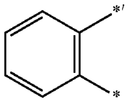
Formula 4-27
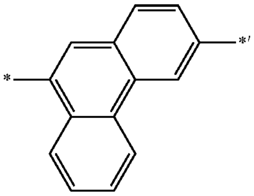
Formula 4-28
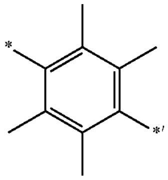
Formula 4-29
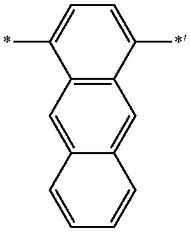
Formula 4-30
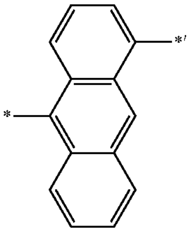
Formula 4-31
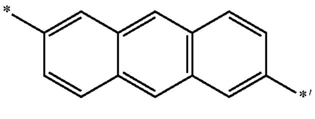
Formula 4-32
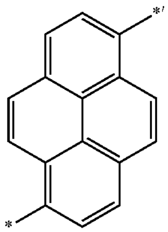

-continued

Formula 4-33

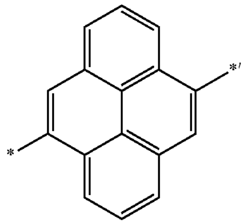

Formula 4-34

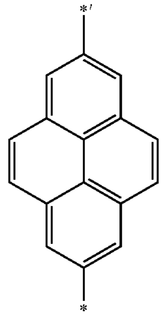

Formula 4-35

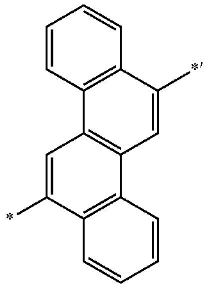

Formula 4-36

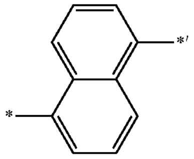

wherein, in Formulae 4-1 to 4-36, *and *' each indicate a binding site to an adjacent atom.

6. The organic light-emitting device as claimed in claim 1, wherein $Ar_1$ to $Ar_8$, $R_{41}$ to $R_{46}$, and $R_{51}$ to $R_{57}$ are each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —$Si(Q_{31})(Q_{32})(Q_{33})$, wherein $Q_{31}$ to $Q_{33}$ are each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

7. The organic light-emitting device as claimed in claim 1, wherein $Ar_1$ to $Ar_8$, $R_{41}$ to $R_{46}$, and $R_{51}$ to $R_{57}$ are each independently selected from groups represented by Formulae 5-1 to 5-87:

Formula 5-1

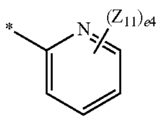

Formula 5-2

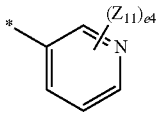

Formula 5-3

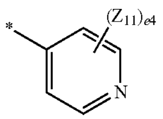

Formula 5-4

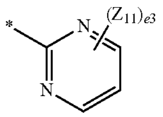

Formula 5-5

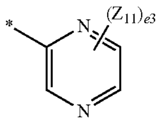

Formula 5-6

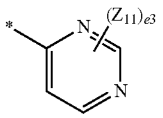

Formula 5-7

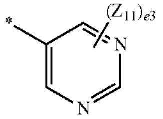

-continued

Formula 5-8

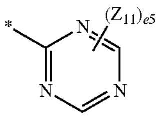

Formula 5-9

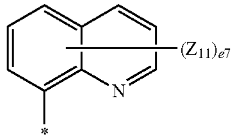

Formula 5-10

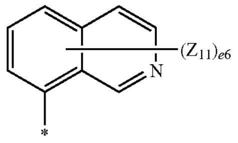

Formula 5-11

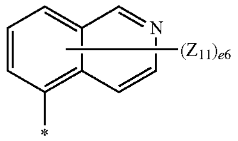

Formula 5-12

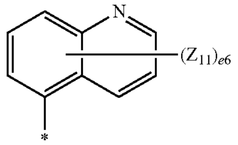

Formula 5-13

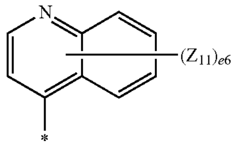

Formula 5-14

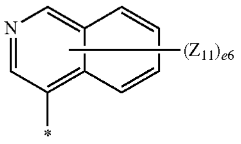

Formula 5-15

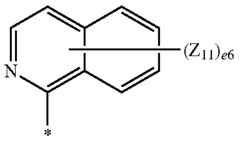

Formula 5-16

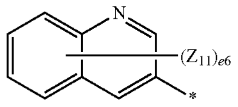

Formula 5-17

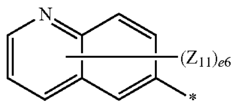

Formula 5-18

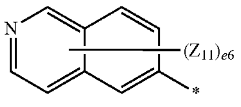

-continued
Formula 5-19
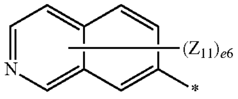
Formula 5-20
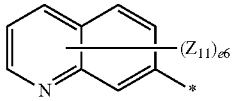
Formula 5-21
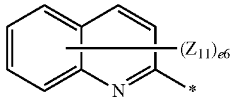
Formula 5-22
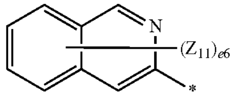
Formula 5-23
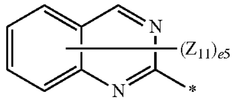
Formula 5-24
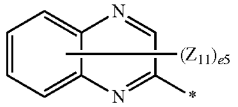
Formula 5-25
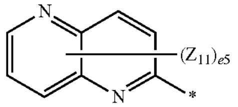
Formula 5-26
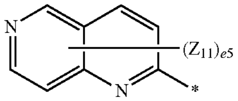
Formula 5-27
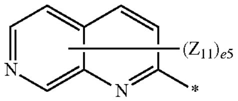
Formula 5-28
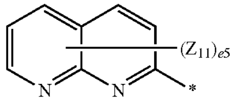
Formula 5-29
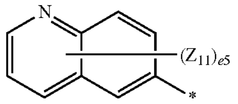
Formula 5-30
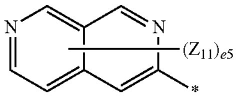
Formula 5-31
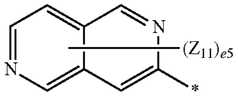
Formula 5-32
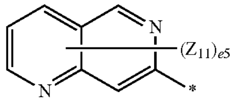
-continued
Formula 5-33
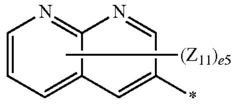
Formula 5-34
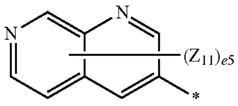
Formula 5-35
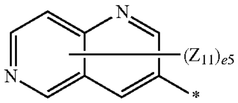
Formula 5-36
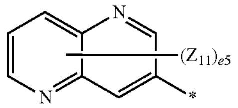
Formula 5-37
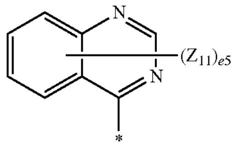
Formula 5-38
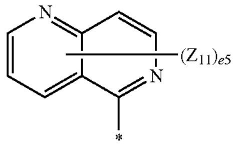
Formula 5-39
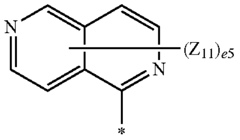
Formula 5-40
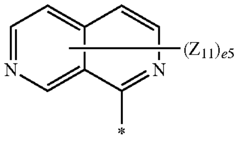
Formula 5-41
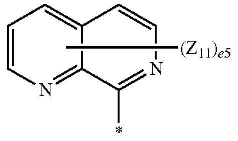
Formula 5-42
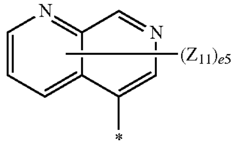
Formula 5-43
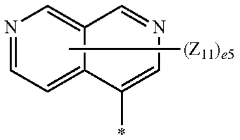

-continued
Formula 5-44
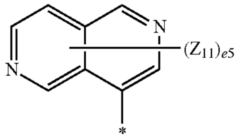
Formula 5-45
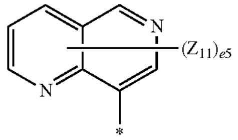
Formula 5-46
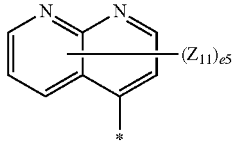
Formula 5-47
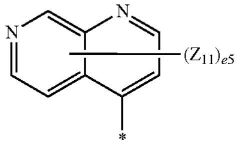
Formula 5-48
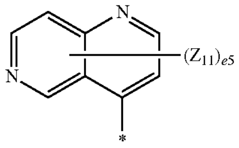
Formula 5-49
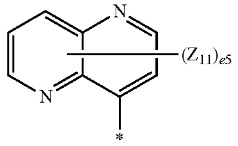
Formula 5-50
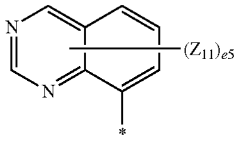
Formula 5-51
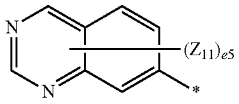
Formula 5-52
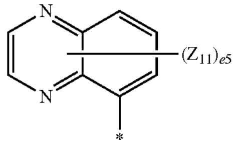
Formula 5-53
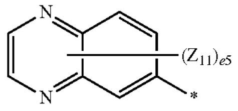
Formula 5-54
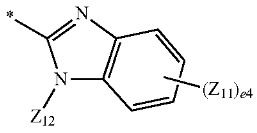
-continued
Formula 5-55
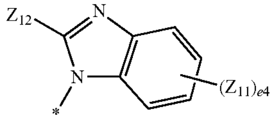
Formula 5-56
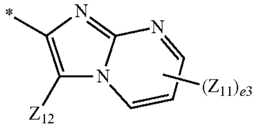
Formula 5-57
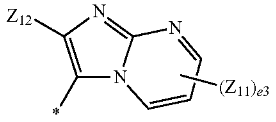
Formula 5-58
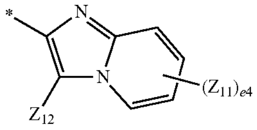
Formula 5-59
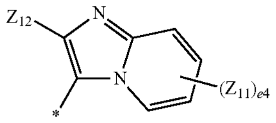
Formula 5-60
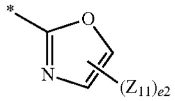
Formula 5-61
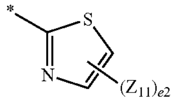
Formula 5-62
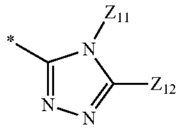
Formula 5-63
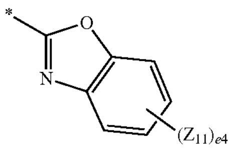
Formula 5-64
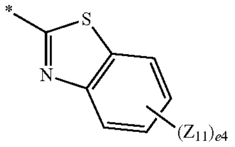
Formula 5-65
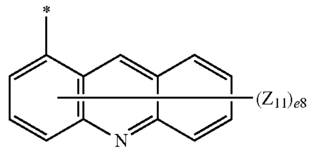

-continued
Formula 5-66
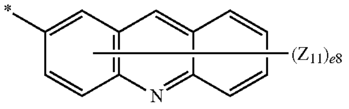
Formula 5-67
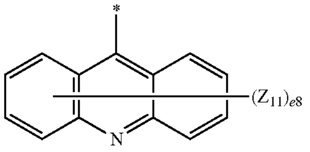
Formula 5-68
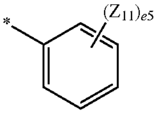
Formula 5-69
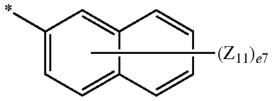
Formula 5-70
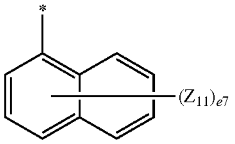
Formula 5-71
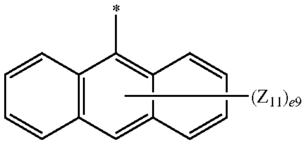
Formula 5-72
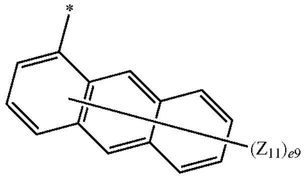
Formula 5-73
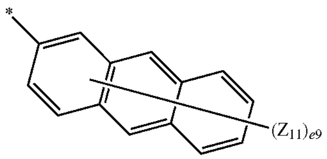
Formula 5-74
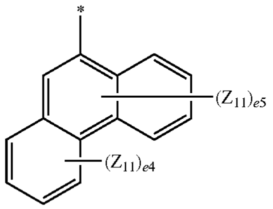
-continued
Formula 5-75
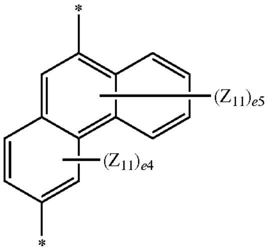
Formula 5-76
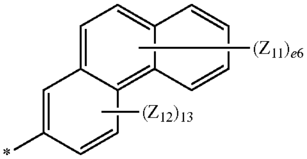
Formula 5-77
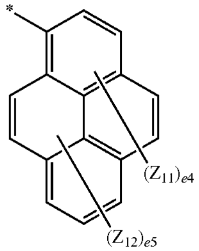
Formula 5-78
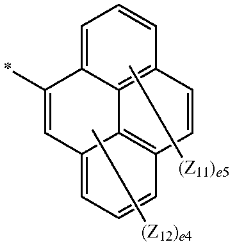
Formula 5-79
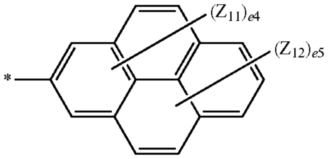
Formula 5-80
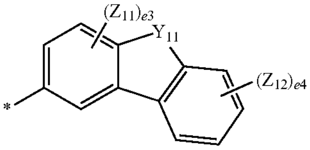
Formula 5-81
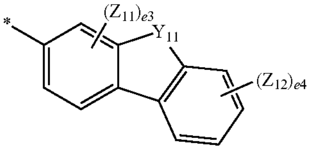
Formula 5-82
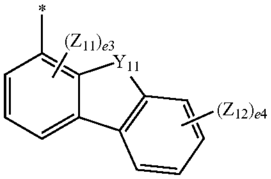

-continued

Formula 5-83

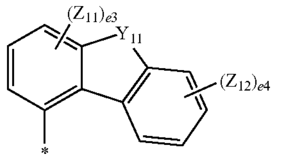

Formula 5-84

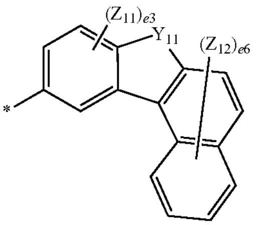

Formula 5-85

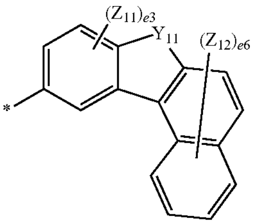

Formula 5-86

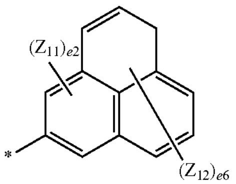

Formula 5-87

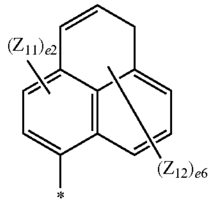

wherein, in Formulae 5-1 to 5-87, $Y_{11}$ is O, S, $C(Z_{13})(Z_{14})$, $N(Z_{15})$, or $Si(Z_{16})(Z_{17})$;

$Z_{11}$ to $Z_{17}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, and a dibenzofuranyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, a dibenzocarbazolyl group, and a dibenzofuranyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group; and —$Si(Q_{31})(Q_{32})(Q_{33})$; and $Z_{11}$ and $Z_{12}$ are optionally linked to each other to form a saturated or unsaturated ring, and $Z_{13}$ and $Z_{14}$ are optionally linked to each other to form a $C_5$ to $C_{20}$ saturated or unsaturated ring, wherein $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group;

e2 is an integer selected from 1 and 2;

e3 is an integer selected from 1 to 3;

e4 is an integer selected from 1 to 4;

e5 is an integer selected from 1 to 5;

e6 is an integer selected from 1 to 6;

e7 is an integer selected from 1 to 7;

e8 is an integer selected from 1 to 8;

e9 is an integer selected from 1 to 9; and

* indicates a binding site to an adjacent atom.

8. The organic light-emitting device as claimed in claim 1, wherein $Ar_1$ to $Ar_8$, $R_{41}$ to $R_{46}$, and $R_{51}$ to $R_{57}$ are each independently selected from groups represented by Formulae 6-1 to 6-170:

Formula 6-1

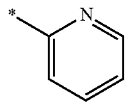

Formula 6-2

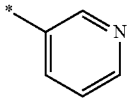

Formula 6-3

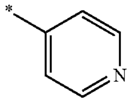

Formula 6-4

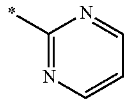

-continued
Formula 6-5
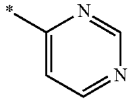
Formula 6-6
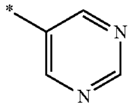
Formula 6-7
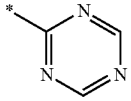
Formula 6-8
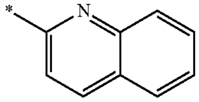
Formula 6-9
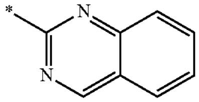
Formula 6-10
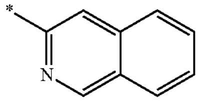
Formula 6-11
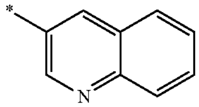
Formula 6-12
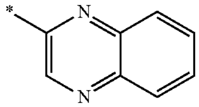
Formula 6-13
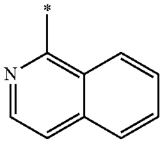
Formula 6-14
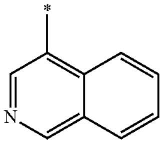
Formula 6-15
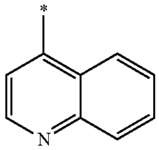
Formula 6-16
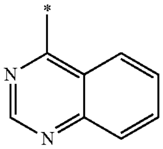
-continued
Formula 6-17
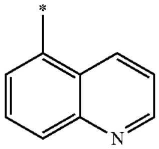
Formula 6-18
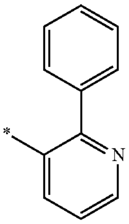
Formula 6-19
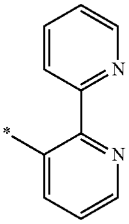
Formula 6-20
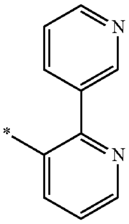
Formula 6-21
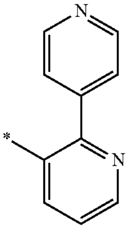
Formula 6-22
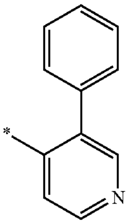
Formula 6-23
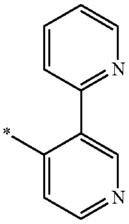

-continued
Formula 6-24
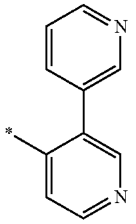
Formula 6-25
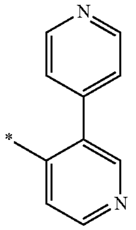
Formula 6-26
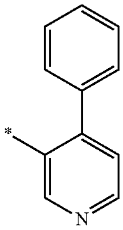
Formula 6-27
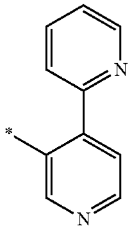
Formula 6-28
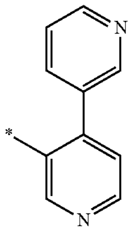
Formula 6-29
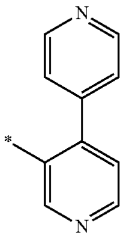
-continued
Formula 6-30
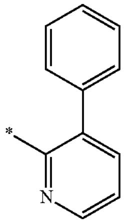
Formula 6-31
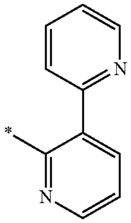
Formula 6-32
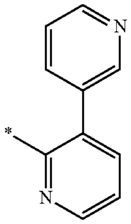
Formula 6-33
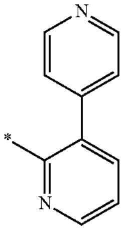
Formula 6-34
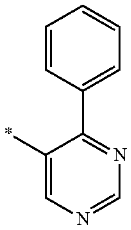
Formula 6-35
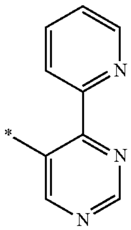

-continued
Formula 6-36
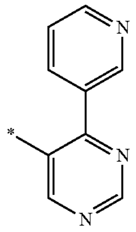
Formula 6-37
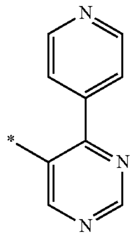
Formula 6-38
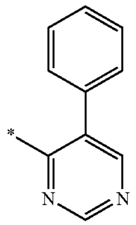
Formula 6-39
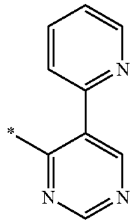
Formula 6-40
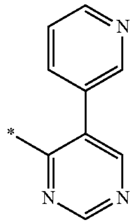
Formula 6-41
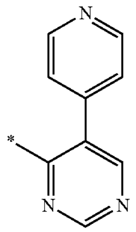
Formula 6-42
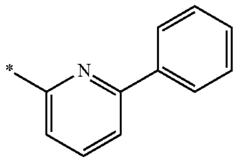
-continued
Formula 6-43
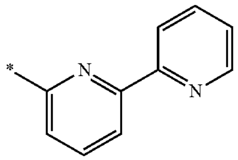
Formula 6-44
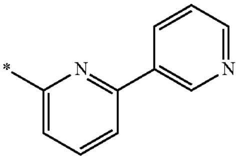
Formula 6-45
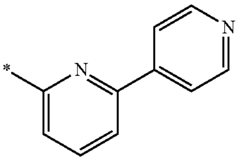
Formula 6-46
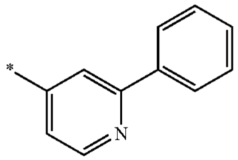
Formula 6-47
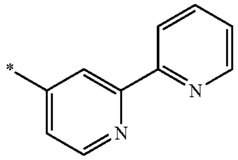
Formula 6-48
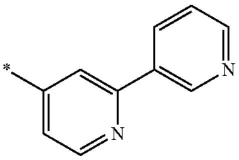
Formula 6-49
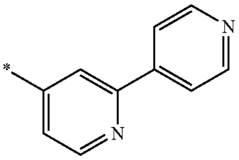
Formula 6-50
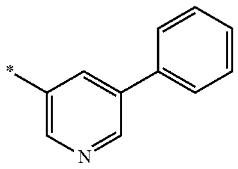
Formula 6-51
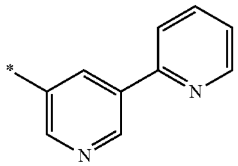

-continued
Formula 6-52
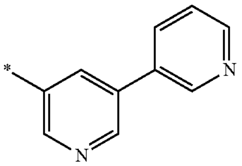
Formula 6-53
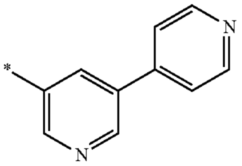
Formula 6-54
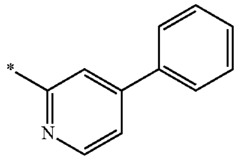
Formula 6-55
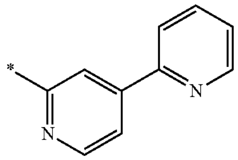
Formula 6-56
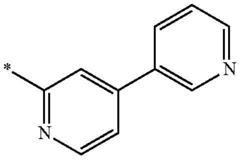
Formula 6-57
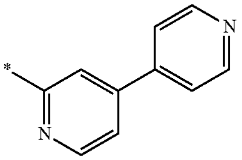
Formula 6-58
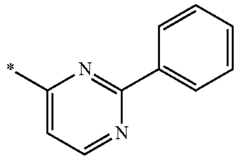
Formula 6-59
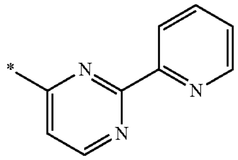
Formula 6-60
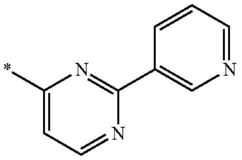
-continued
Formula 6-61
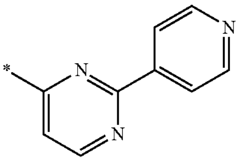
Formula 6-62
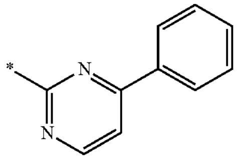
Formula 6-63
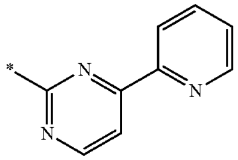
Formula 6-64
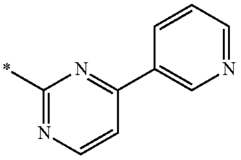
Formula 6-65
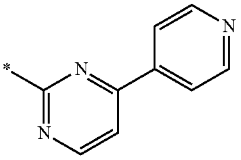
Formula 6-66
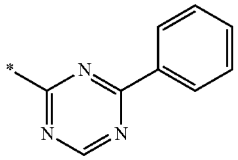
Formula 6-67
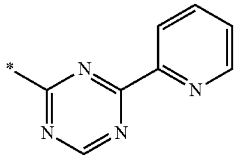
Formula 6-68
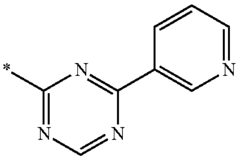
Formula 6-69
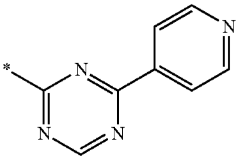

-continued
Formula 6-70
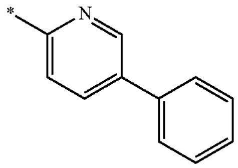
Formula 6-71
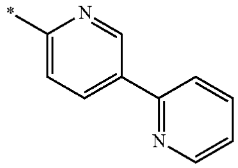
Formula 6-72
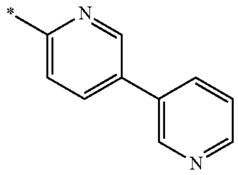
Formula 6-73
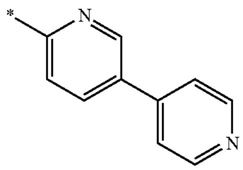
Formula 6-74
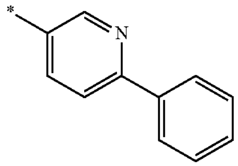
Formula 6-75
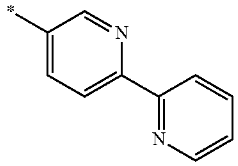
Formula 6-76
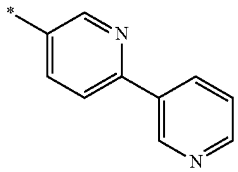
Formula 6-77
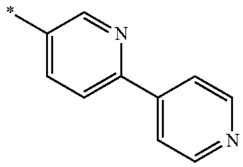
Formula 6-78
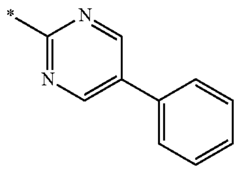
-continued
Formula 6-79
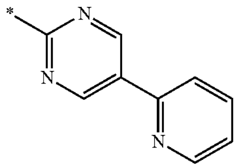
Formula 6-80
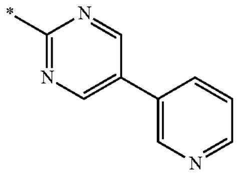
Formula 6-81
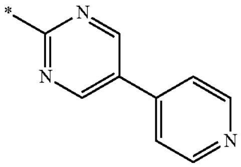
Formula 6-82
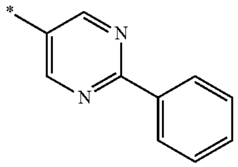
Formula 6-83
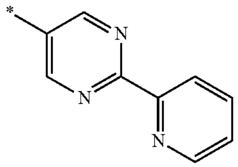
Formula 6-84
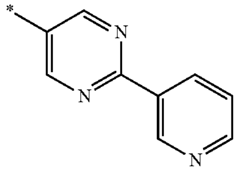
Formula 6-85
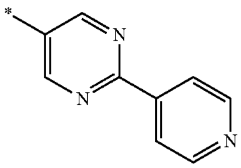
Formula 6-86
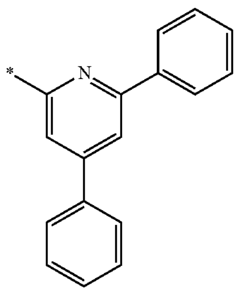

-continued
Formula 6-87
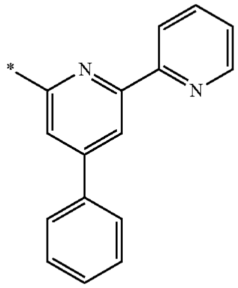
Formula 6-88
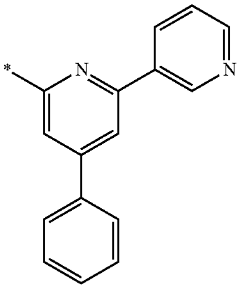
Formula 6-89
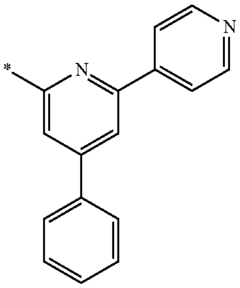
Formula 6-90
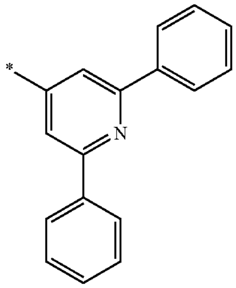
Formula 6-91
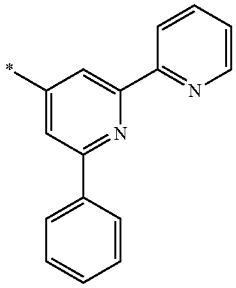
-continued
Formula 6-92
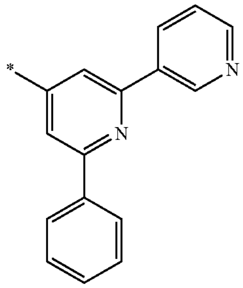
Formula 6-93
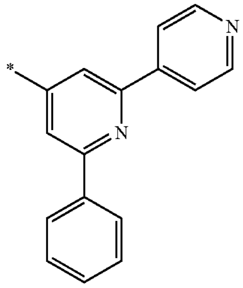
Formula 6-94
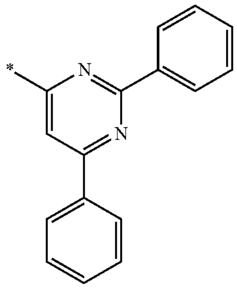
Formula 6-95
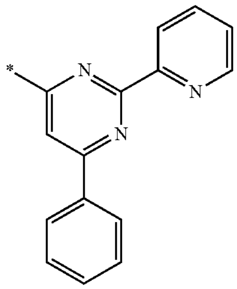
Formula 6-96
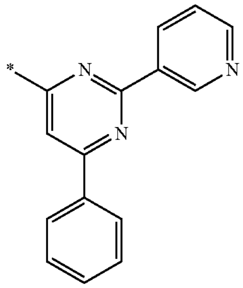

Formula 6-97
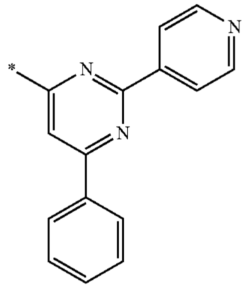
Formula 6-98
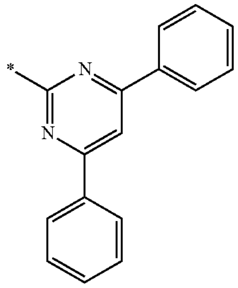
Formula 6-99
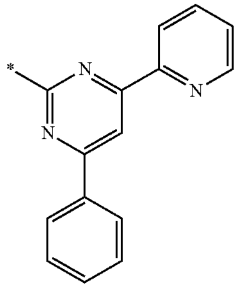
Formula 6-100
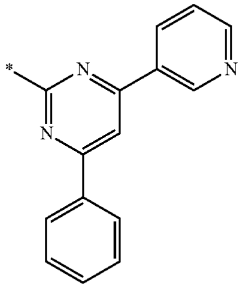
Formula 6-101
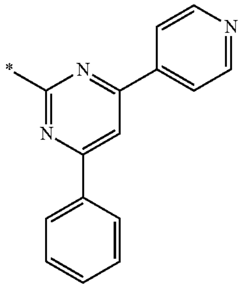
Formula 6-102
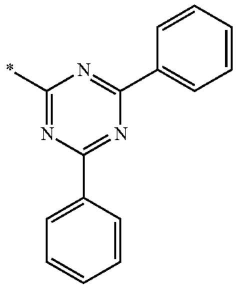
Formula 6-103
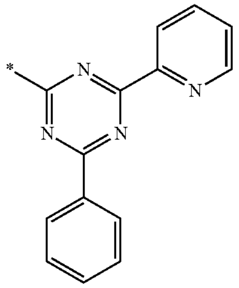
Formula 6-104
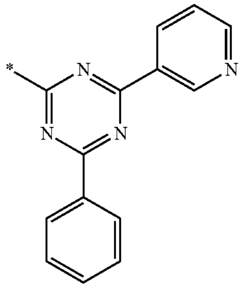
Formula 6-105
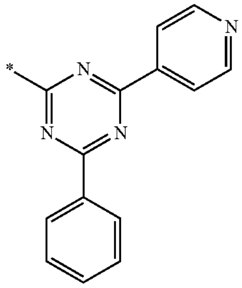
Formula 6-106
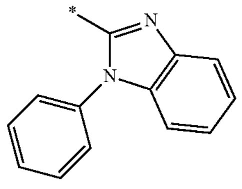
Formula 6-107
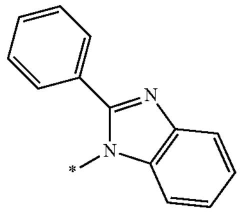

-continued
Formula 6-108
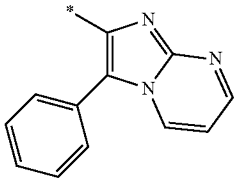
Formula 6-109
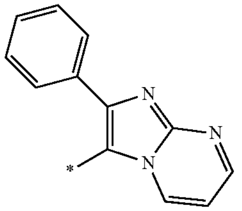
Formula 6-110
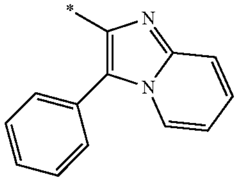
Formula 6-111
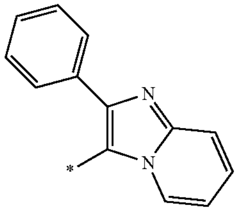
Formula 6-112
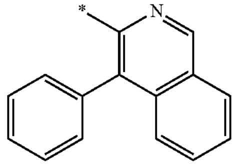
Formula 6-113
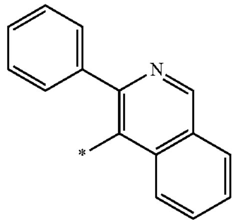
Formula 6-114
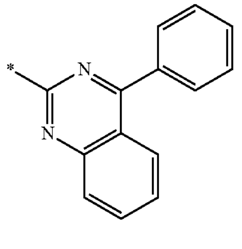
-continued
Formula 6-115
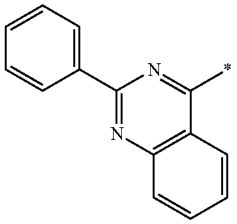
Formula 6-116
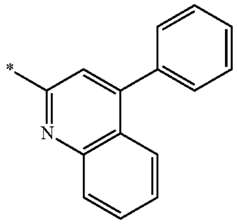
Formula 6-117
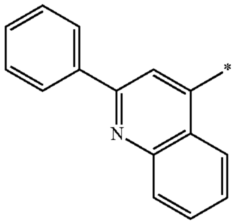
Formula 6-118
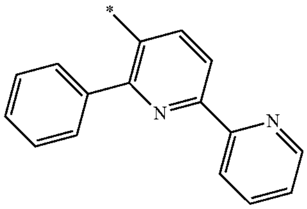
Formula 6-119
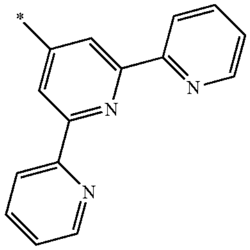
Formula 6-120
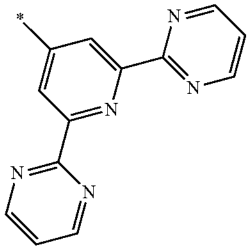
Formula 6-121
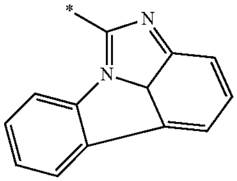

-continued
Formula 6-122
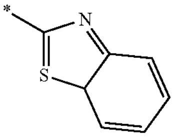
Formula 6-123
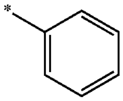
Formula 6-124
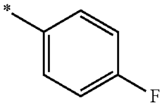
Formula 6-125
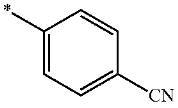
Formula 6-126
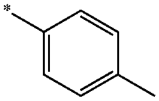
Formula 6-127
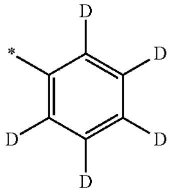
Formula 6-128
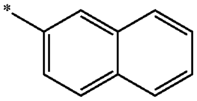
Formula 6-129
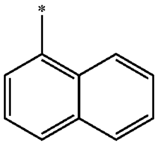
Formula 6-130
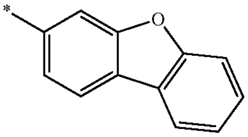
Formula 6-131
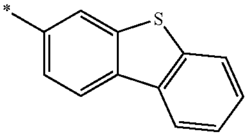
Formula 6-132
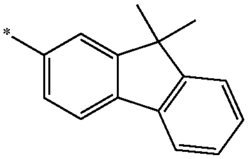
-continued
Formula 6-133
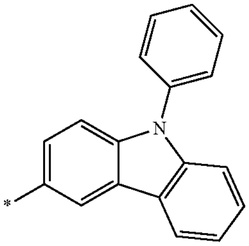
Formula 6-134
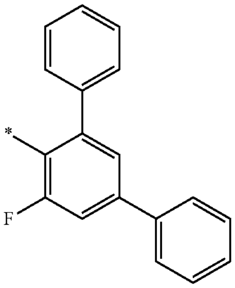
Formula 6-135
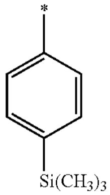
Formula 6-136
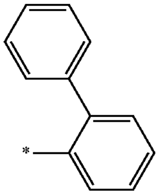
Formula 6-137
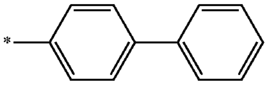
Formula 6-138
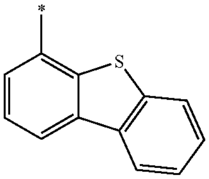
Formula 6-139
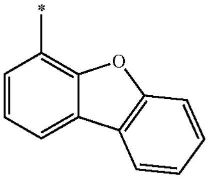

-continued
Formula 6-140
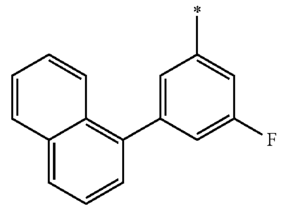
Formula 6-141
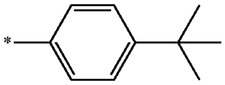
Formula 6-142
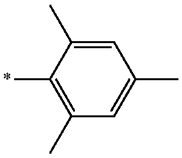
Formula 6-143
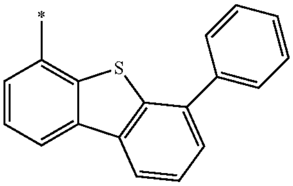
Formula 6-144
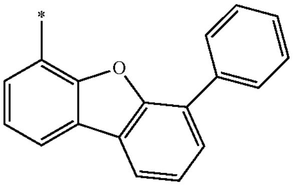
Formula 6-145
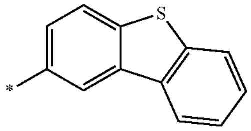
Formula 6-146
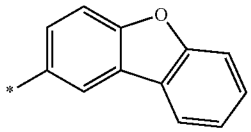
Formula 6-147
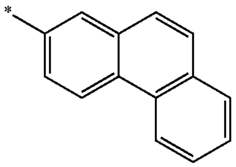
Formula 6-148
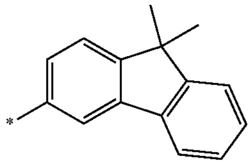
-continued
Formula 6-149
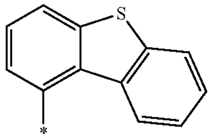
Formula 6-150
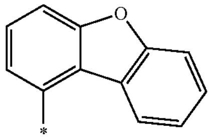
Formula 6-151
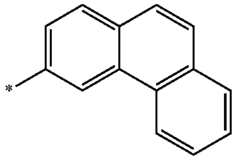
Formula 6-152
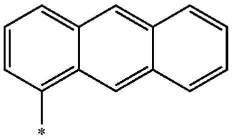
Formula 6-153
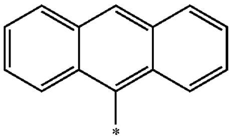
Formula 6-154
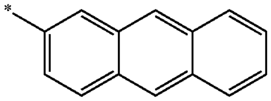
Formula 6-155
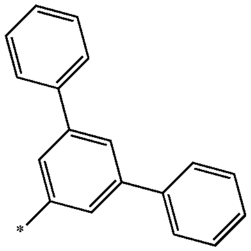
Formula 6-156
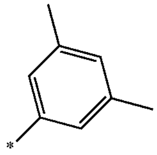
Formula 6-157
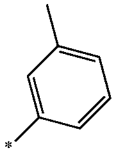
Formula 6-158
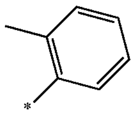

-continued
Formula 6-159
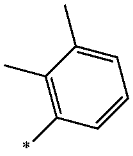
Formula 6-160
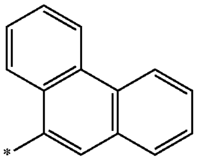
Formula 6-161
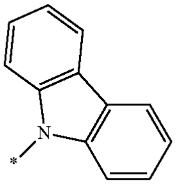
Formula 6-162
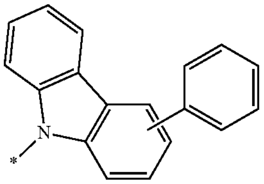
Formula 6-163
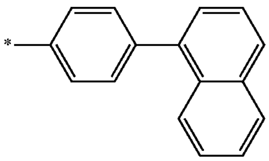
Formula 6-164
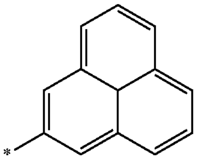
Formula 6-165
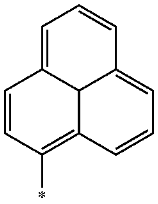
Formula 6-166
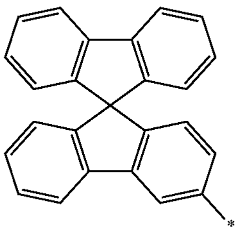
-continued
Formula 6-167
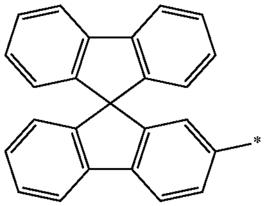
Formula 6-168
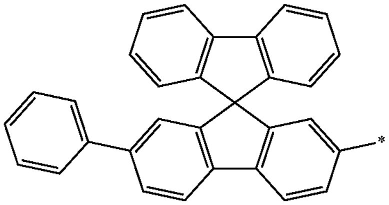
Formula 6-169
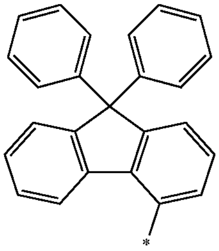
Formula 6-170
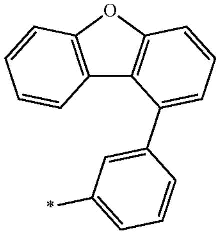
wherein, in Formulae 6-1 to 6-170, * indicates a binding site to an adjacent atom.
9. The organic light-emitting device as claimed in claim 1, wherein, in Formulae 1A to 1C, at least one of
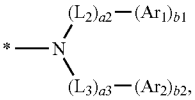
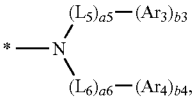
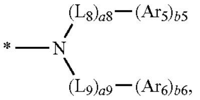
and
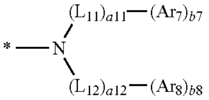
is selected from groups represented by Formulae 7-1 and 7-2:
Formula 7-1
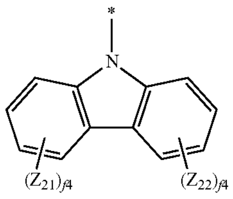

-continued

Formula 7-2

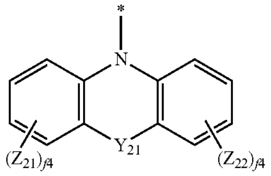

wherein, in Formulae 7-1 and 7-2, $Y_{21}$ is selected from O, S, $C(Z_{23})(Z_{24})$, $N(Z_{25})$, and $Si(Z_{26})(Z_{27})$; and $Z_{21}$ to $Z_{27}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and $—Si(Q_{31})(Q_{32})(Q_{33})$, wherein $Q_{31}$ to $Q_{33}$ are each independently selected from a $C_1$-$C_{10}$ alkyl group, a $C_1$-$C_{10}$ alkoxy group, a phenyl group, and a naphthyl group;

f4 is an integer selected from 1 to 4; and

* indicates a binding site to an adjacent atom.

10. The organic light-emitting device as claimed in claim 1, wherein at least one of $R_{41}$ to $R_{46}$ in Formula 40A or at least one of $R_{51}$ to $R_{57}$ in Formula 40B is selected from groups represented by Formulae 5-1 to 5-67:

Formula 5-1

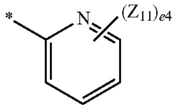

Formula 5-2

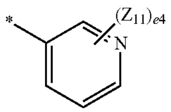

Formula 5-3

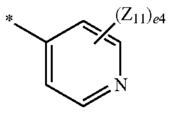

Formula 5-4

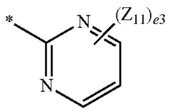

Formula 5-5

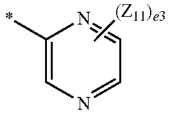

-continued

Formula 5-6

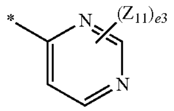

Formula 5-7

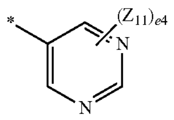

Formula 5-8

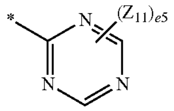

Formula 5-9

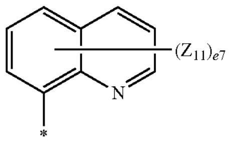

Formula 5-10

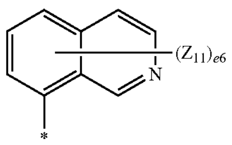

Formula 5-11

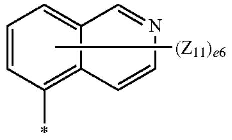

Formula 5-12

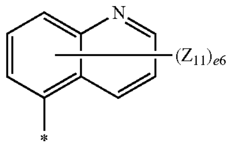

Formula 5-13

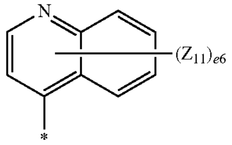

Formula 5-14

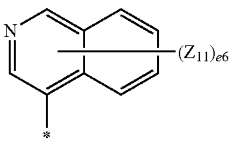

Formula 5-15

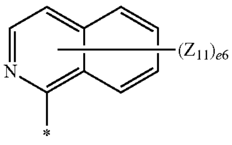

Formula 5-16

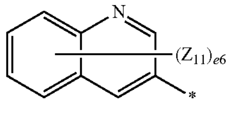

-continued
Formula 5-17
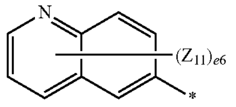
Formula 5-18
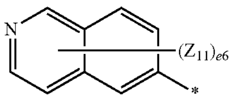
Formula 5-19
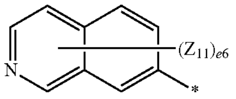
Formula 5-20
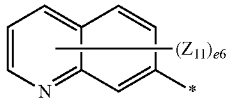
Formula 5-21
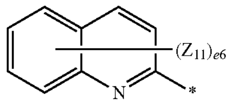
Formula 5-22
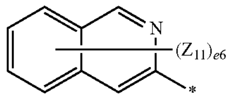
Formula 5-23
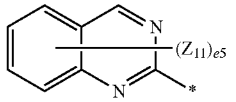
Formula 5-24
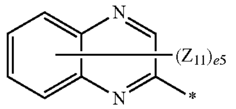
Formula 5-25
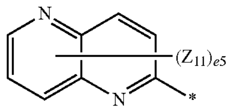
Formula 5-26
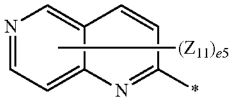
Formula 5-27
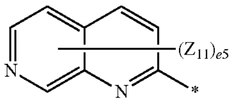
Formula 5-28
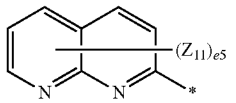
Formula 5-29
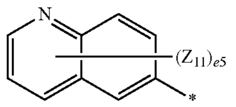
Formula 5-30
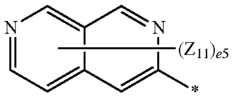
-continued
Formula 5-31
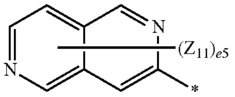
Formula 5-32
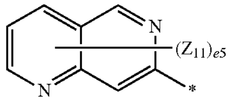
Formula 5-33
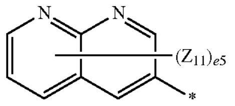
Formula 5-34
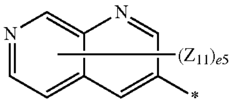
Formula 5-35
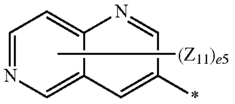
Formula 5-36
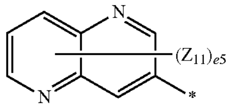
Formula 5-37
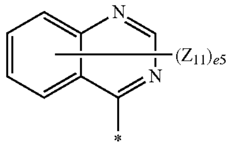
Formula 5-38
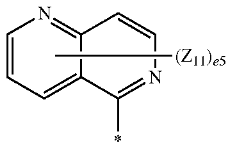
Formula 5-39
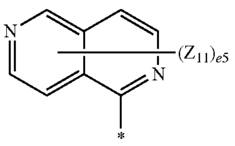
Formula 5-40
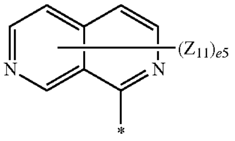
Formula 5-41
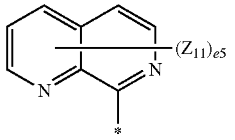
Formula 5-42
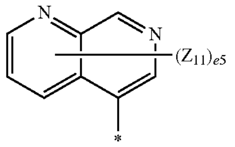

-continued
Formula 5-43
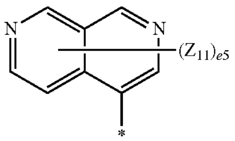
Formula 5-44
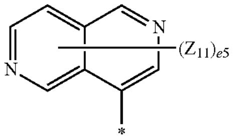
Formula 5-45
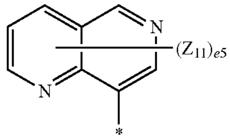
Formula 5-46
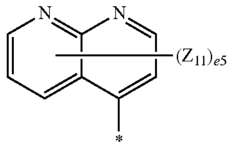
Formula 5-47
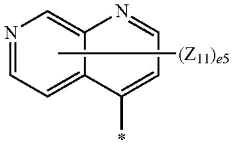
Formula 5-48
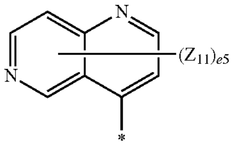
Formula 5-49
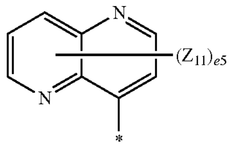
Formula 5-50
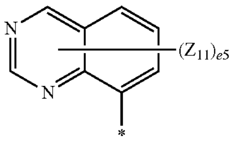
Formula 5-51
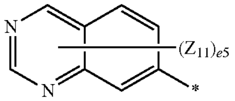
Formula 5-52
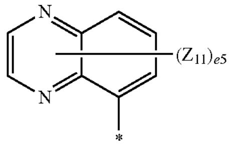
Formula 5-53
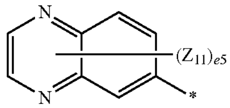
-continued
Formula 5-54
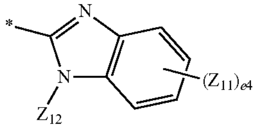
Formula 5-55
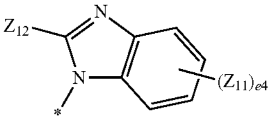
Formula 5-56
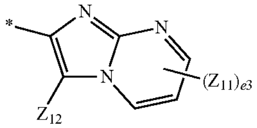
Formula 5-57
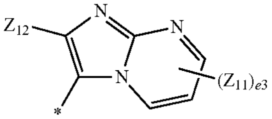
Formula 5-58
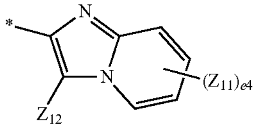
Formula 5-59
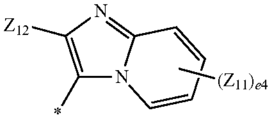
Formula 5-60
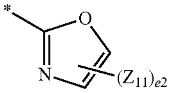
Formula 5-61
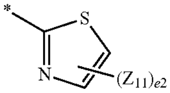
Formula 5-62
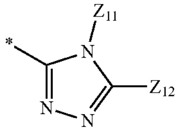
Formula 5-63
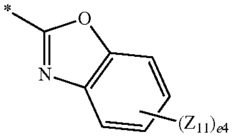
Formula 5-64
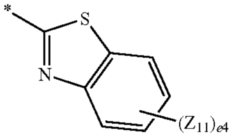

-continued

Formula 5-65

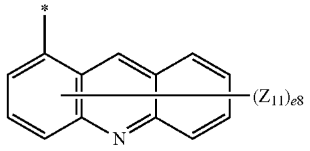

Formula 5-66

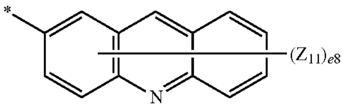

Formula 5-67

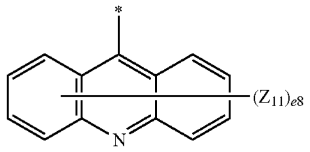

wherein, in Formulae 5-1 to 5-67, $Z_{11}$ and $Z_{12}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a Spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group;

a phenyl group, a naphthyl group, a pyridinyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, and a pyridinyl group; and —$Si(Q_{31})(Q_{32})(Q_{33})$, $Z_{11}$ and $Z_{12}$ are optionally linked to each other to form a $C_5$ to $C_{20}$ saturated or unsaturated ring, wherein $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group;

e2 is an integer selected from 1 and 2;

e3 is an integer selected from 1 to 3;

e4 is an integer selected from 1 to 4;

e5 is an integer selected from 1 to 5;

e6 is an integer selected from 1 to 6;

e7 is an integer selected from 1 to 7;

e8 is an integer selected from 1 to 8;

e9 is an integer selected from 1 to 9; and

* indicates a binding site to an adjacent atom.

11. The organic light-emitting device as claimed in claim 1, wherein at least one of $R_{41}$ to $R_{46}$ in Formula 40A or at least one of $R_{51}$ to $R_{57}$ in Formula 40B is selected from groups represented by Formulae 10-1 to 10-123:

Formula 10-1

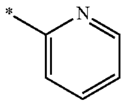

Formula 10-2

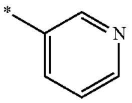

Formula 10-3

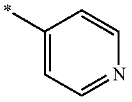

Formula 10-4

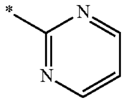

Formula 10-5

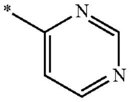

Formula 10-6

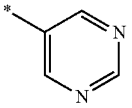

Formula 10-7

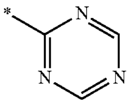

Formula 10-8

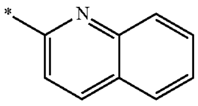

Formula 10-9

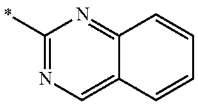

-continued
Formula 10-10
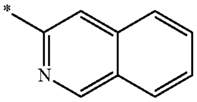
Formula 10-11
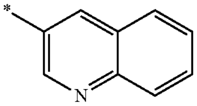
Formula 10-12
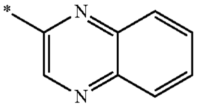
Formula 10-13
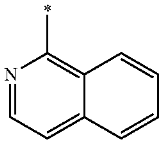
Formula 10-14
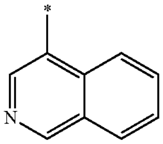
Formula 10-15
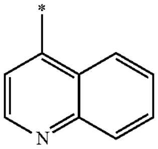
Formula 10-16
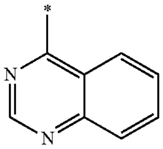
Formula 10-17
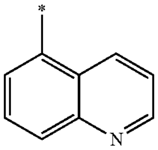
Formula 10-18
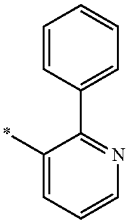
Formula 10-19
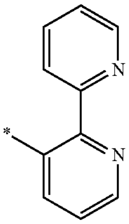
-continued
Formula 10-20
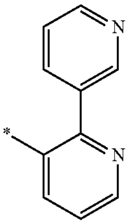
Formula 10-21
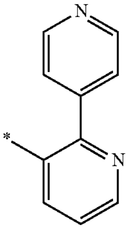
Formula 10-22
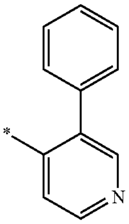
Formula 10-23
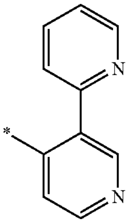
Formula 10-24
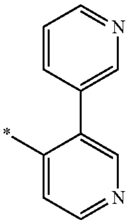
Formula 10-25
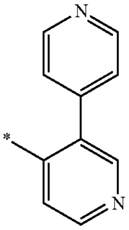
Formula 10-26
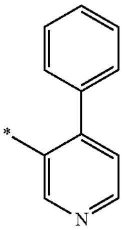

-continued
Formula 10-27
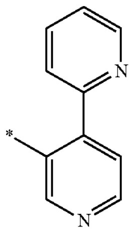
Formula 10-28
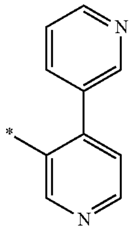
Formula 10-29
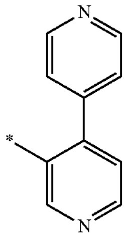
Formula 10-30
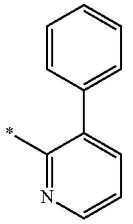
Formula 10-31
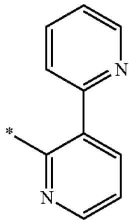
Formula 10-32
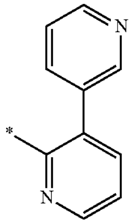
-continued
Formula 10-33
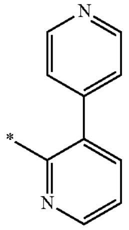
Formula 10-34
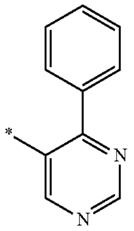
Formula 10-35
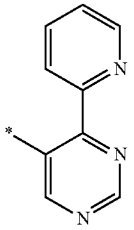
Formula 10-36
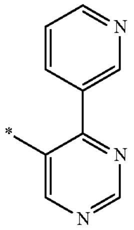
Formula 10-37
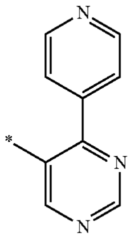
Formula 10-38
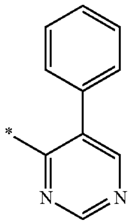

-continued
Formula 10-39
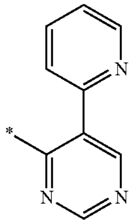
Formula 10-40
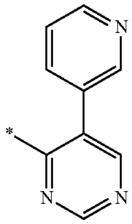
Formula 10-41
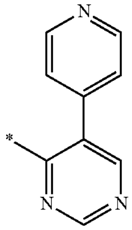
Formula 10-42
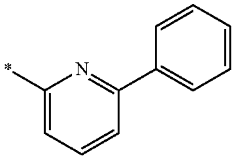
Formula 10-43
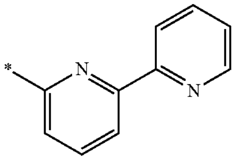
Formula 10-44
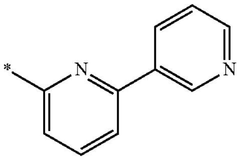
Formula 10-45
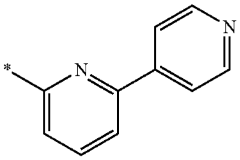
Formula 10-46
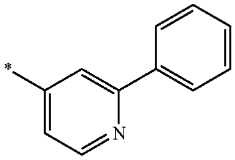
-continued
Formula 10-47
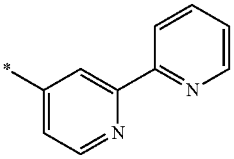
Formula 10-48
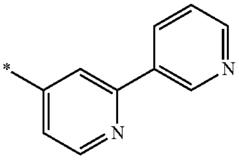
Formula 10-49
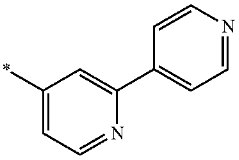
Formula 10-50
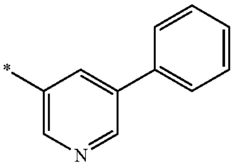
Formula 10-51
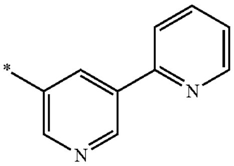
Formula 10-52
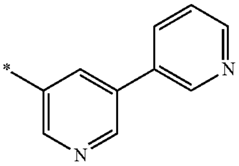
Formula 10-53
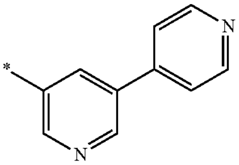
Formula 10-54
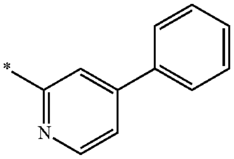
Formula 10-55
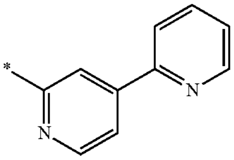

-continued
Formula 10-56
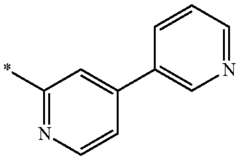
Formula 10-57
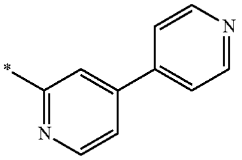
Formula 10-58
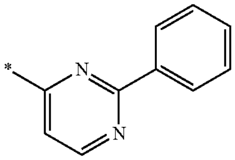
Formula 10-59
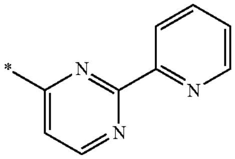
Formula 10-60
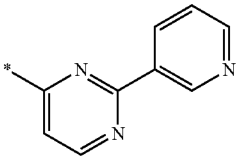
Formula 10-61
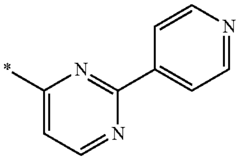
Formula 10-62
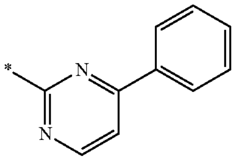
Formula 10-63
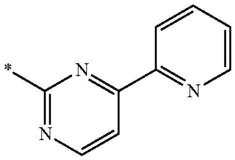
Formula 10-64
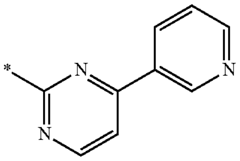
-continued
Formula 10-65
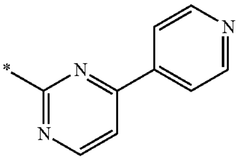
Formula 10-66
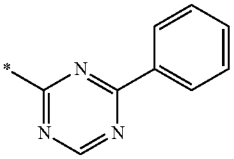
Formula 10-67
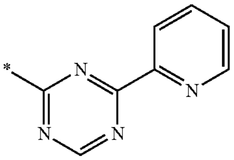
Formula 10-68
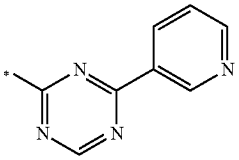
Formula 10-69
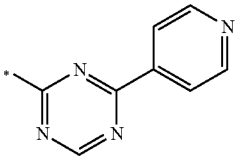
Formula 10-70
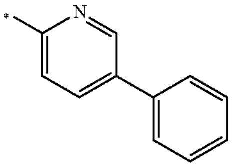
Formula 10-71
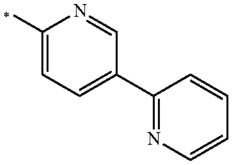
Formula 10-72
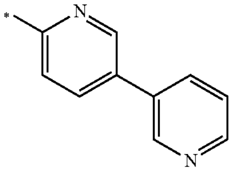
Formula 10-73
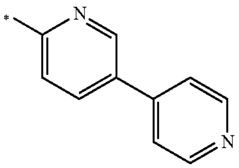

-continued
Formula 10-74
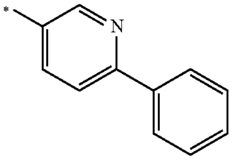
Formula 10-75
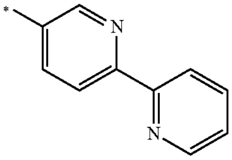
Formula 10-76
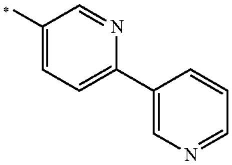
Formula 10-77
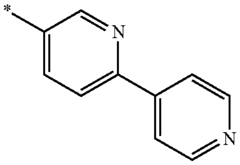
Formula 10-78
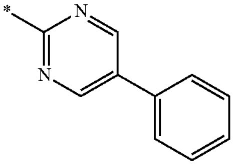
Formula 10-79
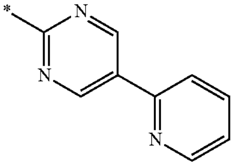
Formula 10-80
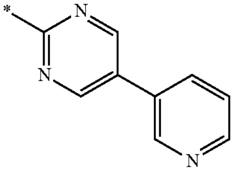
Formula 10-81
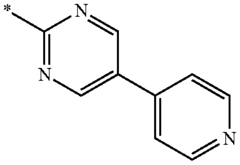
Formula 10-82
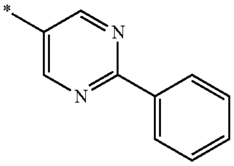
-continued
Formula 10-83
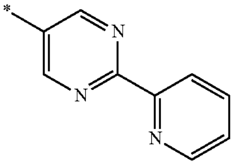
Formula 10-84
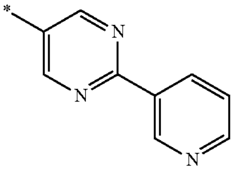
Formula 10-85
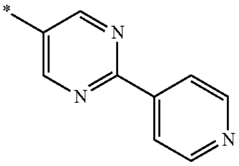
Formula 10-86
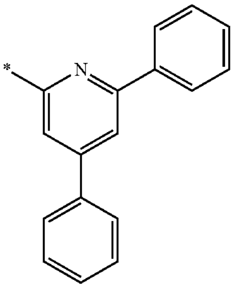
Formula 10-87
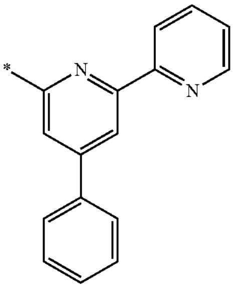
Formula 10-88
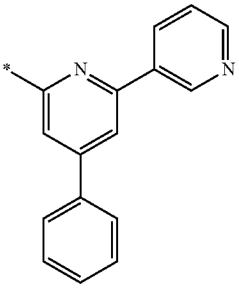

-continued
Formula 10-89
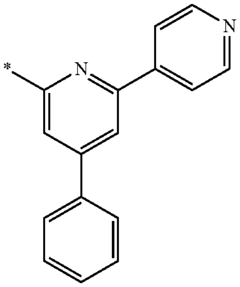
Formula 10-90
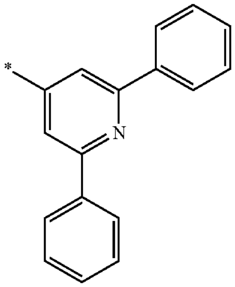
Formula 10-91
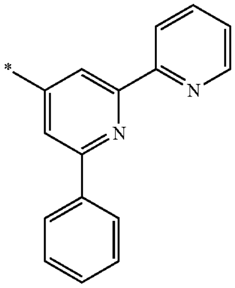
Formula 10-92
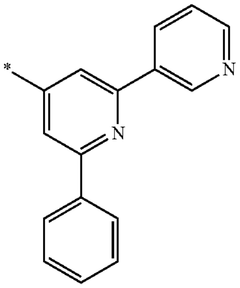
Formula 10-93
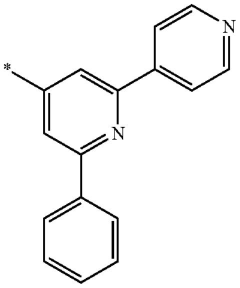
-continued
Formula 10-94
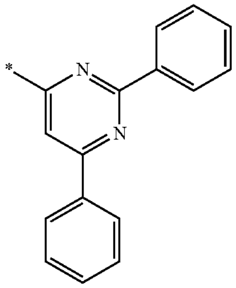
Formula 10-95
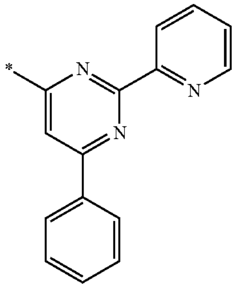
Formula 10-96
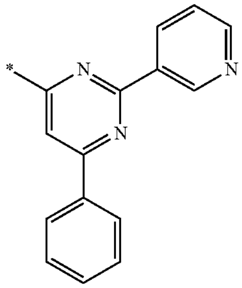
Formula 10-97
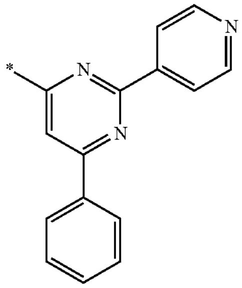
Formula 10-98
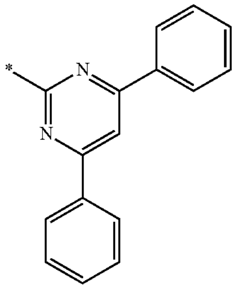

-continued
Formula 10-99
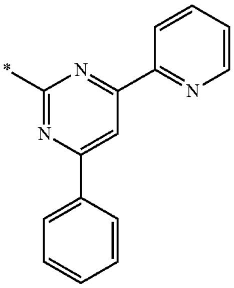
Formula 10-100
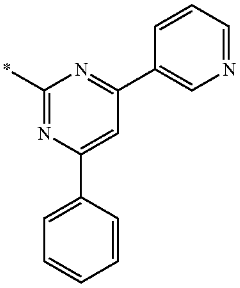
Formula 10-101
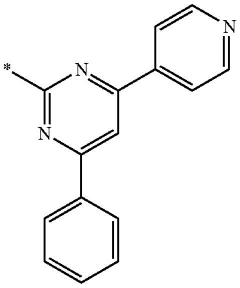
Formula 10-102
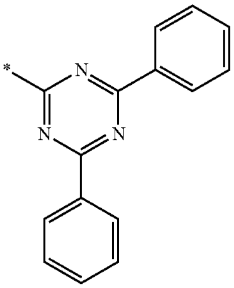
Formula 10-103
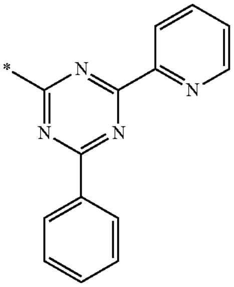
-continued
Formula 10-104
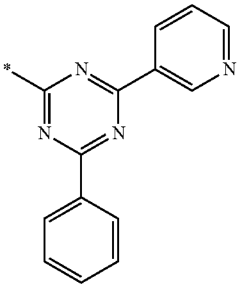
Formula 10-105
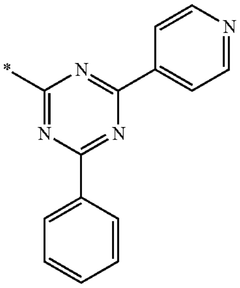
Formula 10-106
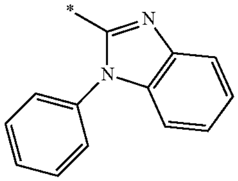
Formula 10-107
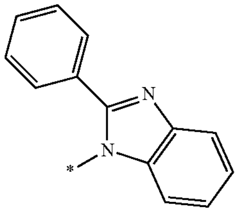
Formula 10-108
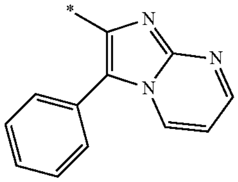
Formula 10-109
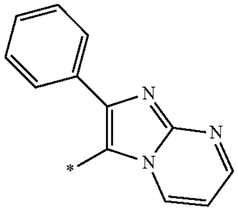
Formula 10-110
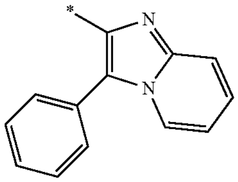

-continued

Formula 10-111

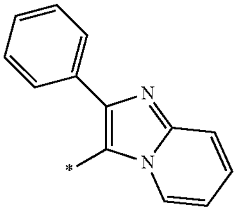

Formula 10-112

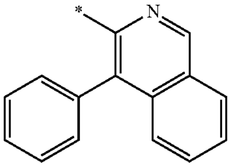

Formula 10-113

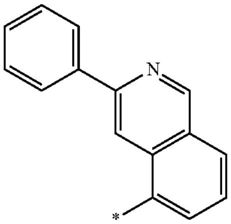

Formula 10-114

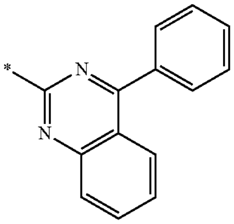

Formula 10-115

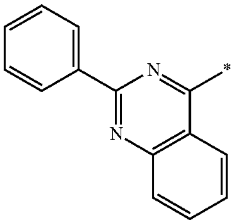

Formula 10-116

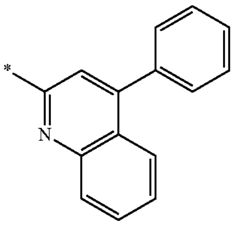

Formula 10-117

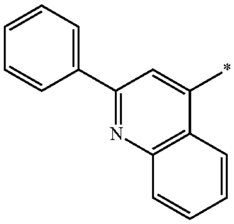

-continued

Formula 10-118

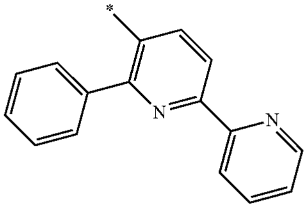

Formula 10-119

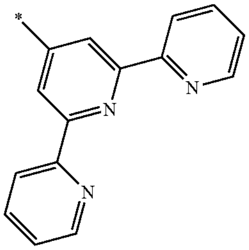

Formula 10-120

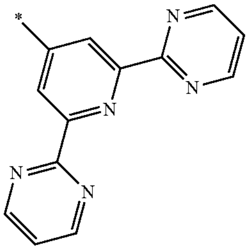

Formula 10-121

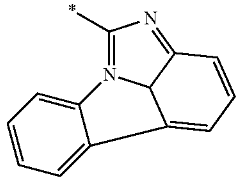

Formula 10-122

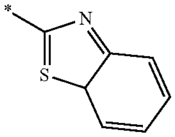

Formula 10-123

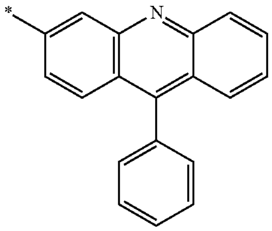

wherein, in Formulae 10-1 to 10-123, * indicates a binding site to an adjacent atom.

12. The organic light-emitting device as claimed in claim 1, wherein $R_1$ to $R_{12}$ and $R_{58}$ to $R_{60}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a phenalenyl group, a pyrenyl group, a dibenzothiophenyl group, and —Si$(Q_1)(Q_2)(Q_3)$.

13. The organic light-emitting device as claimed in claim 1, wherein the first compound is represented by one of Formulae 1A-1 to 1A-10, 1B-1 to 1B-4, 1C-1, and 1C-2, and the second compound is represented by one of Formulae 40A-1 to 40A-3, 40B-1, and 40B-2:

<Formula 1A-1>

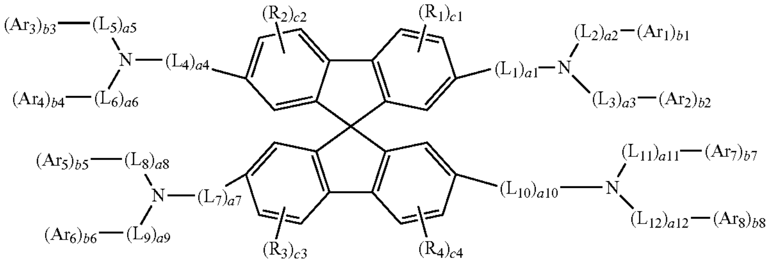

<Formula 1A-2>

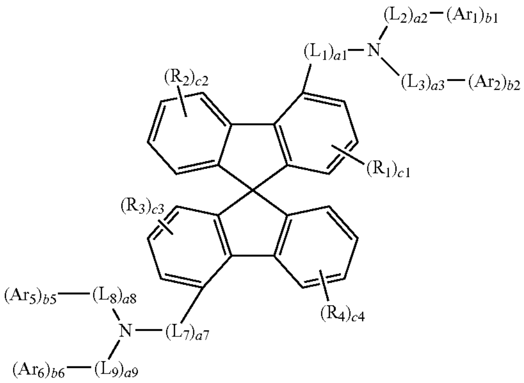

<Formula 1A-3>

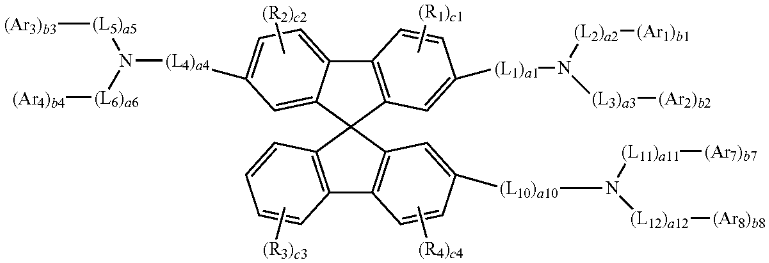

<Formula 1A-4>

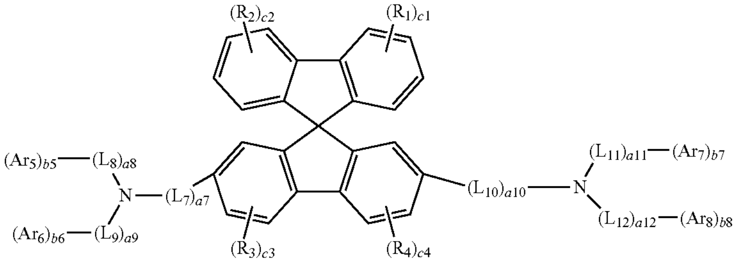

-continued
<Formula 1A-5>
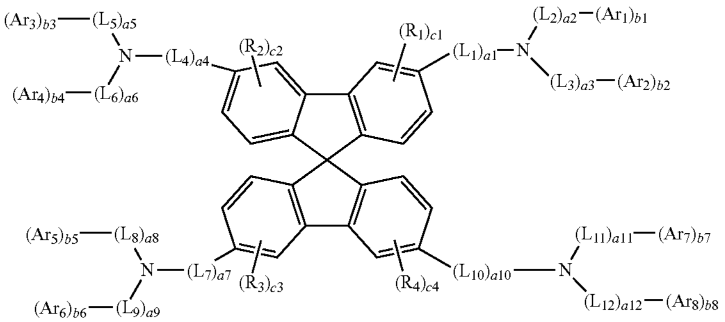
<Formula 1A-6>
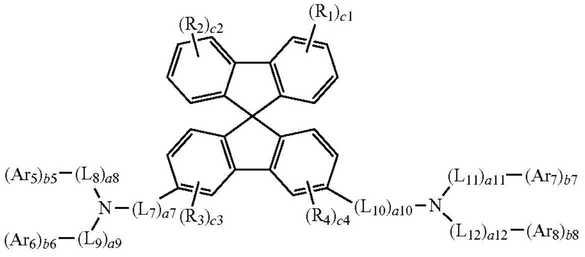
<Formula 1A-7>
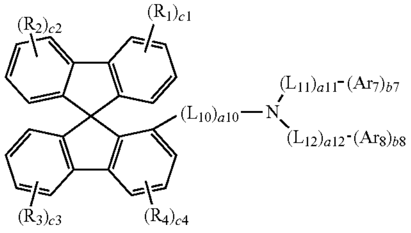
<Formula 1A-8>
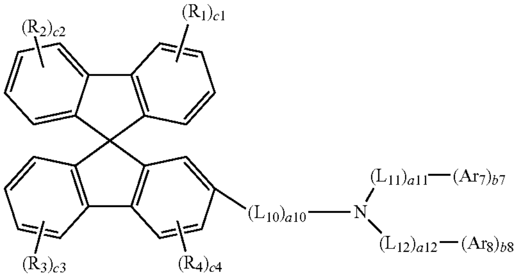
<Formula 1A-9>
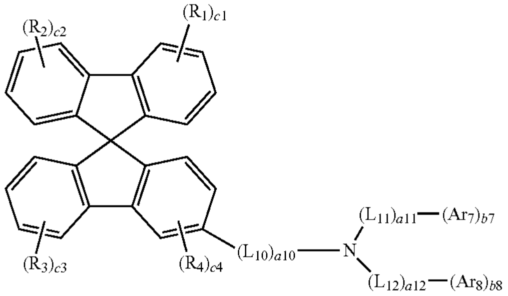
<Formula 1A-10>
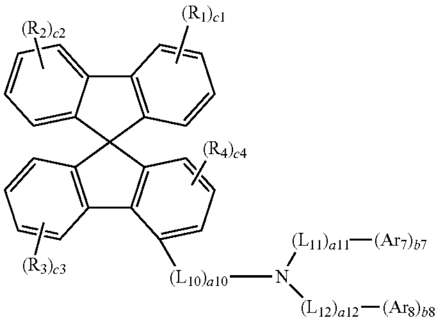
<Formula 1B-1>
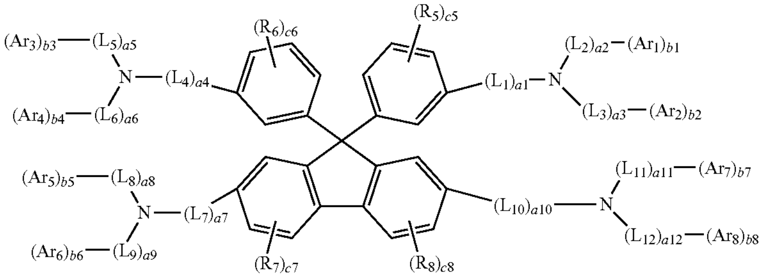

-continued
<Formula 1B-2>
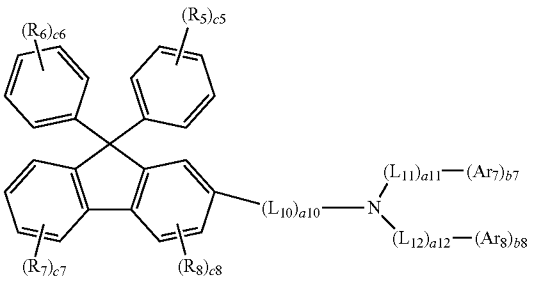
<Formula 1B-3>
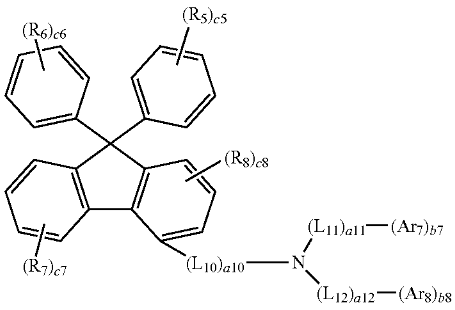
<Formula 1B-4>
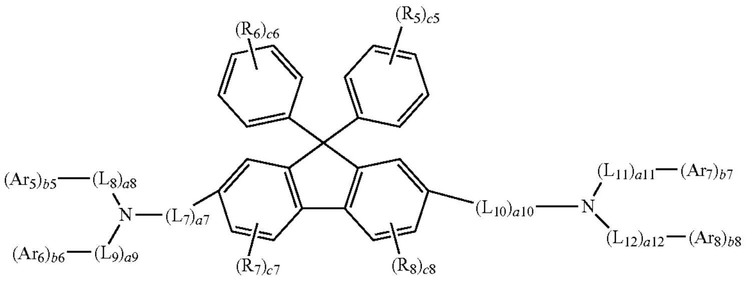
<Formula 1C-1>
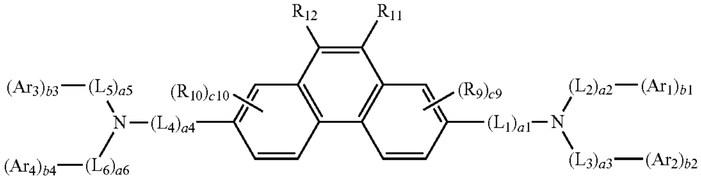
<Formula 40A-1>
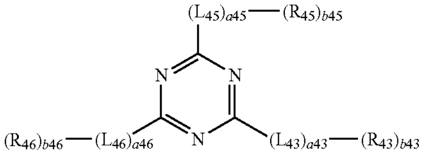
<Formula 40A-2>
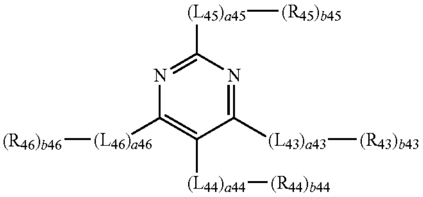
<Formula 40A-3>
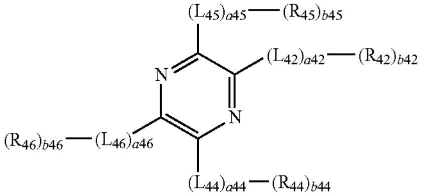
<Formula 40B-1>
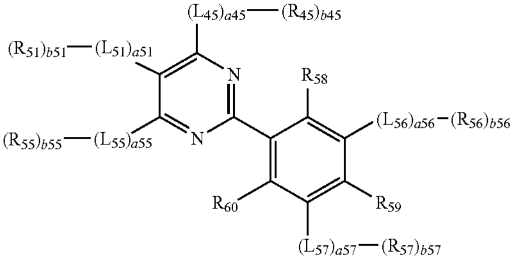
<Formula 40B-2>
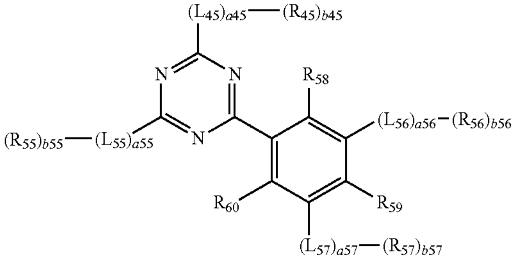

wherein, in the Formulae above, descriptions of $L_1$ to $L_{12}$, $L_{41}$ to $L_{46}$, $L_{51}$ to $L_{57}$, a1 to a12, a41 to a46, a51 to a57, $Ar_1$ to $Ar_8$, $R_1$ to $R_{12}$, $R_{42}$ to $R_{46}$, $R_{51}$, $R_{54}$ to $R_{60}$, b1 to b20, b42 to b46, b51 to b57, and c1 to c10 are the same as described in claim 1.

14. The organic light-emitting device as claimed in claim 1, wherein the first compound is represented by Formulae 1A-1(1), 1A-2(1), 1A-2(2), 1A-3(1), 1A-4(1), 1A-4(2), 1A-5(1), 1A-6(1), 1A-7(1), 1A-8(1), 1A-8(2), 1A-9(1), 1A-9(2), 1A-9(3), 1A-10(1), 1A-10(2), 1B-(1), 1B-2(1), 1B-3(1), 1B-4(1), 1C-1(1), and 1C-1(2), and the second compound is represented by Formulae 40A-1(1), 40A-1(2), 40A-1(3), 40A-2(1), 40A-3(1), 40B-1(1), 40B-1(2), 40B-2(1), and 40B-2(1) to 40B-2(5):

<Formula 1A-1(1)>

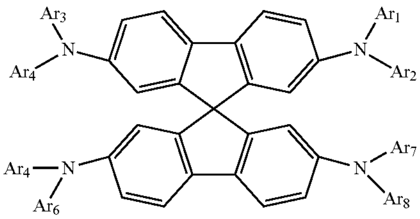

<Formula 1A-2(1)>

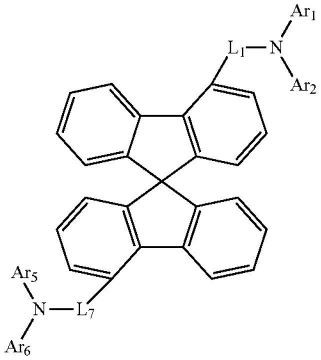

<Formula 1A-2(2)>

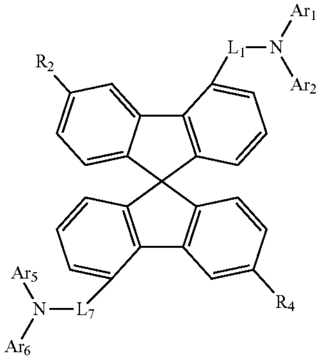

<Formula 1A-3(1)>

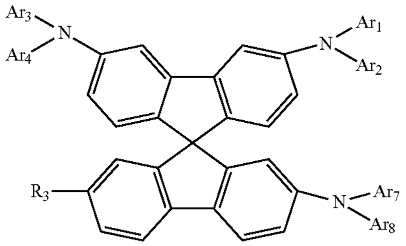

-continued

<Formula 1A-4(1)>

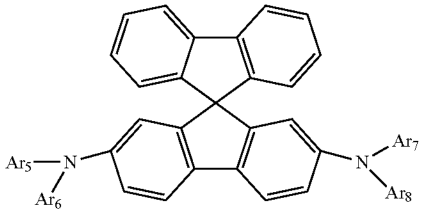

<Formula 1A-4(2)>

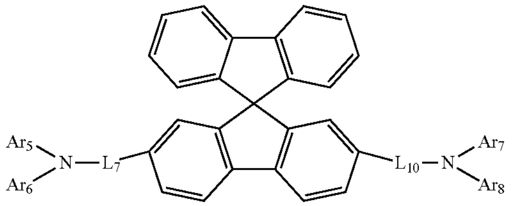

<Formula 1A-5(1)>

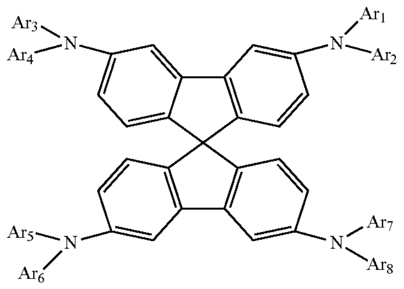

<Formula 1A-6(1)>

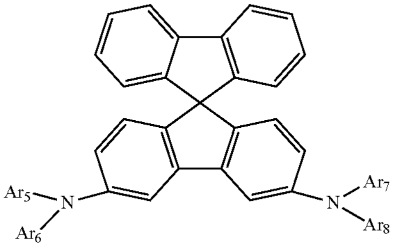

<Formula 1A-7(1)>

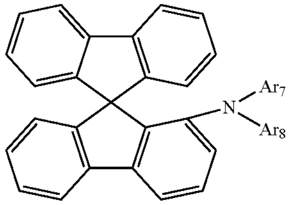

<Formula 1A-8(1)>

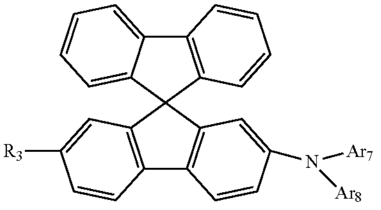

-continued
<Formula 1A-8(2)>
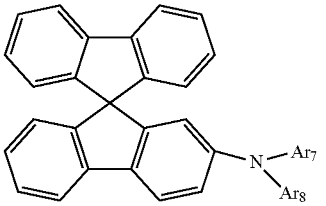
<Formula 1A-9(1)>
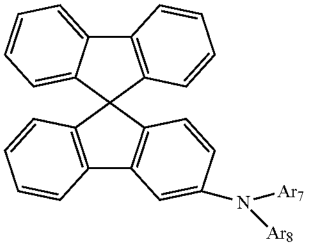
<Formula 1A-9(2)>
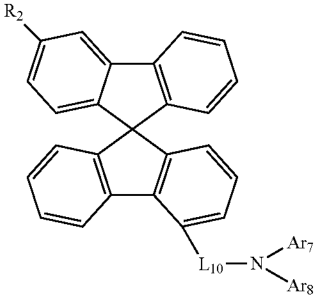
<Formula 1A-9(3)>
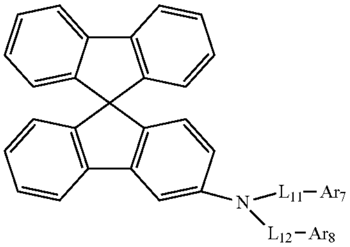
<Formula 1A-10(1)>
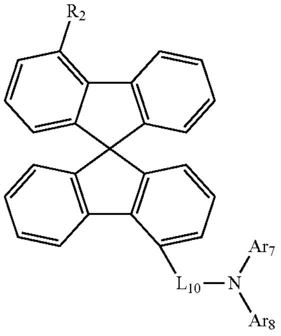
-continued
<Formula 1A-10(2)>
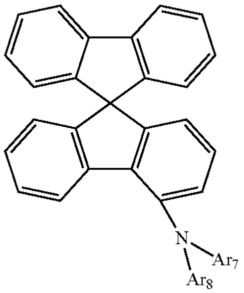
<Formula 1B-1(1)>
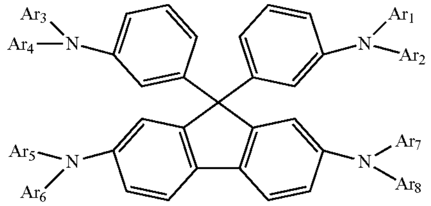
<Formula 1B-2(1)>
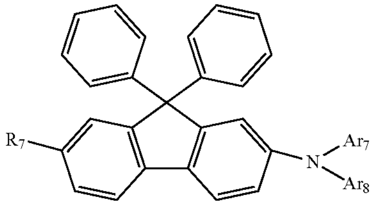
<Formula 1B-3(1)>
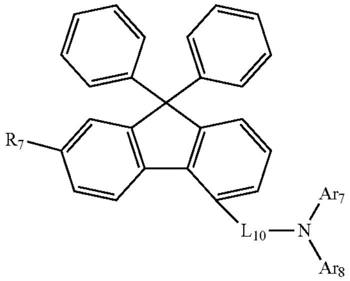
<Formula 1B-4(1)>
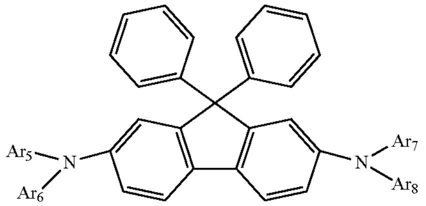
<Formula 1C-1(1)>
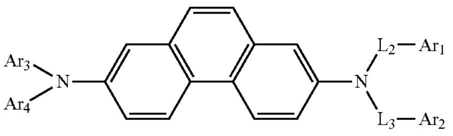

-continued
<Formula 1C-1(2)>
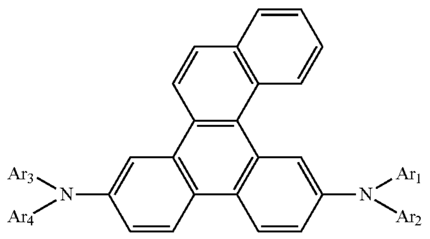
<Formula 40A-1(1)>
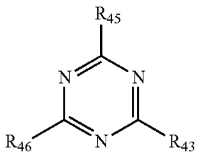
<Formula 40A-1(2)>
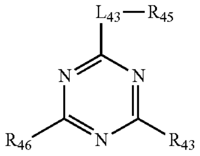
<Formula 40A-1(3)>
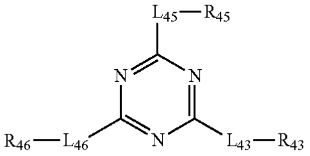
<Formula 40A-2(1)>
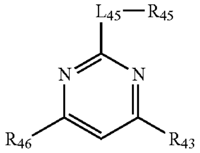
<Formula 40A-3(1)>
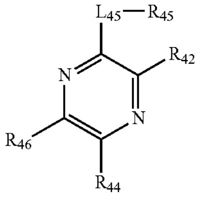
<Formula 40B-1(1)>
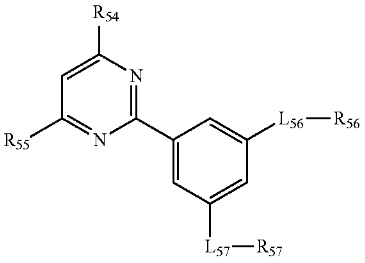
-continued
<Formula 40B-1(2)>
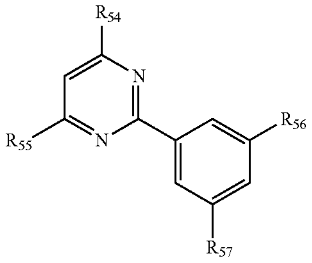
<Formula 40B-2(1)>
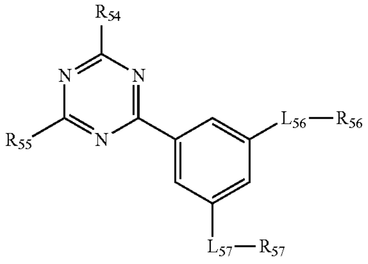
<Formula 40B-2(2)>
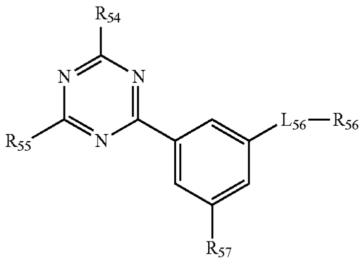
<Formula 40B-2(3)>
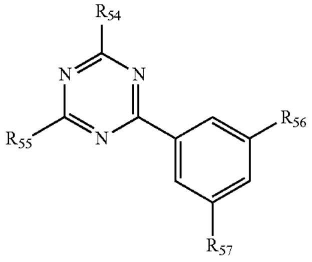
<Formula 40B-2(4)>
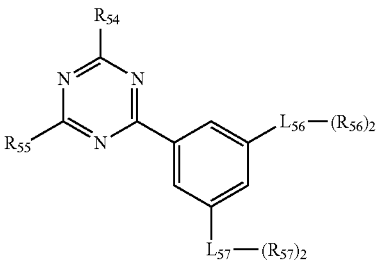

-continued

<Formula 40B-2(5)>

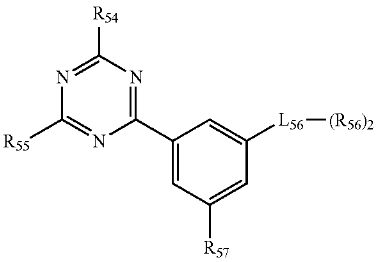

wherein, in the Formulae above, descriptions of $L_1$ to $L_3$, $L_7$, $L_{10}$, $L_{12}$, $L_{43}$, $L_{45}$, $L_{46}$, $L_{56}$, $L_{57}$, $Ar_1$ to $Ar_8$, $R_2$, $R_3$, $R_7$, $R_{42}$ to $R_{44}$, $R_{46}$, $R_{54}$, and $R_{55}$ are the same as described in claim 1, $R_{45}$ is selected from groups represented by Formulae 10-1 to 10-123, and at least one of $R_{56}$ and $R_{57}$ is selected from groups represented by Formulae 10-1 to 10-123:

Formula 10-1

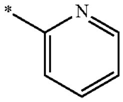

Formula 10-2

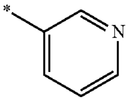

Formula 10-3

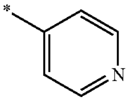

Formula 10-4

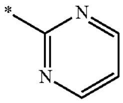

Formula 10-5

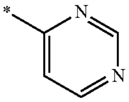

Formula 10-6

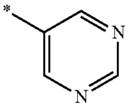

Formula 10-7

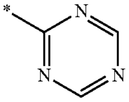

Formula 10-8

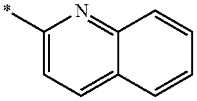

Formula 10-9

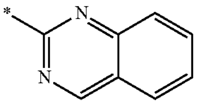

-continued

Formula 10-10

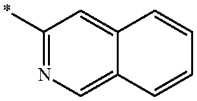

Formula 10-11

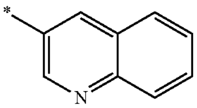

Formula 10-12

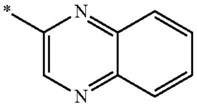

Formula 10-13

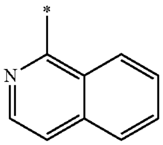

Formula 10-14

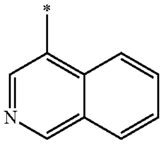

Formula 10-15

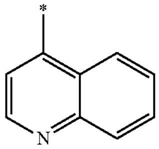

Formula 10-16

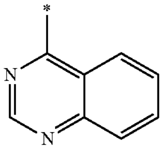

Formula 10-17

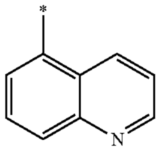

Formula 10-18

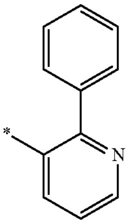

Formula 10-19

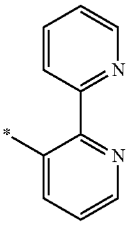

-continued
Formula 10-20
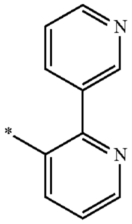
Formula 10-21
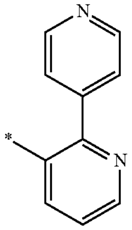
Formula 10-22
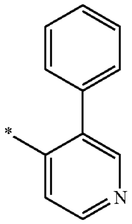
Formula 10-23
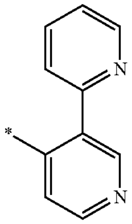
Formula 10-24
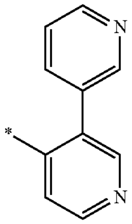
Formula 10-25
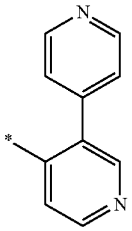
-continued
Formula 10-26
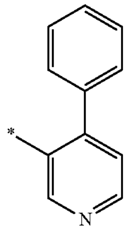
Formula 10-27
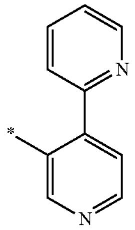
Formula 10-28
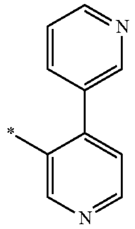
Formula 10-29
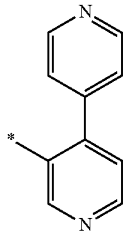
Formula 10-30
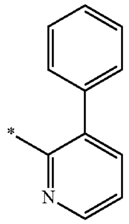
Formula 10-31
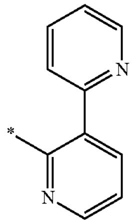

-continued
Formula 10-32
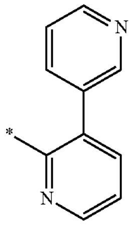
Formula 10-33
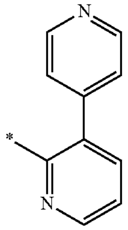
Formula 10-34
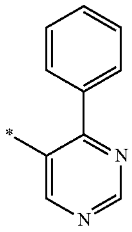
Formula 10-35
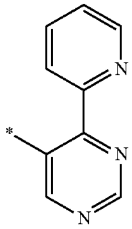
Formula 10-36
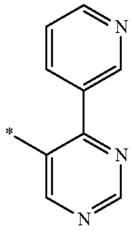
Formula 10-37
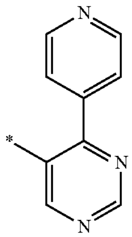
-continued
Formula 10-38
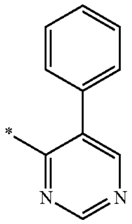
Formula 10-39
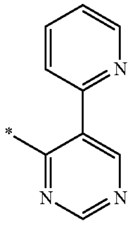
Formula 10-40
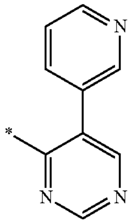
Formula 10-41
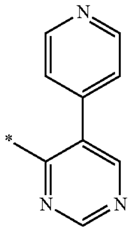
Formula 10-42
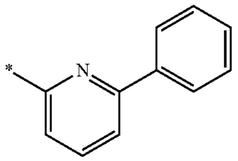
Formula 10-43
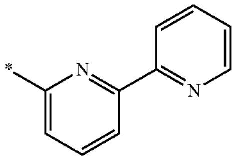
Formula 10-44
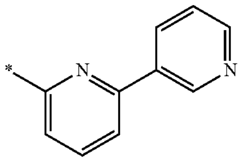
Formula 10-45
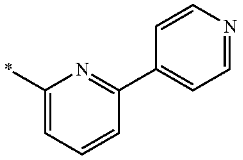

-continued
Formula 10-46
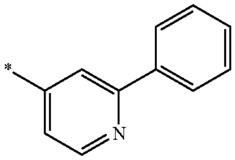
Formula 10-47
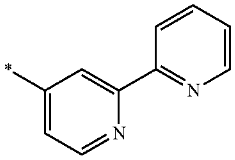
Formula 10-48
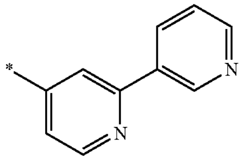
Formula 10-49
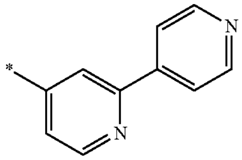
Formula 10-50
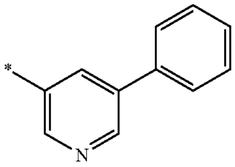
Formula 10-51
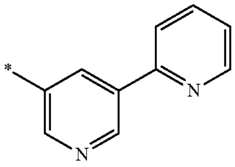
Formula 10-52
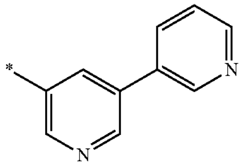
Formula 10-53
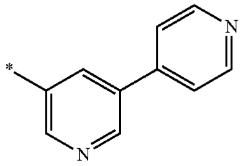
Formula 10-54
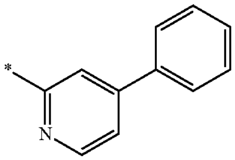
-continued
Formula 10-55
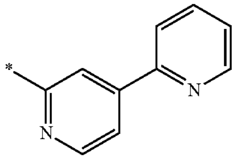
Formula 10-56
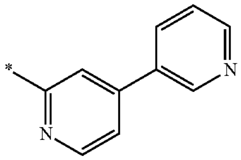
Formula 10-57
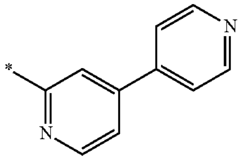
Formula 10-58
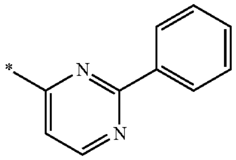
Formula 10-59
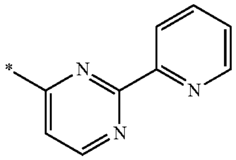
Formula 10-60
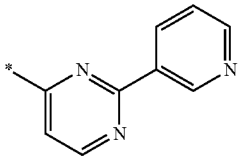
Formula 10-61
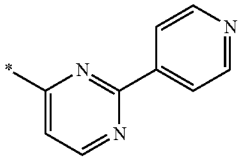
Formula 10-62
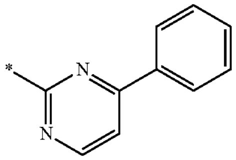
Formula 10-63
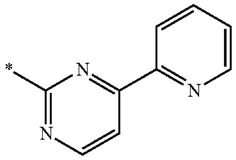

-continued
Formula 10-64
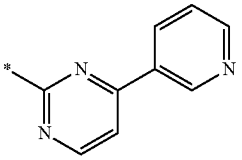
Formula 10-65
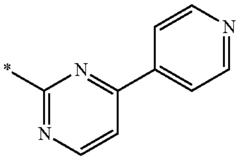
Formula 10-66
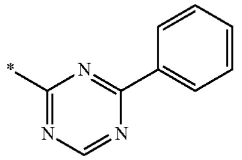
Formula 10-67
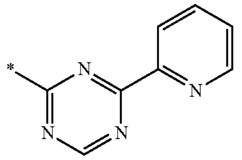
Formula 10-68
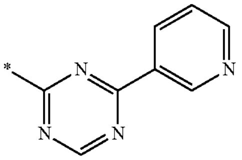
Formula 10-69
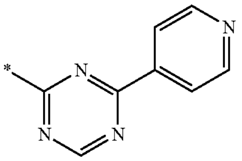
Formula 10-70
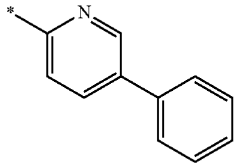
Formula 10-71
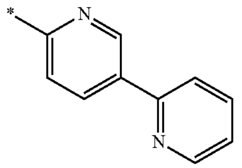
Formula 10-72
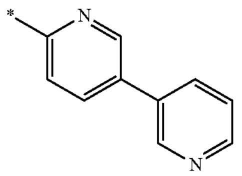
-continued
Formula 10-73
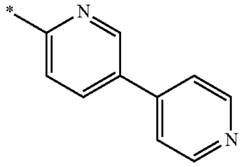
Formula 10-74
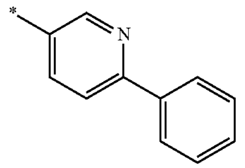
Formula 10-75
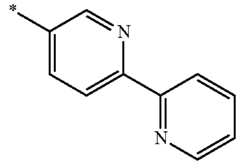
Formula 10-76
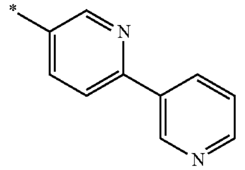
Formula 10-77
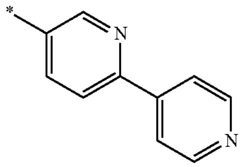
Formula 10-78
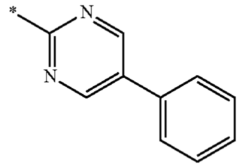
Formula 10-79
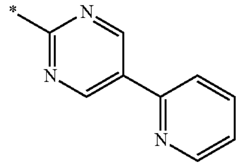
Formula 10-80
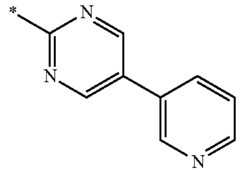
Formula 10-81
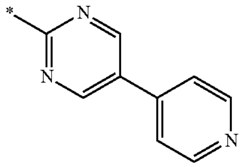

-continued
Formula 10-82
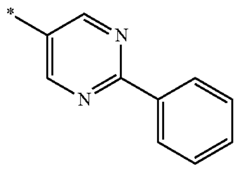
Formula 10-83
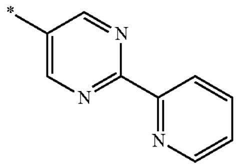
Formula 10-84
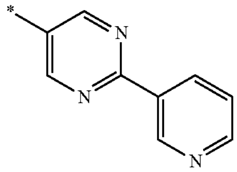
Formula 10-85
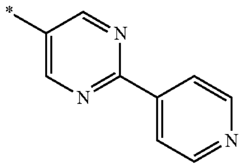
Formula 10-86
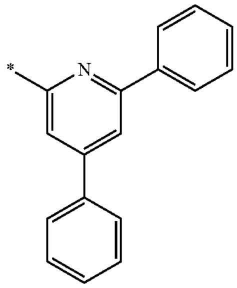
Formula 10-87
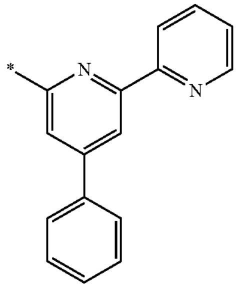
-continued
Formula 10-88
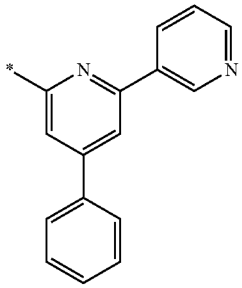
Formula 10-89
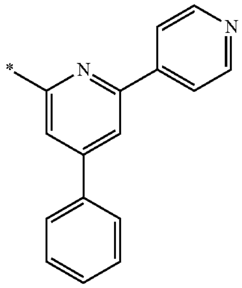
Formula 10-90
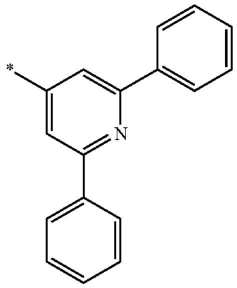
Formula 10-91
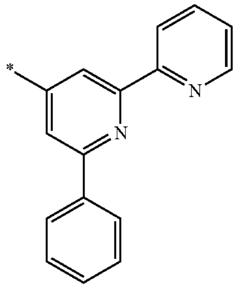
Formula 10-92
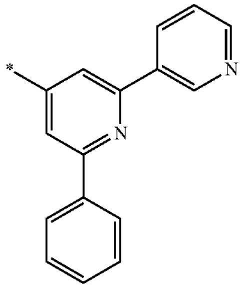

-continued
Formula 10-93
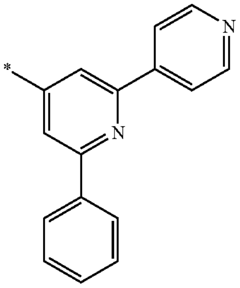
Formula 10-94
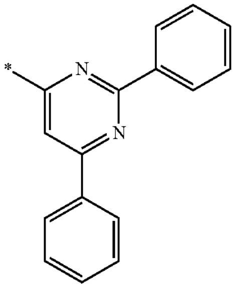
Formula 10-95
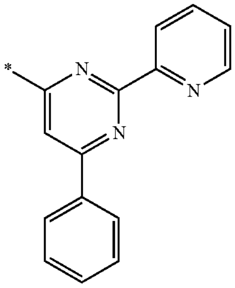
Formula 10-96
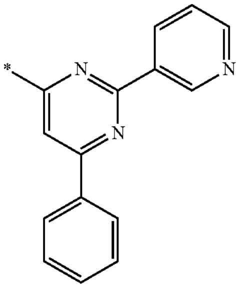
Formula 10-97
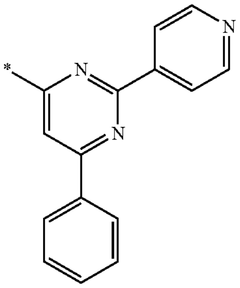
-continued
Formula 10-98
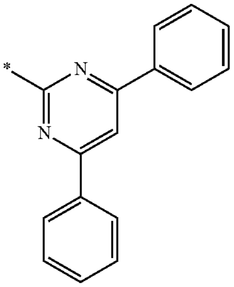
Formula 10-99
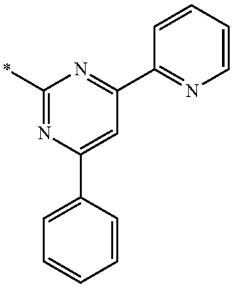
Formula 10-100
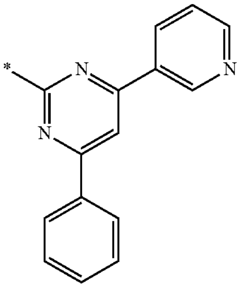
Formula 10-101
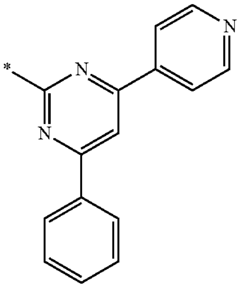
Formula 10-102
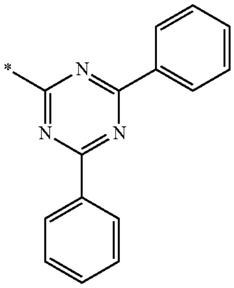

-continued
Formula 10-103
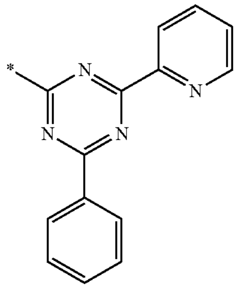
Formula 10-104
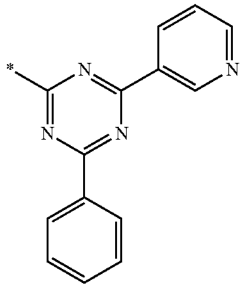
Formula 10-105
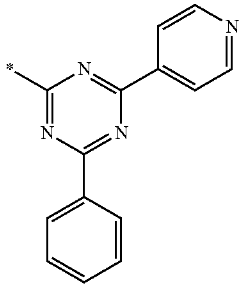
Formula 10-106
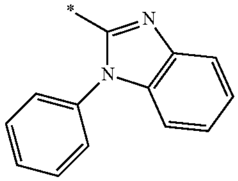
Formula 10-107
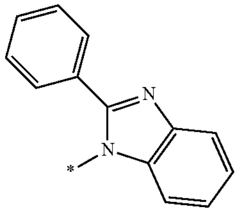
-continued
Formula 10-108
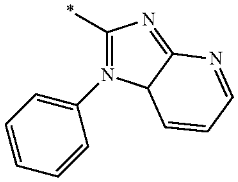
Formula 10-109
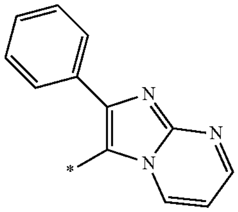
Formula 10-110
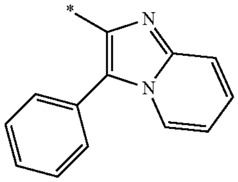
Formula 10-111
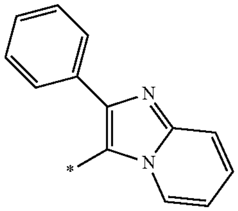
Formula 10-112
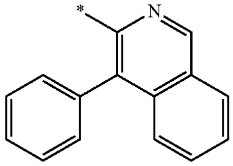
Formula 10-113
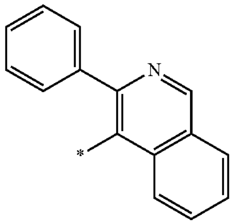
Formula 10-114
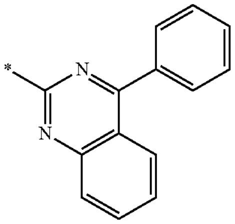

-continued

Formula 10-115

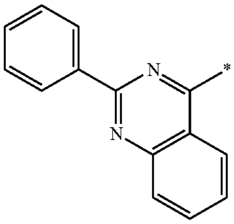

Formula 10-116

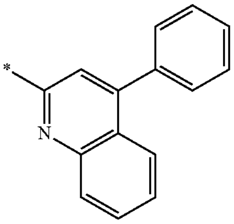

Formula 10-117

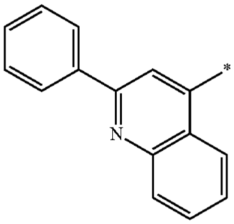

Formula 10-118

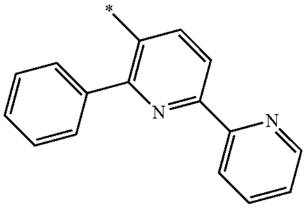

Formula 10-119

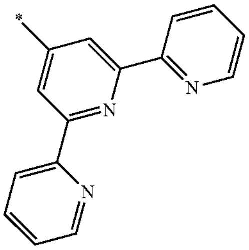

-continued

Formula 10-120

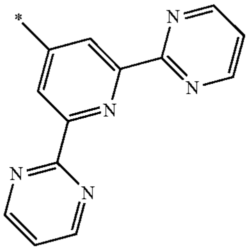

Formula 10-121

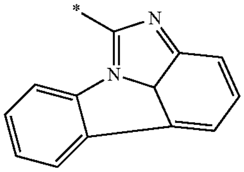

Formula 10-122

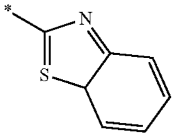

Formula 10-123

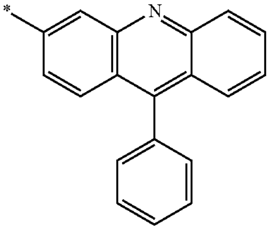

wherein, in Formulae 10-1 to 10-123, * indicates a binding site to an adjacent atom.

15. The organic light-emitting device as claimed in claim 1, wherein the first compound is a compound represented by one of Compounds 1 to 53, and the second compound is a compound represented by one of Compounds A 1 to A32:

1

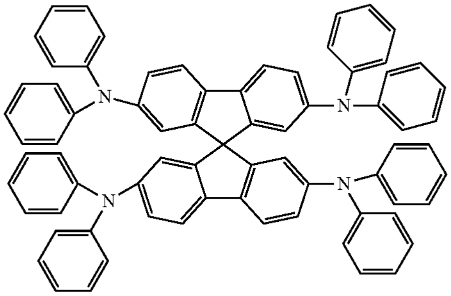

2

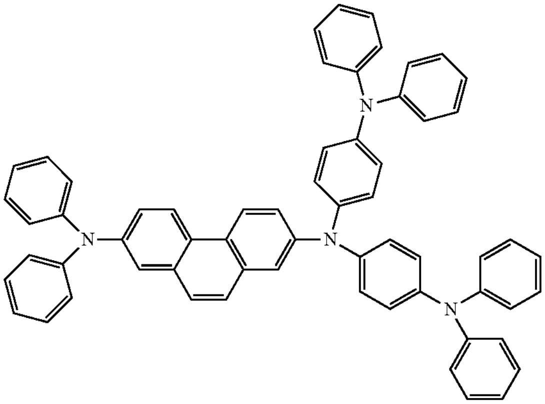

-continued
3
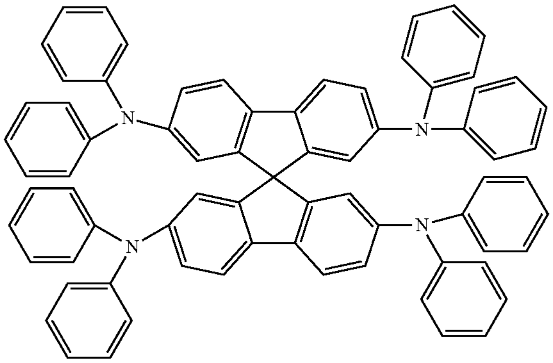
4
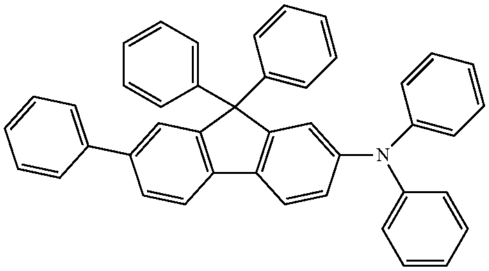
5
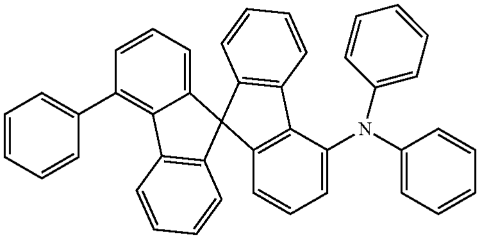
6
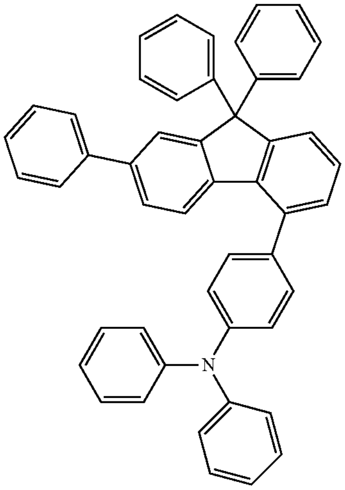
7
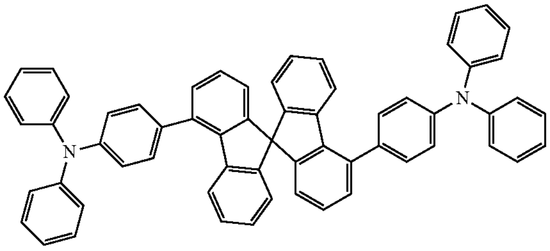
8
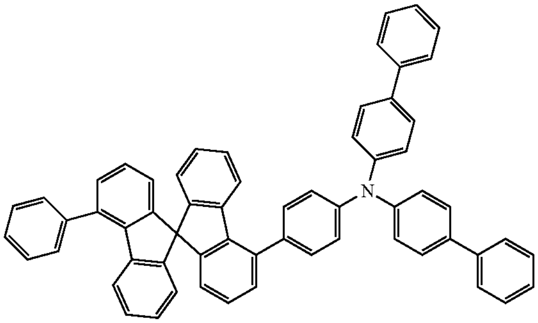

-continued
9
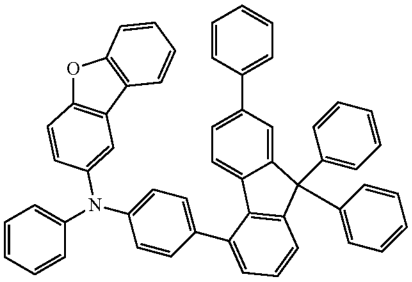
10
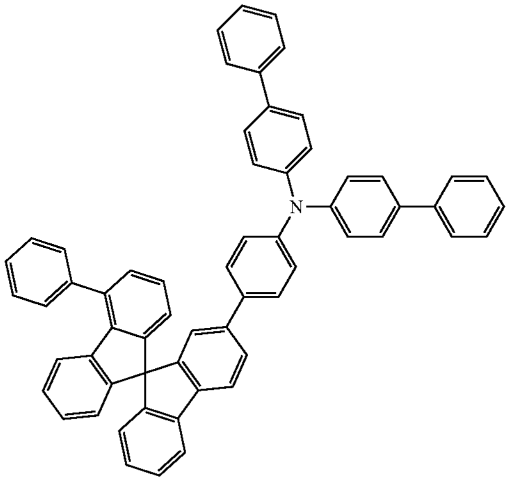
11
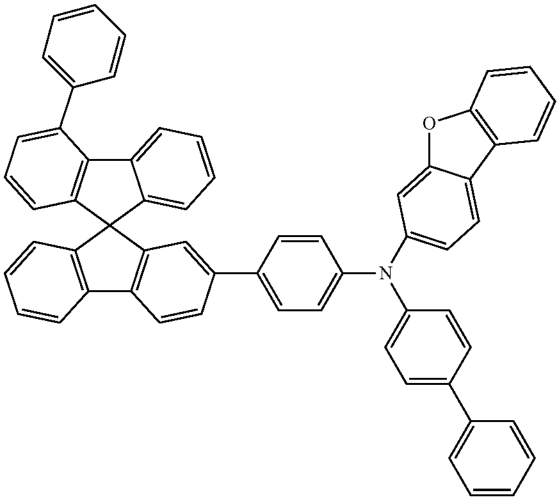
12
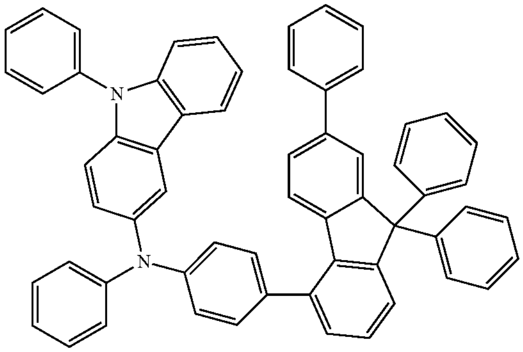
13
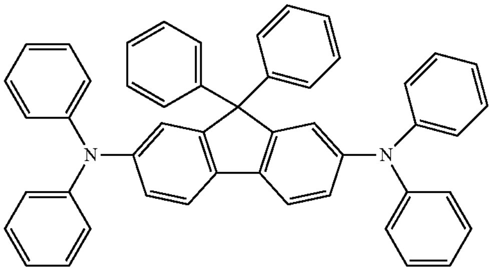
14
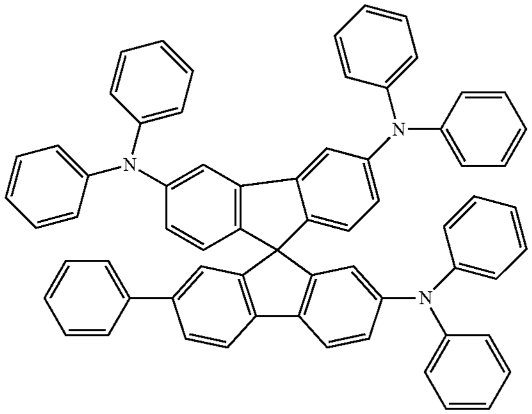

-continued
15
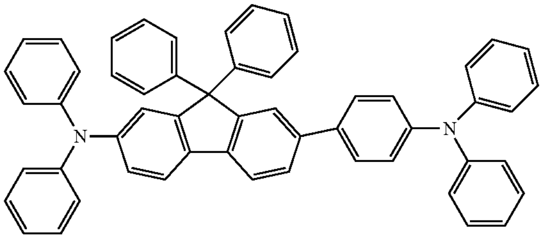
16
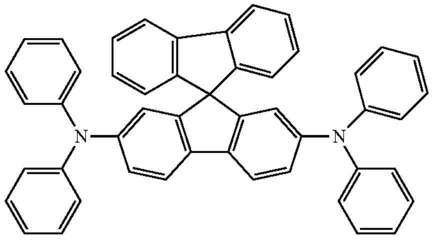
17
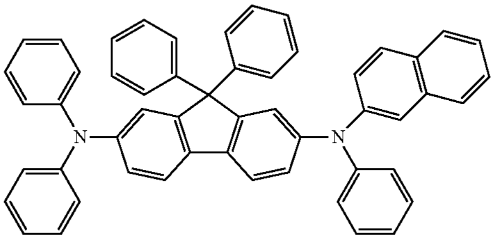
18
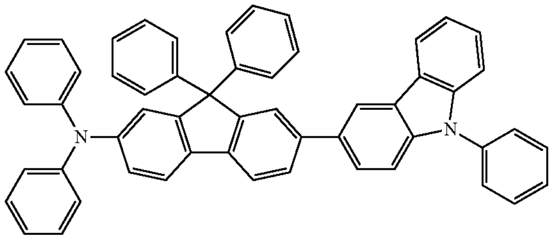
19
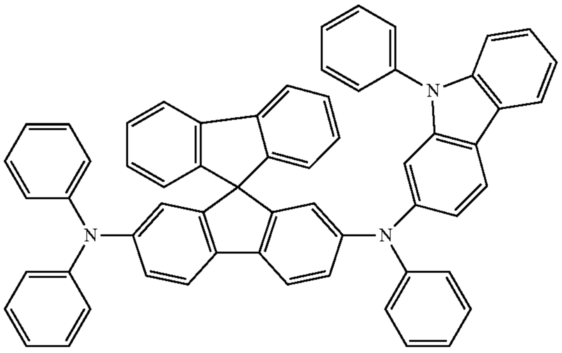
20
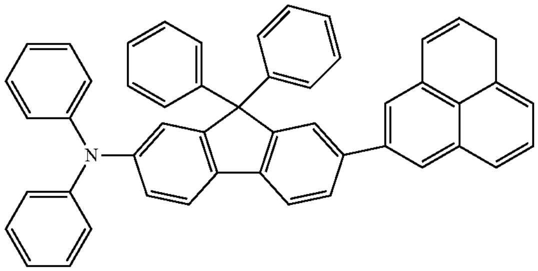
21
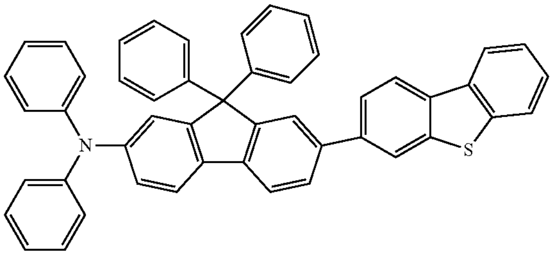
22
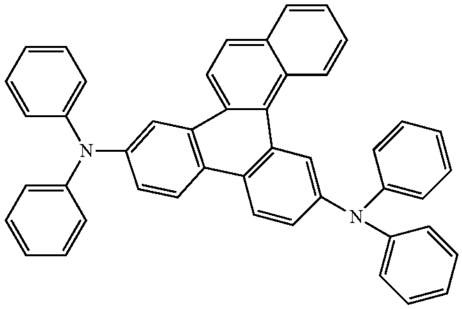

-continued
23
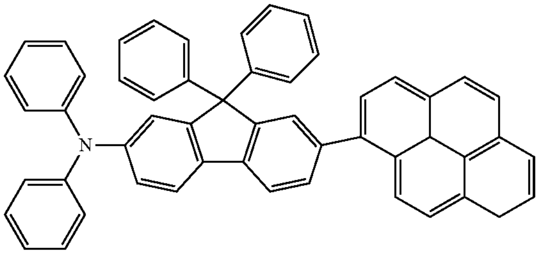
24
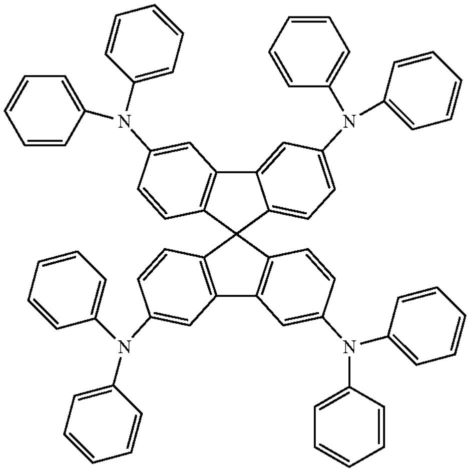
25
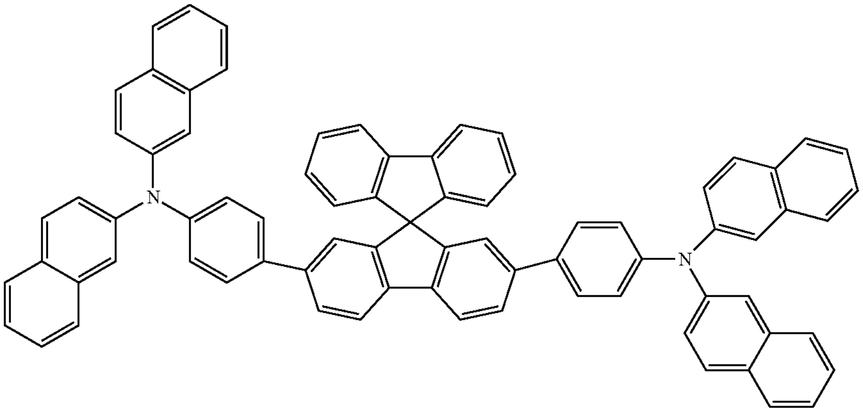
26
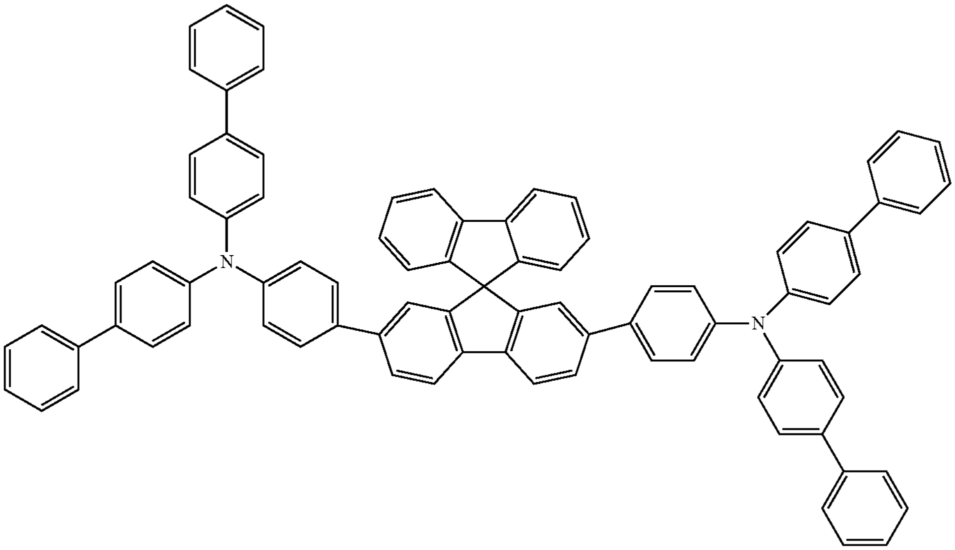

-continued
27
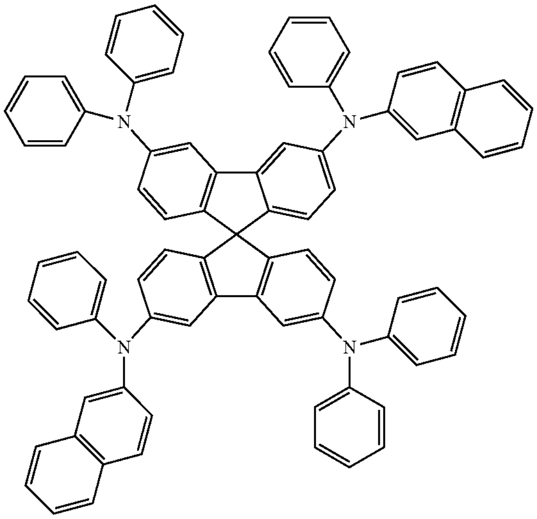
28
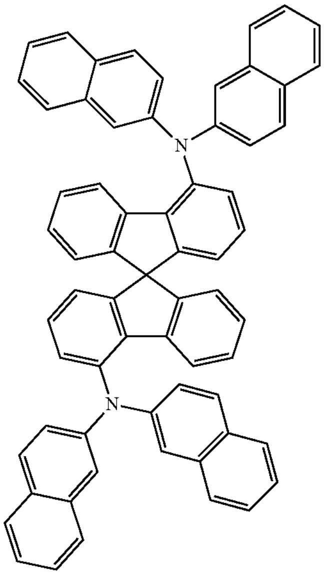
29
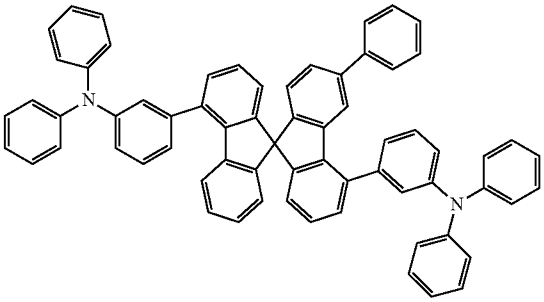
30
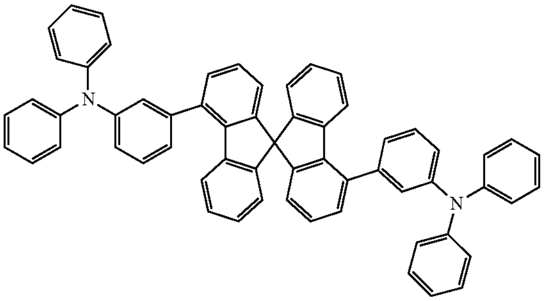
31
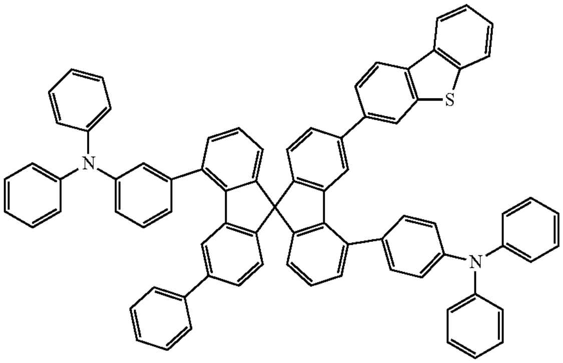
32
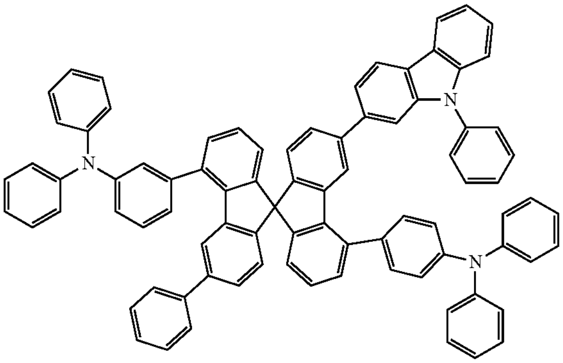

-continued
33
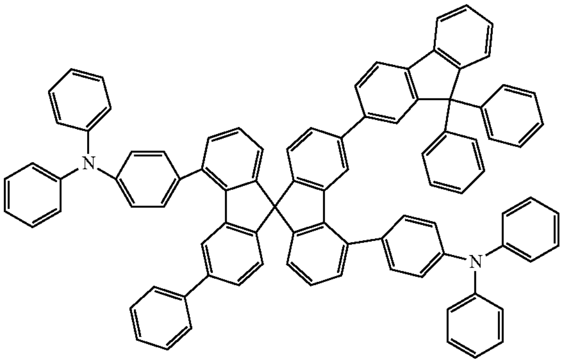
34
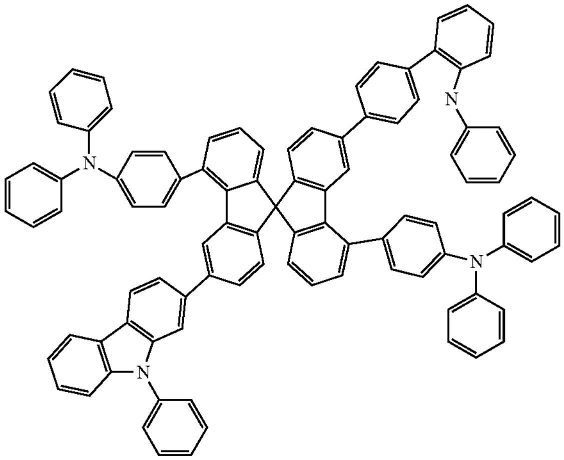
35
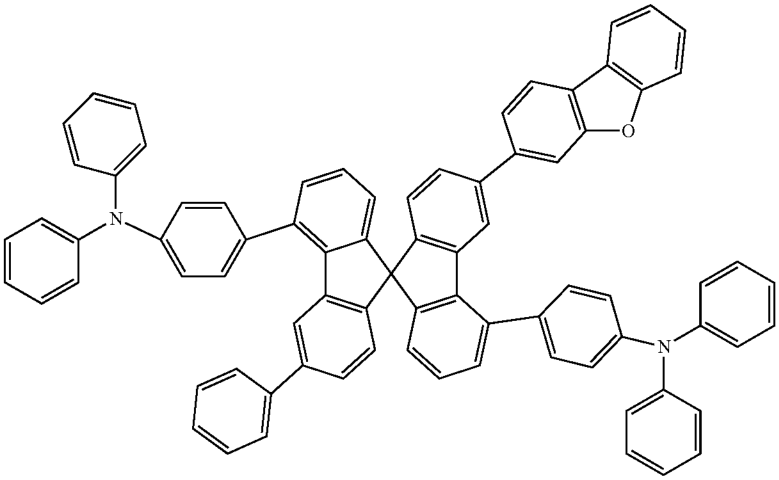
36
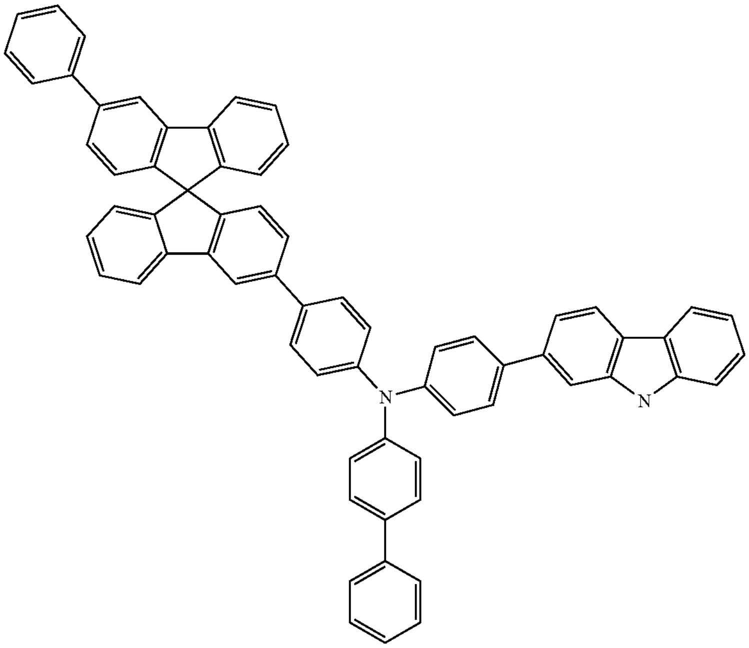

-continued
37
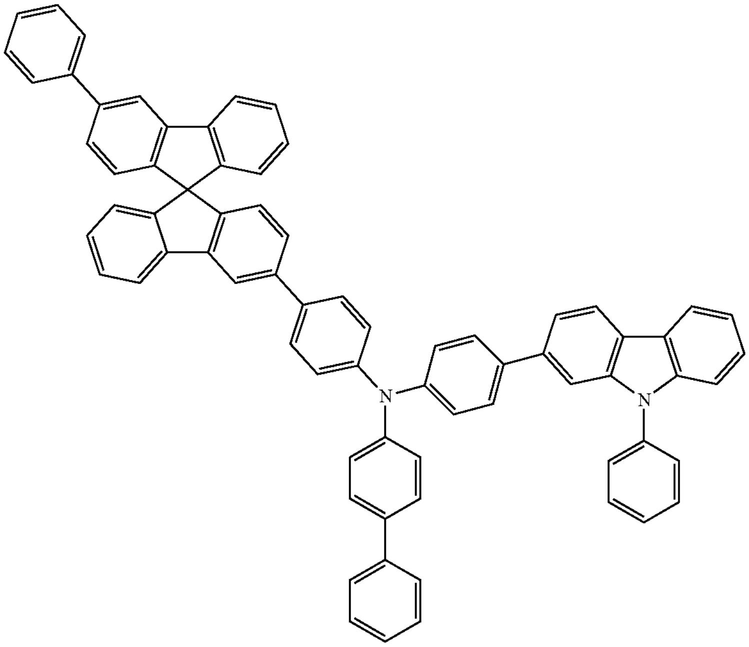
38
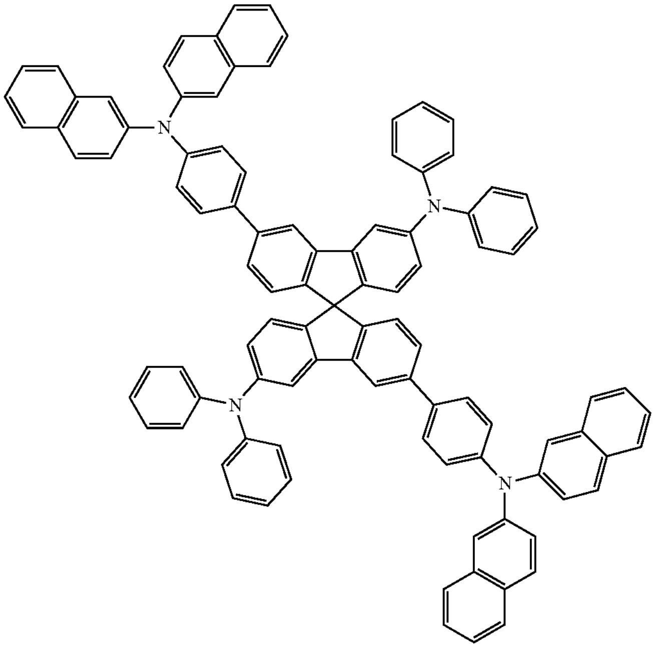

-continued
39
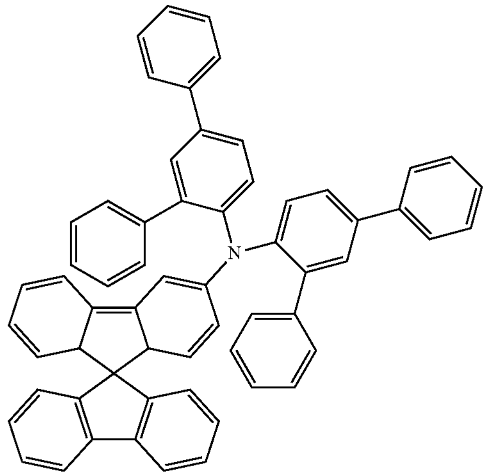
40
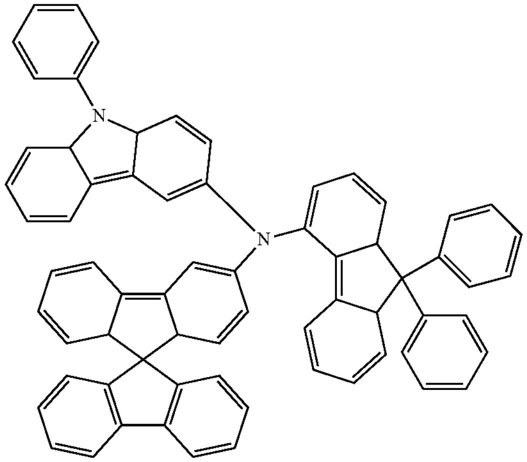
41
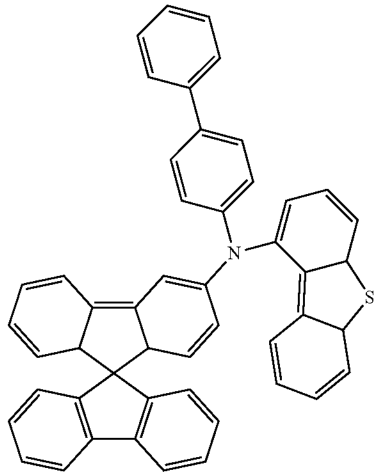
42
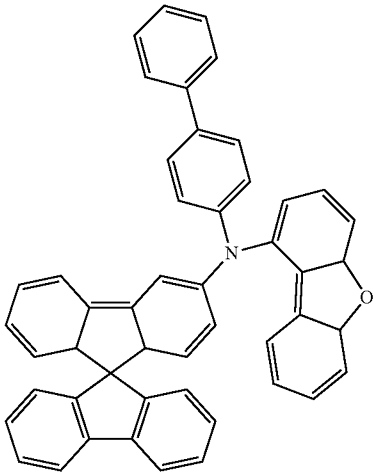
43
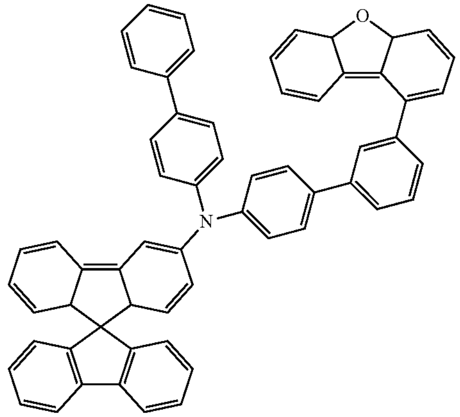
44
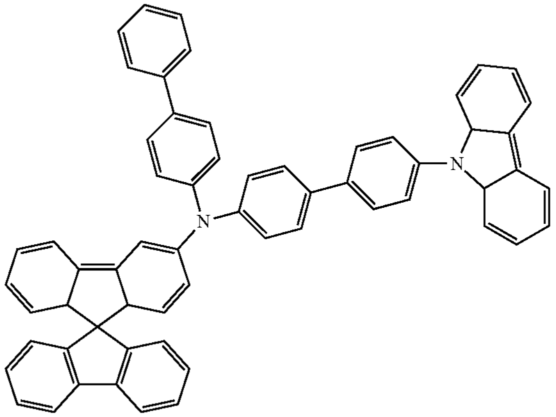

-continued
45
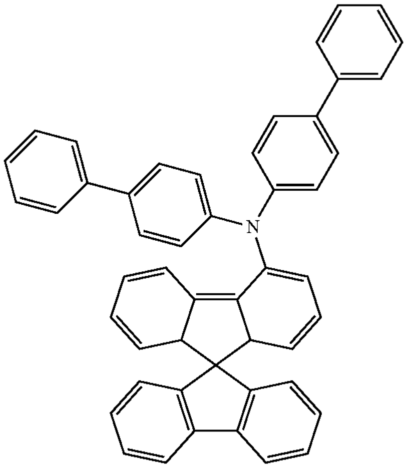
46
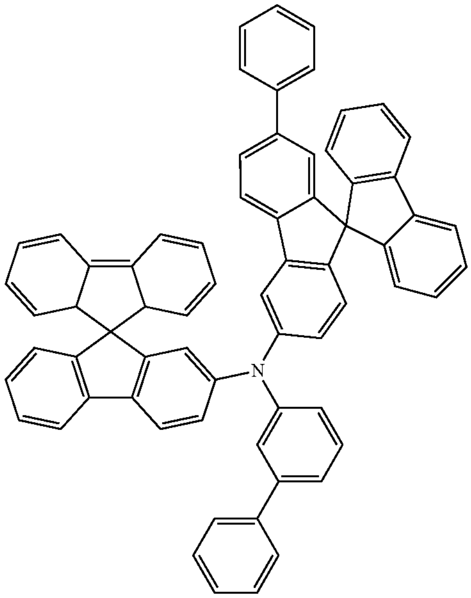
47
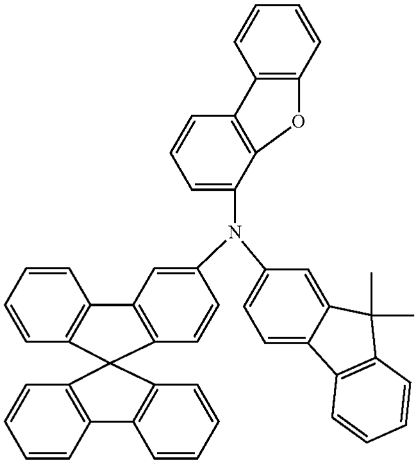
48
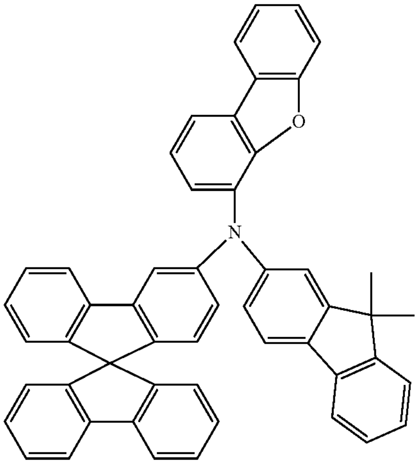
49
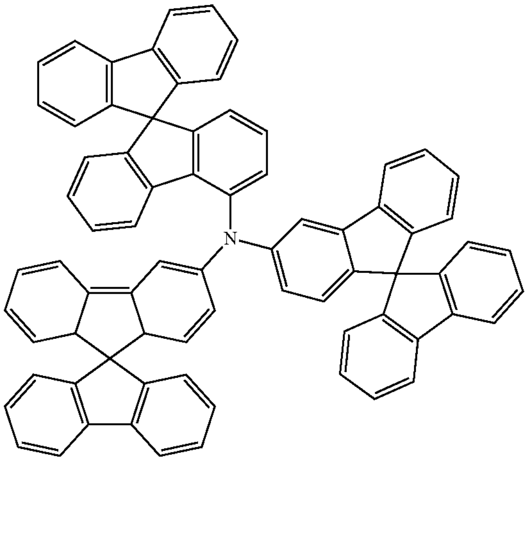
50
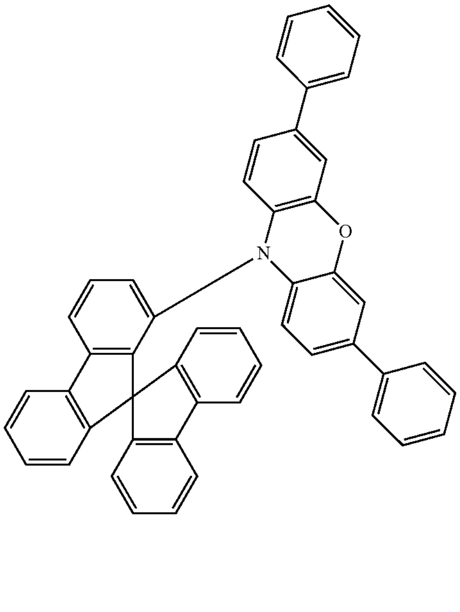

-continued
51
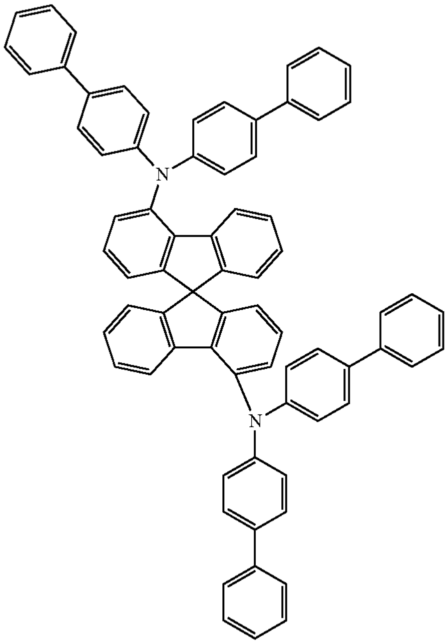
52
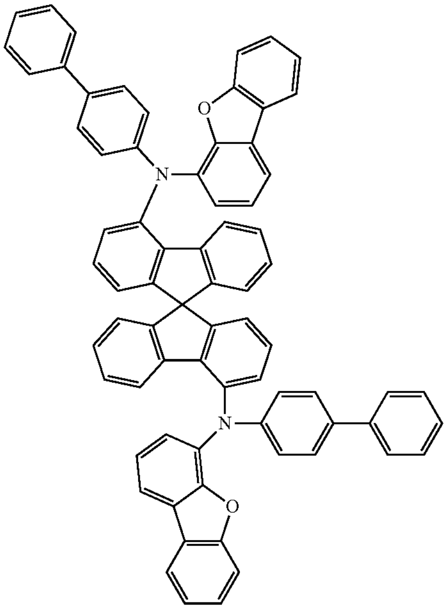
53
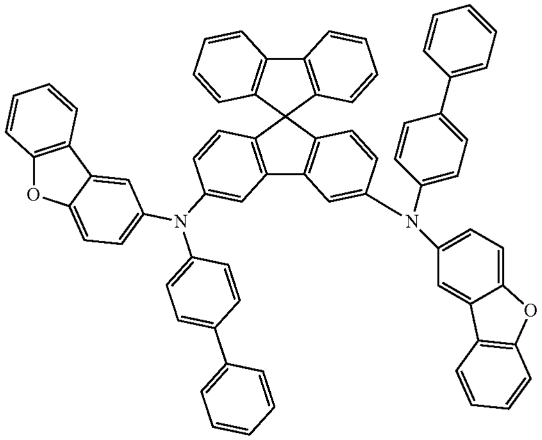
A1
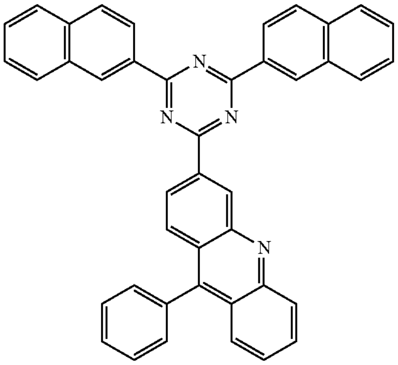
A2
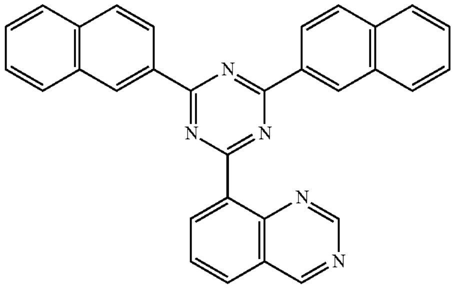
A3
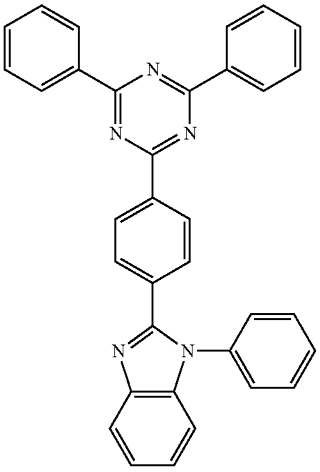

-continued
A4
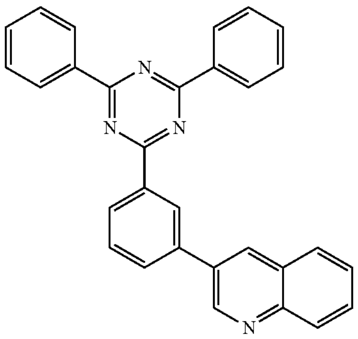
A5
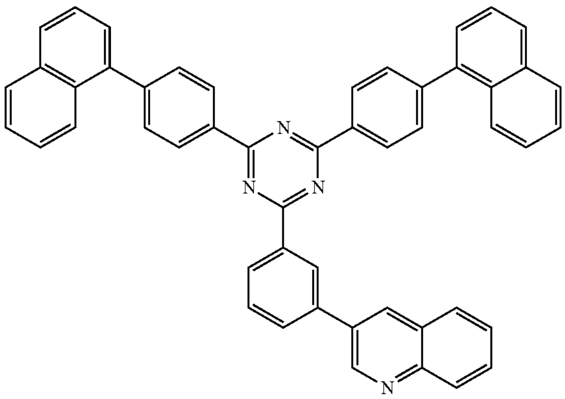
A6
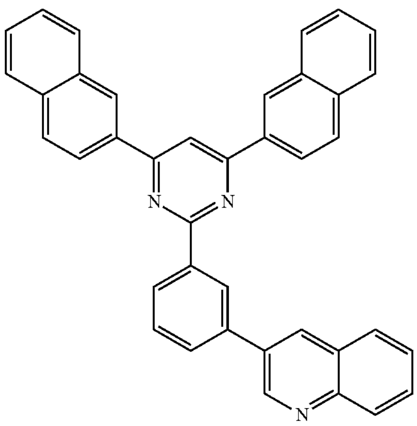
A7
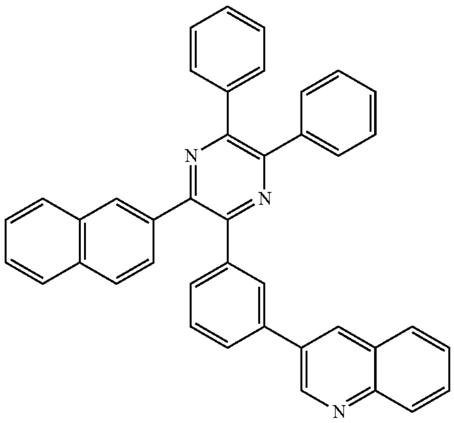
A8
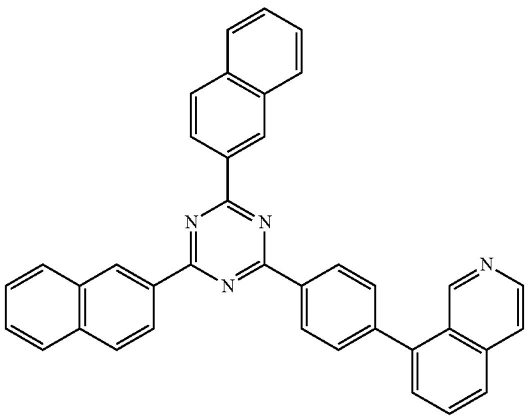
A9
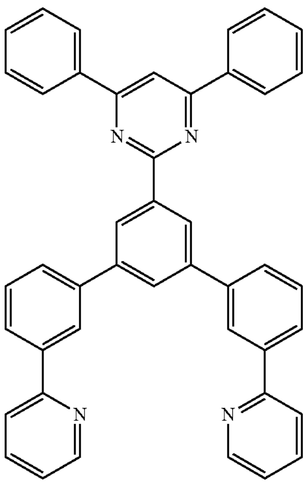

-continued
A10
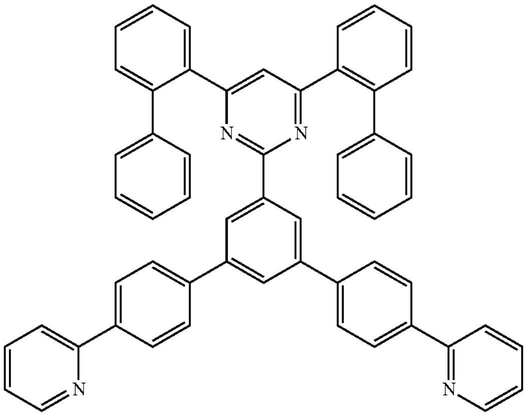
A11
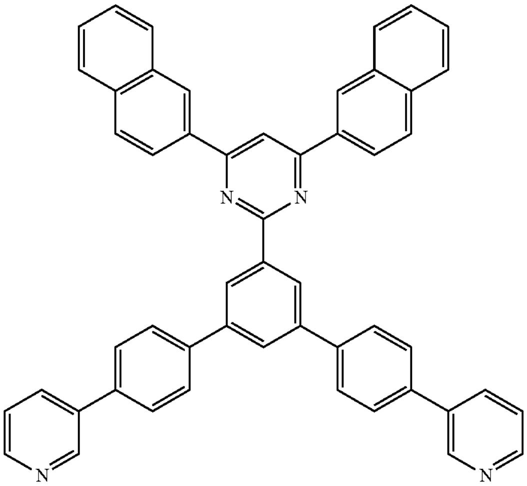
A12
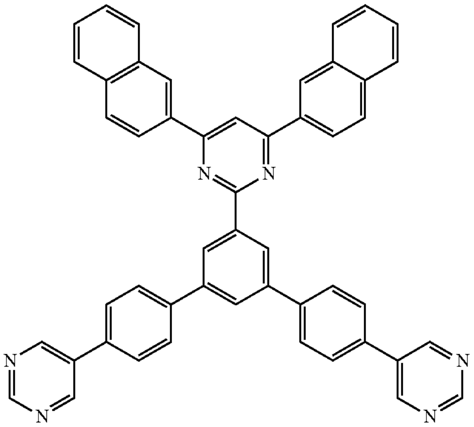
A13
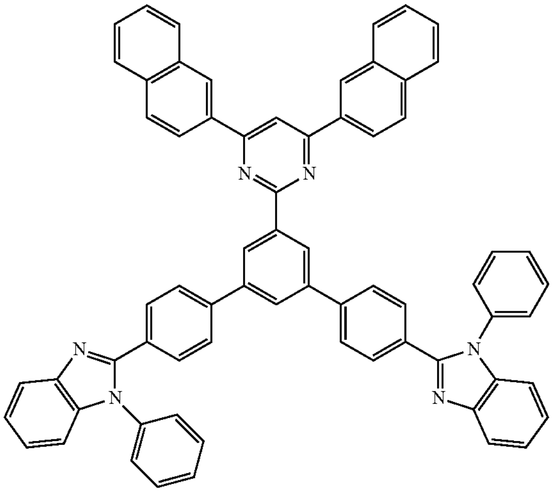
A14
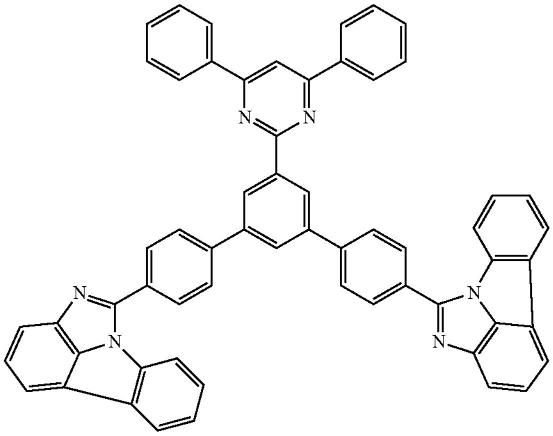
A15
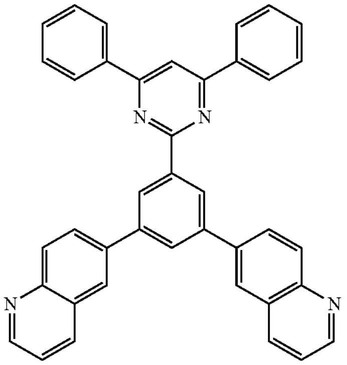

-continued
A16
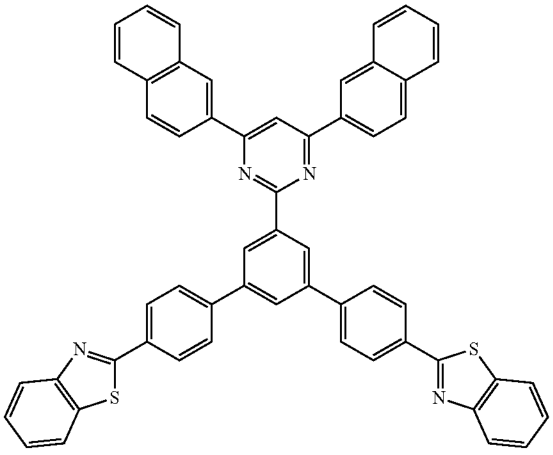
A17
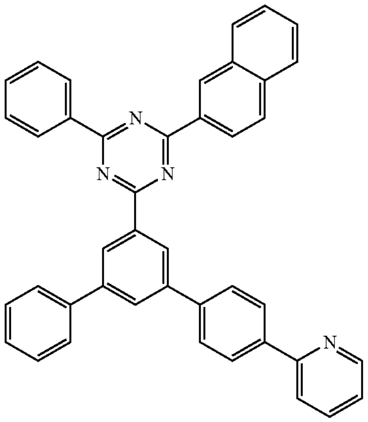
A18
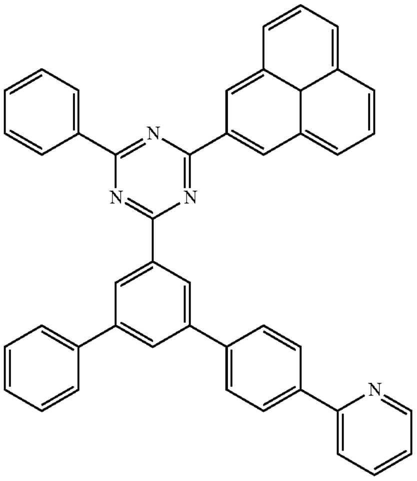
A19
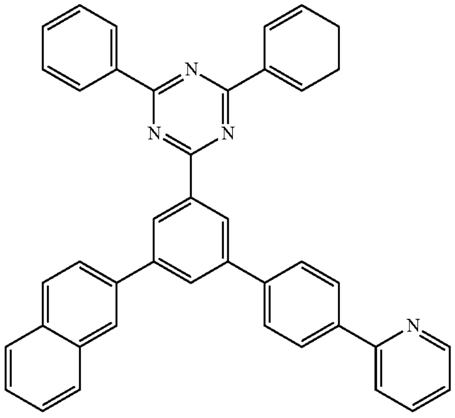
A20
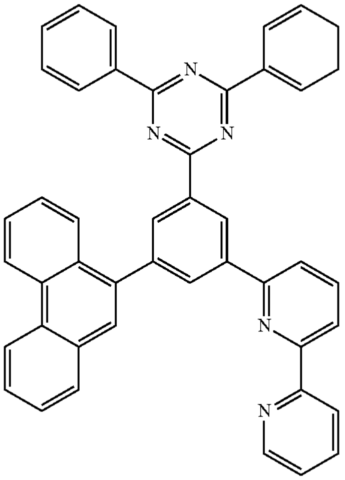
A21
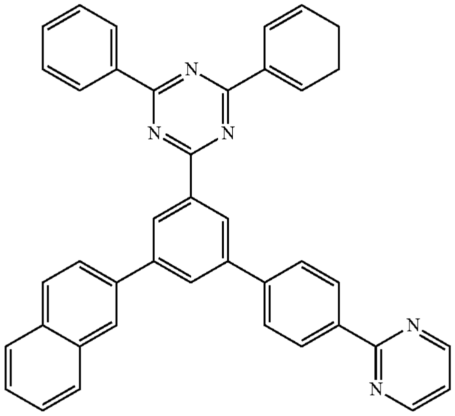

-continued
A22
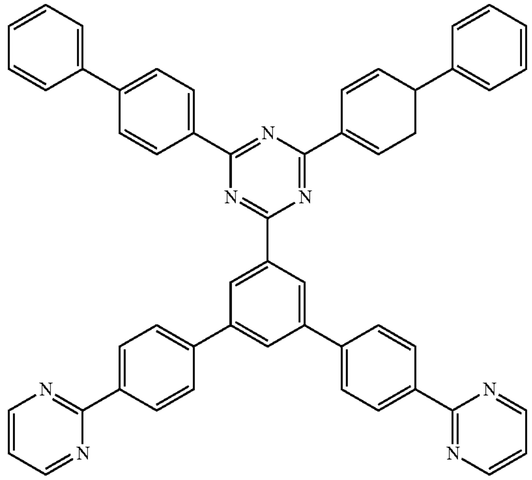
A23
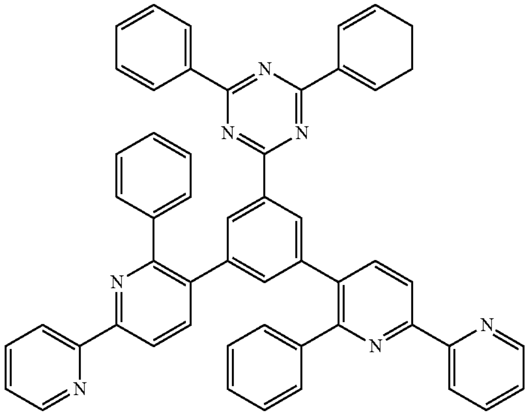
A24
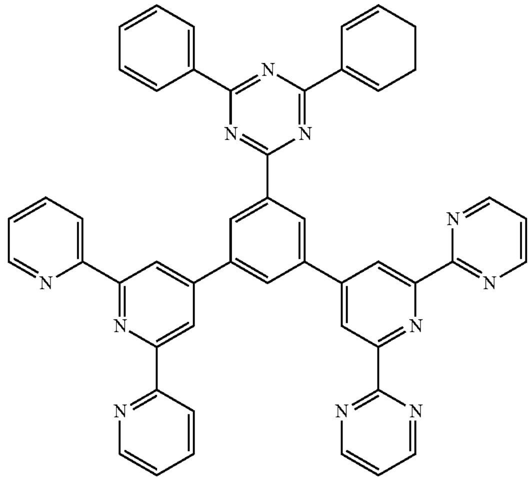
A25
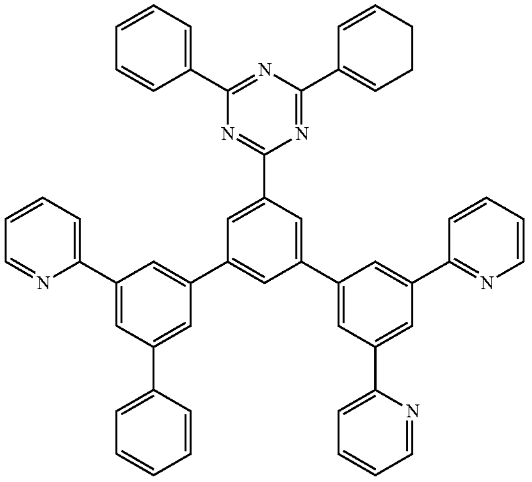
A26
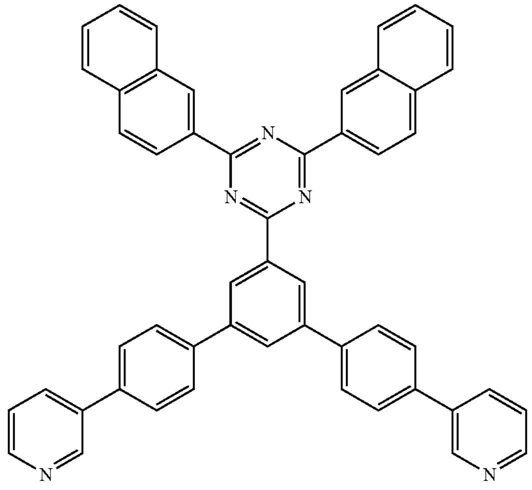
A27
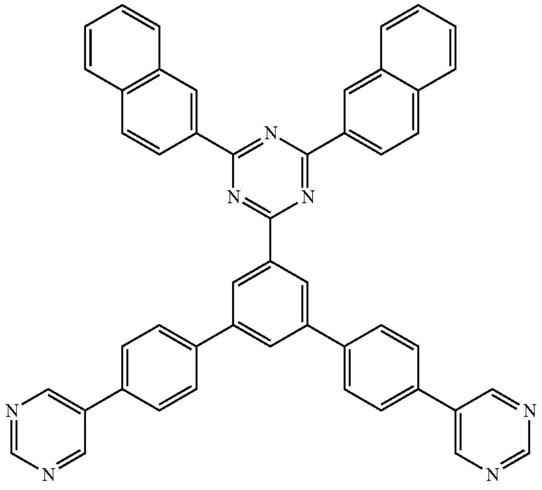

-continued
A28
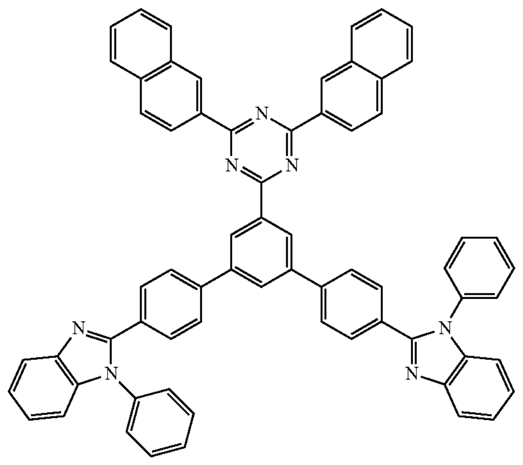
A29
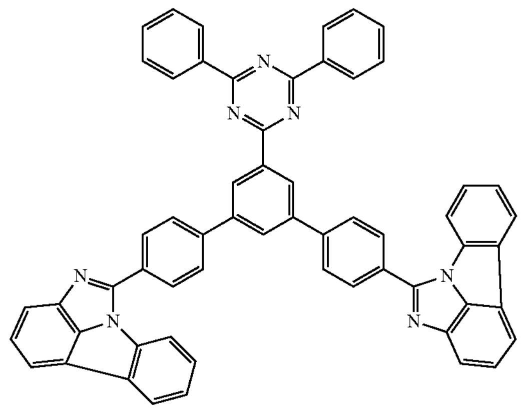
A30
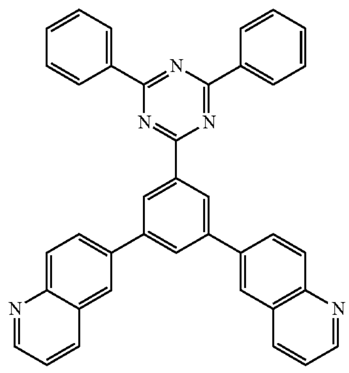
A31
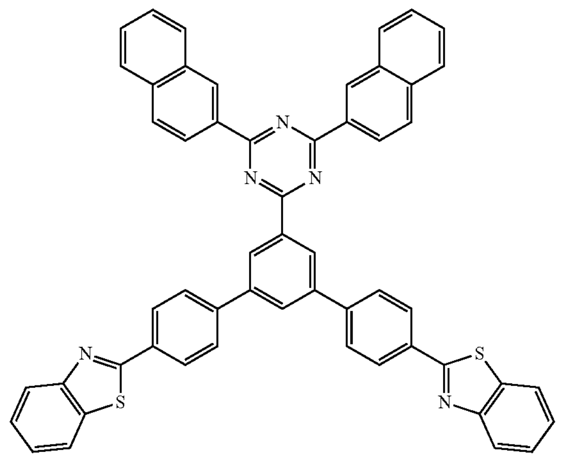
A32
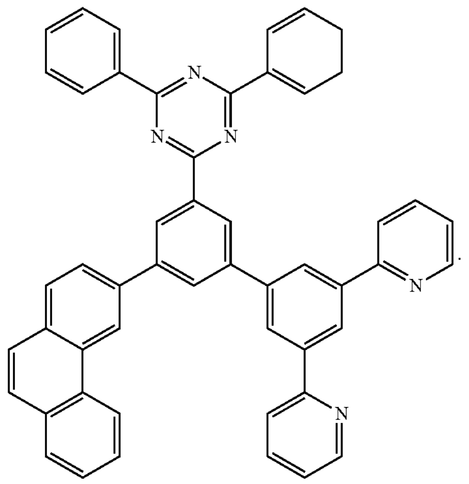

16. The organic light-emitting device as claimed in claim 1, wherein the emission layer includes at least one selected from a first host represented by Formula 101, a second host represented by Formula 201, a third host represented by Formula 202, a fourth host represented by Formula 301, and a fifth host represented by Formula 302:

<Formula 101>

$$Ar_{101}—[(L_{101})_{a101}—R_{101}]_{n101}$$

<Formula 201>

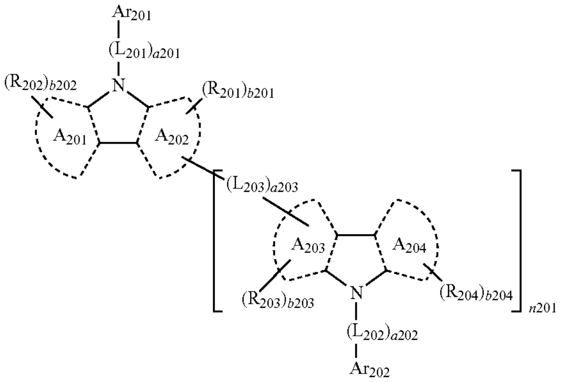

<Formula 202>

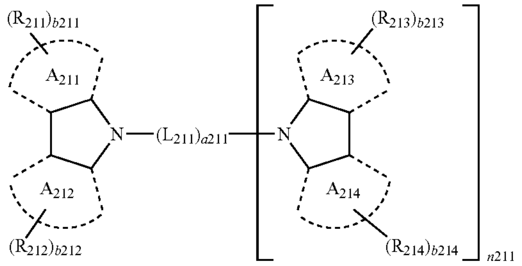

<Formula 301>

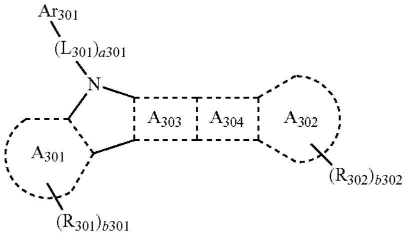

<Formula 302>

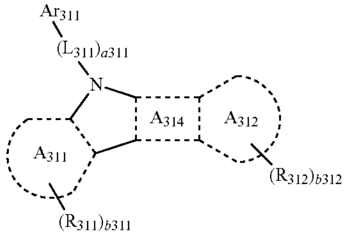

<Formula 303>

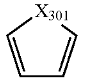

wherein, in the Formulae above, $Ar_{101}$, $A_{201}$ to $A_{204}$, $A_{211}$ to $A_{214}$, $A_{301}$ to $A_{303}$, $A_{311}$, and $A_{312}$ are each independently a substituted or unsubstituted $C_6$-$C_{20}$ aromatic ring;

$A_{304}$ and $A_{314}$ are each independently a group represented by Formula 303;

$X_{301}$ is selected from $N(L_{302})_{a302}$-$Ar_{302}$, an oxygen (O) atom, a sulfur (S) atom, $C(R_{303})(R_{304})$, $Si(R_{303})(R_{304})$, $P(R_{303})$, $B(R_{303})$, and $P(=O)(R_{303})$;

$L_{101}$, $L_{201}$ to $L_{203}$, $L_{211}$, $L_{301}$, $L_{302}$, and $L_{311}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a101, a201 to a203, a211, a301, a302, and a311 are each independently an integer selected from 0 to 3;

$R_{101}$, $Ar_{201}$, $Ar_{202}$, $Ar_{301}$, $Ar_{302}$, and $Ar_{311}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted heteroaryl group, a substituted or unsubstituted monovalent non-aromatic condensed polycyclic group, and a substituted or unsubstituted monovalent non-aromatic condensed heteropolycyclic group;

$R_{201}$ to $R_{204}$, $R_{211}$ to $R_{214}$, $R_{301}$ to $R_{304}$, $R_{311}$, and $R_{312}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_{101})(Q_{102})$, —$Si(Q_{103})(Q_{104})(Q_{105})$, and —$B(Q_{106})(Q_{107})$;

b201 and b203 are each independently an integer selected from 0 to 3, b202, b204, b211 to b214, b301, b302, b311, and b312 are each independently an integer selected from 0 to 4;

n101 is an integer selected from 0 to 3, n201 and n202 are each independently an integer selected from 0 to 4, n211 is an integer selected from 1 and 2;

at least one of substituents of the substituted $C_6$-$C_{20}$ aromatic ring, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{101}$)($Q_{102}$), —Si($Q_{103}$)($Q_{104}$)($Q_{105}$), and —B($Q_{106}$)($Q_{107}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, aryloxy group, a $C_6$-$C_{60}$, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{111}$)($Q_{112}$), —Si($Q_{113}$)($Q_{114}$)($Q_{115}$), and —B($Q_{116}$)($Q_{117}$); and —N($Q_{121}$)($Q_{122}$), —Si($Q_{123}$)($Q_{124}$)($Q_{125}$), and —B($Q_{126}$)($Q_{127}$), wherein $Q_{101}$ to $Q_{107}$, $Q_{111}$ to $Q_{117}$, and $Q_{121}$ to $Q_{127}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

17. The organic light-emitting device as claimed in claim 16, wherein the first host is represented by one of Formulae 101A to 101D, the second host is represented by Formula 201A, the third host is represented by one of Formulae 202A and 202B, the fourth host is represented by one of Formulae 301A to 301H, and the fifth host is represented by one of Formulae 302A and 302B:

<Formula 101A>

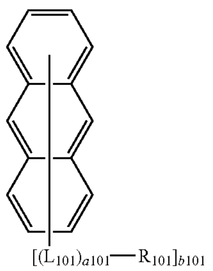

<Formula 101B>

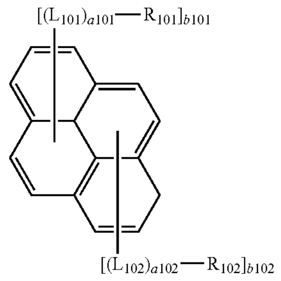

<Formula 101C>

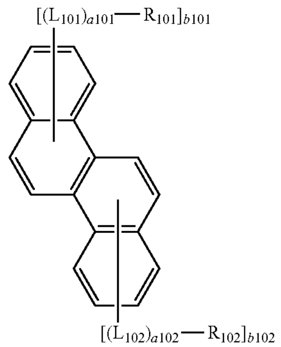

-continued
<Formula 101D>
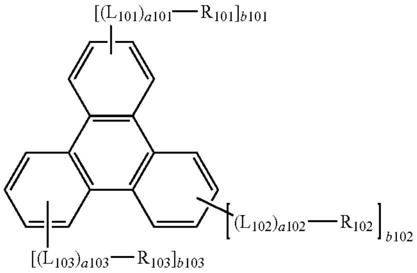
<Formula 201A>
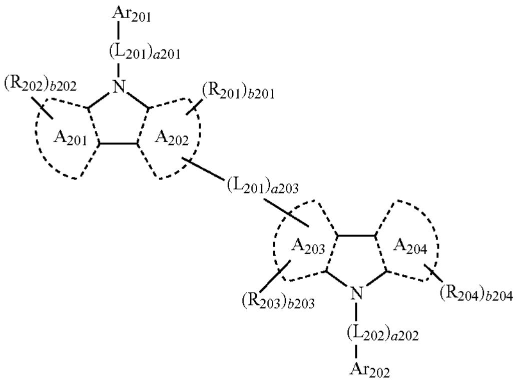
<Formula 202A>
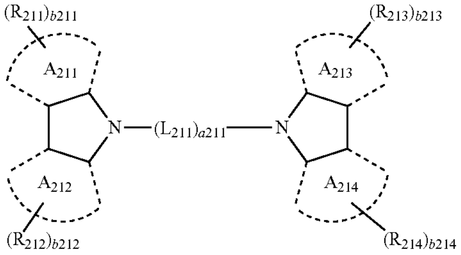
<Formula 202B>
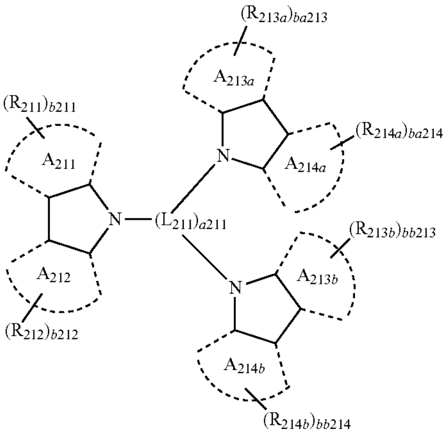
-continued
<Formula 301A>
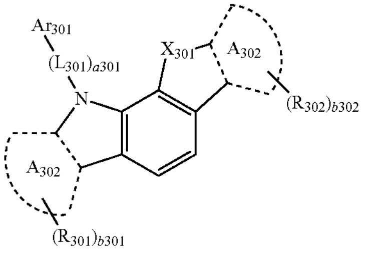
<Formula 301B>
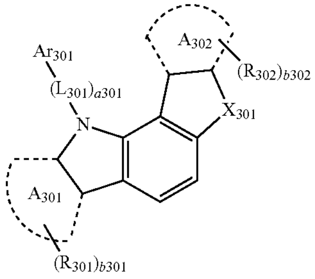
<Formula 301C>
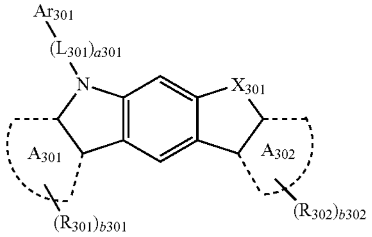
<Formula 301D>
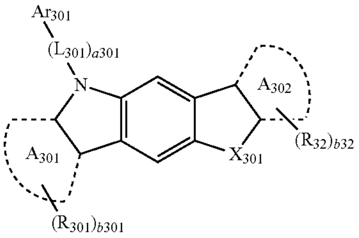
<Formula 301E>
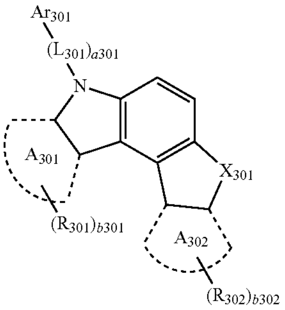

-continued

<Formula 301F>

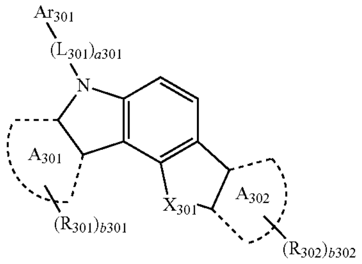

<Formula 301G>

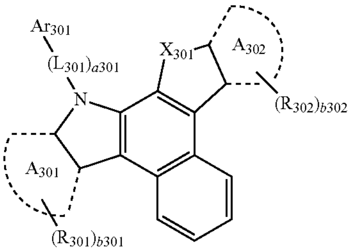

<Formula 301H>

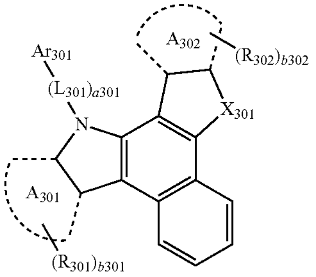

<Formula 302A>

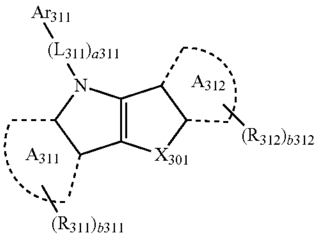

<Formula 302B>

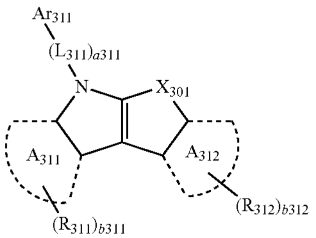

wherein, in the Formulae above, descriptions of $Ar_{101}$, $A_{201}$ to $A_{204}$, $A_{211}$ to $A_{214}$, $A_{301}$ to $A_{304}$, $A_{311}$, $A_{312}$, $A_{314}$, $X_{301}$, $L_{101}$, $L_{201}$ to $L_{203}$, $L_{301}$, $L_{302}$, $L_{311}$, a101, a201 to a203, a301, a302, a311, $Ar_{201}$, $Ar_{202}$, $Ar_{301}$, $Ar_{302}$, $Ar_{311}$, $R_{101}$, $R_{201}$ to $R_{204}$, $R_{211}$ to $R_{214}$, $R_{301}$, $R_{302}$, $R_{311}$, $R_{312}$, b101, b201 to b204, b211 to b214, b301, b302, b311, and b312 are the same as described in claim 15, descriptions of $L_{102}$ and $L_{103}$ are each the same as descriptions of $L_{101}$, descriptions of a102 and a103 are each the same as descriptions of a101, descriptions of $R_{102}$ and $R_{103}$ are each the same as descriptions of $R_{101}$, and descriptions of b102 and b103 are each the same as descriptions of b101, and descriptions of $A_{213a}$ and $A_{213b}$ are each the same as descriptions of $A_{213}$, descriptions of $A_{214a}$ and $A_{214b}$ are each the same as descriptions of $A_{214}$, descriptions of $R_{213a}$ and $R_{213b}$ are each the same as descriptions of $R_{213}$, descriptions of $R_{214b}$ and $R_{214b}$ are each the same as descriptions of $R_{214}$, descriptions of ba213 and bb213 are each the same as descriptions of b213, and descriptions of ba214 and bb214 are each the same as descriptions of b214.

18. The organic light-emitting device as claimed in claim 1, wherein the hole transport region includes a hole transport layer and a hole injection layer between the first electrode and the hole transport layer, the hole transport region includes a hole transport layer and a hole injection layer between the first electrode and the hole transport layer, the first compound is included in the hole injection layer and the hole transport layer, the first compound included in the hole injection layer and the first compound included in the hole transport layer are identical to or different from each other, the electron transport region includes an electron transport layer and an electron injection layer between the second electrode and the electron transport layer, and the second compound is included in the electron transport layer.

19. An organic light-emitting device, comprising:

a first electrode;

a second electrode facing the first electrode;

an emission layer between the first electrode and the second electrode;

a hole transport region between the first electrode and the emission layer;

an electron transport region between the second electrode and the emission layer, wherein the hole transport region includes a hole transport layer, a hole injection layer between the first electrode and the hole transport layer, and an auxiliary emission layer between the hole transport layer and the emission layer, the electron transport region includes an electron transport layer and an electron injection layer between the second electrode and the electron transport layer, wherein the hole injection layer, the hole transport layer, and the auxiliary emission layer each include a first compound represented by one of Formulae 1A, 1B, and 1C, the first compound included in the hole injection layer, the first compound included in the hole transport layer, and the first compound included in the auxiliary emission layer are identical to or different from each other, the electron transport layer includes a second compound represented by one of Formulae 40A and 40B:

<Formula 1A>

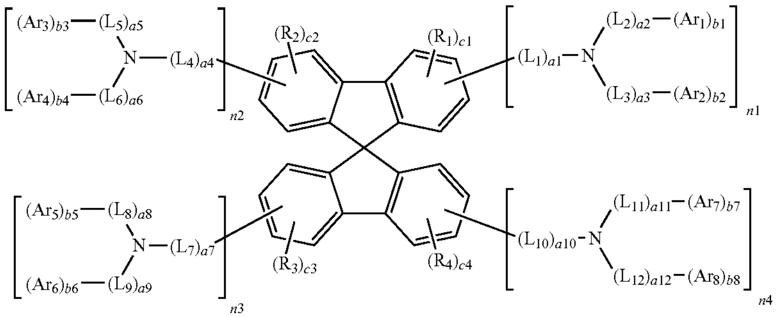

<Formula 1B>

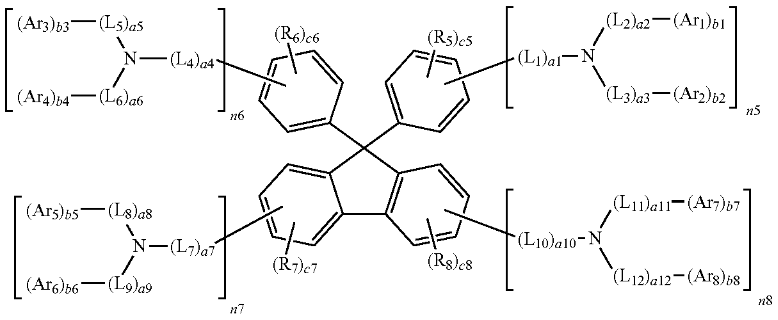

<Formula 1C>

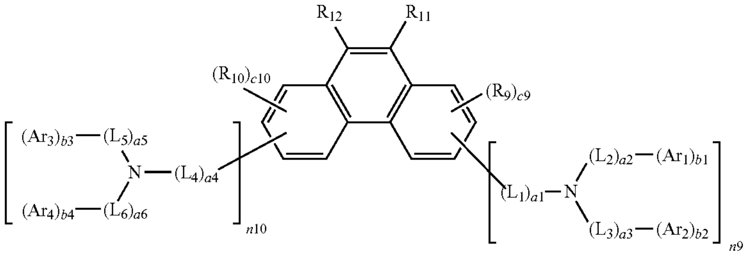

<Formula 40A>

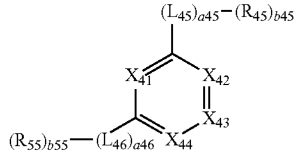

<Formula 40B>

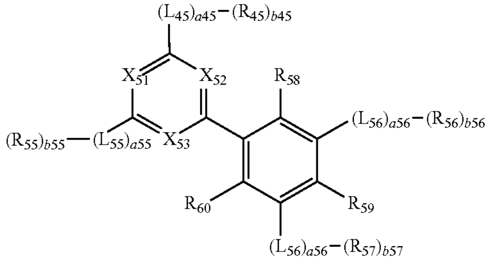

wherein, in Formulae 1A, 1B, 1C, 40A, and 40B, $X_{41}$ is N or C-$(L_{41})_{a41}$-$(R_{41})_{b41}$, $X_{42}$ is N or C-$(L_{42})_{a42}$-$(R_{42})_{b42}$, $X_{43}$ is N or C-$(L_{43})_{a43}$-$(R_{43})_{b43}$, $X_{44}$ is N or C-$(L_{44})_{a44}$-$(R_{44})_{b44}$, and at least one selected from $X_{41}$ to $X_{44}$ is N;

$X_{51}$ is N or C-$(L_{51})_{a51}$-$(R_{51})_{b51}$, $X_{52}$ is N or C-$(L_{52})_{a52}$-$(R_{52})_{b52}$, $X_{53}$ is N or C-$(L_{53})_{a53}$-$(R_{53})_{b53}$, and at least one selected from $X_{51}$ to $X_{53}$ is N;

$L_1$ to $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

$L_{41}$ to $L_{46}$ and $L_{51}$ to $L_{57}$ are each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent non-aromatic condensed polycyclic group;

a1 to a12, a41 to a46, and a51 to a57 are each independently an integer selected from 0 to 3;

$Ar_1$ to $Ar_8$, $R_{41}$ to $R_{46}$, and $R_{51}$ to $R_{57}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$Ar_1$ and $Ar_7$ are optionally linked to each other to form a saturated or unsaturated ring, $Ar_3$ and $Ar_4$ are optionally linked to each other to form a saturated or unsaturated ring, $Ar_5$ and $Ar_6$ are optionally linked to each other to form a saturated or unsaturated ring, and $Ar_7$ and $Ar_8$ are optionally linked to each other to form a saturated or unsaturated ring;

at least one of $R_{41}$ to $R_{46}$ or at least one of $R_{51}$ to $R_{57}$ is selected from a substituted or unsubstituted $C_1$-$C_{10}$ heterocycloalkyl group, a substituted or unsubstituted $C_1$-$C_{10}$ heterocycloalkenyl group, a substituted or unsubstituted $C_1$-$C_{60}$ heteroaryl group, and a substituted or unsubstituted monovalent non-aromatic condensed heteropolycyclic group;

b1 to b8, b41 to b46, and b51 to b57 are each independently an integer selected from 1 to 4;

$R_1$ to $R_{12}$ and $R_{58}$ to $R_{60}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

$R_{11}$ and $R_{12}$ are optionally linked to each other to form a saturated or unsaturated ring;

c1 to c10 are each independently an integer selected from 0 to 4;

n1 to n4 and n7 to n10 are each independently an integer selected from 0 to 4, and n5 and n6 are each independently an integer selected from 0 to 5, provided that n1+n2+n3+n4 is 1 or more, n5+n6+n7+n8 is 1 or more, and n9+n10 is 1 or more;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_7$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group(arylthio), a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{20}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_7$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

20. The organic light-emitting device as claimed in claim 18, wherein the hole injection layer further includes a charge-generating material, the charge-generating material is a p-dopant, and the electron transport layer further includes a metal-containing material.

* * * * *

US009896621C1

(12) EX PARTE REEXAMINATION CERTIFICATE (11774th)

United States Patent

Kim et al.

(10) Number: US 9,896,621 C1

(45) Certificate Issued: Dec. 16, 2020

(54) ORGANIC LIGHT-EMITTING DEVICE

(71) Applicant: SAMSUNG DISPLAY CO., LTD., Yongin-si (KR)

(72) Inventors: Myeong-Suk Kim, Yongin-si (KR); Tae-Kyung Kim, Yongin-si (KR); Sung-Wook Kim, Yongin-si (KR); Hwan-Hee Cho, Yongin-si (KR); Chang-Woong Chu, Yongin-si (KR)

(73) Assignee: SAMSUNG DISPLAY CO., LTD., Yongin-si (KR)

Reexamination Request:
No. 90/014,463, Feb. 25, 2020

Reexamination Certificate for:
Patent No.: 9,896,621
Issued: Feb. 20, 2018
Appl. No.: 14/923,850
Filed: Oct. 27, 2015

(30) Foreign Application Priority Data

Mar. 6, 2015 (KR) ........................ 10-2015-0031964

(51) Int. Cl.
*C09K 11/02* (2006.01)
*H01L 51/00* (2006.01)
(Continued)

(52) U.S. Cl.
CPC .......... *C09K 11/025* (2013.01); *C07C 211/43* (2013.01); *C07C 211/44* (2013.01);
(Continued)

(58) Field of Classification Search
None
See application file for complete search history.

(56) References Cited

To view the complete listing of prior art documents cited during the proceeding for Reexamination Control Number 90/014,463, please refer to the USPTO's public Patent Application Information Retrieval (PAIR) system under the Display References tab.

*Primary Examiner* — Ling X Xu

(57) ABSTRACT

An organic light-emitting device includes a first electrode, a second electrode facing the first electrode, an emission layer between the first electrode and the second electrode, a hole transport region between the first electrode and the emission layer, and an electron transport region between the second electrode and the emission layer. The hole transport region includes a first compound represented by one of Formulae 1A, 1B, and 1C, and the electron transport region includes a second compound represented by one of Formulae 40A and 40B:

<Formula 1A>

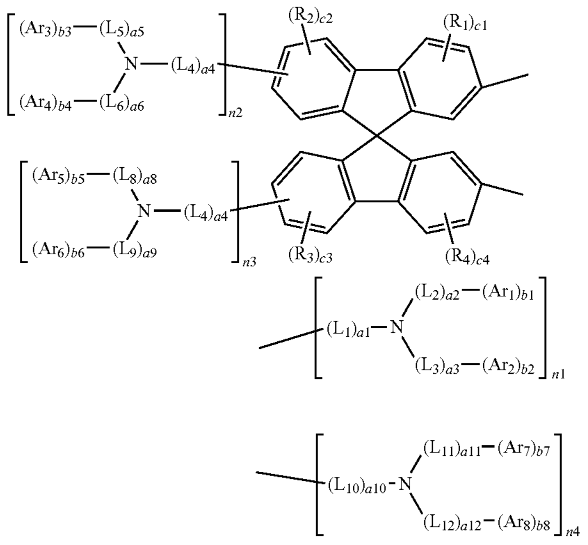

<Formula 1B>

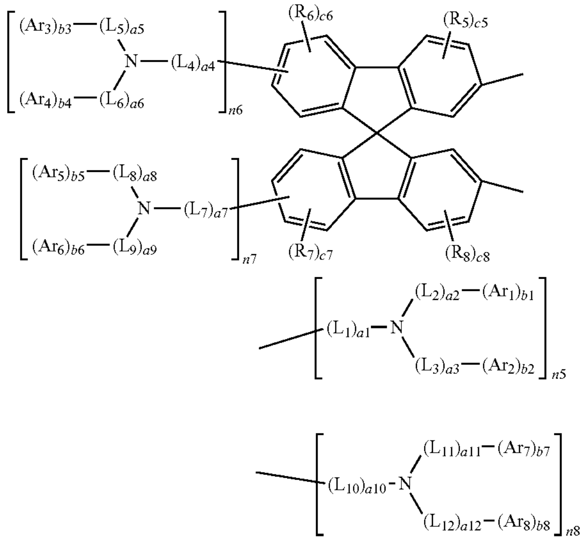

<Formula 1C>

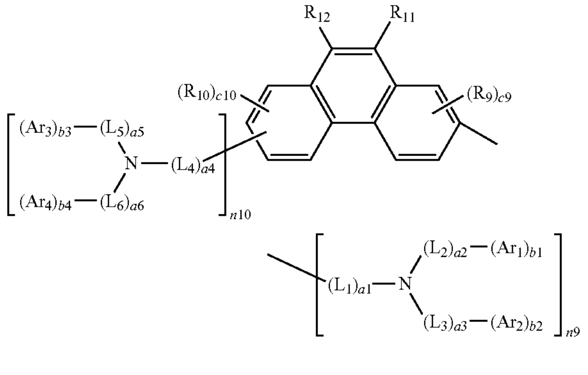

(Continued)

-continued
<Formula 40A>
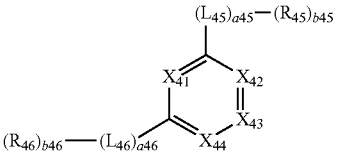
<Formula 40B>
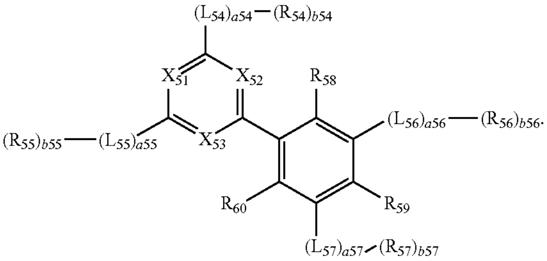
(51) Int. Cl.
| | |
|---|---|
| ***C07C 211/43*** | (2006.01) |
| ***C07D 403/10*** | (2006.01) |
| ***C07C 211/61*** | (2006.01) |
| ***C07D 401/14*** | (2006.01) |
| ***C07C 211/49*** | (2006.01) |
| ***C07C 211/44*** | (2006.01) |
| ***H01L 51/50*** | (2006.01) |
(52) U.S. Cl.
CPC .......... *C07C 211/49* (2013.01); *C07C 211/61* (2013.01); *C07D 401/14* (2013.01); *C07D 403/10* (2013.01); *H01L 51/006* (2013.01); *H01L 51/0052* (2013.01); *H01L 51/0059* (2013.01); *H01L 51/0067* (2013.01); *H01L 51/0072* (2013.01); *H01L 51/5056* (2013.01); *H01L 51/5072* (2013.01); *H01L 51/5088* (2013.01)

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-2 are cancelled.

Claims 3-6, 13-14 and 16-19 are determined to be patentable as amended.

Claim 20, dependent on an amended claim, is determined to be patentable.

New claim 21 is added and determined to be patentable.

Claims 7-12 and 15 were not reexamined.

3. The organic light-emitting device as claimed in claim [1] *21*, wherein

[$L_1$ to $L_{12}$,]

*$L_1$ to $L_{12}$ are each independently selected from:*

*a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoguinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and*

*a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a*

*triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;*

$L_{41}$ to $L_{46}$, and $L_{51}$ to $L_{57}$ are each independently selected from a phenylene group, a pentalenylene group, an indenylene group, a naphthylene group, an azulenylene group, a heptalenylene group, an indacenylene group, an acenaphthylene group, [a fluorenylene group, a spiro-fluorenylene group, a benzofluorenylene group, a dibenzofluorenylene group,] a phenalenylene group, a phenanthrenylene group, an anthracenylene group, a fluoranthenylene group, a triphenylenylene group, a pyrenylene group, a chrysenylene group, *and* a naphthacenylene group, [a picenylene group, a perylenylene group, a pentaphenylene group, a hexacenylene group, a pentacenylene group, a rubicenylene group, a coronenylene group, a ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group]; and a phenylene group, a pentalenylene group, an indenylene group, a naphthylene group, an azulenylene group, a heptalenylene group, an indacenylene group, an acenaphthylene group, [a fluorenylene group, a spiro-fluorenylene group, a benzofluorenylene group, a dibenzofluorenylene group,] a phenalenylene group, a phenanthrenylene group, an anthracenylene group, a fluoranthenylene group, a triphenylenylene group, a pyrenylene group, a chrysenylene group, *and* a naphthacenylene group, [a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group], each substituted with at least one selected from a deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

4. The organic light-emitting device as claimed in claim [1] *21*, wherein $L_1$ to $L_{12}$ are each independently selected from groups represented by Formulae 3-1 to 3-41, and [$L_{41}$ to $L_{46}$ and $L_{51}$ to] *$L_{43}$, $L_{45}$, $L_{46}$, $L_{56}$ and* $L_{57}$ are each independently selected from groups represented by Formulae 3-1, *3-2, 3-5* to 3-9, 3-25, and 3-33 to 3-41:

Formula 3-1

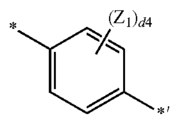

Formula 3-2

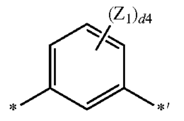

-continued
Formula 3-3
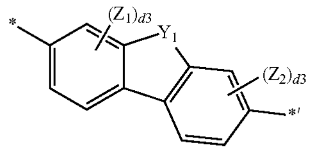
Formula 3-4
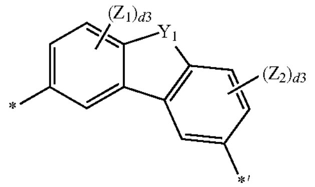
Formula 3-5
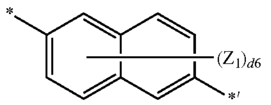
Formula 3-6
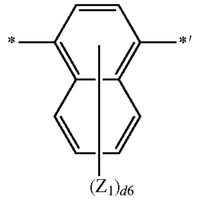
Formula 3-7
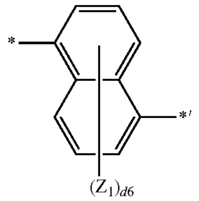
Formula 3-8
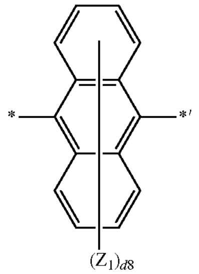
Formula 3-9
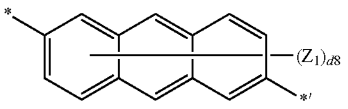
Formula 3-10
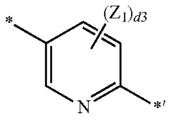
Formula 3-11
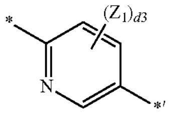
-continued
Formula 3-12
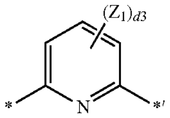
Formula 3-13
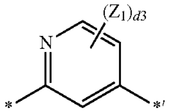
Formula 3-14
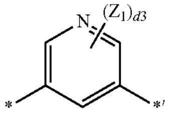
Formula 3-15
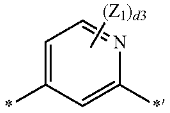
Formula 3-16
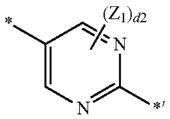
Formula 3-17
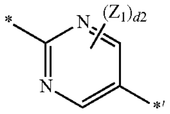
Formula 3-18
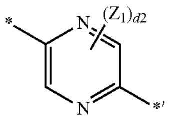
Formula 3-19
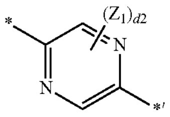
Formula 3-20
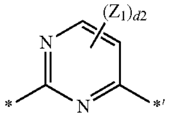
Formula 3-21
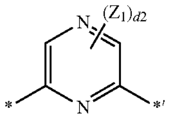
Formula 3-22
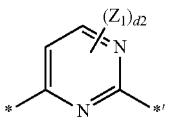
Formula 3-23
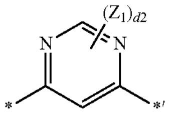

-continued
Formula 3-24
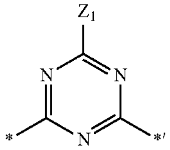
Formula 3-25
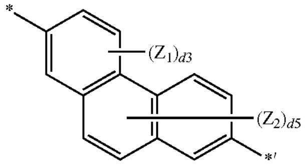
Formula 3-26
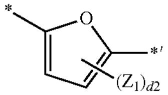
Formula 3-27
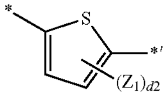
Formula 3-28
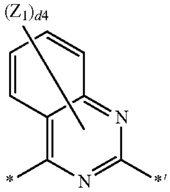
Formula 3-29
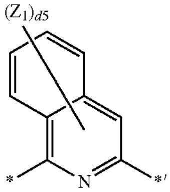
Formula 3-30
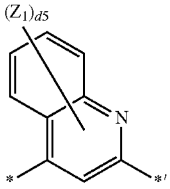
Formula 3-31
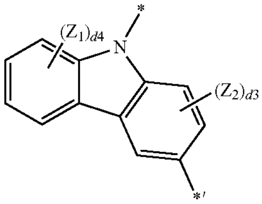
Formula 3-32
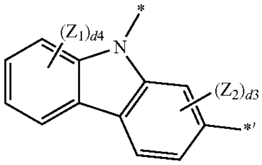
-continued
Formula 3-33
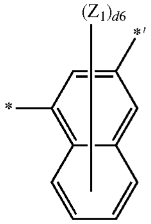
Formula 3-34
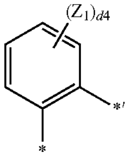
Formula 3-35
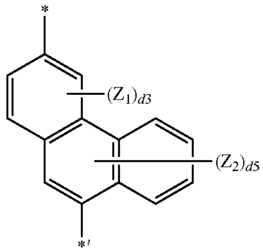
Formula 3-36
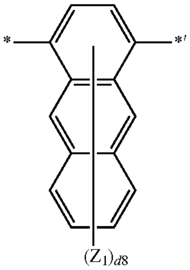
Formula 3-37
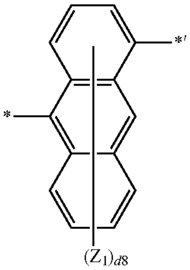
Formula 3-38
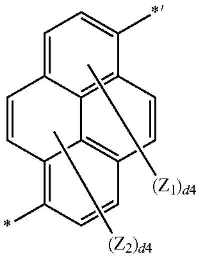

-continued

Formula 3-39

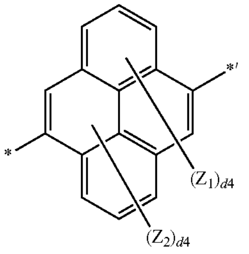

Formula 3-40

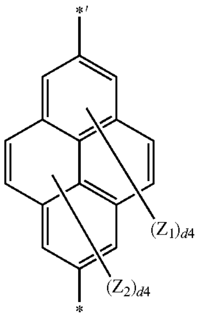

Formula 3-41

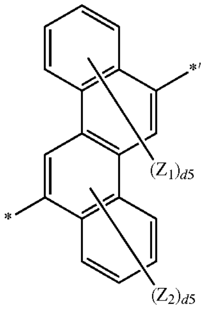

wherein, in Formulae 3-1 to 3-41, $Y_1$ is O, S, $C(Z_3)(Z_4)$, $N(Z_5)$, or $Si(Z_6)(Z_7)$, provided that in Formulae 3-3 and 3-4, $Y_1{=}C(Z_3)(Z_4)$;

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a carbazolyl group, a benzocarbazolyl group, and a dibenzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, and a naphthyl group; and $-Si(Q_{31})(Q_{32})(Q_{33})$, wherein $Q_1$ to $Q_3$ and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, and a carbazolyl group;

d2 is an integer selected from 1 and 2;

d3 is an integer selected from 1 to 3;

d4 is an integer selected from 1 to 4;

d5 is an integer selected from 1 to 5;

d6 is an integer selected from 1 to 6;

d8 is an integer selected from 1 to 8; and

* and *' each indicate a binding site to an adjacent atom.

5. The organic light-emitting device as claimed in claim [1] *21*, wherein $L_1$ to $L_{12}$ are each independently selected from groups represented by Formulae 4-1 to 4-36, and [$L_{41}$ to $L_{46}$ and $L_{51}$ to] *$L_{43}$, $L_{45}$, $L_{46}$, $L_{56}$ and* $L_{57}$ are each independently selected from groups represented by Formulae 4-1, 4-3, 4-5, 4-7 to *4-11,* 4-13, 4-17, and 4-24 to 4-36:

Formula 4-1

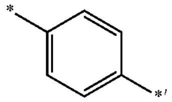

Formula 4-2

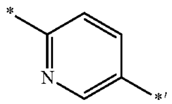

Formula 4-3

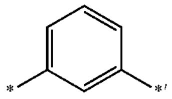

Formula 4-4

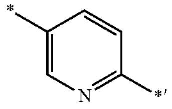

Formula 4-5

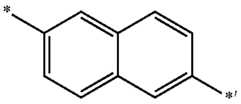

Formula 4-6

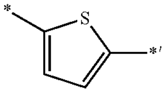

-continued
Formula 4-7
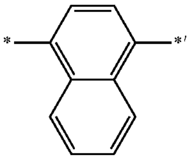
Formula 4-8
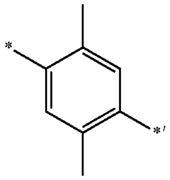
Formula 4-9
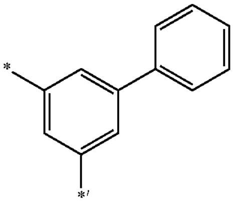
Formula 4-10
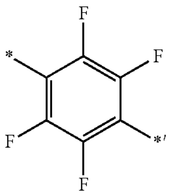
Formula 4-11
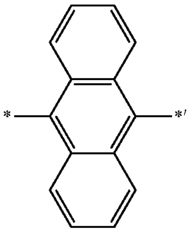
Formula 4-12
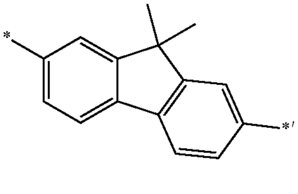
Formula 4-13
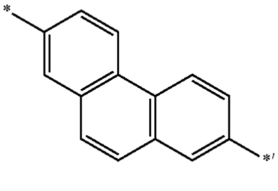
-continued
Formula 4-14
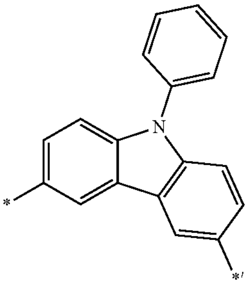
Formula 4-15
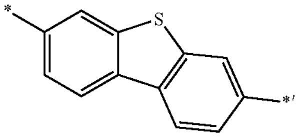
Formula 4-16
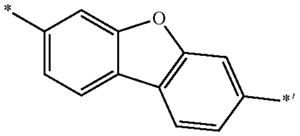
Formula 4-17
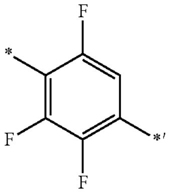
Formula 4-18
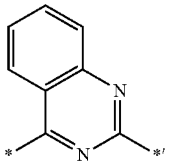
Formula 4-19
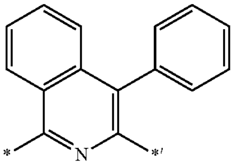
Formula 4-20
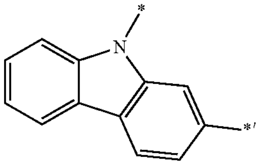
Formula 4-21
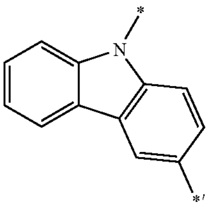

-continued

Formula 4-22

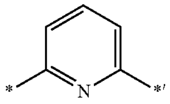

Formula 4-23

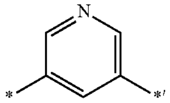

Formula 4-24

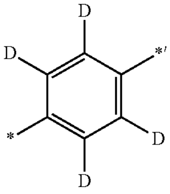

Formula 4-25

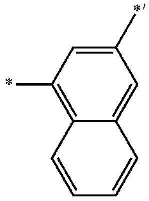

Formula 4-26

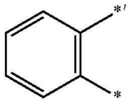

Formula 4-27

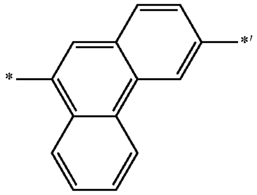

Formula 4-28

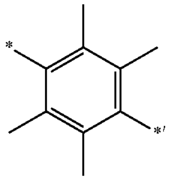

Formula 4-29

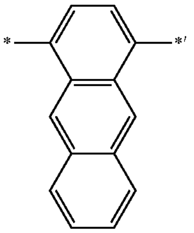

Formula 4-30

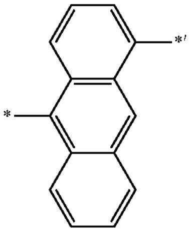

-continued

Formula 4-31

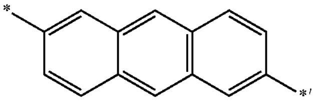

Formula 4-32

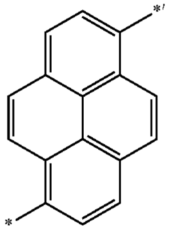

Formula 4-33

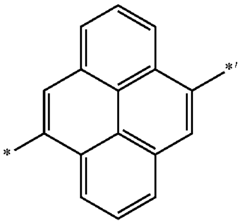

Formula 4-34

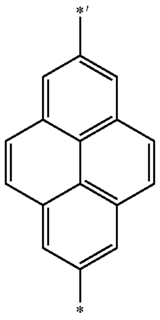

Formula 4-35

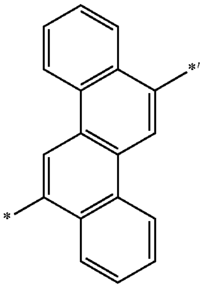

Formula 4-36

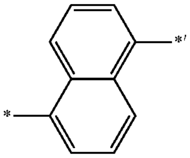

wherein, in Formulae 4-1 to 4-36, * and *' each indicate a binding site to an adjacent atom.

6. The organic light-emitting device as claimed in claim [1] *21*, wherein

[$Ar_1$ to $Ar_8$, $R_{41}$ to $R_{46}$, and $R_{51}$ to]

*$Ar_1$ to $Ar_8$, are each independently selected from*

*a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group,*

*a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and*

*a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a guinolinyl group, and an isoguinolinyl group;*

*$R_{43}$, $R_{45}$, $R_{46}$, and $R_{54}$ to* $R_{57}$ are each independently selected from a phenyl group, a pentalenyl group, an indenyl group, a naphthyl group, an azulenyl group, a heptalenyl group, an indacenyl group, an acenaphthyl group, [a fluorenyl group, a spiro-fluorenyl group, a benzofluorenyl group, a dibenzofluorenyl group,] a phenalenyl group, a phenanthrenyl group, an anthracenyl group, a fluoranthenyl group, a triphenylenyl group, a pyrenyl group, a chrysenyl group, a naphthacenyl group, [a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group,] an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, [an isoindolyl group, an indolyl group,] an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, [a carbazolyl group,] a phenanthridinyl group, an acridinyl group, a phenanthrolinyl group, a phenazinyl group, a benzoimidazolyl group, [a benzofuranyl group, a benzothiophenyl group,] an isobenzothiazolyl group, a benzoxazolyl group, an isobenzoxazolyl group, a triazolyl group, a tetrazolyl group, an oxadiazolyl group, a triazinyl group, [a dibenzofuranyl group, a dibenzothiophenyl group, a benzocarbazolyl group, a dibenzocarbazolyl group,] a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, [a fluorenyl group, a spiro-fluorenyl group, a benzofluorenyl group, a dibenzofluorenyl group,] a phenalenyl group, a phenanthrenyl group, an anthracenyl group, a fluoranthenyl group, a triphenylenyl group, a pyrenyl group, a chrysenyl group, a naphthacenyl group, [a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group,] an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, [an isoindolyl group, an indolyl group,] an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, [a carbazolyl group,] a phenanthridinyl group, an acridinyl group, a phenanthrolinyl group, a phenazinyl group, a benzoimidazolyl group, [a benzofuranyl group, a benzothiophenyl group,] an isobenzothiazolyl group, a benzoxazolyl group, an isobenzoxazolyl group, a triazolyl group, a tetrazolyl group, an oxadiazolyl group, a triazinyl group, [a dibenzofuranyl group, a dibenzothiophenyl group, a benzocarbazolyl group, a dibenzocarbazolyl group,] a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and - $Si(Q_{31})(Q_{32})(Q_{33})$, wherein $Q_{31}$ to $Q_{33}$ are each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group,

*wherein at least two of $R_{43}$, $R_{45}$ and $R_{46}$ are not identical to each other, and*

*at least one of $R_{43}$, $R_{45}$ and $R_{46}$ and at least one of $R_{56}$ and $R_{57}$ is selected from an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group; and*

*an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indazolyl group, a purinyl group, a guinolinyl group, an isoguinolinyl group, a benzoguinolinyl group, a phthalazinyl group, a naphthyridinyl group, a guinoxalinyl group, a guinazolinyl group, a cinnolinyl group, a phenanthridinyl group, an acridinyl group, a phenanthrolinyl group, a phenazinyl group, a benzoimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridi-*

*nyl group, a pyrazinyl group, a pyrimidinyl group, a pyridazinyl group, an isoindolyl group, an indolyl group, an indazolyl group, a purinyl group, a guinolinyl group, an isoguinolinyl group, a benzoguinolinyl group, a phthalazinyl group, a naphthyridinyl group, a guinoxalinyl group, a guinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.*

13. The organic light-emitting device as claimed in claim [1] *21*, wherein the first compound is represented by one of Formulae 1A-1 to 1A-10, 1B-1 to 1B-4, 1C-1, and 1C-2[, and the second compound is represented by one of Formulae 40A-1 to 40A-3, 40B-1, and 40B-2]:

<Formula 1A-1>

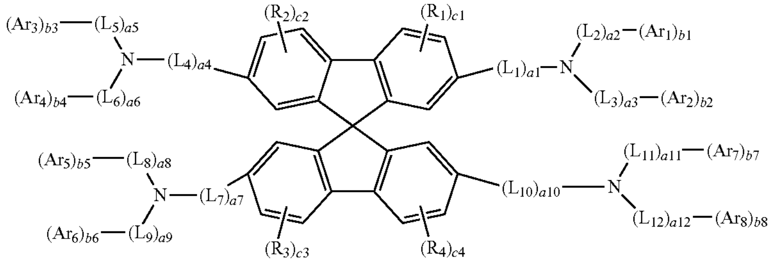

<Formula 1A-2>

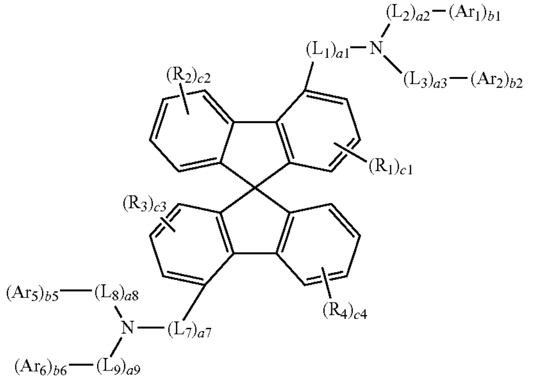

<Formula 1A-3>

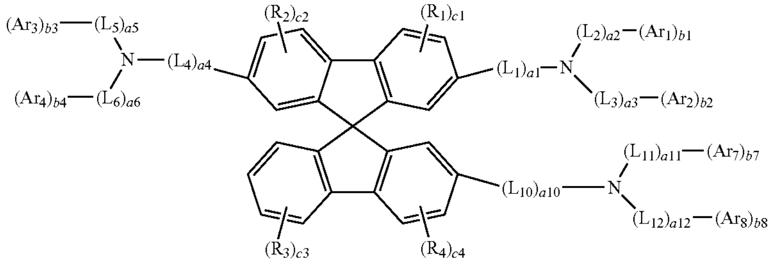

<Formula 1A-4>

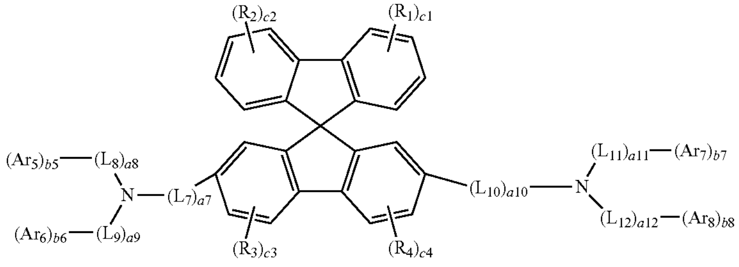

-continued
<Formula 1A-5>
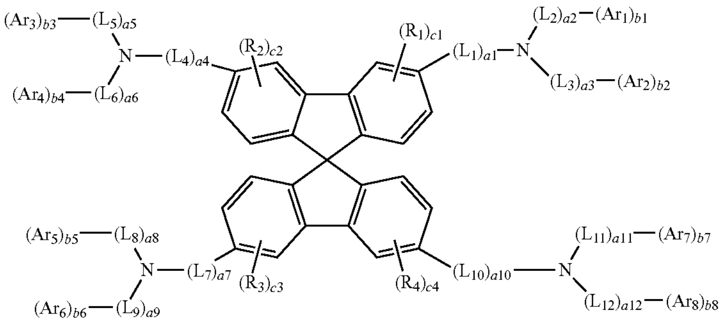
<Formula 1A-6>
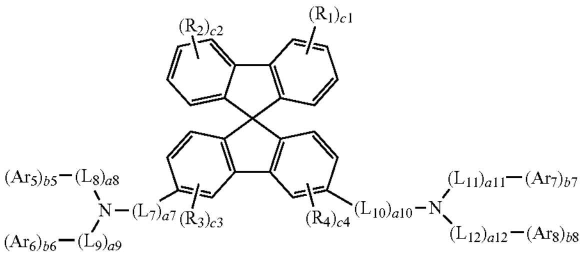
<Formula 1A-7>
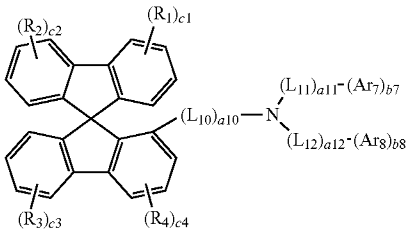
<Formula 1A-8>
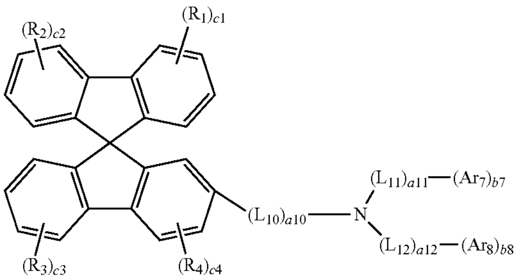
<Formula 1A-9>
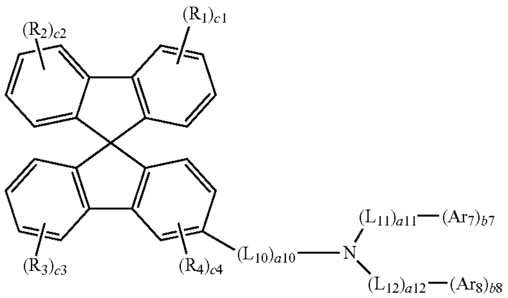
<Formula 1A-10>
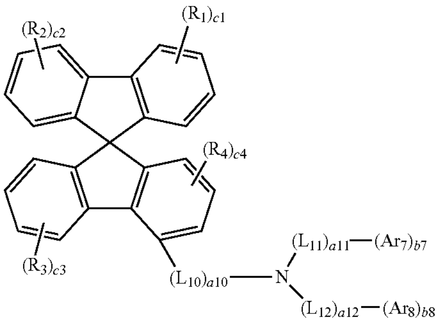
<Formula 1B-1>
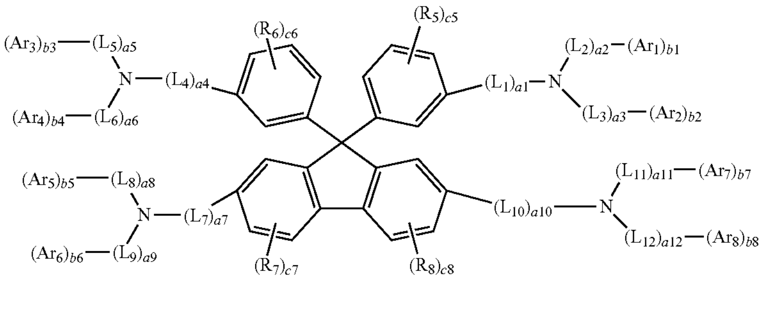

-continued
<Formula 1B-2>
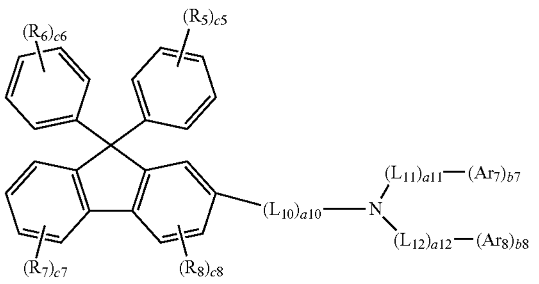
<Formula 1B-3>
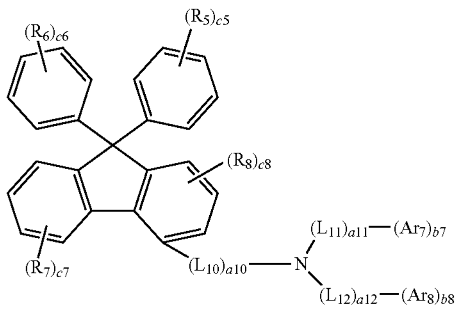
<Formula 1B-4>
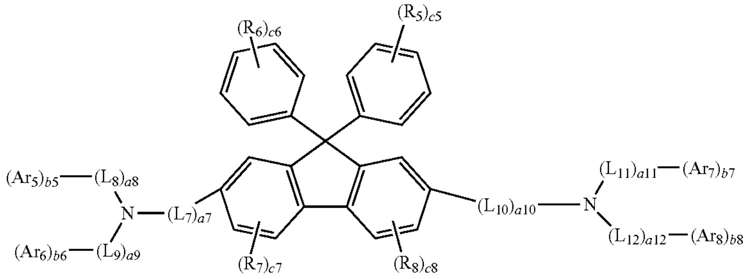
<Formula 1C-1>
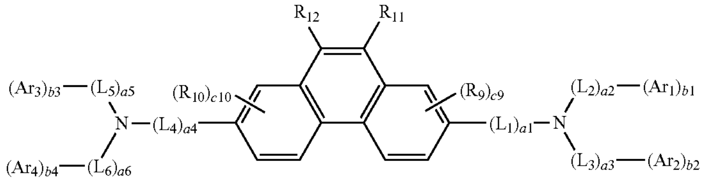
<Formula 40A-1>
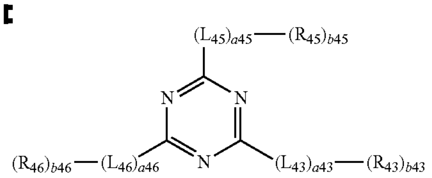
<Formula 40A-2>
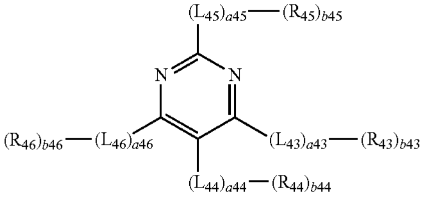
<Formula 40A-3>
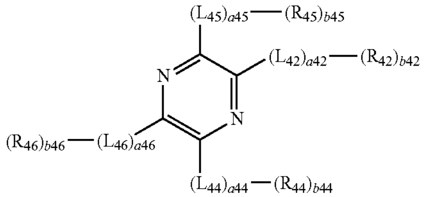
<Formula 40B-1>
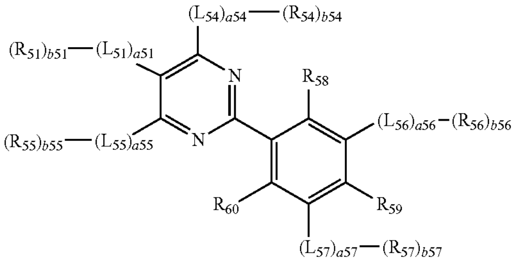
<Formula 40B-2>
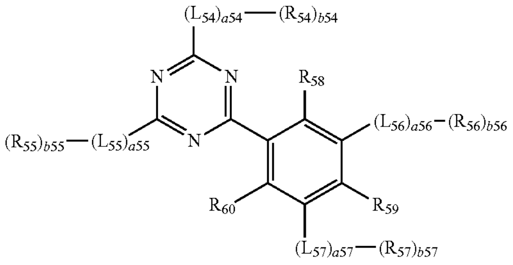

wherein, in the Formulae above, descriptions of $L_1$ to $L_{12}$, [$L_{41}$ to $L_{46}$, $L_{51}$ to $L_{57}$,] a1 to $a_{12}$, [a41 to a46, a51 to a57,] $Ar_1$ to $Ar_8$, $R_1$ to $R_{12}$, [$R_{42}$ to $R_{46}$, $R_{51}$, $R_{54}$ to $R_{60}$,] b1 to b20, [b42 to b46, b51 to b57,] and c1 to c10 are the same as described in claim 1.

14. The organic light-emitting device as claimed in claim [1] *21*, wherein the first compound is represented by Formulae 1A-1(1), 1A-2(1), 1A-2(2), 1A-3(1), 1A-4(1), 1A-4(2), 1A-5(1), 1A-6(1), 1A-7(1), 1A-8(1), 1A-8(2), 1A-9(1), 1A-9(2), 1A-9(3), 1A-10(1), 1A-10(2), 1B-(1), 1B-2(1), 1B-3 (1), 1B-4(1), 1C-1(1), and 1C-1(2)[, and the second compound is represented by Formulae 40A-1 (1), 40A-1(2), 40A-1(3), 40A-2(140A-3(1), 40B-1(1), 40B-1(2), 40B-2(1), and 40B-2(1) to 40B-2(5)]:

<Formula 1A-1(1)>

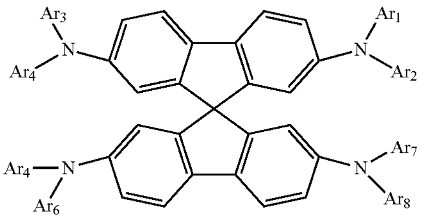

<Formula 1A-2(1)>

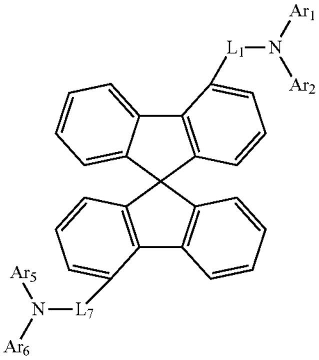

<Formula 1A-2(2)>

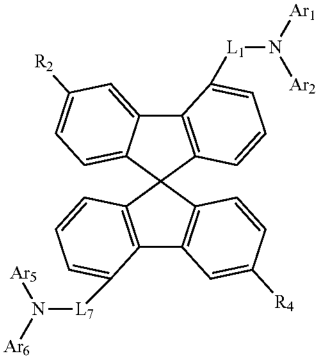

<Formula 1A-3(1)>

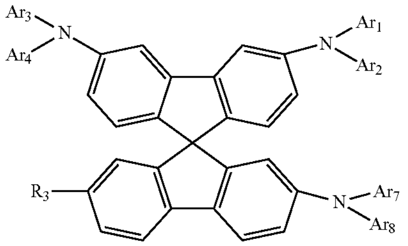

-continued

<Formula 1A-4(1)>

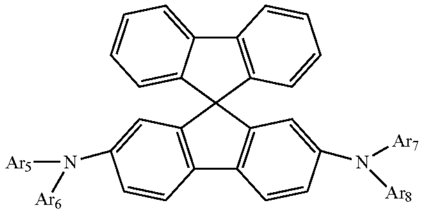

<Formula 1A-4(2)>

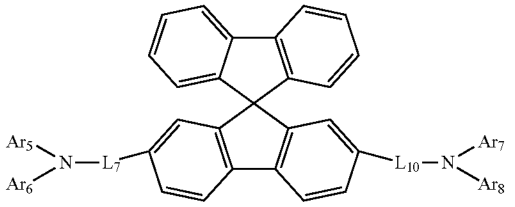

<Formula 1A-5(1)>

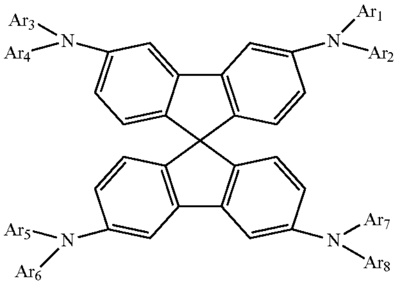

<Formula 1A-6(1)>

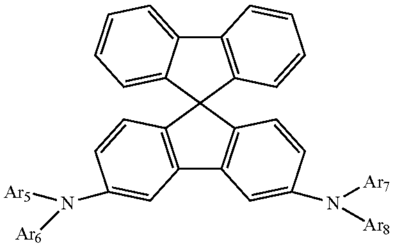

<Formula 1A-7(1)>

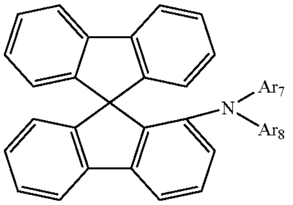

<Formula 1A-8(1)>

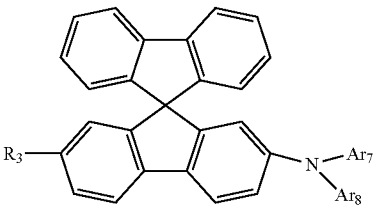

-continued
<Formula 1A-8(2)>
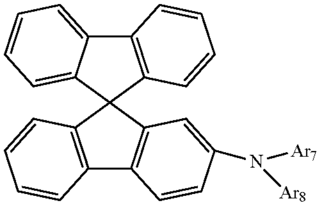
<Formula 1A-9(1)>
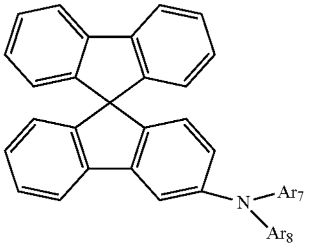
<Formula 1A-9(2)>
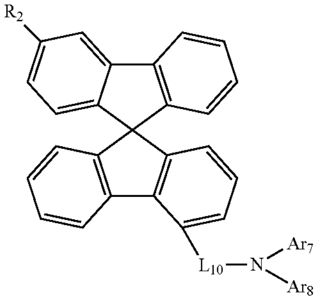
<Formula 1A-9(3)>
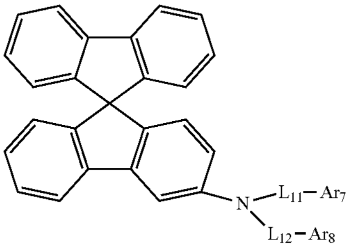
<Formula 1A-10(1)>
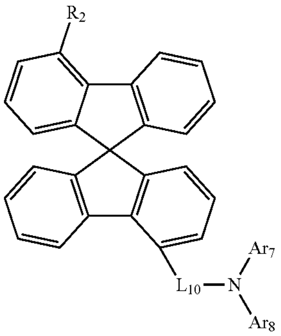
-continued
<Formula 1A-10(2)>
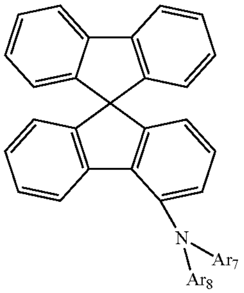
<Formula 1B-1(1)>
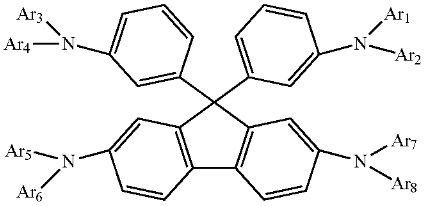
<Formula 1B-2(1)>
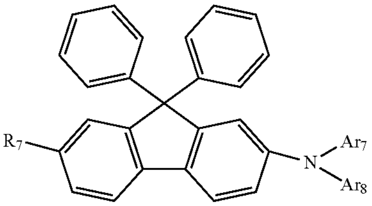
<Formula 1B-3(1)>
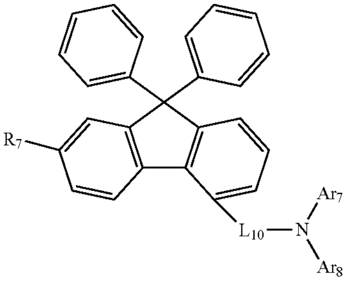
<Formula 1B-4(1)>
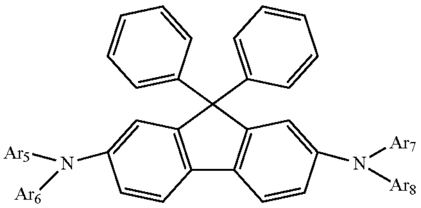
<Formula 1C-1(1)>
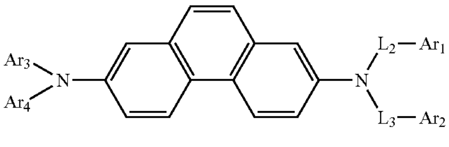

-continued
<Formula 1C-1(2)>
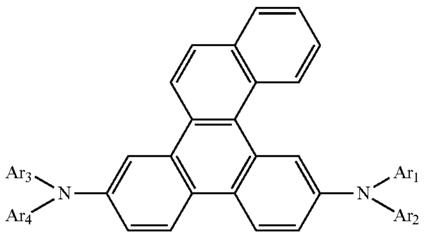
<Formula 40A-1(1)>
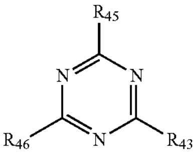
<Formula 40A-1(2)>
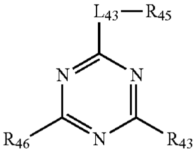
<Formula 40A-1(3)>
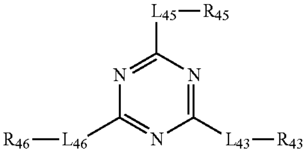
<Formula 40A-2(1)>
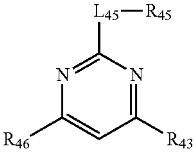
<Formula 40A-3(1)>
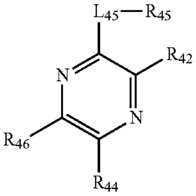
<Formula 40B-1(1)>
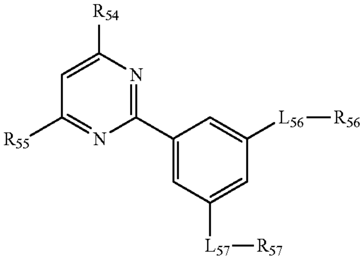
-continued
<Formula 40B-1(2)>
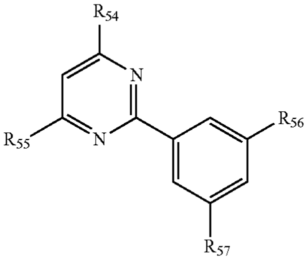
<Formula 40B-2(1)>
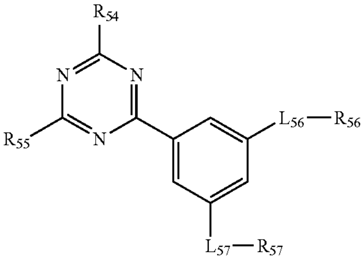
<Formula 40B-2(2)>
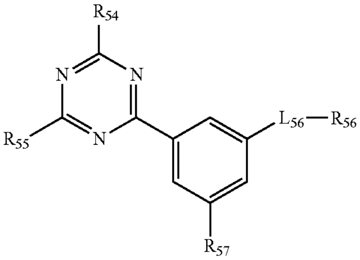
<Formula 40B-2(3)>
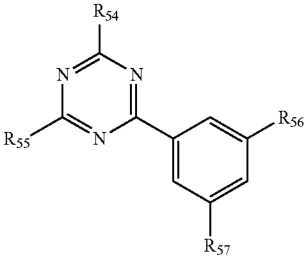
<Formula 40B-2(4)>
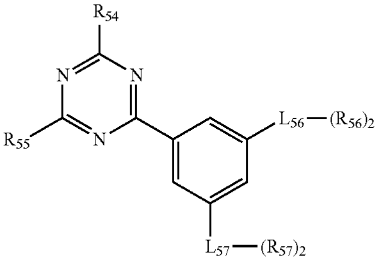

-continued

<Formula 40B-2(5)>

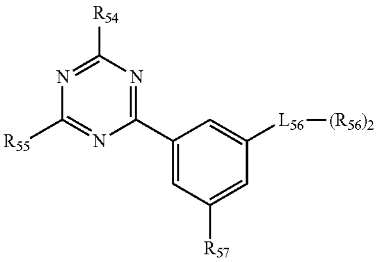

]

wherein, in the Formulae above, descriptions of $L_1$ to $L_3$, $L_7$, $L_{10}$, $L_{12}$, [$L_{43}$, $L_{45}$, $L_{46}$, $L_{56}$, $L_{57}$,] $Ar_1$ to $Ar_8$, $R_2$, $R_3$, $R_7$[, $R_{42}$ to $R_{44}$, $R_{46}$, $R_{54}$, and $R_{55}$] are the same as described in claim 1, $R_{45}$ is selected from groups represented by Formulae 10-1 to 10-123, and at least one of $R_{56}$ and $R_{57}$ is selected from groups represented by Formulae 10-1 to 10-123:

Formula 10-1

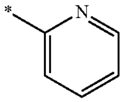

Formula 10-2

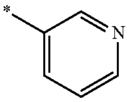

Formula 10-3

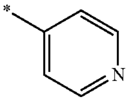

Formula 10-4

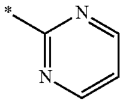

Formula 10-5

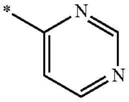

Formula 10-6

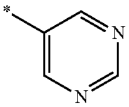

Formula 10-7

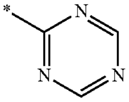

Formula 10-8

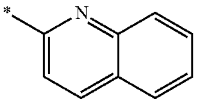

Formula 10-9

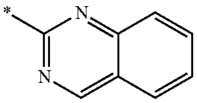

-continued

Formula 10-10

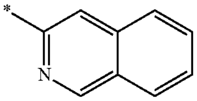

Formula 10-11

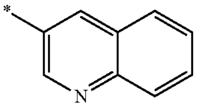

Formula 10-12

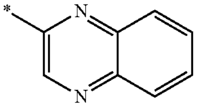

Formula 10-13

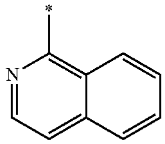

Formula 10-14

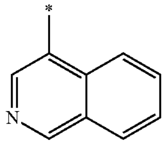

Formula 10-15

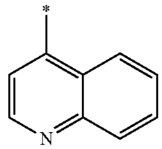

Formula 10-16

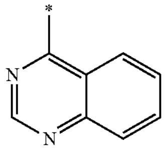

Formula 10-17

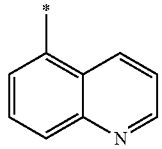

Formula 10-19

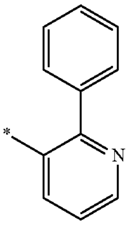

Formula 10-19

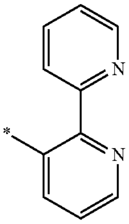

-continued
Formula 10-20
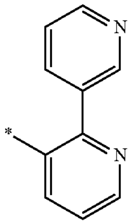
Formula 10-21
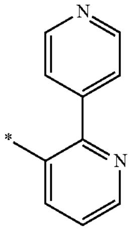
Formula 10-22
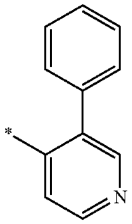
Formula 10-23
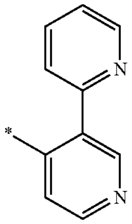
Formula 10-24
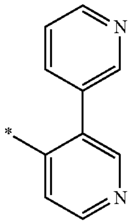
Formula 10-25
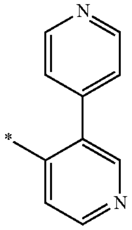
Formula 10-26
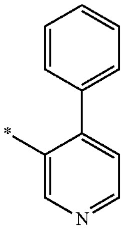
-continued
Formula 10-27
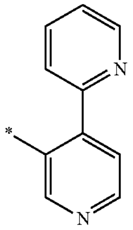
Formula 10-28
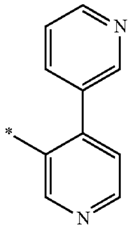
Formula 10-29
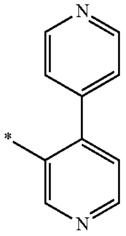
Formula 10-30
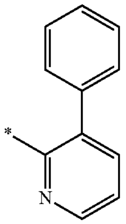
Formula 10-31
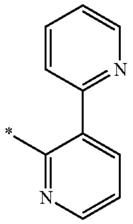
Formula 10-32
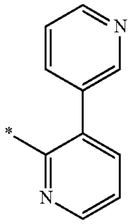

-continued
Formula 10-33
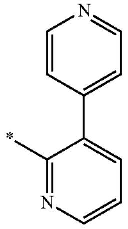
Formula 10-34
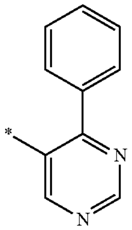
Formula 10-35
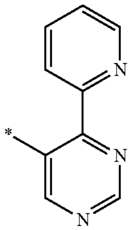
Formula 10-36
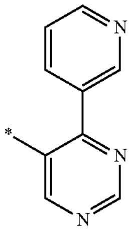
Formula 10-37
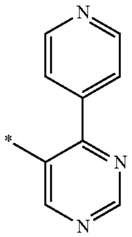
Formula 10-38
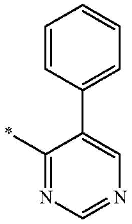
-continued
Formula 10-39
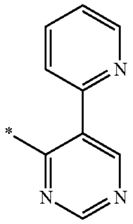
Formula 10-40
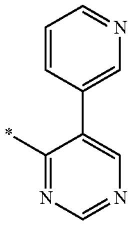
Formula 10-41
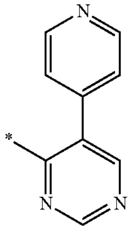
Formula 10-42
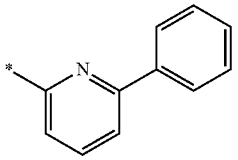
Formula 10-43
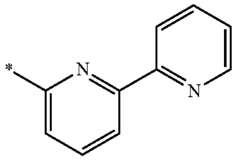
Formula 10-44
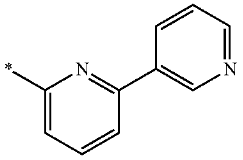
Formula 10-45
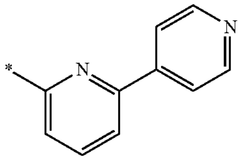
Formula 10-46
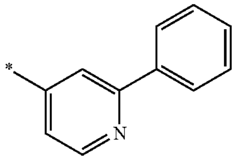

-continued
Formula 10-47
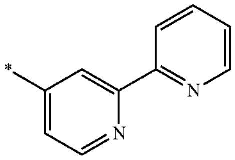
Formula 10-48
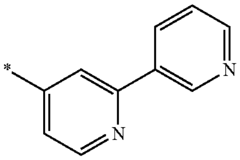
Formula 10-49
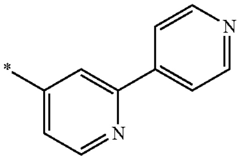
Formula 10-50
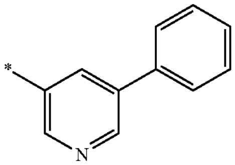
Formula 10-51
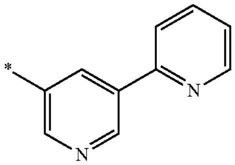
Formula 10-52
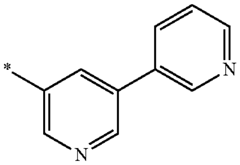
Formula 10-53
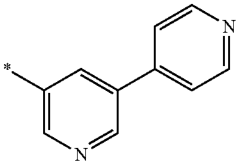
Formula 10-54
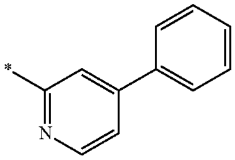
Formula 10-55
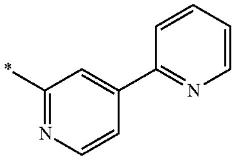
-continued
Formula 10-56
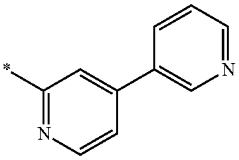
Formula 10-57
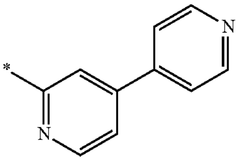
Formula 10-58
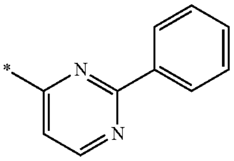
Formula 10-59
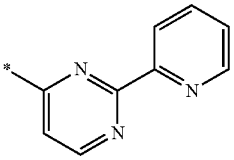
Formula 10-60
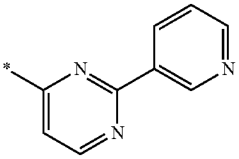
Formula 10-61
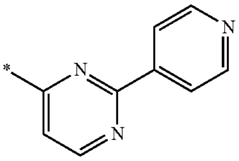
Formula 10-62
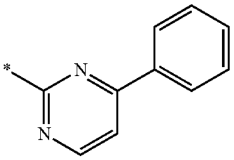
Formula 10-63
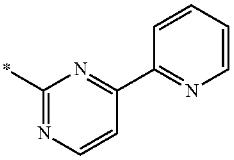
Formula 10-64
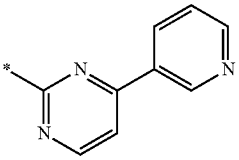

-continued
Formula 10-65
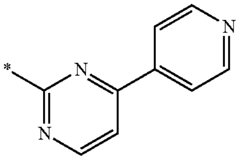
Formula 10-66
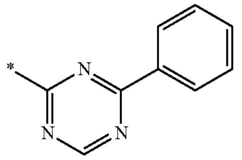
Formula 10-67
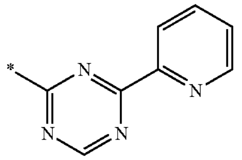
Formula 10-68
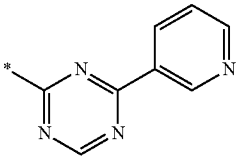
Formula 10-69
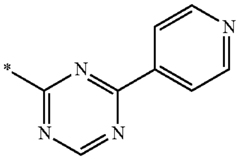
Formula 10-70
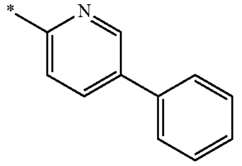
Formula 10-71
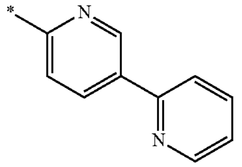
Formula 10-72
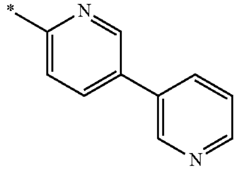
Formula 10-73
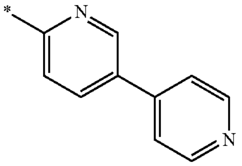
-continued
Formula 10-74
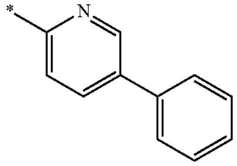
Formula 10-75
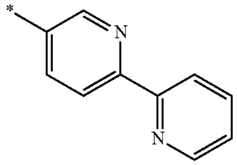
Formula 10-76
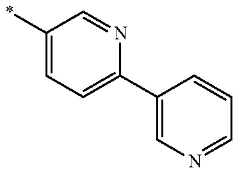
Formula 10-77
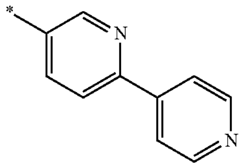
Formula 10-78
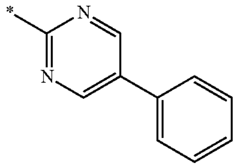
Formula 10-79
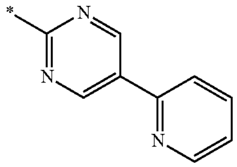
Formula 10-80
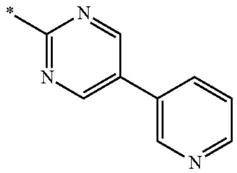
Formula 10-81
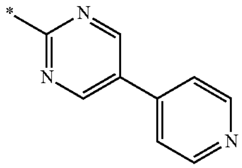
Formula 10-82
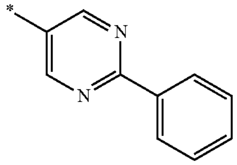

-continued
Formula 10-83
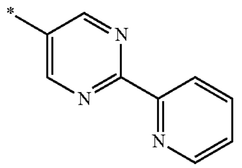
Formula 10-84
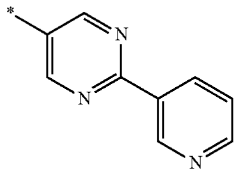
Formula 10-85
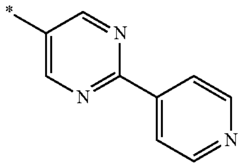
Formula 10-86
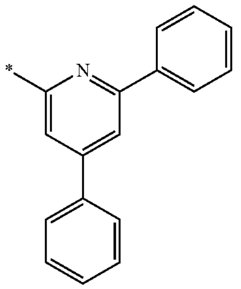
Formula 10-87
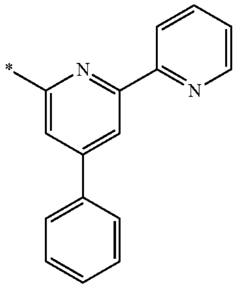
Formula 10-88
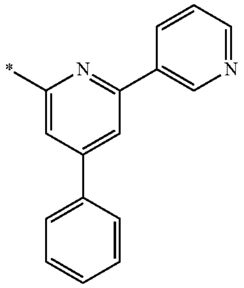
-continued
Formula 10-89
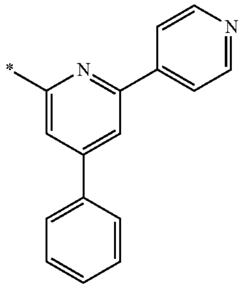
Formula 10-90
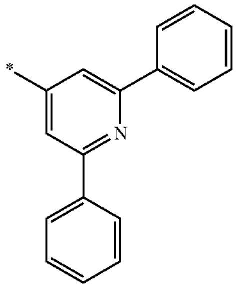
Formula 10-91
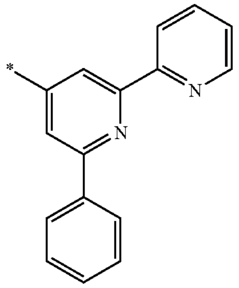
Formula 10-92
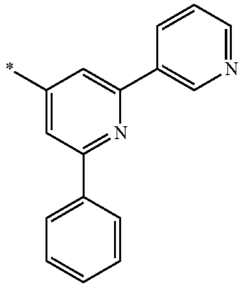
Formula 10-93
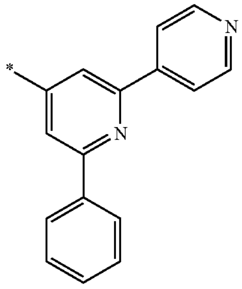

-continued
Formula 10-94
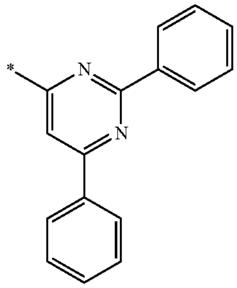
Formula 10-95
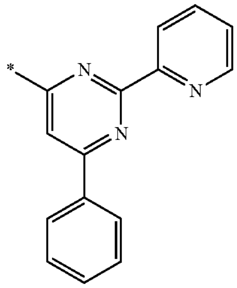
Formula 10-96
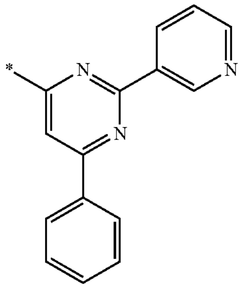
Formula 10-97
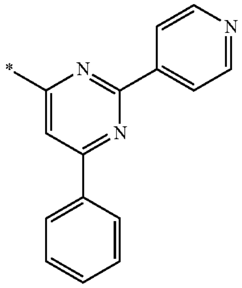
Formula 10-98
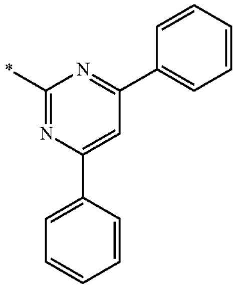
-continued
Formula 10-99
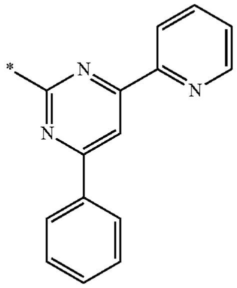
Formula 10-100
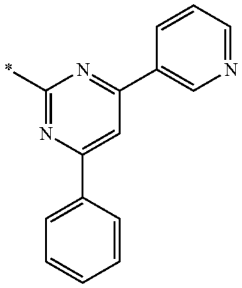
Formula 10-101
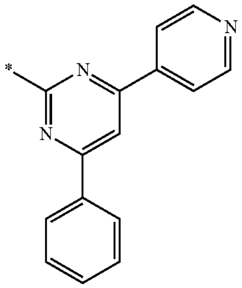
Formula 10-102
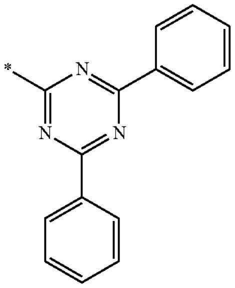
Formula 10-103
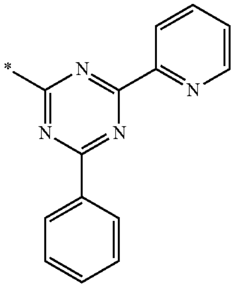

Formula 10-104
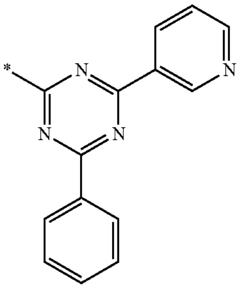
Formula 10-105
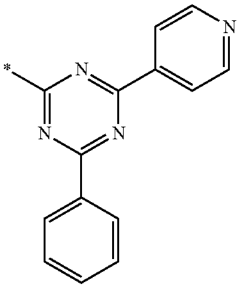
Formula 10-106
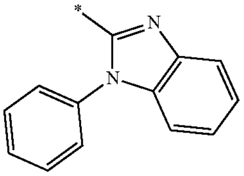
Formula 10-107
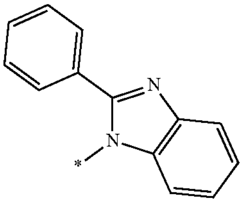
Formula 10-108
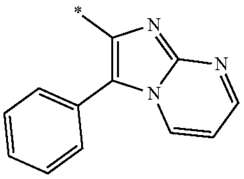
Formula 10-109
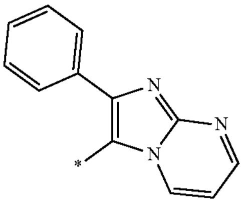
Formula 10-110
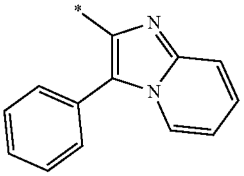
Formula 10-111
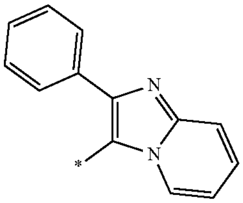
Formula 10-112
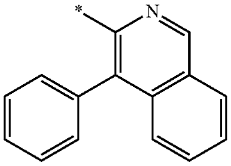
Formula 10-113
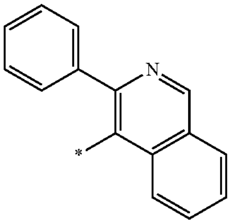
Formula 10-114
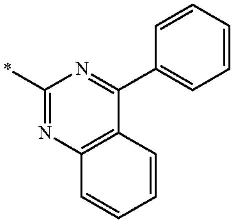
Formula 10-115
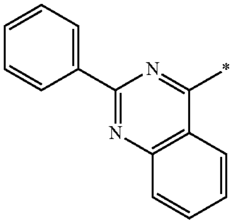
Formula 10-116
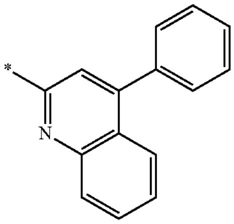
Formula 10-117
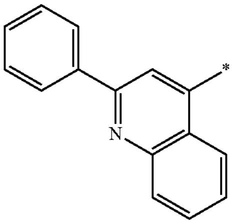

-continued

Formula 10-118

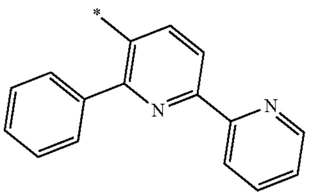

Formula 10-119

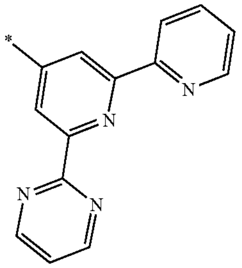

Formula 10-120

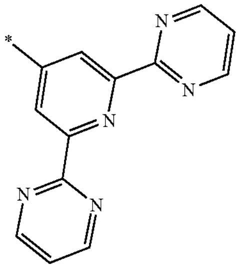

Formula 10-121

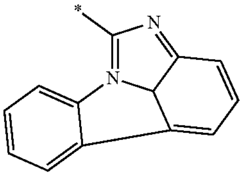

Formula 10-122

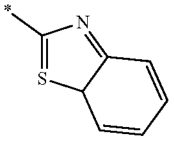

Formula 10-123

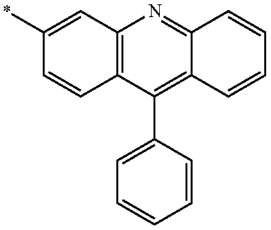

wherein, in Formulae 10-1 to 10-123, * indicates a binding site to an adjacent atom.

16. The organic light-emitting device as claimed in claim [1] *21*, wherein the emission layer includes at least one selected from a first host represented by Formula 101, a second host represented by Formula 201, a third host represented by Formula 202, a fourth host represented by Formula 301, and a fifth host represented by Formula 302:

<Formula 101>

$$—Ar_{101}—[(L_{101})_{a101}—R_{101}]_{n101}$$

<Formula 201>

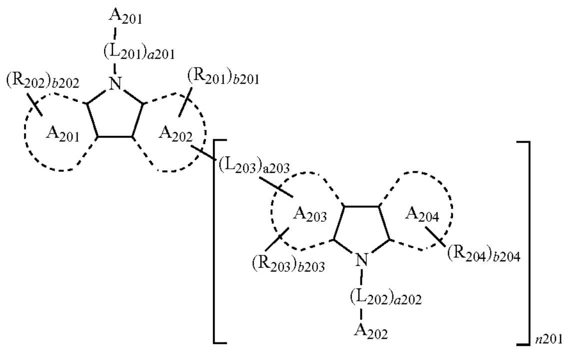

<Formula 202>

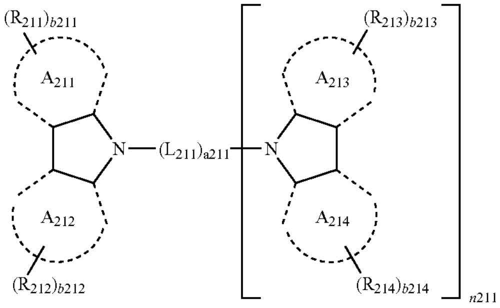

<Formula 301>

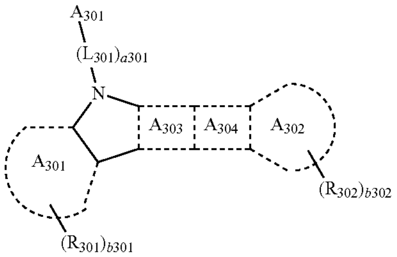

<Formula 302>

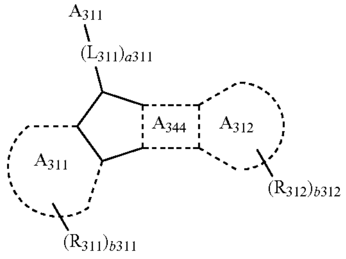

<Formula 303>

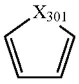

wherein, in the Formulae above, $Ar_{101}$, $A_{201}$ to $A_{204}$, $A_{211}$ to $A_{214}$, $A_{301}$ to $A_{303}$, $A_{311}$, and $A_{312}$ are each independently a substituted or unsubstituted $C_6$-$C_{20}$ aromatic ring;

$A_{304}$ and $A_{314}$ are each independently a group represented by Formula 303;

$X_{301}$ is selected from N-$(L_{302})_{a302}$-$Ar_{302}$, an oxygen (O) atom, a sulfur (S) atom, $C(R_{303})(R_{304})$, $Si(R_{303})(R_{304})$, $P(R_{303})$, $B(R_{303})$, and $P(=O)(R_{303})$, $L_{101}$, $L_{201}$ to $L_{203}$, $L_{211}$, $L_{301}$, $L_{302}$, and $L_{311}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

a101, a201 to a203, a211, a301, a302, and a311 are each independently an integer selected from 0 to 3;

$R_{101}$, $Ar_{201}$, $Ar_{202}$, $Ar_{301}$, $Ar_{302}$, and $Ar_{311}$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$R_{201}$ to $R_{204}$, $R_{211}$ to $R_{214}$, $R_{301}$ to $R_{304}$, $R_{311}$, and $R_{312}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_{101}$)($Q_{102}$), —Si($Q_{103}$)($Q_{104}$)($Q_{105}$), and —B($Q_{106}$)($Q_{107}$);

b201 and b203 are each independently an integer selected from 0 to 3, b202, b204, b211 to b214, b301, b302, b311, and b312 are each independently an integer selected from 0 to 4;

n101 is an integer selected from 0 to 3, n201 and n202 are each independently an integer selected from 0 to 4, n211 is an integer selected from 1 and 2;

at least one of substituents of the substituted $C_6$-$C_{20}$ aromatic ring, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_1$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{101}$)($Q_{102}$), —Si($Q_{103}$)($Q_{104}$)($Q_{105}$), and —B($Q_{106}$)($Q_{107}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{111}$)($Q_{112}$), —Si($Q_{113}$)($Q_{114}$)($Q_{115}$), and —B($Q_{116}$)($Q_{117}$); and —N($Q_{121}$)($Q_{122}$), —Si($Q_{123}$)($Q_{124}$)($Q_{125}$), and -B($Q_{126}$)($Q_{127}$), wherein $Q_{101}$ to $Q_{107}$, $Q_{111}$ to $Q_{117}$, and $Q_{121}$ to $Q_{127}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

17. The organic light-emitting device as claimed in claim 16, wherein the first host is represented by one of Formulae 101A to 101D, the second host is represented by Formula 201A, the third host is represented by one of Formulae 202A and 202B, the fourth host is represented by one of Formulae 301A to 301H, and the fifth host is represented by one of Formulae 302A and 302B:

<Formula 101A>

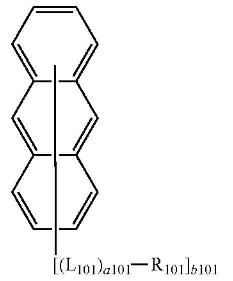

<Formula 101B>

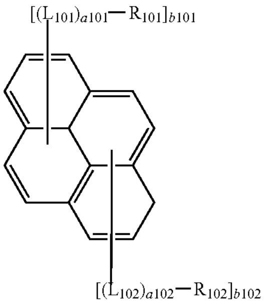

<Formula 101C>

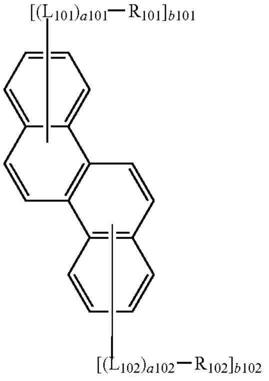

-continued

<Formula 101D>

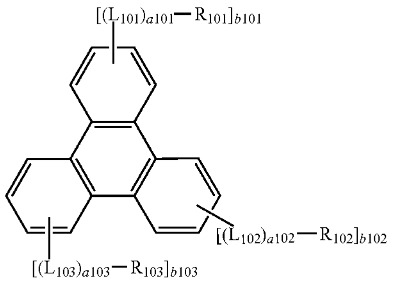

<Formula 201A>

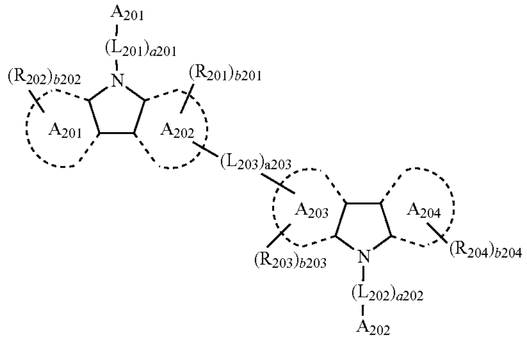

<Formula 202A>

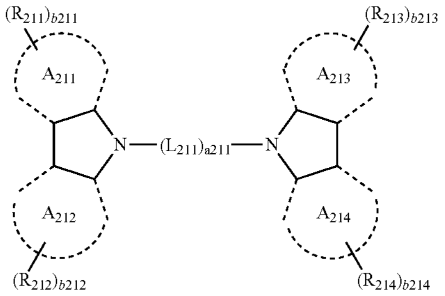

<Formula 202B>

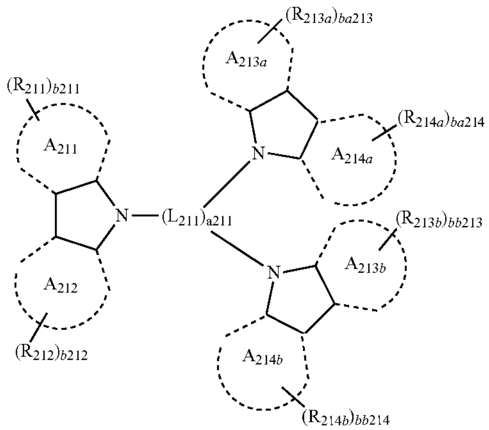

-continued
<Formula 301A>
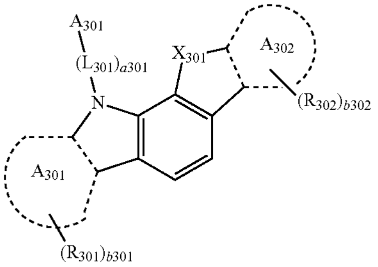
<Formula 301B>
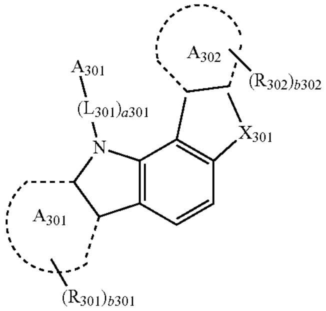
<Formula 301C>
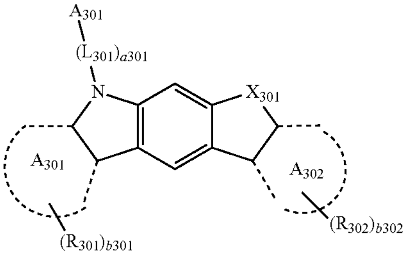
<Formula 301D>
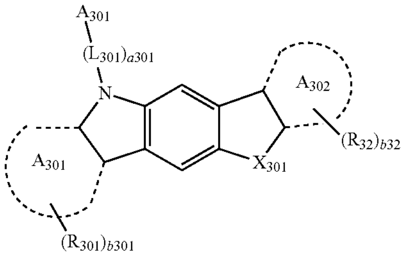
*<Formula 301D>*
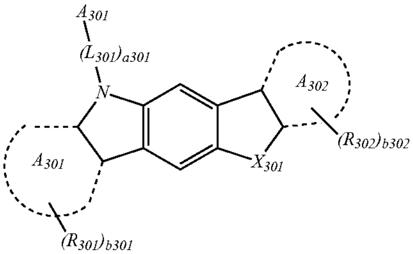
-continued
<Formula 301E>
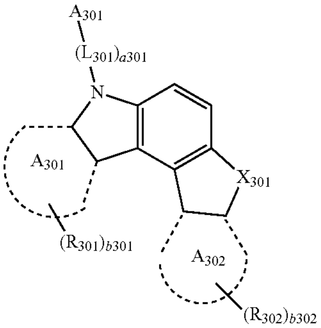
<Formula 301F>
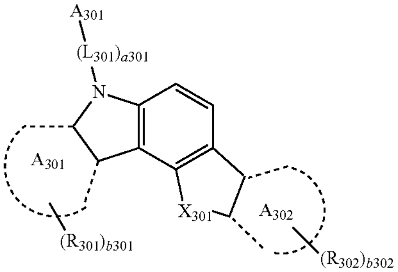
<Formula 30GF>
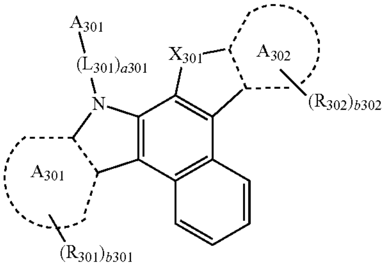
<Formula 301H>
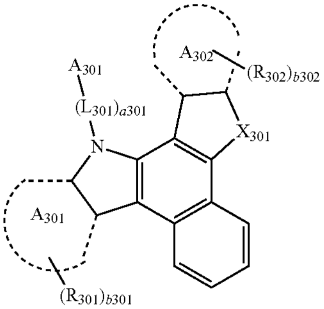
<Formula 302A>
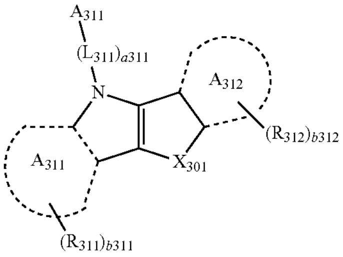

-continued

<Formula 302B>

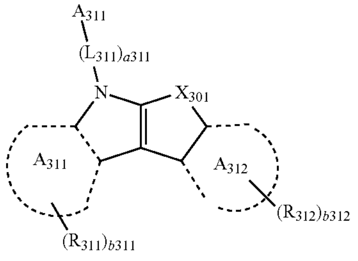

wherein, in the Formulae above, descriptions of $Ar_{101}$, $Ar_{201}$ to $A_{204}$, $A_{211}$ to $A_{214}$, $A_{301}$ to $A_{304}$, $A_{311}$, $A_{312}$, $A_{314}$, $X_{301}$, $L_{101}$, $L_{201}$ to $L_{203}$, $L_{301}$, $L_{302}$, $L_{311}$, a101, a201 to a203, a301, a302, a311, $Ar_{201}$, $Ar_{202}$, $Ar_{301}$, $Ar_{302}$, $Ar_{311}$, $R_{101}$, $R_{201}$ to $R_{204}$, $R_{211}$ to $R_{214}$, $R_{301}$, $R_{302}$, $R_{311}$, $R_{312}$, b101, b201 to b204, b211 to b214, b301, b302, b311, and b312 are the same as described in claim [15] *16*, descriptions of $L_{102}$ and $L_{103}$ are each the same as descriptions of $L_{101}$, descriptions of a102 and a103 are each the same as descriptions of a101, descriptions of $R_{102}$ and $R_{103}$ are each the same as descriptions of $R_{101}$, and descriptions of b102 and b103 are each the same as descriptions of b101, and descriptions of $A_{213a}$ and $A_{213b}$ are each the same as descriptions of $A_{213}$, descriptions of $A_{214a}$ and $A_{214b}$ are each the same as descriptions of $A_{214}$, descriptions of $R_{213a}$ and $R_{213b}$ are each the same as descriptions of $R_{213}$, descriptions of $R_{214b}$ and $R_{214b}$ are each the same as descriptions of $R_{214}$, descriptions of ba213 and bb213 are each the same as descriptions of b213, and descriptions of ba214 and bb214 are each the same as descriptions of b214.

18. The organic light-emitting device as claimed in claim [1] *21*, wherein

[the hole transport region includes a hole transport layer and a hole injection layer between the first electrode and the hole transport layer,]

the hole transport region includes a hole transport layer and a hole injection layer between the first electrode and the hole transport layer, the first compound is included in the hole injection layer and the hole transport layer, the first compound included in the hole injection layer and the first compound included in the hole transport layer are identical to or different from each other, the electron transport region includes an electron transport layer and an electron injection layer between the second electrode and the electron transport layer, and the second compound is included in the electron transport layer.

19. An organic light-emitting device, comprising:

a first electrode;

a second electrode facing the first electrode;

an emission layer between the first electrode and the second electrode;

a hole transport region between the first electrode and the emission layer;

an electron transport region between the second electrode and the emission layer, wherein the hole transport region includes a hole transport layer, a hole injection layer between the first electrode and the hole transport layer, and an auxiliary emission layer between the hole transport layer and the emission layer, the electron transport region includes an electron transport layer and an electron injection layer between the second electrode and the electron transport layer, wherein the hole injection layer, the hole transport layer, and the auxiliary emission layer each include a first compound represented by one of Formulae 1A, 1B, and 1C, the first compound included in the hole injection layer, the first compound included in the hole transport layer, and the first compound included in the auxiliary emission layer are identical to or different from each other, the electron transport layer includes a second compound represented by one of Formulae [40A and 40 B] *40A-1(1) to 40A-1(3) and 40B-2(1) to 40B-2(5)*:

<Formula 1A>

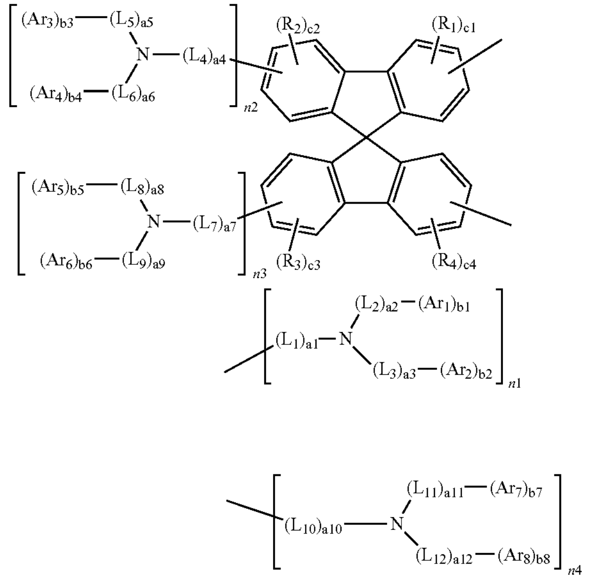

<Formula 1B>

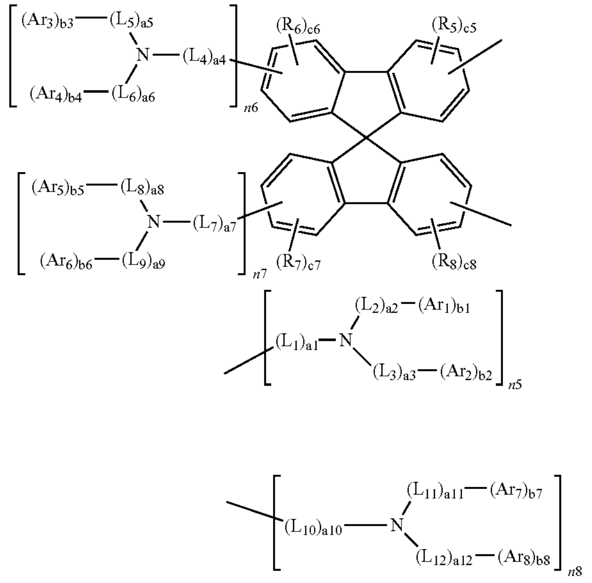

-continued

<Formula 1C>

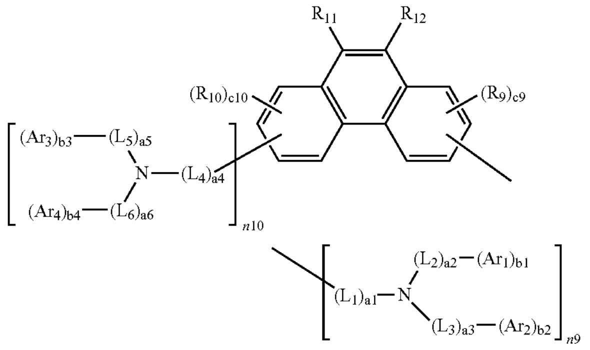

[

<Formula 40A>

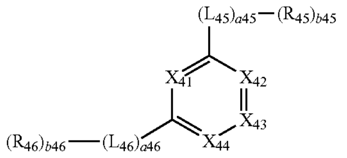

<Formula 40B>

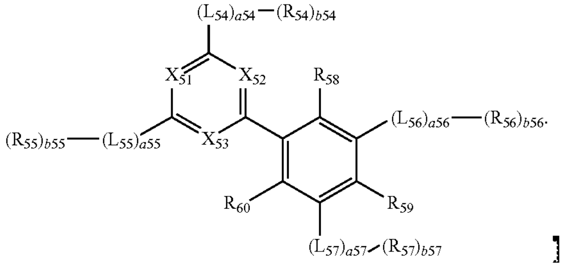

]

*<Formula 40A-1(1)>*

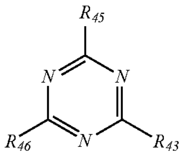

*<Formula 40A-1(2)>*

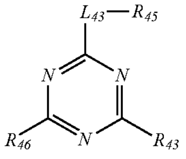

*<Formula 40A-1(3)>*

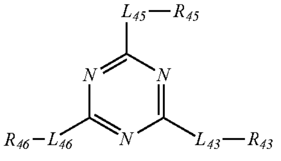

*<Formula 40B-2(1)>*

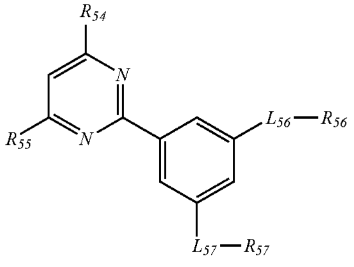

-continued

*<Formula 40B-2(2)>*

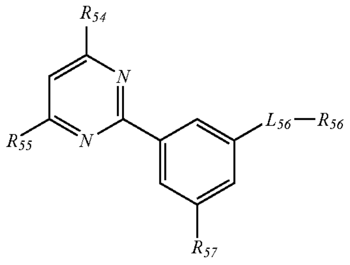

*<Formula 40B-2(3)>*

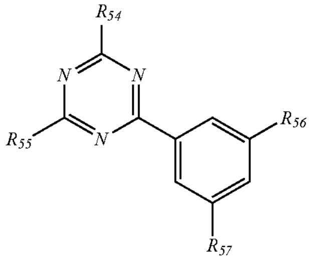

*<Formula 40B-2(4)>*

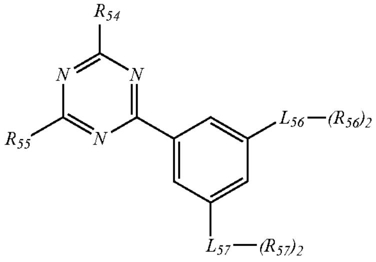

*<Formula 40B-2(5)>*

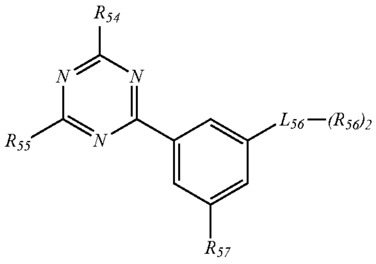

wherein, in Formulae 1A, 1B, 1C, [40A, and 40B] *40A-1(1) to 40A-1(3) and 40B-2(1) to 40B-2(5)*,

[$X_{41}$ is N or C-$(L_{41})_{a41}$-$(R_{41})_{b41}$, $X_{42}$ is N or C-$(L_{42})_{a42}$-$(R_{42})_{b42}$, $X_{43}$ is N or C-$(L_{43})_{a43}$-$(R_{43})_{b43}$, $X_{44}$ is N or C-$(L_{44})_{a44}$-$(R_{44})_{b44}$, and at least one selected from $X_{41}$ to $X_{44}$ is N;

$X_{51}$ is N or C-$(L_{51})_{a51}(R_{51})_{b51}$, $X_{52}$ is N or C-$(L_{52})_{a52}(R_{52})_{b52}$, $X_{53}$ is N or C-$(L_{53})_{a53}(R_{52})_{b53}$, and at least one selected from $X_{51}$ to $X_{53}$ is N;]

$L_1$ to $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

[$L_{41}$ to $L_{46}$ and $L_{51}$ to $L_{57}$] *$L_{43}$, $L_{45}$, $L_{46}$, $L_{56}$ and $L_{57}$* are each independently selected from a substituted or unsubstituted $C_3$-$C_{10}$ cycloalkylene group, a substituted or unsubstituted $C_3$-$C_{10}$ cycloalkenylene group, a substituted or unsubstituted $C_6$-$C_{60}$ arylene group, and a substituted or unsubstituted divalent non-aromatic condensed polycyclic group*, wherein $L_{41}$ to $L_{46}$ are not identical to each other and $L_{51}$ to $L_{57}$ are not identical to each other, and wherein $L_{41}$ to $L_{46}$ and $L_{51}$ to $L_{57}$ do not include a carbazolylene group, a fluorenylene group, or a spiro-fluorenylene group*;

a1 to a12[, a41 to a46, and a51 to a57] are each independently an integer selected from 0 to 3;

$Ar_1$ to $Ar_8$ [, $R_{41}$ to $R_{46}$, and $R_{51}$ to $R_{57}$] are each independently selected from a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted Ca-Cao aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$Ar_1$ and $Ar_2$ are optionally linked to each other to form a saturated or unsaturated ring, $Ar_3$ and $Ar_4$ are optionally linked to each other to form a saturated or unsaturated ring, $Ar_5$ and $Ar_6$ are optionally linked to each other to form a saturated or unsaturated ring, and $Ar_7$ and $Ar_8$ are optionally linked to each other to form a saturated or unsaturated ring;

[at least one of $R_{41}$ to $R_{46}$ or at least one of $R_{51}$ to $R_{57}$ is selected from a substituted or unsubstituted $C_1$-$C_{10}$ heterocycloalkyl group, a substituted or unsubstituted $C_1$-$C_{10}$ heterocycloalkenyl group, a substituted or unsubstituted $C_1$-$C_{60}$ heteroaryl group, and a substituted or unsubstituted monovalent non-aromatic condensed heteropolycyclic group;] *$R_{43}$, $R_{45}$, $R_{46}$, and $R_{54}$ to $R_{57}$ are each independently selected from a substituted or unsubstituted $C_6$-$C_{18}$ aryl group and an electron transporting group including at least one N as a ring-forming atom, wherein $R_{43}$, $R_{45}$, $R_{46}$, and $R_{54}$ to $R_{57}$ do not include a fluorenyl group or a spiro-fluorenyl group;*

*wherein in Formulae 40A-1(1) to 40A-1(3), at least two of $R_{43}$, $R_{45}$ and $R_{46}$ are not identical to each other, and at least one of $R_{43}$, $R_{45}$ and $R_{46}$ is an electron transporting group including at least one N as a ring-forming atom; and*

*wherein in Formulae 40B-2(1) to 40B-2(5), at least one of $R_{56}$ and $R_{57}$ is an electron transporting group including at least one N as a ring-forming atom;* b1 to b8[, b41 to b46, and b51 to b57] are each independently an integer selected from 1 to 4;

$R_1$ to $R_{12}$ [and $R_{58}$ to $R_{60}$] are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted Ci-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —$Si(Q_1)(Q_2)(Q_3)$;

$R_{11}$ and $R_{12}$ are optionally linked to each other to form a saturated or unsaturated ring;

c1 to c10 are each independently an integer selected from 0 to 4;

n1 to n4 and n7 to n10 are each independently an integer selected from 0 to 4, and n5 and n6 are each independently an integer selected from 0 to 5, provided that n1+n2+n3+n4 is 1 or more, n5+n6+n7+n8 is 1 or more, and n9+n10 is 1 or more;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group(arylthio), a $C_1$-$C_{60}$ heteroaryl group, a monovalent non-aromatic condensed polycyclic group, a monovalent non-aromatic condensed heteropolycyclic group, and —$Si(Q_{11})(Q_{12})(Q_{13})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group,a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Qi_1$ to $Q_3$, $Q_{11}$ to $Q_{13}$, $Q_{21}$ to $Q_{23}$, and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

*21. An organic light-emitting device, comprising:*

*a first electrode;*

*a second electrode facing the first electrode;*

*an emission layer between the first electrode and the second electrode;*

*a hole transport region between the first electrode and the emission layer; and*

*an electron transport region between the second electrode and the emission layer, wherein the hole transport region includes a first compound represented by one of Formulae 1A, 1B, and 1C, and the electron transport region includes a second compound represented by one of Formulae 40A-1(1) to 40A-1(3) and 40B-2(1) to 40B-2(5):*

<Formula 1A>

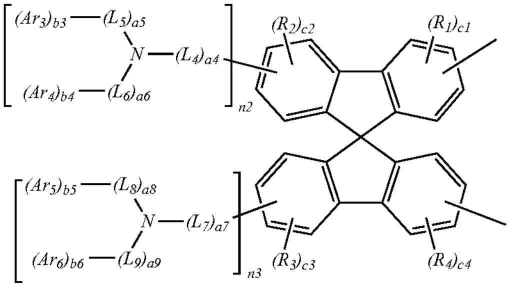

*-continued*

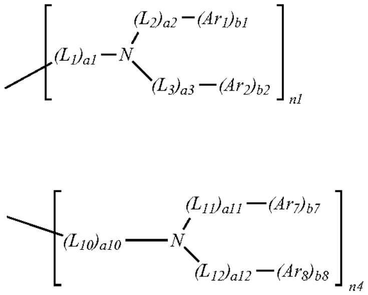

<Formula 1B>

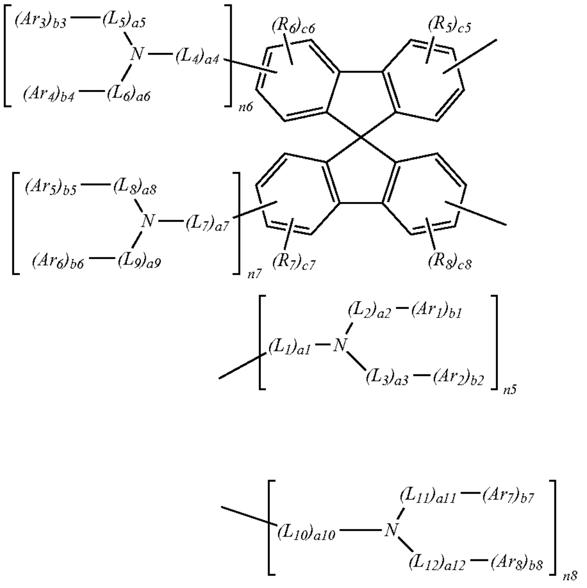

<Formula 1C>

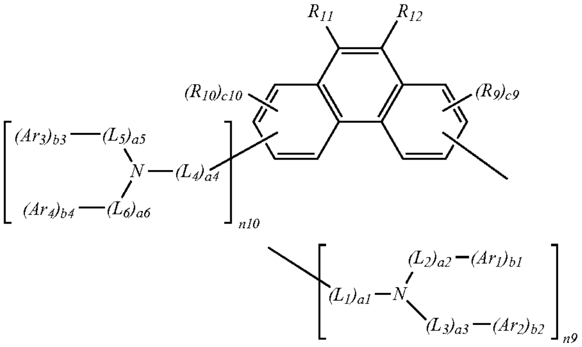

<Formula 40A-1(1)>

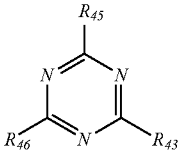

<Formula 40A-1(2)>

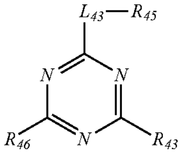

-continued

<Formula 40A-1(3)>

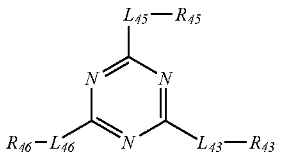

<Formula 40B-2(1)>

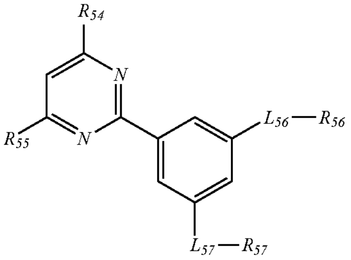

<Formula 40B-2(2)>

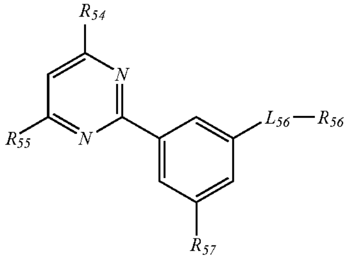

<Formula 40B-2(3)>

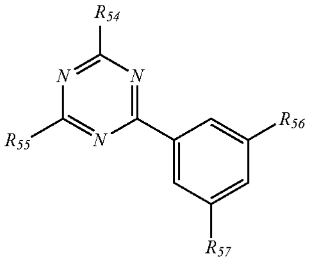

<Formula 40B-2(4)>

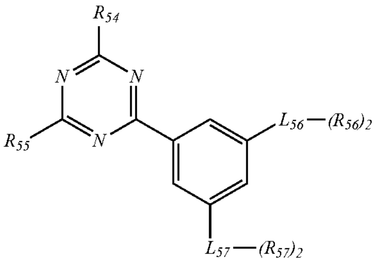

<Formula 40B-2(5)>

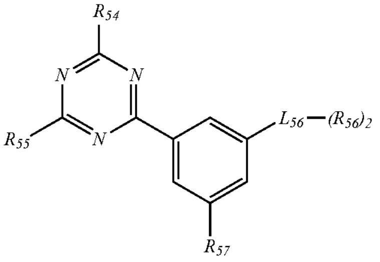

*wherein, in Formulae 1A, 1B, 1C, 40A-1(1) to 40A-1(3) and 40B-2(1) to 40B-2(5),*

*$L_1$ to $L_{12}$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{10}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;*

*$L_{43}$, $L_{45}$, $L_{46}$, $L_{56}$ and $L_{57}$ are each independently selected from a substituted or unsubstituted $C_6$-$C_{18}$ arylene group, wherein $L_{43}$, $L_{45}$, $L_{46}$, $L_{56}$ and $L_{57}$ do not include a fluorenylene group or a spiro-fluorenylene group;*

*a1 to a12 are each independently an integer selected from 0 to 3;*

*$Ar_1$ to $Ar_8$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;*

*$Ar_1$ and $Ar_2$ are optionally linked to each other to form a saturated or unsaturated ring, $Ar_2$ and $Ar_4$ are optionally linked to each other to form a saturated or unsaturated ring, $Ar_5$ and $Ar_6$ are optionally linked to each other to form a saturated or unsaturated ring, and $Ar_7$ and $Ar_8$ are optionally linked to each other to form a saturated or unsaturated ring;*

*$R_{43}$, $R_{45}$, $R_{46}$, and $R_{54}$ to $R_{57}$ are each independently selected from a substituted or unsubstituted $C_6$-$C_{18}$ aryl group and an electron transporting group including at least one N as a ring-forming atom, wherein $R_{43}$, $R_{45}$, $R_{46}$, and $R_{54}$ to $R_{57}$ do not include a fluorenyl group or a spiro-fluorenyl group;*

*wherein in Formulae 40A-1(1) to 40A-1(3), at least two of $R_{43}$, $R_{45}$ and $R_{46}$ are not identical to each other, and at least one of $R_{43}$, $R_{45}$ and $R_{46}$ is an electron transporting group including at least one N as a ring-forming atom; and*

*wherein in Formulae 40B-2(1) to 40B-2(5), at least one of $R_{56}$ and $R_{57}$ is an electron transporting group including at least one N as a ring-forming atom;*

*b1 to b8 are each independently an integer selected from 1 to 4;*

*$R_1$ to $R_{12}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substi-* tuted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

$R_{11}$ and $R_{12}$ are optionally linked to each other to form a saturated or unsaturated ring;

c1 to c10 are each independently an integer selected from 0 to 4;

n1 to n4 and n7 to n10 are each independently an integer selected from 0 to 4, and n5 and n6 are each independently an integer selected from 0 to 5, provided that n1+n2+n3+n4 is 1 or more, n5+n6+n7+n8 is 1 or more, and n9+n10 is 1 or more;

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group(arylthio), a $C_1$-$C_{60}$ heteroaryl group, a monovalent non-aromatic condensed polycyclic group, a monovalent non-aromatic condensed heteropolycyclic group, and —Si($C_{211}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group,a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$); and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

* * * * *